United States Patent
Subramanian et al.

(10) Patent No.: US 11,679,161 B2
(45) Date of Patent: *Jun. 20, 2023

(54) MUSCLE TARGETING COMPLEXES AND USES THEREOF FOR TREATING FACIOSCAPULOHUMERAL MUSCULAR DYSTROPHY

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US); Cody A. Desjardins, Waltham, MA (US); Brendan Quinn, Boston, MA (US); John Najim, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,795

(22) Filed: Dec. 9, 2022

(65) Prior Publication Data
US 2023/0118799 A1    Apr. 20, 2023

Related U.S. Application Data

(63) Continuation of application No. 17/811,380, filed on Jul. 8, 2022.

(60) Provisional application No. 63/220,155, filed on Jul. 9, 2021.

(51) Int. Cl.
| | | |
|---|---|---|
| A61K 39/395 | (2006.01) | |
| A61K 47/68 | (2017.01) | |
| C07K 14/47 | (2006.01) | |
| C12N 15/113 | (2010.01) | |
| C07K 16/28 | (2006.01) | |
| A61K 38/00 | (2006.01) | |
| A61K 39/00 | (2006.01) | |

(52) U.S. Cl.
CPC ...... *A61K 47/6807* (2017.08); *A61K 47/6849* (2017.08); *C07K 14/4707* (2013.01); *C07K 16/2881* (2013.01); *C12N 15/113* (2013.01); *A61K 38/00* (2013.01); *A61K 2039/505* (2013.01); *C07K 2317/24* (2013.01); *C07K 2317/33* (2013.01); *C07K 2317/55* (2013.01); *C07K 2317/77* (2013.01); *C07K 2317/92* (2013.01); *C07K 2317/94* (2013.01); *C12N 2310/11* (2013.01); *C12N 2310/14* (2013.01); *C12N 2310/3513* (2013.01)

(58) Field of Classification Search
None
See application file for complete search history.

(56) References Cited

U.S. PATENT DOCUMENTS

| | | |
|---|---|---|
| 2,631,173 A | 3/1953 | Hillyer et al. |
| 6,214,345 B1 | 4/2001 | Firestone et al. |
| 7,015,315 B1 | 3/2006 | Cook et al. |
| 7,064,142 B2 | 6/2006 | Sato et al. |
| 7,265,131 B2 | 9/2007 | Johnson et al. |
| 7,534,879 B2 | 5/2009 | van Deutekom et al. |
| 7,575,886 B2 | 8/2009 | Venkataraman et al. |
| 7,960,541 B2 | 6/2011 | Wilton et al. |
| 7,973,015 B2 | 7/2011 | Dunnen et al. |
| 8,084,601 B2 | 12/2011 | Graham et al. |
| 8,232,384 B2 | 7/2012 | Wilton et al. |
| 8,324,371 B2 | 12/2012 | Graham et al. |
| 8,361,979 B2 | 1/2013 | van Ommen et al. |
| 8,455,636 B2 | 6/2013 | Fletcher et al. |
| 8,486,907 B2 | 7/2013 | Wilton et al. |
| 8,524,880 B2 | 9/2013 | Mcclorey et al. |
| 8,580,756 B2 | 11/2013 | Hansen et al. |
| 8,759,507 B2 | 6/2014 | van Deutekom et al. |
| 8,802,437 B2 | 8/2014 | Tremblay et al. |
| 8,846,639 B2 | 9/2014 | Swayze et al. |
| 8,859,629 B2 | 10/2014 | van Delft et al. |
| 8,865,883 B2 | 10/2014 | Kole et al. |
| 8,952,147 B2 | 2/2015 | Bouchard et al. |
| 9,018,368 B2 | 4/2015 | Wilton et al. |

(Continued)

FOREIGN PATENT DOCUMENTS

| | | |
|---|---|---|
| EP | 1619249 A1 | 1/2006 |
| EP | 2149605 A2 | 2/2010 |

(Continued)

OTHER PUBLICATIONS

[No Author Listed] GenBank: AF095738.1. Mus musculus dystrophin gene, exons 22-25 and partial CDs. 2016. Retrieved from the internet Oct. 30, 2019: https://www.ncbi.nlm.nih.gov/nucleotide/AF095738.1?report=genbank&log$=nuclalign&blast_rank=3&RID=VKBMZ9WW014, 5 pages.

(Continued)

*Primary Examiner* — Meera Natarajan
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits expression or activity of DUX4. In some embodiments, the molecular payload is an oligonucleotide, such as an antisense oligonucleotide or RNAi oligonucleotide.

25 Claims, 21 Drawing Sheets

Specification includes a Sequence Listing.

(56) References Cited

U.S. PATENT DOCUMENTS

| | | |
|---|---|---|
| 9,024,007 B2 | 5/2015 | Wilton et al. |
| 9,045,754 B2 | 6/2015 | Bhanot et al. |
| 9,078,911 B2 | 7/2015 | Lu et al. |
| 9,079,934 B2 | 7/2015 | Takeda et al. |
| 9,222,940 B2 | 12/2015 | van Delft et al. |
| 9,228,187 B2 | 1/2016 | Meloni et al. |
| 9,243,245 B2 | 1/2016 | De Kimpe et al. |
| 9,260,371 B2 | 2/2016 | Bertozzi et al. |
| 9,416,361 B2 | 8/2016 | Iversen et al. |
| 9,422,555 B2 | 8/2016 | Wilton et al. |
| 9,428,534 B2 | 8/2016 | Christensen et al. |
| 9,447,415 B2 | 9/2016 | Wilton et al. |
| 9,504,758 B2 | 11/2016 | van Delft et al. |
| 9,506,058 B2 | 11/2016 | Kaye |
| 9,512,424 B2 | 12/2016 | Wantanabe et al. |
| 9,550,834 B2 | 1/2017 | Shirai et al. |
| 9,550,988 B2 | 1/2017 | Swayze |
| 9,610,362 B2 | 4/2017 | Armstrong |
| 9,617,540 B2 | 4/2017 | Bhanot et al. |
| 9,657,049 B2 | 5/2017 | Koizumi et al. |
| 9,657,050 B2 | 5/2017 | Koizumi et al. |
| 9,695,418 B2 | 7/2017 | Seth et al. |
| 9,708,361 B2 | 7/2017 | Takeda et al. |
| 9,708,406 B2 | 7/2017 | Zhang et al. |
| 9,708,614 B2 | 7/2017 | Christensen et al. |
| 9,758,783 B2 | 9/2017 | Meloni et al. |
| 9,765,338 B2 | 9/2017 | Bennett et al. |
| 9,840,706 B2 | 12/2017 | Tetsuya et al. |
| 9,970,010 B2 | 5/2018 | Graham et al. |
| 9,988,628 B2 | 6/2018 | Belayew et al. |
| 9,988,629 B2 | 6/2018 | Takeda et al. |
| 9,994,851 B2 | 6/2018 | Wilton et al. |
| 10,100,304 B2 | 10/2018 | van Deutkom et al. |
| 10,131,682 B2 | 11/2018 | Zhao |
| 10,144,931 B2 | 12/2018 | Enya et al. |
| 10,190,116 B2 | 1/2019 | van Deutekom et al. |
| 10,238,753 B2 | 3/2019 | Armstrong |
| 10,239,807 B2 | 3/2019 | van Delft et al. |
| 10,266,502 B2 | 4/2019 | van Delft et al. |
| 10,287,586 B2 | 5/2019 | Wilson et al. |
| 10,337,003 B2 | 7/2019 | Kaye |
| 10,364,431 B2 | 7/2019 | Kaye |
| 10,385,092 B2 | 8/2019 | Watanabe et al. |
| 10,407,461 B2 | 9/2019 | Watanabe et al. |
| 10,434,111 B2 | 10/2019 | Bertozzi et al. |
| 10,450,568 B2 | 10/2019 | Butler et al. |
| 10,487,106 B2 | 11/2019 | Watanabe et al. |
| RE47,751 E | 12/2019 | Wilton et al. |
| RE47,769 E | 12/2019 | Wilton et al. |
| 10,493,092 B2 | 12/2019 | Swayze |
| 10,533,171 B2 | 1/2020 | van Deutekom et al. |
| 10,533,174 B2 | 1/2020 | Iversen et al. |
| 10,538,763 B2 | 1/2020 | Rigo et al. |
| 10,550,188 B2 | 2/2020 | Geall et al. |
| 10,704,060 B2 | 7/2020 | Gersbach et al. |
| 10,752,898 B2 | 8/2020 | Pietri et al. |
| 10,781,451 B2 | 9/2020 | Wilton et al. |
| 10,865,445 B2 | 12/2020 | van der Maarel et al. |
| 10,876,114 B2 | 12/2020 | van Deutekom et al. |
| 10,881,743 B2 | 1/2021 | Geall et al. |
| 10,907,157 B2 | 2/2021 | Belayew et al. |
| RE48,468 E | 3/2021 | De Kimpe et al. |
| 11,111,309 B2 | 9/2021 | Subramanian et al. |
| 11,168,141 B2 | 11/2021 | Subramanian et al. |
| 11,230,605 B2 * | 1/2022 | Launay ............... A61P 35/00 |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 11,497,815 B2 | 11/2022 | Subramanian et al. |
| 11,518,816 B2 | 12/2022 | Subramanian et al. |
| 2004/0063654 A1 | 4/2004 | Davis et al. |
| 2005/0004026 A1 | 1/2005 | Kashibatla et al. |
| 2005/0084906 A1 | 4/2005 | Goetsch et al. |
| 2005/0255487 A1 | 11/2005 | Khvorova et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2007/0050146 A1 | 3/2007 | Bentwich et al. |
| 2007/0082861 A1 | 4/2007 | Matsuo et al. |
| 2007/0105805 A1 | 5/2007 | Kmiec et al. |
| 2008/0199960 A1 | 8/2008 | Juliano et al. |
| 2009/0269755 A1 | 10/2009 | Aartsma-Rus et al. |
| 2010/0130591 A1 | 5/2010 | Sazani et al. |
| 2010/0168212 A1 | 7/2010 | Popplewell et al. |
| 2011/0263682 A1 | 10/2011 | De Kimpe et al. |
| 2012/0077860 A1 | 3/2012 | Garcia et al. |
| 2012/0122801 A1 | 5/2012 | Platenburg |
| 2012/0201809 A1 | 8/2012 | Bhat et al. |
| 2012/0225034 A1 | 9/2012 | Belayew et al. |
| 2012/0270925 A1 | 10/2012 | Wilton et al. |
| 2013/0028891 A1 | 1/2013 | Penichet et al. |
| 2013/0041017 A1 | 2/2013 | Kaplan et al. |
| 2013/0066063 A1 | 3/2013 | Berry et al. |
| 2013/0072541 A1 | 3/2013 | Garcia et al. |
| 2013/0137763 A1 | 5/2013 | van Delft et al. |
| 2013/0177579 A1 | 7/2013 | Lin et al. |
| 2013/0237585 A1 | 9/2013 | Bennett et al. |
| 2014/0105873 A1 | 4/2014 | Belayew et al. |
| 2014/0193436 A1 | 7/2014 | Prudent |
| 2014/0323552 A1 | 10/2014 | Burghes et al. |
| 2014/0336178 A1 | 11/2014 | Kazantsev et al. |
| 2014/0363455 A1 | 12/2014 | Stull et al. |
| 2015/0191725 A1 | 7/2015 | van Deutekom et al. |
| 2015/0196670 A1 | 7/2015 | Dickson et al. |
| 2015/0258210 A1 | 9/2015 | van Delft et al. |
| 2016/0032286 A1 | 2/2016 | Montgomery et al. |
| 2016/0107999 A1 | 4/2016 | Debets et al. |
| 2016/0175460 A1 | 6/2016 | Arathoon et al. |
| 2016/0201064 A1 | 7/2016 | Ozsolak |
| 2016/0235861 A1 | 8/2016 | van Delft et al. |
| 2016/0250347 A1 | 9/2016 | van Delft et al. |
| 2016/0264976 A1 | 9/2016 | Laporte et al. |
| 2016/0272973 A1 | 9/2016 | Shehadeh |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0029849 A1 | 2/2017 | Harper et al. |
| 2017/0072068 A1 | 3/2017 | Verkade et al. |
| 2017/0130256 A1 | 5/2017 | van Berkel et al. |
| 2017/0151348 A1 | 6/2017 | Kaspar et al. |
| 2017/0226554 A1 | 8/2017 | Wasiel et al. |
| 2017/0281795 A1 | 10/2017 | Geall et al. |
| 2017/0283799 A1 | 10/2017 | Kaye et al. |
| 2017/0348416 A1 | 12/2017 | Hasler et al. |
| 2018/0002433 A1 | 1/2018 | Zhang et al. |
| 2018/0021449 A1 | 1/2018 | Armstrong |
| 2018/0028554 A1 | 2/2018 | De Visser et al. |
| 2018/0094262 A1 | 4/2018 | Montgomery et al. |
| 2018/0111983 A1 | 4/2018 | Hatsell et al. |
| 2018/0134797 A1 | 5/2018 | Zhang et al. |
| 2018/0142245 A1 | 5/2018 | Watanabe et al. |
| 2018/0171333 A1 | 6/2018 | Meloni et al. |
| 2018/0179538 A1 | 6/2018 | Takeda et al. |
| 2018/0216111 A1 | 8/2018 | Wilton et al. |
| 2018/0265859 A1 | 9/2018 | Tremblay et al. |
| 2018/0265870 A1 | 9/2018 | Belayew et al. |
| 2018/0369400 A1 | 12/2018 | Levin et al. |
| 2019/0000986 A1 | 1/2019 | Levin et al. |
| 2019/0008986 A1 | 1/2019 | Butler et al. |
| 2019/0038765 A1 | 2/2019 | van Berkel et al. |
| 2019/0060488 A1 | 2/2019 | Tadin-Strapps et al. |
| 2019/0092833 A1 | 3/2019 | Lin et al. |
| 2019/0092870 A1 | 3/2019 | Launay et al. |
| 2019/0112604 A1 | 4/2019 | De Kimpe et al. |
| 2019/0119679 A1 | 4/2019 | De Kimpe et al. |
| 2019/0127733 A1 | 5/2019 | Butler et al. |
| 2019/0153083 A1 | 5/2019 | Juste et al. |
| 2019/0177723 A1 | 6/2019 | Dickson et al. |
| 2019/0177725 A1 | 6/2019 | De Kimpe et al. |
| 2019/0209604 A1 | 7/2019 | Zhang et al. |
| 2019/0211362 A1 | 7/2019 | Lundberg et al. |
| 2019/0240346 A1 | 8/2019 | Sugo et al. |
| 2019/0249173 A1 | 8/2019 | Vargeese et al. |

(56) References Cited

U.S. PATENT DOCUMENTS

| | | |
|---|---|---|
| 2019/0270994 A1 | 9/2019 | Wilton et al. |
| 2019/0284556 A1 | 9/2019 | Sazani et al. |
| 2019/0298847 A1 | 10/2019 | Geall et al. |
| 2019/0323010 A1 | 10/2019 | Wilton et al. |
| 2019/0330626 A1 | 10/2019 | Rigo et al. |
| 2019/0338311 A1 | 11/2019 | Amoasii et al. |
| 2019/0359982 A1 | 11/2019 | Kaye et al. |
| 2019/0364862 A1 | 12/2019 | Amoasii et al. |
| 2019/0390197 A1 | 12/2019 | Butler et al. |
| 2020/0040337 A1 | 2/2020 | Kaye et al. |
| 2020/0046742 A1 | 2/2020 | Bertozzi et al. |
| 2020/0046854 A1 | 2/2020 | Zhang et al. |
| 2020/0048174 A1 | 2/2020 | van Delft et al. |
| 2020/0123267 A1 | 4/2020 | Zhang et al. |
| 2020/0239886 A1 | 7/2020 | De Kimpe et al. |
| 2020/0248179 A1 | 8/2020 | Harper |
| 2020/0282074 A1 | 9/2020 | Levin et al. |
| 2020/0325237 A1 | 10/2020 | Darimont et al. |
| 2021/0163941 A1 | 6/2021 | Belayew et al. |
| 2021/0163942 A1 | 6/2021 | Belayew et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |

FOREIGN PATENT DOCUMENTS

| | | |
|---|---|---|
| EP | 2284264 A1 | 2/2011 |
| EP | 2410053 A1 | 1/2012 |
| EP | 2410054 A1 | 1/2012 |
| EP | 2426203 A2 | 3/2012 |
| EP | 2801618 A1 | 11/2014 |
| EP | 3031920 A1 | 6/2016 |
| EP | 3067421 A1 | 9/2016 |
| EP | 2623609 B1 | 1/2017 |
| EP | 3192880 A1 | 7/2017 |
| EP | 2736539 B1 | 8/2017 |
| EP | 3202905 A1 | 8/2017 |
| EP | 3238737 A1 | 11/2017 |
| EP | 2922818 B1 | 9/2018 |
| EP | 3473270 A1 | 4/2019 |
| EP | 3489360 A2 | 5/2019 |
| IL | 54795 A | 10/1980 |
| JP | 2007104971 A | 4/2007 |
| WO | WO 1989/007970 A1 | 9/1989 |
| WO | WO 1991/004753 A1 | 4/1991 |
| WO | WO 2001/083740 A1 | 11/2001 |
| WO | WO 2004/069991 A2 | 8/2004 |
| WO | WO 2005/023825 A2 | 3/2005 |
| WO | WO 2006/000057 A1 | 1/2006 |
| WO | WO 2007/089612 A2 | 8/2007 |
| WO | WO 2007/135105 A1 | 11/2007 |
| WO | WO 2008/018795 A1 | 2/2008 |
| WO | WO 2008/049085 A1 | 4/2008 |
| WO | WO 2009/054725 A2 | 4/2009 |
| WO | WO 2009/144481 A2 | 12/2009 |
| WO | WO 2010/048586 A1 | 4/2010 |
| WO | WO 2010/050801 A1 | 5/2010 |
| WO | WO 2011/057350 A1 | 5/2011 |
| WO | WO 2011/078797 A2 | 6/2011 |
| WO | WO 2011/136645 A1 | 11/2011 |
| WO | WO 2011/150408 A2 | 12/2011 |
| WO | WO 2011/154427 A1 | 12/2011 |
| WO | WO 2012/012443 A2 | 1/2012 |
| WO | WO 2012/029986 A1 | 3/2012 |
| WO | WO 2012/144906 A1 | 10/2012 |
| WO | WO 2013/016352 A1 | 1/2013 |
| WO | WO 2013/019623 A2 | 2/2013 |
| WO | WO 2013/085550 A2 | 6/2013 |
| WO | WO 2013/100190 A1 | 7/2013 |
| WO | WO 2014/065661 A1 | 5/2014 |
| WO | WO 2014/144978 A2 | 9/2014 |
| WO | WO 2014/153240 A2 | 9/2014 |
| WO | WO 2015/021457 A2 | 2/2015 |
| WO | WO 2015/055859 A1 | 4/2015 |
| WO | WO 2015/070158 A1 | 5/2015 |
| WO | WO 2015/143062 A1 | 9/2015 |
| WO | WO 2015/179741 A1 | 11/2015 |
| WO | WO 2016/039796 A2 | 3/2016 |
| WO | WO 2016/081643 A1 | 5/2016 |
| WO | WO 2016/081670 A2 | 5/2016 |
| WO | WO 2016/187425 A1 | 11/2016 |
| WO | WO 2017/047707 A1 | 3/2017 |
| WO | WO 2017/050836 A1 | 3/2017 |
| WO | WO 2017/100467 A2 | 6/2017 |
| WO | WO 2017/143156 A1 | 8/2017 |
| WO | WO 2017/173408 A1 | 10/2017 |
| WO | WO 2017/184529 A1 | 10/2017 |
| WO | WO 2017/192679 A1 | 11/2017 |
| WO | WO 2017/205191 A1 | 11/2017 |
| WO | WO 2017/221883 A1 | 12/2017 |
| WO | WO 2018/007475 A1 | 1/2018 |
| WO | WO 2018/014042 A1 | 1/2018 |
| WO | WO 2018/017754 A1 | 1/2018 |
| WO | WO 2018/057575 A1 | 3/2018 |
| WO | WO 2018/091544 A1 | 5/2018 |
| WO | WO 2018/098480 A1 | 5/2018 |
| WO | WO 2018/100010 A1 | 6/2018 |
| WO | WO 2018/107003 A1 | 6/2018 |
| WO | WO 2018/129296 A1 | 7/2018 |
| WO | WO 2018/129384 A1 | 7/2018 |
| WO | WO 2018/226861 A1 | 12/2018 |
| WO | WO 2019/014772 A1 | 1/2019 |
| WO | WO 2019/059973 A1 | 3/2019 |
| WO | WO 2019/060432 A2 | 3/2019 |
| WO | WO 2019/060775 A1 | 3/2019 |
| WO | WO 2019/067975 A1 | 4/2019 |
| WO | WO 2019/071028 A1 | 4/2019 |
| WO | WO 2019/092507 A2 | 5/2019 |
| WO | WO 2019/110725 A1 | 6/2019 |
| WO | WO 2019/113393 A1 | 6/2019 |
| WO | WO 2019/126641 A2 | 6/2019 |
| WO | WO 2019/136180 A2 | 7/2019 |
| WO | WO 2019/136216 A1 | 7/2019 |
| WO | WO 2019/152609 A1 | 8/2019 |
| WO | WO 2019/152820 A1 | 8/2019 |
| WO | WO 2019/157224 A1 | 8/2019 |
| WO | WO 2019/200185 A1 | 10/2019 |
| WO | WO 2019/215333 A1 | 11/2019 |
| WO | WO 2019/229658 A1 | 12/2019 |
| WO | WO 2019/241385 A2 | 12/2019 |
| WO | WO 2019/246480 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |

(56) References Cited

FOREIGN PATENT DOCUMENTS

| | | |
|---|---|---|
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/219820 A1 | 10/2020 |
| WO | WO 2020/247738 A1 | 12/2020 |
| WO | WO 2020/247782 A1 | 12/2020 |
| WO | WO 2020/247818 A1 | 12/2020 |
| WO | WO 2021/003573 A1 | 1/2021 |
| WO | WO 2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051332 A1 | 3/2022 |
| WO | WO 2022/051665 A1 | 3/2022 |
| WO | WO 2022/115745 A1 | 6/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/159712 A1 | 7/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |

OTHER PUBLICATIONS

[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.

[No Author Listed] Wikipedia, Dystrophin, Mar. 9, 2018. Retrieved from the internet Nov. 5, 2019: https://en.wikipedia.org/w/index.php?title=Dystrophin&oldid=829543258, 10 pages.

[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.

[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.

[No Author Listed], Alessandra Baleyew—Abstract. MDA National Scientific Conference. Neuromuscular Therapeutic Strategies: Overcoming the Barriers from Microscope to Marketplace. Mar. 13-16, 2011. Las Vegas, Nevada. 2 pages.

[No Author Listed], Baliforsen—Ionis Pharmaceuticals Drug Profile. Springer Nature Switzerland AG. Nov. 15, 2016. 9 pages.

[No Author Listed], Building the world's leading muscle disease company. Dyne Company Overview. Jun. 2021. 46 pages.

[No Author Listed], Highlights of prescribing information EXONDYS 51. FDA. <accessdata.fda.gov> Sep. 2016. Retrieved May 22, 2021. 11 pages.

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.

[No Author Listed], NCBI "NM_004006.2(DMD)". Published Oct. 30, 2020. Accessed from ncbi.nlm.nih.gov on May 21, 2021. 2 pages.

[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.

Aartsma-Rus et al., Antisense-induced multiexon skipping for Duchenne muscular dystrophy makes more sense. Am J Hum Genet. Jan. 2004;74(1):83-92. Epub Dec. 16, 2003.

Aartsma-Rus et al., Antisense-mediated exon skipping: a versatile tool with therapeutic and research applications. RNA. Oct. 2007;13(10):1609-24. doi: 10.1261/rna.653607. Epub Aug. 7, 2007.

Aartsma-Rus et al., Antisense-mediated modulation of splicing: therapeutic implications for Duchenne muscular dystrophy. RNA Biol. Jul.-Aug. 2010;7(4):453-61. doi: 10.4161/rna.7.4.12264. Epub Jul. 1, 2010.

Aartsma-Rus et al., Guidelines for antisense oligonucleotide design and insight into splice-modulating mechanisms. Mol Ther. Mar. 2009;17(3):548-53. doi: 10.1038/mt.2008.205. Epub Sep. 23, 2008.

Aartsma-Rus et al., Less is more: therapeutic exon skipping for Duchenne muscular dystrophy. Lancet Neurol. Oct. 2009;8(10):873-5. doi: 10.1016/S1474-4422(09)70229-7. Epub Aug. 25, 2009.

Aartsma-Rus et al., Progress in therapeutic antisense applications for neuromuscular disorders. Eur J Hum Genet. Feb. 2010;18(2):146-53. Epub Oct. 7, 2009.

Aartsma-Rus et al., Targeted exon skipping as a potential gene correction therapy for Duchenne muscular dystrophy. Neuromuscul Disord. Oct. 2002; 12 Suppl 1:S71-7. doi: 10.1016/s0960-8966(02)00086-x.

Adams et al., Antisense oligonucleotide induced exon skipping and the dystrophin gene transcript: cocktails and chemistries. BMC Mol Biol. Jul. 2, 2007;8:57.

Agard et al., A Comparative Study of Bioorthogonal Reactions with Azides. ACS Chem. Biol. 2006;1(10):644-8. Epub Oct. 20, 2006.

Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.

Alter et al., Systemic delivery of morpholino oligonucleotide restores dystrophin expression bodywide and improves dystrophic pathology. Nat Med. Feb. 2006; 12(2):175-7. doi: 10.1038/nm1345. Epub Jan. 29, 2006.

Anciaux et al., Transition-metal-catalyzed reactions of diazo compounds. 1. Cyclopropanation of double bonds. The Journal of Organic Chemistry. Feb. 1980;45(4):695-702.

Ansseau et al., Antisense Oligonucleotides Used to Target the DUX4 mRNA as Therapeutic Approaches in FaciosScapuloHumeral Muscular Dystrophy (FSHD). Genes (Basel). Mar. 3, 2017;8(3):93. doi: 10.3390/genes8030093.

Ansseau et al., DUX4c is up-regulated in FSHD. It induces the MYF5 protein and human myoblast proliferation. PLoS One. Oct. 15, 2009;4(10):e7482. 11 pages.

Antony-Mayer et al., Bicyclo[6.1.0]nonine. Chemische Berichte. Nov. 1988;121(11):2013-8.

Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.

Arechavala-Gomeza et al., Comparative analysis of antisense oligonucleotide sequences for targeted skipping of exon 51 during dystrophin pre-mRNA splicing in human muscle. Hum Gene Ther. Sep. 2007;18(9):798-810. doi: 10.1089/hum.2006.061.

(56) References Cited

OTHER PUBLICATIONS

Arnett et al., Therapy for neuromuscular disorders. Curr Opin Genet Dev. Jun. 2009;19(3):290-7. doi: 10.1016/j.gde.2009.03.005. Epub May 4, 2009.

Arzumanov et al., A structure-activity study of the inhibition of HIV-1 Tat-dependent transactivation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.

Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.

Ast et al., Estergruppenhaltige Polyalkenylene durch Olefin-Metathese. Die Makromolekulare Chemie. May 1976;177(5):1349-55.

Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.

Baskin et al., Copper-free click chemistry for dynamic in vivo imaging. PNAS. Oct. 2007; 104(43):16793-7.

Baskin et al., Copper-free click chemistry: Bioorthogonal Reagents for Tagging Azides. Aldrichimica Acta. 2010;43(1):15-23.

Behlke et al., Chemical modification of siRNAs for in vivo use. Oligonucleotides. Dec. 2008;18(4):305-19.

Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.

Bien-Ly et al., Transferrin receptor (TfR) trafficking determines brain uptake of TfR antibody affinity variants. J Exp Med. Feb. 10, 2014;211(2):233-44. Epub Jan. 27, 2014.

Black, 9.13.4.1.1.3.2 Variation 2: C-Alkylation (and Arylation) by Carbenes and Free Radicals. Science of Synthesis. 2001;9:514.

Böhm et al., Mutation spectrum in the large GTPase dynamin 2, and genotype-phenotype correlation in autosomal dominant centronuclear myopathy. Hum Mutat. Jun. 2012;33(6):949-59. doi: 10.1002/humu.22067. Epub Apr. 4, 2012.

Bortolanza et al., AAV6-mediated systemic shRNA delivery reverses disease in a mouse model of facioscapulohumeral muscular dystrophy. Mol Ther. Nov. 2011;19(11):2055-64. doi: 10.1038/mt.2011.153. Epub Aug. 9, 2011.

Buntz et al., Quantitative fluorescence imaging determines the absolute number of locked nucleic acid oligonucleotides needed for suppression of target gene expression. Nucleic Acids Res. Jan. 25, 2019;47(2):953-969. doi: 10.1093/nar/gky1158.

Bushel et al., Blood gene expression signatures predict exposure levels. Proc Natl Acad Sci U S A. Nov. 13, 2007;104(46):18211-6. doi: 10.1073/pnas.0706987104. Epub Nov. 2, 2007.

Campbell et al., Deflazacort for the treatment of Duchenne Dystrophy: a systematic review. BMC Neurol. Sep. 8, 2003;3:7. doi: 10.1186/1471-2377-3-7. Epub Sep. 8, 2003.

Campbell et al., NuRD and CAF-1-mediated silencing of the D4Z4 array is modulated by DUX4-induced MBD3L proteins. eLife. May 2018;7:e31023. 27 pages.

Candelaria et al., Antibodies Targeting the Transferrin Receptor 1 (TfR1) as Direct Anti-cancer Agents. Front Immunol. Mar. 17, 2021;12:607692.

Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.

Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Chamberlain et al., Validity of RNAi-based therapeutics as a treatment for FSHD as demonstrated in a mouse model of muscular dystrophy. MDA National Scientific Conference—Neuromuscular Therapeutic Strategies: Overcoming the Barriers from Microscope to Marketplace (Book of Abstracts) Mar. 13-16, 2011; p. 40. Abstract.

Chen et al., Morpholino-mediated Knockdown of DUX4 Toward Facioscapulohumeral Muscular Dystrophy Therapeutics. Mol Ther. Aug. 2016;24(8):1405-11. doi: 10.1038/mt.2016.111. Epub Jun. 3, 2016.

Cho et al., Myotonic dystrophy: emerging mechanisms for DM1 and DM2. Biochim Biophys Acta. Feb. 2007;1772(2):195-204. Epub Jun. 20, 2006.

Chothia et al., Canonical structures for the hypervariable regions of immunoglobulins. J Mol Biol. Aug. 20, 1987;196(4):901-17. doi: 10.1016/0022-2836(87)90412-8.

Cirak et al., Exon skipping and dystrophin restoration in patients with Duchenne muscular dystrophy after systemic phosphorodiamidate morpholino oligomer treatment: an open-label, phase 2, dose-escalation study. Lancet. Aug. 13, 2011;378(9791):595-605. doi: 10.1016/S0140-6736(11)60756-3. Epub Jul. 23, 2011.

Clark et al., Increased brain uptake of targeted nanoparticles by adding an acid-cleavable linkage between transferrin and the nanoparticle core. PNAS. Oct. 2015;112(40):12586-91.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., Antisense research and applications. 1993. p. 15-35.

Crooke et al., Kinetic characteristics of *Escherichia coli* RNase H1: cleavage of various antisense oligonucleotide-RNA duplexes. Biochem J. Dec. 1, 1995;312 ( Pt 2)(Pt 2):599-608. doi: 10.1042/bj3120599.

Crooke et al., The Effects of 2'-0-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Davis et al., Improved targeting of miRNA with antisense oligonucleotides. Nucleic Acids Res. May 11, 2006;34(8):2294-304. doi: 10.1093/nar/gkl183. Print 2006.

Daxinger et al., Genetic and epigenetic contributors to FSHD. Current Opinion in Genetics & Development. Aug. 2015;33:56-61. Author manuscript. 11 pages.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Dixit et al., DUX4, a candidate gene of facioscapulohumeral muscular dystrophy, encodes a transcriptional activator of PITX1. Proc Natl Acad Sci U S A. Nov. 13, 2007;104(46):18157-62. doi: 10.1073/pnas.0708659104. Epub Nov. 5, 2007.

Dommerholt et al., Readily accessible bicyclononynes for bioorthogonal labeling and three-dimensional imaging of living cells. Angew Chem Int Ed Engl. Dec. 3, 2010;49(49):9422-5.

Dommerholt et al., Strain-Promoted 1,3-Dipolar Cycloaddition of Cycloalkynes and Organic Azides. Top Curr Chem (Cham). Apr. 2016;374(2):16. doi: 10.1007/s41061-016-0016-4. Epub Mar. 22, 2016.

Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.

(56) References Cited

OTHER PUBLICATIONS

Echigoya et al., Effects of systemic multiexon skipping with peptide-conjugated morpholinos in the heart of a dog model of Duchenne muscular dystrophy. Proc Natl Acad Sci U S A. Apr. 18, 2017;114(16):4213-4218. doi: 10.1073/pnas.1613203114. Epub Apr. 3, 2017.
Echigoya et al., Exons 45-55 Skipping Using Mutation-Tailored Cocktails of Antisense Morpholinos in the DMD Gene. Mol Ther. Nov. 6, 2019;27(11):2005-2017. doi: 10.1016/j.ymthe.2019.07.012. Epub Jul. 26, 2019.
Echigoya et al., Quantitative Antisense Screening and Optimization for Exon 51 Skipping in Duchenne Muscular Dystrophy. Mol Ther. Nov. 1, 2017;25(11):2561-2572. doi: 10.1016/j.ymthe.2017.07.014. Epub Jul. 28, 2017.
Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.
Elangkovan et al., Gene Therapy for Duchenne Muscular Dystrophy. J Neuromuscul Dis. 2021;8(s2):S303-S316.
Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.
Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.
Freed et al., Pharmacology Review(s) for Application No. 206488Orig1s000. Center for Drug Evaluation and Research (CDER). Published May 25, 2016. Accessed from accessdata.fda.gov on May 21, 2021. 97 pages.
Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.
Furling et al., Abstract R.P.1.01—Nucleotide Repeat Expansion Disorders I: Poster Presentations. Neuromuscular Disorders. 2004;14:585. 2 pages total.
Furling et al., Viral vector producing antisense RNA restores myotonic dystrophy myoblast functions. Gene Ther. May 2003;10(9):795-802.
Gagnon et al., RNAi factors are present and active in human cell nuclei. Cell Rep. Jan. 16, 2014;6(1):211-21. Epub Jan. 2, 2014.
Galderisi et al., Myotonic dystrophy: antisense oligonucleotide inhibition of DMPK gene expression in vitro. Biochem Biophys Res Commun. Apr. 25, 1996;221(3):750-4.
Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.
Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.
Gebski et al., Morpholino antisense oligonucleotide induced dystrophin exon 23 skipping in mdx mouse muscle. Hum Mol Genet. Aug. 1, 2003;12(15):1801-11.
Geng et al., DUX4 activates germline genes, retroelements, and immune mediators: implications for facioscapulohumeral dystrophy. Dev Cell. Jan. 17, 2012;22(1):38-51. doi: 10.1016/j.devcel.2011.11.013. Epub Dec. 29, 2011.
Giles et al., Enhanced RNase H activity with methylphosphonodiester/phosphodiester chimeric antisense oligodeoxynucleotides. Anticancer Drug Des. Feb. 1992;7(1):37-48.
Girones et al. Comparison of the kinetics of cycling of the transferrin receptor in the presence or absence of bound diferric transferrin. Biochem J. Nov. 15, 1989;264(1):35-46.
Goemans et al., Systemic administration of PRO051 in Duchenne's muscular dystrophy. N Engl J Med. Apr. 21, 2011;364(16):1513-22. doi: 10.1056/NEJMoa1011367. Epub Mar. 23, 2011. Erratum in: N Engl J Med. Oct. 6, 2011;365(14):1361.
Gong et al., Simple Method to Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.
Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.
Griggs et al., Prednisone in Duchenne dystrophy. A randomized, controlled trial defining the time course and dose response. Clinical Investigation of Duchenne Dystrophy Group. Arch Neurol. Apr. 1991;48(4):383-8. doi: 10.1001/archneur.1991.00530160047012.
Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.
Henry et al., Chemically modified oligonucleotides exhibit decreased immune stimulation in mice. J Pharmacol Exp Ther. Feb. 2000;292(2):468-79.
Iwaki et al., Preparation of Chiral Stationary Phase via Activated Carbamate Intermediate for Liquid Chromatographic Optical Resolution. Chromatographia. Oct. 1987;23:727-30.
Jain et al., Current ADC Linker Chemistry. Pharm Res. Nov. 2015;32(11):3526-40. Epub Mar. 11, 2015.
Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.
Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.
Jepsen et al., Locked nucleic acid: a potent nucleic acid analog in therapeutics and biotechnology. Oligonucleotides. 2004;14(2):130-46. doi: 10.1089/1545457041526317.
Jirka et al., Cyclic Peptides to improve Delivery and Exon Skipping of Antisense Oligonucleotides in a Mouse Model for Duchenne Muscular Dystrophy. Mol Ther. Jan. 3, 2018;26(1):132-147. doi: 10.1016/j.ymthe.2017.10.004. Epub Oct. 12, 2017.
Juliano, The delivery of therapeutic oligonucleotides. Nucleic Acids Res. Aug. 19, 2016;44(14):6518-48. doi: 10.1093/nar/gkw236. Epub Apr. 15, 2016.
Khan et al., Silencing Myostatin Using Cholesterol-conjugated siRNAs Induces Muscle Growth. Mol Ther Nucleic Acids. Aug. 2, 2016;5(8):e342. doi: 10.1038/mtna.2016.55.
Kher et al., Antisense Oligonucleotides and RNA Interference. Challenges in Delivery of Therapeutic Genomics and Proteomics. Aug. 2011;325-86.
Kim et al., Strategies for silencing human disease using RNA interference. Nat Rev Genet. Mar. 2007;8(3):173-84. doi: 10.1038/nrg2006.
Kinali et al., Local restoration of dystrophin expression with the morpholino oligomer AVI-4658 in Duchenne muscular dystrophy: a single-blind, placebo-controlled, dose-escalation, proof-of-concept study. Lancet Neurol. Oct. 2009;8(10):918-28. doi: 10.1016/S1474-4422(09)70211-X. Epub Aug. 25, 2009. Erratum in: Lancet Neurol. Dec. 2009;8(12):1083.
Kline et al., Methods to Make Homogenous Antibody Drug Conjugates. Pharm Res. Nov. 2015;32(11):3480-93. Epub Dec. 16, 2014.
Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

(56) References Cited

OTHER PUBLICATIONS

Koshelev et al., Heart-specific overexpression of CUGBP1 reproduces functional and molecular abnormalities of myotonic dystrophy type 1. Hum Mol Genet. Mar. 15, 2010; 19(6):1066-75. Epub Jan. 5, 2010.

Kumar et al., Antisense RNA: Function and Fate of Duplex RNA in Cells of Higher Eukaryotes. Microbiol Mol Biol Rev. Dec. 1998; 62(4): 1415-34.

Kuran et al., Investigations on the Catalytic Systems Diethylzinc/ Di- and Trihydroxybenzenes in the Copolymerization of Carbon Dioxide with Propylene Oxide. Makromol. Chem. 1976;177:1283-92.

Kurreck et al., Design of antisense oligonucleotides stabilized by locked nucleic acids. Nucleic Acids Res. May 1, 2002;30(9):1911-8. doi: 10.1093/nar/30.9.1911.

Kurreck, Antisense technologies. Improvement through novel chemical modifications. Eur J Biochem. Apr. 2003;270(8):1628-44.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Lam et al., siRNA Versus miRNA as Therapeutics for Gene Silencing. Mol Ther Nucleic Acids. Sep. 15, 2015;4(9):e252. 20 pages.

Langlois et al., Abstract 831—Ribozyme and Antisense RNA-Based Gene Therapies for Myotonic Dystrophy. Molecular Therapy. May 2003;7(5):S320.

Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.

Langlois et al., Hammerhead ribozyme-mediated destruction of nuclear foci in myotonic dystrophy myoblasts. Mol Ther. May 2003;7(5 Pt 1):670-80.

Lawrence et al., Crystal structure of the ectodomain of human transferrin receptor. Science. Oct. 22, 1999;286(5440):779-82. doi: 10.1126/science.286.5440.779.

Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lemmers et al., A unifying genetic model for facioscapulohumeral muscular dystrophy. Science. Sep. 24, 2010;329(5999): 1650-3. Epub Aug. 19, 2010.

Lemmers et al., Facioscapulohumeral muscular dystrophy is uniquely associated with one of the two variants of the 4q subtelomere. Nat Genet. Oct. 2002;32(2):235-6.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.

Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.

Liu et al. Myostatin antisense RNA-mediated muscle growth in normal and cancer cachexia mice. Gene Ther. Feb. 2008;15(3):155-60. doi: 10.1038/sj.gt.3303016. Epub Nov. 22, 2007.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Lu et al., Functional amounts of dystrophin produced by skipping the mutated exon in the mdx dystrophic mouse. Nat Med. Aug. 2003;9(8):1009-14. Epub Jul. 6, 2003.

Lu et al., Systemic delivery of antisense oligoribonucleotide restores dystrophin expression in body-wide skeletal muscles. Proc Natl Acad Sci U S A. Jan. 4, 2005;102(1):198-203. doi: 10.1073/pnas.0406700102. Epub Dec. 17, 2004.

Mann et al., Antisense-induced exon skipping and synthesis of dystrophin in the mdx mouse. Proc Natl Acad Sci U S A. Jan. 2, 2001;98(1):42-7.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mignon, Update on Ionis-DMPKRX Program. 2018 MDF Annual Conference. Nashville, TN. Sep. 14-15, 2018:22 pages.

Mojsov et al., A Quantitative Evaluation of Methods for Coupling Asparagine. The Journal of Organic Chemistry. Feb. 1980;45(4):555-60.

Monia et al., Evaluation of 2'-modified oligonucleotides containing 2'-deoxy gaps as antisense inhibitors of gene expression. J Biol Chem. Jul. 5, 1993;268(19):14514-22.

Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.

Mulders et al., Molecular therapy in myotonic dystrophy: focus on RNA gain-of-function. Human Molecular Genetics. 2010;19(1):R90-7. Epub Apr. 20, 2010.

Mulders et al., Triplet-repeat oligonucleotide-mediated reversal of RNA toxicity in myotonic dystrophy. PNAS. Aug. 18, 2009;106(33):13915-20. Supporting information included. 13 pages.

Nguyen et al., Antisense oligonucleotides for the treatment of cardiomyopathy in Duchenne muscular dystrophy. Am J Transl Res. Mar. 15, 2019;11(3):1202-1218.

Ohrt et al., In situ fluorescence analysis demonstrates active siRNA exclusion from the nucleus by Exportin 5. Nucleic Acids Res. Mar. 6, 2006;34(5):1369-80. doi: 10.1093/nar/gkl001. Print 2006.

Overby et al., RNA-mediated therapies in myotonic dystrophy. Drug Discov Today. Dec. 2018;23(12):2013-2022. Epub Aug. 4, 2018.

Padlan et al., A possible procedure for reducing the immunogenicity of antibody variable domains while preserving their ligand-binding properties. Molecular Immunology. Apr.-May 1991;28(4-5):489-98.

Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.

Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.

Pradhan et al., Prednisolone in Duchenne muscular dystrophy with imminent loss of ambulation. J Neurol. Oct. 2006;253(10):1309-16. doi: 10.1007/s00415-006-0212-1. Epub Jun. 19, 2006.

(56) References Cited

OTHER PUBLICATIONS

Qian et al., Targeted drug delivery via the transferrin receptor-mediated endocytosis pathway. Pharmacol Rev. Dec. 2002;54(4):561-87. doi: 10.1124/pr.54.4.561.
Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-28.
Rando et al., Rescue of dystrophin expression in mdx mouse muscle by RNA/DNA oligonucleotides. Proc Natl Acad Sci U S A. May 9, 2000;97(10):5363-8. doi: 10.1073/pnas.97.10.5363.
Roberts et al., Advances in oligonucleotide drug delivery. Nat Rev Drug Discov. Oct. 2020;19(10):673-694. doi: 10.1038/s41573-020-0075-7. Epub Aug. 11, 2020.
Roberts et al., The Halogenation of Ethylenes. J. Am. Chem. Soc. May 1937;59(5):947-8.
Sahenk et al., The muscular dystrophies: distinct pathogenic mechanisms invite novel therapeutic approaches. Curr Rheumatol Rep. Jun. 2011;13(3):199-207.
Saito et al., Antisense PMO found in dystrophic dog model was effective in cells from exon 7-deleted DMD patient. PLoS One. Aug. 18, 2010;5(8):e12239.
Sazani et al., Safety pharmacology and genotoxicity evaluation of AVI-4658. Int J Toxicol. Mar.-Apr. 2010;29(2):143-56. doi: 10.1177/1091581809359206. Epub Jan. 28, 2010.
Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.
Scanlon, Anti-genes: siRNA, ribozymes and antisense. Curr Pharm Biotechnol. Oct. 2004;5(5):415-20.
Scherr et al., Detection of antisense and ribozyme accessible sites on native mRNAs: application to NCOA3 mRNA. Mol Ther. Nov. 2001;4(5):454-60.
Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Chemistry, mechanism and clinical status of antisense oligonucleotides and duplex RNAs. Nucleic Acids Res. Feb. 28, 2018;46(4):1584-1600.
Singh et al., Catalytic Enantioselective Cyclopropanation of Olefins Using Carbenoid Chemistry. Synthesis. Feb. 1997;137-49.
Sklar et al., Methylprednisolone increases dystrophin levels by inhibiting myotube death during myogenesis of normal human muscle in vitro. J Neurol Sci. Jan. 1991;101(1):73-81. doi: 10.1016/0022-510x(91)90019-4.
Snider et al., Facioscapulohumeral dystrophy: incomplete suppression of a retrotransposed gene. PLoS Genet. Oct. 28, 2010;6(10):e1001181. 14 pages.
Snider et al., RNA transcripts, miRNA-sized fragments and proteins produced from D4Z4 units: new candidates for the pathophysiology of facioscapulohumeral dystrophy. Hum Mol Genet. Jul. 1, 2009;18(13):2414-30. Epub Apr. 9, 2009.
Stein, The experimental use of antisense oligonucleotides: a guide for the perplexed. J Clin Invest. Sep. 2001;108(5):641-4.
Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.
Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.
Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.
Summerton et al..Morpholino antisense oligomers: design, preparation, and properties. Antisense Nucleic Acid Drug Dev. Jun. 1997;7(3):187-95.
Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.
Swayze et al., The medicinal chemistry of oligonucleotides. In: Antisense Drug Technology, Second Edition. 2007. Crooke, Ed. Chapter 6: 143-182.
Tasfaout et al., Single Intramuscular Injection of AAV-shRNA Reduces DNM2 and Prevents Myotubular Myopathy in Mice. Mol Ther. Apr. 4, 2018;26(4):1082-1092. doi: 10.1016/j.ymthe.2018.02.008. Epub Feb. 14, 2018.
Tawil et al., Facioscapulohumeral dystrophy: the path to consensus on pathophysiology. Skelet Muscle. Jun. 10, 2014;4:12.
Thomas et al., Myotonic Dystrophy and Developmental Regulation of RNA Processing. Comprehensive Physiology. Apr. 2018;8(2):509-53. Epub Mar. 25, 2018.
Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.
Trollet et al., Gene therapy for muscular dystrophy: current progress and future prospects. Expert Opin Biol Ther. Jul. 2009;9(7):849-66.
Tron et al., Click chemistry reactions in medicinal chemistry: applications of the 1,3-dipolar cycloaddition between azides and alkynes. Med Res Rev. Mar. 2008;28(2):278-308.
Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.
Van Den Bergen et al., Forty-Five Years of Duchenne Muscular Dystrophy in the Netherlands. J Neuromuscul Dis. 2014;1(1):99-109.
Van Der Maarel et al., Facioscapulohumeral muscular dystrophy and DUX4: breaking the silence. Trends Mol Med. May 2011;17(5):252-8. Epub Feb. 1, 2011.
Van Deutekom et al., Local dystrophin restoration with antisense oligonucleotide PRO051. N Engl J Med. Dec. 27, 2007;357(26):2677-86. doi: 10.1056/NEJMoa073108.
Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.
Vanderplanck et al., Abstract Keynote 5—Suppression of DUX4 or DUX4C expression by antisense strategies in a therapeutic approach for FSHD. 7th Australian Gene Therapy Society Meeting. The Journal of Gene Medicine. May 2011;13:414.
Vanderplanck et al., Suppression of DUX4 or DUX4c protein expression by antisense strategies in a therapeutic approach for FSHD. MDA National Scientific Conference—Neuromuscular Therapeutic Strategies: Overcoming the Barriers from Microscope to Marketplace (Book of Abstracts) Mar. 13-16, 2011; p. 8. Abstract.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
Wagner et al., Transferrin-polycation conjugates as carriers for DNA uptake into cells. Proc Natl Acad Sci U S A. May 1990;87(9):3410-4. doi: 10.1073/pnas.87.9.3410.
Walder et al., Role of RNase H in hybrid-arrested translation by antisense oligonucleotides. Proc. Natl. Acad. Sci. Jul. 1988;85:5011-5.
Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.
Wallace et al., Abstract 387—Developing RNAi Therapy for FSHD. Molecular Therapy. May 2009;17(1):S151.
Wallace et al., RNA interference inhibits DUX4-induced muscle toxicity in vivo: implications for a targeted FSHD therapy. Mol Ther. Jul. 2012;20(7):1417-23. doi: 10.1038/mt.2012.68. Epub Apr. 17, 2012.

(56) References Cited

OTHER PUBLICATIONS

Walles et al., ADME and Safety Aspects of Non-cleavable Linkers in Drug Discovery and Development. Curr Top Med Chem. 2017;17(32):3463-3475. doi: 10.2174/1568026618666180118153502.

Wei et al., Therapeutic RNAi for dominant muscle disease. Muse Conn Tissue—Antisense and Stem Cells. Abstract. 2009. S200.

Wheeler et al., Myotonic dystrophy: therapeutic strategies for the future. Neurotherapeutics. Oct. 2008;5(4):592-600.

Wheeler et al., Reversal of RNA dominance by displacement of protein sequestered on triplet repeat RNA. Science. Jul. 17, 2009;325(5938):336-9.

Wheeler et al., Targeting nuclear RNA for in vivo correction of myotonic dystrophy. Nature. Aug. 2, 2012;488(7409):111-5. doi: 10.1038/nature11362.

Wilton et al., Antisense oligonucleotide-induced exon skipping across the human dystrophin gene transcript. Mol Ther. Jul. 2007;15(7):1288-96. doi: 10.1038/sj.mt.6300095. Epub Feb. 6, 2007.

Wilton et al., Antisense oligonucleotides, exon skipping and the dystrophin gene transcript. Acta Myol. Dec. 2005;24(3):222-9.

Wilton et al., Exon skipping and Duchenne muscular dystrophy: hope, hype and how feasible? Neurol India. Jul.-Sep. 2008;56(3):254-62. doi: 10.4103/0028-3886.43443.

Wu et al., Determination of the role of the human RNase H1 in the pharmacology of DNA-like antisense drugs. J Biol Chem. Apr. 23, 2004;279(17):17181-9. Epub Feb. 11, 2004.

Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.

Yao et al., DUX4-induced gene expression is the major molecular signature in FSHD skeletal muscle. Hum Mol Genet. Oct. 15, 2014; 23(20): 5342-5352. Epub May 26, 2014.

Yao et al., Targeted Delivery of ASOs Demonstrates Potential to Treat Duchenne Muscular Dystrophy. Poster. Presented at ASGCT; May 12, 2020. 1 page.

Ye et al., Generation and functional characterization of the anti-transferrin receptor single-chain antibody-GAL4 (TfRscFv-GAL4) fusion protein. BMC Biotechnol. Nov. 28, 2012;12:91.

Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at ASGST Annual Meeting; May 14, 2021. 13 pages.

\* cited by examiner

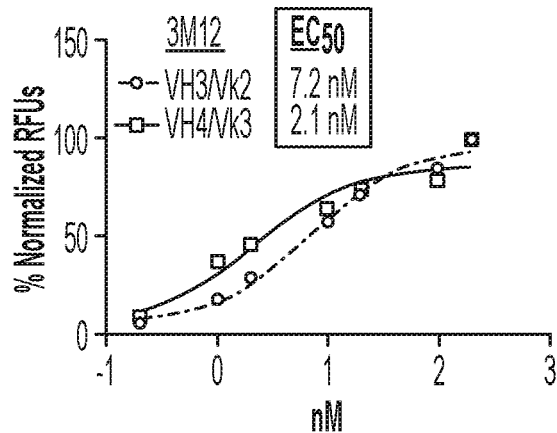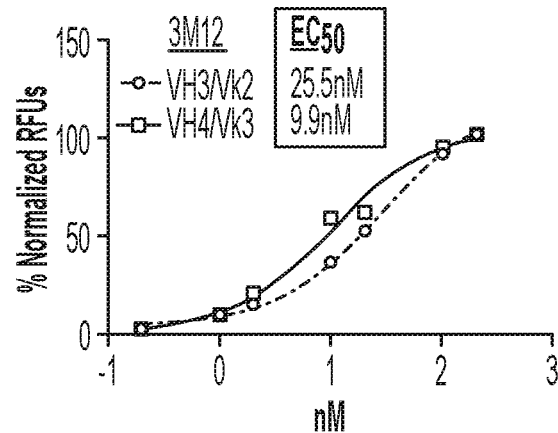
FIG. 9A  FIG. 9B
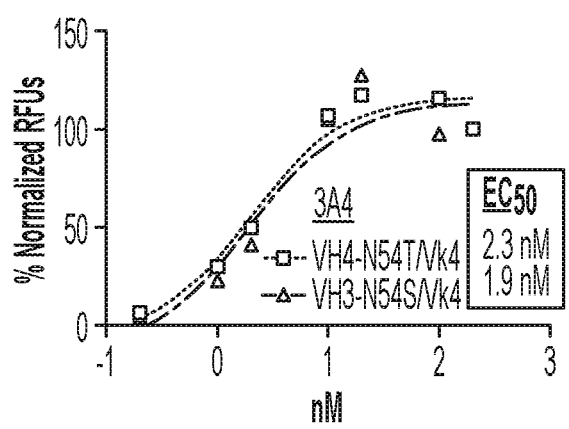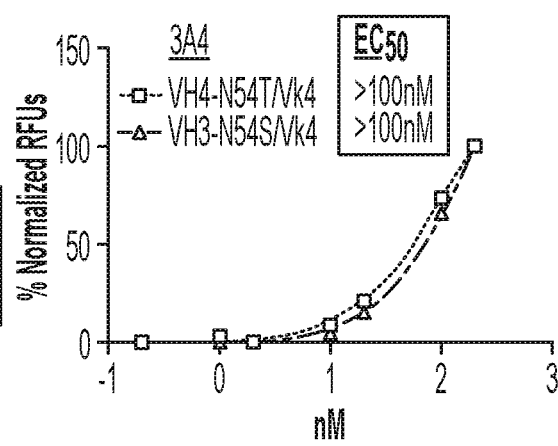
FIG. 9C  FIG. 9D
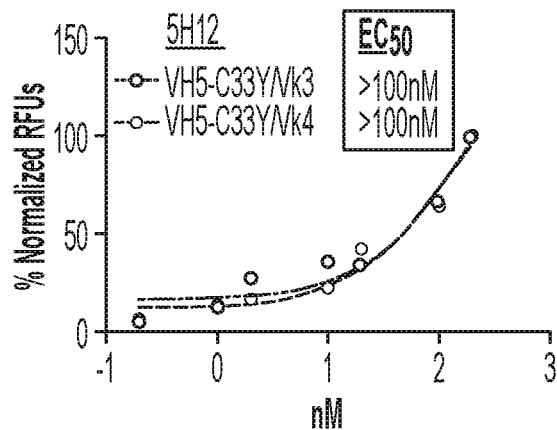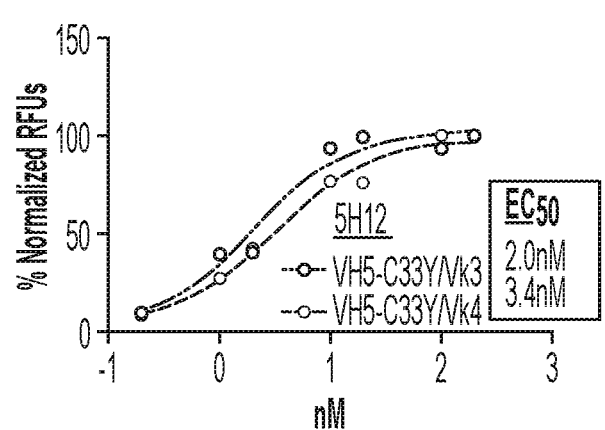
FIG. 9E  FIG. 9F

MUSCLE TARGETING COMPLEXES AND USES THEREOF FOR TREATING FACIOSCAPULOHUMERAL MUSCULAR DYSTROPHY

RELATED APPLICATIONS

This application is a continuation of U.S. application Ser. No. 17/811,380, filed Jul. 8, 2022, entitled "MUSCLE TARGETING COMPLEXES AND USES THEREOF FOR TREATING FACIOSCAPULOHUMERAL MUSCULAR DYSTROPHY", which claims priority under 35 U.S.C. § 119(e) to U.S. Provisional Patent Application No. 63/220,155, filed Jul. 9, 2021, entitled "MUSCLE TARGETING COMPLEXES AND USES THEREOF FOR TREATING FACIOSCAPULOHUMERAL MUSCULAR DYSTROPHY," which are hereby incorporated by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO AN ELECTRONIC SEQUENCE LISTING

The contents of the electronic sequence listing (D082470069US03-SEQ-ZJG.xml; Size: 205,469 bytes; and Date of Creation: Dec. 5, 2022) is herein incorporated by reference in its entirety.

BACKGROUND OF INVENTION

Muscular dystrophies (MDs) are a group of diseases characterized by the progressive weakness and loss of muscle mass. These diseases are caused by mutations in genes which encode proteins needed to form healthy muscle tissue. Facioscapulohumeral muscular dystrophy (FSHD) is a dominantly inherited type of MD which primarily affects muscles of the face, shoulder blades, and upper arms. Other symptoms of FSHD include abdominal muscle weakness, retinal abnormalities, hearing loss, and joint pain and inflammation. FSHD is the most prevalent of the nine types of MD affecting both adults and children, with a worldwide incidence of about 1 in 8,300 people. FSHD is caused by aberrant production of double homeobox 4 (DUX4), a protein whose function is unknown. The DUX4 gene, which encodes the DUX4 protein, is located in the D4Z4 repeat region on chromosome 4 and is typically expressed only in fetal development, after which it is repressed by hypermethylation of the D4Z4 repeats which surround and compact the DUX4 gene. Two types of FSHD, Type 1 and Type 2 have been described. Type 1, which accounts for about 95% of cases, is associated with deletions of D4Z4 repeats on chromosome 4. Unaffected individuals generally have more than 10 repeats arrayed in the subtelomeric region of chromosome 4, whereas the most common form of FSHD (FSHD1) is caused by a contraction of the array to fewer than 10 repeats, associated with decreased epigenetic repression and variegated expression of DUX4 in skeletal muscle. Two allelic variants of chromosome 4q (4qA and 4qB) exist in the region distal to D4Z4. 4qA is in cis with a functional polyadenylation consensus site. Contractions on 4qA alleles are pathogenic because the DUX4 transcript is polyadenylated and translated into stable protein. Type 2 FSHD, which accounts for about 5% of cases, is associated with mutations of the SMCHD1 gene on chromosome 18. Besides supportive care and treatments to address the symptoms of the disease, there are no effective therapies for FSHD.

SUMMARY OF INVENTION

According to some aspects, the disclosure provides complexes that target muscle cells for purposes of delivering molecular payloads to those cells. In some embodiments, complexes provided herein are particularly useful for delivering molecular payloads that inhibit the expression or activity of DUX4, e.g., in a subject having or suspected of having Facioscapulohumeral muscular dystrophy (FSHD). Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can inhibit DUX4 gene expression in the muscle cells. In some embodiments, the oligonucleotides are released by endosomal cleavage of covalent linkers connecting oligonucleotides and muscle-targeting agents of the complexes.

One aspect of the present disclosure relates to a complex comprising an anti-transferrin receptor (TfR) antibody covalently linked to a molecular payload configured for reducing expression or activity of DUX4, wherein the antibody comprises:

(i) a heavy chain variable region (VH) comprising an amino acid sequence at least 95% identical to SEQ ID NO: 76; and/or a light chain variable region (VL) comprising an amino acid sequence at least 95% identical to SEQ ID NO: 75;

(ii) a heavy chain variable region (VH) comprising an amino acid sequence at least 95% identical to SEQ ID NO: 69; and/or a light chain variable region (VL) comprising an amino acid sequence at least 95% identical to SEQ ID NO: 70;

(iii) a heavy chain variable region (VH) comprising an amino acid sequence at least 95% identical to SEQ ID NO: 71; and/or a light chain variable region (VL) comprising an amino acid sequence at least 95% identical to SEQ ID NO: 70;

(iv) a heavy chain variable region (VH) comprising an amino acid sequence at least 95% identical to SEQ ID NO: 72; and/or a light chain variable region (VL) comprising an amino acid sequence at least 95% identical to SEQ ID NO: 70;

(v) a heavy chain variable region (VH) comprising an amino acid sequence at least 95% identical to SEQ ID NO: 73; and/or a light chain variable region (VL) comprising an amino acid sequence at least 95% identical to SEQ ID NO: 74;

(vi) a heavy chain variable region (VH) comprising an amino acid sequence at least 95% identical to SEQ ID NO: 73; and/or a light chain variable region (VL) comprising an amino acid sequence at least 95% identical to SEQ ID NO: 75;

(vii) a heavy chain variable region (VH) comprising an amino acid sequence at least 95% identical to SEQ ID NO:

76; and/or a light chain variable region (VL) comprising an amino acid sequence at least 95% identical to SEQ ID NO: 74;

(viii) a heavy chain variable region (VH) comprising an amino acid sequence at least 95% identical to SEQ ID NO: 77; and/or a light chain variable region (VL) comprising an amino acid sequence at least 95% identical to SEQ ID NO: 78;

(ix) a heavy chain variable region (VH) comprising an amino acid sequence at least 95% identical to SEQ ID NO: 79; and/or a light chain variable region (VL) comprising an amino acid sequence at least 95% identical to SEQ ID NO: 80; or (x) a heavy chain variable region (VH) comprising an amino acid sequence at least 95% identical to SEQ ID NO: 77; and/or a light chain variable region (VL) comprising an amino acid sequence at least 95% identical to SEQ ID NO: 80.

In some embodiments, the antibody comprises:

(i) a VH comprising the amino acid sequence of SEQ ID NO: 76 and a VL comprising the amino acid sequence of SEQ ID NO: 75;

(ii) a VH comprising the amino acid sequence of SEQ ID NO: 69 and a VL comprising the amino acid sequence of SEQ ID NO: 70;

(iii) a VH comprising the amino acid sequence of SEQ ID NO: 71 and a VL comprising the amino acid sequence of SEQ ID NO: 70;

(iv) a VH comprising the amino acid sequence of SEQ ID NO: 72 and a VL comprising the amino acid sequence of SEQ ID NO: 70;

(v) a VH comprising the amino acid sequence of SEQ ID NO: 73 and a VL comprising the amino acid sequence of SEQ ID NO: 74;

(vi) a VH comprising the amino acid sequence of SEQ ID NO: 73 and a VL comprising the amino acid sequence of SEQ ID NO: 75;

(vii) a VH comprising the amino acid sequence of SEQ ID NO: 76 and a VL comprising the amino acid sequence of SEQ ID NO: 74;

(viii) a VH comprising the amino acid sequence of SEQ ID NO: 77 and a VL comprising the amino acid sequence of SEQ ID NO: 78;

(ix) a VH comprising the amino acid sequence of SEQ ID NO: 79 and a VL comprising the amino acid sequence of SEQ ID NO: 80; or (x) a VH comprising the amino acid sequence of SEQ ID NO: 77 and a VL comprising the amino acid sequence of SEQ ID NO: 80.

In some embodiments, the antibody is selected from the group consisting of a Fab fragment, a Fab' fragment, a F(ab')2 fragment, a scFv, a Fv, and a full-length IgG. In some embodiments, the antibody is a Fab fragment.

In some embodiments, the antibody comprises:

(i) a heavy chain comprising an amino acid sequence at least 85% identical to SEQ ID NO: 101; and/or a light chain comprising an amino acid sequence at least 85% identical to SEQ ID NO: 90;

(ii) a heavy chain comprising an amino acid sequence at least 85% identical to SEQ ID NO: 97; and/or a light chain comprising an amino acid sequence at least 85% identical to SEQ ID NO: 85;

(iii) a heavy chain comprising an amino acid sequence at least 85% identical to SEQ ID NO: 98; and/or a light chain comprising an amino acid sequence at least 85% identical to SEQ ID NO: 85;

(iv) a heavy chain comprising an amino acid sequence at least 85% identical to SEQ ID NO: 99; and/or a light chain comprising an amino acid sequence at least 85% identical to SEQ ID NO: 85;

(v) a heavy chain comprising an amino acid sequence at least 85% identical to SEQ ID NO: 100; and/or a light chain comprising an amino acid sequence at least 85% identical to SEQ ID NO: 89;

(vi) a heavy chain comprising an amino acid sequence at least 85% identical to SEQ ID NO: 100; and/or a light chain comprising an amino acid sequence at least 85% identical to SEQ ID NO: 90;

(vii) a heavy chain comprising an amino acid sequence at least 85% identical to SEQ ID NO: 101; and/or a light chain comprising an amino acid sequence at least 85% identical to SEQ ID NO: 89;

(viii) a heavy chain comprising an amino acid sequence at least 85% identical to SEQ ID NO: 102; and/or a light chain comprising an amino acid sequence at least 85% identical to SEQ ID NO: 93;

(ix) a heavy chain comprising an amino acid sequence at least 85% identical to SEQ ID NO: 103; and/or a light chain comprising an amino acid sequence at least 85% identical to SEQ ID NO: 95; or (x) a heavy chain comprising an amino acid sequence at least 85% identical to SEQ ID NO: 102; and/or a light chain comprising an amino acid sequence at least 85% identical to SEQ ID NO: 95.

In some embodiments, the antibody comprises:

(i) a heavy chain comprising the amino acid sequence of SEQ ID NO: 101; and a light chain comprising the amino acid sequence of SEQ ID NO: 90;

(ii) a heavy chain comprising the amino acid sequence of SEQ ID NO: 97; and a light chain comprising the amino acid sequence of SEQ ID NO: 85;

(iii) a heavy chain comprising the amino acid sequence of SEQ ID NO: 98; and a light chain comprising the amino acid sequence of SEQ ID NO: 85;

(iv) a heavy chain comprising the amino acid sequence of SEQ ID NO: 99; and a light chain comprising the amino acid sequence of SEQ ID NO: 85;

(v) a heavy chain comprising the amino acid sequence of SEQ ID NO: 100; and a light chain comprising the amino acid sequence of SEQ ID NO: 89;

(vi) a heavy chain comprising the amino acid sequence of SEQ ID NO: 100; and a light chain comprising the amino acid sequence of SEQ ID NO: 90;

(vii) a heavy chain comprising the amino acid sequence of SEQ ID NO: 101; and a light chain comprising the amino acid sequence of SEQ ID NO: 89;

(viii) a heavy chain comprising the amino acid sequence of SEQ ID NO: 102; and a light chain comprising the amino acid sequence of SEQ ID NO: 93;

(ix) a heavy chain comprising the amino acid sequence of SEQ ID NO: 103; and a light chain comprising the amino acid sequence of SEQ ID NO: 95; or (x) a heavy chain comprising the amino acid sequence of SEQ ID NO: 102; and a light chain comprising the amino acid sequence of SEQ ID NO: 95.

In some embodiments, the antibody does not specifically bind to the transferrin binding site of the transferrin receptor and/or wherein the antibody does not inhibit binding of transferrin to the transferrin receptor. In some embodiments, the antibody is cross-reactive with extracellular epitopes of two or more of a human, non-human primate and rodent transferrin receptor. In some embodiments, the complex is configured to promote transferrin receptor mediated internalization of the molecular payload into a muscle cell.

In some embodiments, the molecular payload is an oligonucleotide. In some embodiments, the oligonucleotide comprises an antisense strand comprising a region of complementarity to a DUX4 RNA. In some embodiments, the oligonucleotide comprises an antisense strand comprising a region of complementarity to a non-coding region of the DUX4 RNA. In some embodiments, the oligonucleotide comprises an antisense strand comprising a region of complementarity to a 5' or 3' UTR of the DUX4 RNA.

In some embodiments, the antisense strand comprises at least 15 consecutive nucleotides of SEQ ID NO: 151 (GGG-CATTTTAATATATCTCTGAACT).

In some embodiments, the antisense strand comprises the nucleotide sequence of SEQ ID NO: 151 (GGGCATTT-TAATATATCTCTGAACT).

In some embodiments, the oligonucleotide further comprises a sense strand that hybridizes to the antisense strand to form a double stranded siRNA. In some embodiments, the oligonucleotide comprises at least one modified internucleoside linkage. In some embodiments, the oligonucleotide comprises one or more modified nucleosides. In some embodiments, the one or more modified nucleosides are 2'-modified nucleosides. In some embodiments, the oligonucleotide is a phosphorodiamidate morpholino oligomer.

In some embodiments, the antibody is covalently linked to the molecular payload via a cleavable linker. In some embodiments, the cleavable linker comprises a valine-citrulline sequence.

In some embodiments, the antibody is covalently linked to the molecular payload via conjugation to a lysine residue or a cysteine residue of the antibody.

In some embodiments, reducing expression or activity of DUX4 comprises reducing DUX4 RNA levels. In some embodiments, reducing expression or activity of DUX4 comprises reducing DUX4 protein levels.

Another aspect of the present disclosure relates to a method of reducing DUX4 expression or activity in a cell, the method comprising contacting the cell with the complex in an effective amount for promoting internalization of the molecular payload in the cell, optionally wherein the cell is a muscle cell.

Another aspect of the present disclosure relates to a method of treating a subject having one or more deletions of a D4Z4 repeat in chromosome 4 that is associated with facioscapulohumeral muscular dystrophy, the method comprising administering to the subject an effective amount of the complex.

BRIEF DESCRIPTION OF THE DRAWINGS

FIGS. 9A-9F show binding of humanized anti-TfR Fabs to human TfR1 (hTfR1) or cynomolgus monkey TfR1 (cTfR1), as measured by ELISA. FIG. 9A shows binding of humanized 3M12 variants to hTfR1. FIG. 9B shows binding of humanized 3M12 variants to cTfR1. FIG. 9C shows binding of humanized 3A4 variants to hTfR1. FIG. 9D shows binding of humanized 3A4 variants to cTfR1. FIG. 9E shows binding of humanized 5H12 variants to hTfR1. FIG. 9F shows binding of humanized 5H12 variants to hTfR1.

FIG. 11A shows the binding of humanized 3M12 variants alone or in conjugates with a DMPK targeting oligo to hTfR1. FIG. 11B shows the binding of humanized 3M12 variants alone or in conjugates with a DMPK targeting oligo to cTfR1. FIG. 11C shows the binding of humanized 3A4 variants alone or in conjugates with a DMPK targeting oligo to hTfR1. FIG. 11D shows the binding of humanized 3A4 variants alone or in conjugates with a DMPK targeting oligo to cTfR1. FIG. 11E shows the binding of humanized 5H12 variants alone or in conjugates with a DMPK targeting oligo to hTfR1. FIG. 11F shows the binding of humanized 5H12 variants alone or in conjugates with a DMPK targeting oligo to cTfR1. The respective $EC_{50}$ values are also shown.

FIG. 18A shows MBD3L2 knockdown in C6 (AB1080) immortalized FSHD1 cells treated with conjugates containing an anti-TfR Fab 3M12 VH4/Vk3 conjugated to a DUX4-targeting oligonucleotide (SEQ ID NO: 151). FIG. 18B shows MBD3L2, TRIM43, and ZSCAN4 knockdown in FSHD patient myotubes treated with conjugates containing an anti-TfR Fab 3M12 VH4/Vk3 conjugated to a DUX4-targeting oligonucleotide (SEQ ID NO: 151). FIG. 18B includes the MBD3L2 data shown in FIG. 18A.

DETAILED DESCRIPTION OF INVENTION

Figure 1:
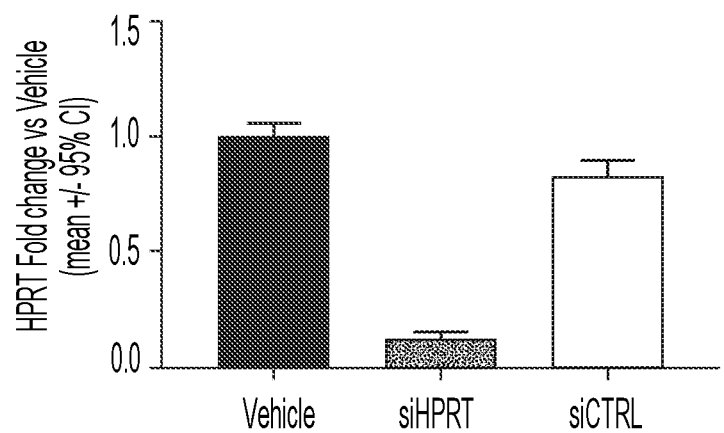
FIG. 1 depicts a non-limiting schematic showing the effect of transfecting cells with an siRNA.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that inhibit the expression or activity of target genes in muscle cells, e.g., in a subject having or suspected of having a rare muscle disease. For example, in some embodiments, complexes are provided for targeting a DUX4 to treat subjects having FSHD. In some embodiments, complexes provided herein comprise oligonucleotides that inhibit expression of DUX4 in a subject that has one or more D4Z4 repeat deletions on chromosome 4. In some embodiments, complexes provided herein comprise molecular payloads such as guide molecules (e.g., guide RNAs) that are capable of targeting nucleic acid programmable nucleases (e.g., Cas9) to a DUX4 gene in order to inactivate the gene in muscle cells, for example, by removing a portion of the DUX4 gene, or by introducing an inactivating mutation or stop codon into the DUX4 gene. In some embodiments, such nucleic programmable nucleases could be used to inactivate DUX4 that is aberrantly expressed in muscle cells.

Further aspects of the disclosure, including a description of defined terms, are provided below.

I. Definitions

Administering: As used herein, the terms "administering" or "administration" means to provide a complex to a subject in a manner that is physiologically and/or (e.g., and) pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a Fab' fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or (e.g., and) a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or (e.g., and) CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or (e.g., and) the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). ee also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems. Examples of CDR definition systems are provided in Table 1.

TABLE 1

CDR Definitions

|  | IMGT[1] | Kabat[2] | Chothia[3] |
| --- | --- | --- | --- |
| CDR-H1 | 27-38 | 31-35 | 26-32 |
| CDR-H2 | 56-65 | 50-65 | 53-55 |
| CDR-H3 | 105-116/117 | 95-102 | 96-101 |

TABLE 1-continued

CDR Definitions

|  | IMGT[1] | Kabat[2] | Chothia[3] |
|---|---|---|---|
| CDR-L1 | 27-38 | 24-34 | 26-32 |
| CDR-L2 | 56-65 | 50-56 | 50-52 |
| CDR-L3 | 105-116/117 | 89-97 | 91-96 |

[1]IMGT ®, the international ImMunoGeneTics information system ®, imgt.org, Lefranc, M.-P. et al., Nucleic Acids Res., 27:209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196:901-917 (1987))

CDR-grafted antibody: The term "CDR-grafted antibody" refers to antibodies which comprise heavy and light chain variable region sequences from one species but in which the sequences of one or more of the CDR regions of VH and/or (e.g., and) VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferrin receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

DUX4: As used herein, the term "DUX4" refers to a gene that encodes double homeobox 4, a protein which is generally expressed during fetal development and in the testes of adult males. In some embodiments, DUX4 may be a human (Gene ID: 100288687), non-human primate (e.g., Gene ID: 750891, Gene ID: 100405864), or rodent gene (e.g., Gene ID: 306226). In humans, expression of the DUX4 gene outside of fetal development and the testes is associated with facioscapulohumeral muscular dystrophy. In addition, multiple human transcript variants (e.g., as annotated under GenBank RefSeq Accession Numbers: NM_001293798.2, NM_001306068.2, NM_001363820.1) have been characterized that encode different protein isoforms.

Facioscapulohumeral muscular dystrophy (FSHD): As used herein, the term "facioscapulohumeral muscular dystrophy (FSHD)" refers to a genetic disease caused by mutations in the DUX4 gene or SMCHD1 gene that is characterized by muscle mass loss and muscle atrophy, primarily in the muscles of the face, shoulder blades, and upper arms. Two types of the disease, Type 1 and Type 2, have been described. Type 1 is associated with deletions in D4Z4 repeat regions on chromosome 4 allelic variant 4qA which contains the DUX4 gene. Type 2 is associated with mutations in the SMCHD1 gene. Both Type 1 and Type 2 FSHD are characterized by aberrant production of the DUX4 protein after fetal development outside of the testes. Facioscapulohumeral dystrophy, the genetic basis for the disease, and related symptoms are described in the art (see, e.g. Campbell, A. E., et al., "Facioscapulohumeral dystrophy: Activating an early embryonic transcriptional program in human skeletal muscle" Human Mol Genet. (2018); and Tawil, R. "Facioscapulohumeral muscular dystrophy" Handbook Clin. Neurol. (2018), 148: 541-548.) FSHD Type 1 is associated with Online Mendelian Inheritance in Man (OMIM) Entry #158900. FSHD Type 2 is associated with OMIM Entry #158901.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or (e.g., and) VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or (e.g., and) an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or (e.g., and) chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidate morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides or nucleosides (e.g. 2'-O-methyl sugar modifications, purine or pyrimidine modifications). In some embodiments, an oligonucleotide may comprise one or more modified internucleotide linkages. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having FSHD.

Transferrin receptor: As used herein, the term, "transferrin receptor" (also known as TFRC, CD71, p90, TFR or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP 001300894.1, and NP_001300895.1).

2'-modified nucleoside: As used herein, the terms "2'-modified nucleoside" and "2'-modified ribonucleoside" are used interchangeably and refer to a nucleoside having a sugar moiety modified at the 2' position. In some embodiments, the 2'-modified nucleoside is a 2'-4' bicyclic nucleoside, where the 2' and 4' positions of the sugar are bridged (e.g., via a methylene, an ethylene, or a (S)-constrained ethyl bridge). In some embodiments, the 2'-modified nucleoside is a non-bicyclic 2'-modified nucleoside, e.g., where the 2' position of the sugar moiety is substituted. Non-limiting examples of 2'-modified nucleosides include: 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-0-dimethylaminoethyloxyethyl (2'-O-DMAEOE), 2'-O—N-methylacetamido (2'-O-NMA), locked nucleic acid (LNA, methylene-bridged nucleic acid), ethylene-bridged nucleic acid (ENA), and (S)-constrained ethyl-bridged nucleic acid (cEt). In some embodiments, the 2'-modified nucleosides described herein are high-affinity modified nucleotides and oligonucleotides comprising the 2'-modified nucleotides have increased affinity to a target sequences, relative to an unmodified oligonucleotide. Examples of structures of 2'-modified nucleosides are provided below:

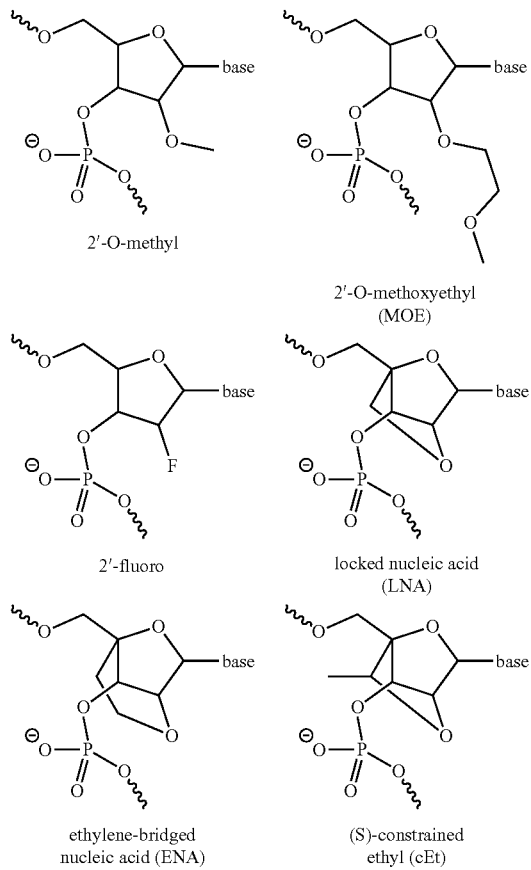

2'-O-methyl

2'-O-methoxyethyl (MOE)

2'-fluoro locked nucleic acid (LNA)

ethylene-bridged nucleic acid (ENA)

(S)-constrained ethyl (cEt)

II. Complexes

Provided herein are complexes that comprise a targeting agent, e.g. an antibody, covalently linked to a molecular payload. In some embodiments, a complex comprises a muscle-targeting antibody covalently linked to an oligonucleotide. A complex may comprise an antibody that specifically binds a single antigenic site or that binds to at least two antigenic sites that may exist on the same or different antigens.

A complex may be used to modulate the activity or function of at least one gene, protein, and/or (e.g., and) nucleic acid. In some embodiments, the molecular payload present with a complex is responsible for the modulation of a gene, protein, and/or (e.g., and) nucleic acids. A molecular payload may be a small molecule, protein, nucleic acid, oligonucleotide, or any molecular entity capable of modulating the activity or function of a gene, protein, and/or (e.g., and) nucleic acid in a cell. In some embodiments, a molecular payload is an oligonucleotide that targets a DUX4 in muscle cells.

In some embodiments, a complex comprises a muscle-targeting agent, e.g. an anti-transferrin receptor antibody, covalently linked to a molecular payload, e.g. an antisense oligonucleotide that targets a DUX4.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or (e.g., and) a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or (e.g., and) cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" Nature 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" J Biol Chem 1996; 271: 15160-5; and Weisbart R. H. et al., "Cell type specific targeted intracellular delivery into muscle of a monoclonal antibody that binds myosin IIb" Mol Immunol. 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to interchangeably as an, transferrin receptor antibody, an anti-transferrin receptor antibody, or an anti-TfR antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or (e.g., and) derivatized using several known methodologies, e.g. library design using phage display. Exemplary methodologies have been characterized in the art and are incorporated by reference (Diez, P. et al. "High-throughput phage-display screening in array format", Enzyme and microbial technology, 2015, 79, 34-41.; Hammers et al., "Antibody Phage Display: Technique and Applications" J Invest Dermatol. 2014, 134: 2.; Engleman, Edgar (Ed.) "Human Hybridomas and Monoclonal Antibodies." 1985, Springer.). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522.; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052.).

Provided herein, in some aspects, are new anti-TfR antibodies for use as the muscle targeting agents (e.g., in muscle targeting complexes). In some embodiments, the anti-TfR antibody described herein binds to transferrin receptor with high specificity and affinity. In some embodiments, the anti-TfR antibody described herein specifically binds to any extracellular epitope of a transferrin receptor or an epitope that becomes exposed to an antibody. In some embodiments, anti-TfR antibodies provided herein bind specifically to transferrin receptor from human, non-human primates, mouse, rat, etc. In some embodiments, anti-TfR antibodies provided herein bind to human transferrin receptor. In some embodiments, the anti-TfR antibody described herein binds to an amino acid segment of a human or non-human primate transferrin receptor, as provided in SEQ ID NOs: 105-108. In some embodiments, the anti-TfR antibody described herein binds to an amino acid segment corresponding to amino acids 90-96 of a human transferrin receptor as set forth in SEQ ID NO: 105, which is not in the apical domain of the transferrin receptor.

corresponding to NCBI sequence NP_003225.2 (transferrin receptor protein 1 isoform 1, *Homo sapiens*) is as follows:

(SEQ ID NO: 105)
MMDQARSAFSNLFGGEPLSYTRFSLARQVDGDNSHVEMKLAVDEEENAD

NNTKANVTKPKRCSGSICYGTIAVIVFFLIGFMIGYLGYCKGVEPKTEC

ERLAGTESPVREEPGEDFPAARRLYWDDLKRKLSEKLDSTDFTGTIKLL

NENSYVPREAGSQKDENLALYVENQFREFKLSKVWRDQHFVKIQVKDSA

QNSVIIVDKNGRLVYLVENPGGYVAYSKAATVTGKLVHANFGTKKDFED

LYTPVNGSIVIVRAGKITFAEKVANAESLNAIGVLIYMDQTKFPIVNAE

LSFFGHAHLGTGDPYTPGFPSFNHTQFPPSRSSGLPNIPVQTISRAAAE

KLFGNMEGDCPSDWKTDSTCRMVTSESKNVKLTVSNVLKEIKILNIFGV

IKGFVEPDHYVVVGAQRDAWGPGAAKSGVGTALLLKLAQMFSDMVLKDG

FQPSRSIIFASWSAGDFGSVGATEWLEGYLSSLHLKAFTYINLDKAVLG

TSNFKVSASPLLYTLIEKTMQNVKHPVTGQFLYQDSNWASKVEKLTLDN

AAFPFLAYSGIPAVSFCFCEDTDYPYLGTTMDTYKELIERIPELNKVAR

AAAEVAGQFVIKLTHDVELNLDYERYNSQLLSFVRDLNQYRADIKEMGL

SLQWLYSARGDFFRATSRLTTDFGNAEKTDRFVMKKLNDRVMRVEYHFL

SPYVSPKESPFRHVFWGSGSHTLPALLENLKLRKQNNGAFNETLFRNQL

ALATWTIQGAANALSGDVWDIDNEF.

An example non-human primate transferrin receptor amino acid sequence, corresponding to NCBI sequence NP_001244232.1 (transferrin receptor protein 1, *Macaca mulatta*) is as follows:

(SEQ ID NO: 106)
MMDQARSAFSNLFGGEPLSYTRFSLARQVDGDNSHVEMKLGVDEEENTD

NNTKPNGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPPLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 107)
MMDQARSAFSNLFGGEPLSYTRFSLARQVDGDNSHVEMKLGVDEEENTD

NNTKANGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPPLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 108)
MMDQARSAFSNLFGGEPLSYTRFSLARQVDGDNSHVEMKLAADEEENAD

NNMKASVRKPKRFNGRLCFAAIALVIFFLIGFMSGYLGYCKRVEQKEEC

VKLAETEETDKSETMETEDVPTSSRLYWADLKTLLSEKLNSIEFADTIK

QLSQNTYTPREAGSQKDESLAYYIENQFHEFKFSKVWRDEHYVKIQVKS

SIGQNMVTIVQSNGNLDPVESPEGYVAFSKPTEVSGKLVHANFGTKKDF

EELSYSVNGSLVIVRAGEITFAEKVANAQSFNAIGVLIYMDKNKFPVVE

ADLALFGHAHLGTGDPYTPGFPSFNHTQFPPSQSSGLPNIPVQTISRAA

AEKLFGKMEGSCPARWNIDSSCKLELSQNQNVKLIVKNVLKERRILNIF

GVIKGYEEPDRYVVVGAQRDALGAGVAAKSSVGTGLLLKLAQVFSDMIS

KDGFRPSRSIIFASWTAGDFGAVGATEWLEGYLSSLHLKAFTYINLDKV

VLGTSNFKVSASPLLYTLMGKIMQDVKHPVDGKSLYRDSNWISKVEKLS

FDNAAYPFLAYSGIPAVSFCFCEDADYPYLGTRLDTYEALTQKVPQLNQ

MVRTAAEVAGQLIIKLTHDVELNLDYEMYNSKLLSFMKDLNQFKTDIRD

MGLSLQWLYSARGDYFRATSRLTTDFHNAEKTNRFVMREINDRIMKVEY

HFLSPYVSPRESPFRHIFWGSGSHTLSALVENLKLRQKNITAFNETLFR

NQLALATWTIQGVANALSGDIWNIDNEF

In some embodiments, an anti-transferrin receptor antibody binds to an amino acid segment of the receptor as follows: FVKIQVKDSAQNSVIIVDKNGRLVYLVENPG-GYVAYSKAATVTGKLVHANFGTKKDFE DLYTPVNG-SIVIVRAGKITFAEKVANAESLNAIGVLIYMDQTK-FPIVNAELSFFGHAHLG TGDPYTPGFPSFNHTQF-PPSRSSGLPNIPVQTISRAAAEKLFGNMEGDCPSD-WKTDSTCR MVTSESKNVKLTVSNVLKE (SEQ ID NO: 109) and does not inhibit the binding interactions between transferrin receptors and transferrin and/or (e.g., and) human hemochromatosis protein (also known as HFE). In some embodiments, the anti-transferrin receptor antibody described herein does not bind an epitope in SEQ ID NO: 109.

Appropriate methodologies may be used to obtain and/or (e.g., and) produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988.).

In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, the anti-TfR antibody of the present disclosure comprises a VL domain and/or (e.g., and) VH domain of any one of the anti-TfR antibodies selected from Table 2, and comprises a constant region comprising the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, agents binding to transferrin receptor, e.g., anti-TfR antibodies, are capable of targeting muscle cell and/or (e.g., and) mediate the transportation of an agent across the blood brain barrier. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Antibodies that bind, e.g. specifically bind, to a transferrin receptor may be internalized into the cell, e.g. through receptor-mediated endocytosis, upon binding to a transferrin receptor.

Provided herein, in some aspects, are humanized antibodies that bind to transferrin receptor with high specificity and affinity. In some embodiments, the humanized anti-TfR antibody described herein specifically binds to any extracellular epitope of a transferrin receptor or an epitope that becomes exposed to an antibody. In some embodiments, the humanized anti-TfR antibodies provided herein bind specifically to transferrin receptor from human, non-human primates, mouse, rat, etc. In some embodiments, the humanized anti-TfR antibodies provided herein bind to human transferrin receptor. In some embodiments, the humanized anti-TfR antibody described herein binds to an amino acid segment of a human or non-human primate transferrin receptor, as provided in SEQ ID NOs: 105-108. In some embodiments, the humanized anti-TfR antibody described herein binds to an amino acid segment corresponding to amino acids 90-96 of a human transferrin receptor as set forth in SEQ ID NO: 105, which is not in the apical domain of the transferrin receptor. In some embodiments, the humanized anti-TfR antibodies described herein binds to TfR1 but does not bind to TfR2.

In some embodiments, an anti-TFR antibody specifically binds a TfR1 (e.g., a human or non-human primate TfR1) with binding affinity (e.g., as indicated by Kd) of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, the anti-TfR antibodies described herein binds to TfR1 with a KD of sub-nanomolar range. In some embodiments, the anti-TfR antibodies described herein selectively binds to transferrin receptor 1 (TfR1) but do not bind to transferrin receptor 2 (TfR2). In some embodiments, the anti-TfR antibodies described herein binds to human TfR1 and cyno TfR1 (e.g., with a Kd of $10^{-7}$ M, $10^{-8}$ M, $10^{-9}$ M, $10^{-10}$ M, $10^{-11}$ M, $10^{-12}$ M, $10^{-13}$ M, or less), but does not bind to a mouse TfR1. The affinity and binding kinetics of the anti-TfR antibody can be tested using any suitable method including but not limited to biosensor technology (e.g., OCTET or BIACORE). In some embodiments, binding of any one of the anti-TfR antibody described herein does not complete with or inhibit transferrin binding to the TfR1. In some embodiments, binding of any one of the anti-TfR antibody described herein does not complete with or inhibit HFE-beta-2-microglobulin binding to the TfR1.

The anti-TfR antibodies described herein are humanized antibodies. The CDR and variable region amino acid sequences of the mouse monoclonal anti-TfR antibody from which the humanized anti-TfR antibodies described herein are derived are provided in Table 2.

TABLE 2

| | | Mouse Monoclonal Anti-TfR Antibodies | | |
|---|---|---|---|---|
| Ab | No. system | IMGT | Kabat | Chothia |
| 3-A4 | CDR-H1 | GFNIKDDY (SEQ ID NO: 1) | DDYMY (SEQ ID NO: 7) | GFNIKDD (SEQ ID NO: 12) |
| | CDR-H2 | IDPENGDT (SEQ ID NO: 2) | WIDPENGDTEYASKFQD (SEQ ID NO: 8) | ENG (SEQ ID NO: 13) |

TABLE 2-continued

Mouse Monoclonal Anti-TfR Antibodies

| Ab | No. system | IMGT | Kabat | Chothia |
|---|---|---|---|---|
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPENGDTEYASKFQDKATVTADTSSNTAYLQLSSLTSEDTAVYYCTLWLRRGLDYWGQGTSVTVSS (SEQ ID NO: 17) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-A4 N54T* | CDR-H1 | GFNIKDDY (SEQ ID NO: 1) | DDYMY (SEQ ID NO: 7) | GFNIKDD (SEQ ID NO: 12) |
| | CDR-H2 | IDPETGDT (SEQ ID NO: 19) | WIDPETGDTEYASKFQD (SEQ ID NO: 20) | ETG (SEQ ID NO: 21) |
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPETGDTEYASKFQDKATVTADTSSNTAYLQLSSLTSEDTAVYYCTLWLRRGLDYWGQGTSVTVSS (SEQ ID NO: 22) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-A4 N54S* | CDR-H1 | GFNIKDDY (SEQ ID NO: 1) | DDYMY (SEQ ID NO: 7) | GFNIKDD (SEQ ID NO: 12) |
| | CDR-H2 | IDPESGDT (SEQ ID NO: 23) | WIDPESGDTEYASKFQD (SEQ ID NO: 24) | ESG (SEQ ID NO: 25) |
| | CDR-H3 | TLWLRRGLDY (SEQ ID NO: 3) | WLRRGLDY (SEQ ID NO: 9) | LRRGLD (SEQ ID NO: 14) |
| | CDR-L1 | KSLLHSNGYTY (SEQ ID NO: 4) | RSSKSLLHSNGYTYLF (SEQ ID NO: 10) | SKSLLHSNGYTY (SEQ ID NO: 15) |
| | CDR-L2 | RMS (SEQ ID NO: 5) | RMSNLAS (SEQ ID NO: 11) | RMS (SEQ ID NO: 5) |
| | CDR-L3 | MQHLEYPFT (SEQ ID NO: 6) | MQHLEYPFT (SEQ ID NO: 6) | HLEYPF (SEQ ID NO: 16) |
| | VH | EVQLQQSGAELVRPGASVKLSCTASGFNIKDDYMYWVKQRPEQGLEWIGWIDPESGDTEYASKFQDKATVTADTSSNTAYLQLSSLTSEDTAVYYCTLWLRRGLDYWGQGTSVTVSS (SEQ ID NO: 26) | | |
| | VL | DIVMTQAAPSVPVTPGESVSISCRSSKSLLHSNGYTYLFWFLQRPGQSPQLLIYRMSNLASGVPDRFSGSGSGTAFTLRISRVEAEDVGVYYCMQHLEYPFTFGGGTKLEIK (SEQ ID NO: 18) | | |
| 3-M12 | CDR-H1 | GYSITSGYY (SEQ ID NO: 27) | SGYYWN (SEQ ID NO: 33) | GYSITSGY (SEQ ID NO: 38) |
| | CDR-H2 | ITFDGAN (SEQ ID NO: 28) | YITFDGANNYNPSLKN (SEQ ID NO: 34) | FDG (SEQ ID NO: 39) |
| | CDR-H3 | TRSSYDYDVLDY (SEQ ID NO: 29) | SSYDYDVLDY (SEQ ID NO: 35) | SYDYDVLD (SEQ ID NO: 40) |
| | CDR-L1 | QDISNF (SEQ ID NO: 30) | RASQDISNFLN (SEQ ID NO: 36) | SQDISNF (SEQ ID NO: 41) |
| | CDR-L2 | YTS (SEQ ID NO: 31) | YTSRLHS (SEQ ID NO: 37) | YTS (SEQ ID NO: 31) |
| | CDR-L3 | QQGHTLPYT (SEQ ID NO: 32) | QQGHTLPYT (SEQ ID NO: 32) | GHTLPY (SEQ ID NO: 42) |
| | VH | DVQLQESGPGLVKPSQSLSLTCSVTGYSITSGYYWNWIRQFPGNKLEWMGYITFDGANNYNPSLKNRISITRDTSKNQFFLKLTSVTTEDTATYYCTRSSYDYDVLDYWGQGTTLTVSS (SEQ ID NO: 43) | | |
| | VL | DIQMTQTTSSLSASLGDRVTISCRASQDISNFLNWYQQRPDGTVKLLIYYTSRLHSGVPSRFSGSGSGTDFSLTVSNLEQEDIATYFCQQGHTLPYTFGGGTKLEIK (SEQ ID NO: 44) | | |
| 5-H12 | CDR-H1 | GYSFTDYC (SEQ ID NO: 45) | DYCIN (SEQ ID NO: 51) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |

TABLE 2-continued

Mouse Monoclonal Anti-TfR Antibodies

| Ab | No. system | IMGT | Kabat | Chothia |
|---|---|---|---|---|
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYCINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 61) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |
| 5-H12 C33Y* | CDR-H1 | GYSFTDYY (SEQ ID NO: 63) | DY YIN (SEQ ID NO: 64) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYYINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 65) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |
| 5-H12 C33D* | CDR-H1 | GYSFTDYD (SEQ ID NO: 66) | DYDIN (SEQ ID NO: 67) | GYSFTDY (SEQ ID NO: 56) |
| | CDR-H2 | IYPGSGNT (SEQ ID NO: 46) | WIYPGSGNTRYSERFKG (SEQ ID NO: 52) | GSG (SEQ ID NO: 57) |
| | CDR-H3 | AREDYYPYHGMDY (SEQ ID NO: 47) | EDYYPYHGMDY (SEQ ID NO: 53) | DYYPYHGMD (SEQ ID NO: 58) |
| | CDR-L1 | ESVDGYDNSF (SEQ ID NO: 48) | RASESVDGYDNSFMH (SEQ ID NO: 54) | SESVDGYDNSF (SEQ ID NO: 59) |
| | CDR-L2 | RAS (SEQ ID NO: 49) | RASNLES (SEQ ID NO: 55) | RAS (SEQ ID NO: 49) |
| | CDR-L3 | QQSSEDPWT (SEQ ID NO: 50) | QQSSEDPWT (SEQ ID NO: 50) | SSEDPW (SEQ ID NO: 60) |
| | VH | QIQLQQSGPELVRPGASVKISCKASGYSFTDYDINWVNQRPGQGLEWIGWIYPGSGNTRYSERFKGKATLTVDTSSNTAYMQLSSLTSEDSAVYFCAREDYYPYHGMDYWGQGTSVTVSS (SEQ ID NO: 68) | | |
| | VL | DIVLTQSPTSLAVSLGQRATISCRASESVDGYDNSFMHWYQQKPGQPPKLLIFRASNLESGIPARFSGSGSRTDFTLTINPVEAADVATYYCQQSSEDPWTFGGGTKLEIK (SEQ ID NO: 62) | | |

*mutation positions are according to Kabat numbering of the respective VH sequences containing the mutations In some embodiments, the anti-TfR antibody of the present disclosure is a humanized variant of any one of the anti-TfR antibodies provided in Table 2. In some embodiments, the anti-TfR antibody of the present disclosure comprises a CDR-H1, a CDR-1H2, a CDR-H3, a CDR-L1, a CDR-L2, and a CDR-L3 that are the same as the CDR-H1, CDR-1H2, and CDR-H3 in any one of the anti-TfR antibodies provided in Table 2, and comprises a humanized heavy chain variable region and/or (e.g., and) a humanized light chain variable region.

Humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more of the original antibody. Humanized antibodies may also involve affinity maturation.

Humanized antibodies and methods of making them are known, e.g., as described in Almagro et al., Front. Biosci. 13:1619-1633 (2008); Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005); Padlan et al., Mol. Immunol. 28:489-498 (1991); Dall'Acqua et al., Methods 36:43-60 (2005); Osbourn et al., Methods 36:61-68 (2005); and Klimka et al., Br. J. Cancer, 83:252-260 (2000), the contents of all of which are incorporated herein by reference. Human framework regions that may be used for humanization are described in e.g., Sims et al. J. Immunol. 151:2296 (1993); Carter et al., Proc. Natl. Acad. Sci. USA, 89:4285 (1992); Presta et al., J. Immunol., 151:2623 (1993); Almagro et al., Front. Biosci. 13:1619-1633 (2008)); Baca et al., J. Biol. Chem. 272:10678-10684 (1997); and Rosok et al., J Biol. Chem. 271:22611-22618 (1996), the contents of all of which are incorporated herein by reference.

In some embodiments, the humanized anti-TfR antibody of the present disclosure comprises a humanized VH comprising one or more amino acid variations (e.g., in the VH framework region) as compared with any one of the VHs listed in Table 2, and/or (e.g., and) a humanized VL comprising one or more amino acid variations (e.g., in the VL framework region) as compared with any one of the VLs listed in Table 2.

In some embodiments, the humanized anti-TfR antibody of the present disclosure comprises a humanized VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH of any of the anti-TfR antibodies listed in Table 2 (e.g., any one of SEQ ID NOs: 17, 22, 26, 43, 61, 65, and 68). Alternatively or in addition (e.g., in addition), the humanized anti-TfR antibody of the present disclosure comprises a humanized VL containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL of any one of the anti-TfR antibodies listed in Table 2 (e.g., any one of SEQ ID NOs: 18, 44, and 62).

In some embodiments, the humanized anti-TfR antibody of the present disclosure comprises a humanized VH comprising an amino acid sequence that is at least 75% (e.g., 75%, 80%, 85%, 90%, 95%, 98%, or 99%) identical in the framework regions to the VH of any of the anti-TfR antibodies listed in Table 2 (e.g., any one of SEQ ID NOs: 17, 22, 26, 43, 61, 65, and 68). Alternatively or in addition (e.g., in addition), In some embodiments, the humanized anti-TfR antibody of the present disclosure comprises a humanized VL comprising an amino acid sequence that is at least 75% (e.g., 75%, 80%, 85%, 90%, 95%, 98%, or 99%) identical in the framework regions to the VL of any of the anti-TfR antibodies listed in Table 2 (e.g., any one of SEQ ID NOs: 18, 44, and 62).

In some embodiments, the humanized anti-TfR antibody of the present disclosure comprises a humanized VH comprising a CDR-H1 having the amino acid sequence of SEQ ID NO: 1 (according to the IMGT definition system), a CDR-H2 having the amino acid sequence of SEQ ID NO: 2, SEQ ID NO: 19, or SEQ ID NO: 23 (according to the IMGT definition system), a CDR-H3 having the amino acid sequence of SEQ ID NO: 3 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22, or SEQ ID NO: 26. Alternatively or in addition (e.g., in addition), the anti-TfR antibody of the present disclosure comprises a humanized VL comprising a CDR-L1 having the amino acid sequence of SEQ ID NO: 4 (according to the IMGT definition system), a CDR-L2 having the amino acid sequence of SEQ ID NO: 5 (according to the IMGT definition system), and a CDR-L3 having the amino acid sequence of SEQ ID NO: 6 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 1 (according to the IMGT definition system), a CDR-H2 having the amino acid sequence of SEQ ID NO: 2, SEQ ID NO: 19, or SEQ ID NO: 23 (according to the IMGT definition system), a CDR-H3 having the amino acid sequence of SEQ ID NO: 3 (according to the IMGT definition system), and is at least 75% (e.g., 75%, 80%, 85%, 90%, 95%, 98%, or 99%) identical in the framework regions to the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 4 (according to the IMGT definition system), a CDR-L2 having the amino acid sequence of SEQ ID NO: 5 (according to the IMGT definition system), and a CDR-L3 having the amino acid sequence of SEQ ID NO: 6 (according to the IMGT definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 7 (according to the Kabat definition system), a CDR-H2 having the amino acid sequence of SEQ ID NO: 8, SEQ ID NO: 20, or SEQ ID NO: 24 (according to the Kabat definition system), a CDR-H3 having the amino acid sequence of SEQ ID NO: 9 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 10 (according to the Kabat definition system), a CDR-L2 having the amino acid sequence of SEQ ID NO: 11 (according to the Kabat definition system), and a CDR-L3 having the amino acid sequence of SEQ ID NO: 6 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 7 (according to the Kabat definition system), a CDR-H2 having the amino acid sequence of SEQ ID NO: 8, SEQ ID NO: 20, or SEQ ID NO: 24 (according to the Kabat definition system), a CDR-H3 having the amino acid sequence of SEQ ID NO: 9 (according to the Kabat definition system), and is at least 75% (e.g., 75%, 80%, 85%, 90%, 95%, 98%, or 99%) identical in the framework regions to the VH as set forth in SEQ ID NO: 17, SEQ ID NO: 22, or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 10 (according to the Kabat definition system), a CDR-L2 having the amino acid sequence of SEQ ID NO: 11 (according to the Kabat definition system), and a CDR-L3 having the amino acid sequence of SEQ ID NO: 6 (according to the Kabat definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 12 (according to the Chothia definition system), a CDR-H2 having the amino acid sequence of SEQ ID NO: 13, SEQ ID NO: 21, or SEQ ID NO: 25 (according to the Chothia definition system), a CDR-H3 having the amino acid sequence of SEQ ID NO: 14 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 17, SEQ ID NO: 22 or SEQ ID NO: 26. Alternatively or in addition (e.g., in addition), the humanized anti-TfR antibody of the present disclosure comprises a humanized VL comprising a CDR-L1 having the amino acid sequence of SEQ ID NO: 15 (according to the Chothia definition system), a CDR-L2 having the amino acid sequence of SEQ ID NO: 5 (according to the Chothia definition system), and a CDR-L3 having the amino acid sequence of SEQ ID NO: 16 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 18.

In some embodiments, the humanized anti-TfR antibody of the present disclosure comprises a humanized VH comprising a CDR-H1 having the amino acid sequence of SEQ ID NO: 12 (according to the Chothia definition system), a CDR-H2 having the amino acid sequence of SEQ ID NO: 13, SEQ ID NO: 21, or SEQ ID NO: 25 (according to the Chothia definition system), a CDR-H3 having the amino acid sequence of SEQ ID NO: 14 (according to the Chothia definition system), and is at least 75% (e.g., 75%, 80%, 85%, 90%, 95%, 98%, or 99%) identical in the framework regions to the VH as set forth in SEQ ID NO: SEQ ID NO: 17, SEQ ID NO: 22 or SEQ ID NO: 26. Alternatively or in addition (e.g., in addition), the anti-TfR antibody of the present disclosure comprises a humanized VL comprising a CDR-L1 having the amino acid sequence of SEQ ID NO: 15 (according to the Chothia definition system), a CDR-L2 having the amino acid sequence of SEQ ID NO: 5 (according to the Chothia definition system), and a CDR-L3 having the amino acid sequence of SEQ ID NO: 16 (according to the Chothia definition system), and is at least 75% (e.g., 75%, 80%, 85%, 90%, 95%, 98%, or 99%) identical in the framework regions to the VL as set forth in any one of SEQ ID NO: 18.

In some embodiments, the humanized anti-TfR antibody of the present disclosure comprises a humanized VH comprising a CDR-H1 having the amino acid sequence of SEQ ID NO: 27 (according to the IMGT definition system), a CDR-H2 having the amino acid sequence of SEQ ID NO: 28 (according to the IMGT definition system), a CDR-H3 having the amino acid sequence of SEQ ID NO: 29 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 30 (according to the IMGT definition system), a CDR-L2 having the amino acid sequence of SEQ ID NO: 31 (according to the IMGT definition system), and a CDR-L3 having the amino acid sequence of SEQ ID NO: 32 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 27 (according to the IMGT definition system), a CDR-H2 having the amino acid sequence of SEQ ID NO: 28 (according to the IMGT definition system), a CDR-H3 having the amino acid sequence of SEQ ID NO: 29 (according to the IMGT definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 30 (according to the IMGT definition system), a CDR-L2 having the amino acid sequence of SEQ ID NO: 31 (according to the IMGT definition system), and a CDR-L3 having the amino acid sequence of SEQ ID NO: 32 (according to the IMGT definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 33 (according to the Kabat definition system), a CDR-H2 having the amino acid sequence of SEQ ID NO: 34 (according to the Kabat definition system), a CDR-H3 having the amino acid sequence of SEQ ID NO: 35 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 36 (according to the Kabat definition system), a CDR-L2 having the amino acid sequence of SEQ ID NO: 37 (according to the Kabat definition system), and a CDR-L3 having the amino acid sequence of SEQ ID NO: 32 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 33 (according to the Kabat definition system), a CDR-H2 having the amino acid sequence of SEQ ID NO: 34 (according to the Kabat definition system), a CDR-H3 having the amino acid sequence of SEQ ID NO: 35 (according to the Kabat definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 36 (according to the Kabat definition system), a CDR-L2 having the amino acid sequence of SEQ ID NO: 37 (according to the Kabat definition system), and a CDR-L3 having the amino acid sequence of SEQ ID NO: 32 (according to the Kabat definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 38 (according to the Chothia definition system), a CDR-H2 having the amino acid sequence of SEQ ID NO: 39 (according to the Chothia definition system), a CDR-H3 having the amino acid sequence of SEQ ID NO: 40 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 41 (according to the Chothia definition system), a CDR-L2 having the amino acid sequence of SEQ ID NO: 31 (according to the Chothia definition system), and a CDR-L3 having the amino acid sequence of SEQ ID NO: 42 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 44.

In some embodiments, the humanized anti-TfR antibody of the present disclosure comprises a humanized VH comprising a CDR-H1 having the amino acid sequence of SEQ ID NO: 38 (according to the Chothia definition system), a CDR-H2 having the amino acid sequence of SEQ ID NO: 39 (according to the Chothia definition system), a CDR-H3 having the amino acid sequence of SEQ ID NO: 40 (according to the Chothia definition system), and is at least 75% (e.g., 75%, 80%, 85%, 90%, 95%, 98%, or 99%) identical in the framework regions to the VH as set forth in SEQ ID NO: 43. Alternatively or in addition (e.g., in addition), the humanized anti-TfR antibody of the present disclosure comprises a humanized VL comprising a CDR-L1 having the amino acid sequence of SEQ ID NO: 41 (according to the Chothia definition system), a CDR-L2 having the amino acid sequence of SEQ ID NO: 31 (according to the Chothia definition system), and a CDR-L3 having the amino acid sequence of SEQ ID NO: 42 (according to the Chothia definition system), and is at least 75% (e.g., 75%, 80%, 85%, 90%, 95%, 98%, or 99%) identical in the framework regions to the VL as set forth in SEQ ID NO: 44.

In some embodiments, the humanized anti-TfR antibody of the present disclosure comprises a humanized VH comprising a CDR-H1 having the amino acid sequence of SEQ ID NO: 45, SEQ ID NO: 63, or SEQ ID NO: 66 (according to the IMGT definition system), a CDR-H2 having the amino acid sequence of SEQ ID NO: 46 (according to the IMGT definition system), a CDR-H3 having the amino acid sequence of SEQ ID NO: 47 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, or SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 48 (according to the IMGT definition system), a CDR-L2 having the amino acid sequence of SEQ ID NO: 49 (according to the IMGT definition system), and a CDR-L3 having the amino acid sequence of SEQ ID NO: 50 (according to the IMGT definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 45, SEQ ID NO: 63, or SEQ ID NO: 66 (according to the IMGT definition system), a CDR-H2 having the amino acid sequence of SEQ ID NO: 46 (according to the IMGT definition system), a CDR-H3 having the amino acid sequence of SEQ ID NO: 47 (according to the IMGT definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 48 (according to the IMGT definition system), a CDR-L2 having the amino acid sequence of SEQ ID NO: 49 (according to the IMGT definition system), and a CDR-L3 having the amino acid sequence of SEQ ID NO: 50 (according to the IMGT definition system), and is at least 75% (e.g., 75%, 80%, 85%, 90%, 95%, 98%, or 99%) identical in the framework regions to the VL as set forth in SEQ ID NO: 62.

In some embodiments, the humanized anti-TfR antibody of the present disclosure comprises a humanized VH comprising a CDR-H1 having the amino acid sequence of SEQ ID NO: 51, SEQ ID NO: 64, or SEQ ID NO: 67 (according to the Kabat definition system), a CDR-H2 having the amino acid sequence of SEQ ID NO: 52 (according to the Kabat definition system), a CDR-H3 having the amino acid sequence of SEQ ID NO: 53 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 54 (according to the Kabat definition system), a CDR-L2 having the amino acid sequence of SEQ ID NO: 55 (according to the Kabat definition system), and a CDR-L3 having the amino acid sequence of SEQ ID NO: 50 (according to the Kabat definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 51, SEQ ID NO: 64, or SEQ ID NO: 67 (according to the Kabat definition system), a CDR-H2 having the amino acid sequence of SEQ ID NO: 52 (according to the Kabat definition system), a CDR-H3 having the amino acid sequence of SEQ ID NO: 53 (according to the Kabat definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 54 (according to the Kabat definition system), a CDR-L2 having the amino acid sequence of SEQ ID NO: 55 (according to the Kabat definition system), and a CDR-L3 having the amino acid sequence of SEQ ID NO: 50 (according to the Kabat definition system), and is at least 75% (e.g., 75%, 80%, 85%, 90%, 95%, 98%, or 99%) identical in the framework regions to the VL as set forth in SEQ ID NO: 62.

In some embodiments, the humanized anti-TfR antibody of the present disclosure comprises a humanized VH comprising a CDR-H1 having the amino acid sequence of SEQ ID NO: 56 (according to the Chothia definition system), a CDR-H2 having the amino acid sequence of SEQ ID NO: 57 (according to the Chothia definition system), a CDR-H3 having the amino acid sequence of SEQ ID NO: 58 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 59 (according to the Chothia definition system), a CDR-L2 having the amino acid sequence of SEQ ID NO: 49 (according to the Chothia definition system), and a CDR-L3 having the amino acid sequence of SEQ ID NO: 60 (according to the Chothia definition system), and containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL as set forth in SEQ ID NO: 62.

In some embodiments, the humanized anti-TfR antibody of the present disclosure comprises a humanized VH comprising a CDR-H1 having the amino acid sequence of SEQ ID NO: 56 (according to the Chothia definition system), a CDR-12 having the amino acid sequence of SEQ ID NO: 57 (according to the Chothia definition system), a CDR-H3 having the amino acid sequence of SEQ ID NO: 58 (according to the Chothia definition system), and is at least 75% (e.g., 75%, 80%, 85%, 90%, 95%, 98%, or 99%) identical in the framework regions to the VH as set forth in SEQ ID NO: 61, SEQ ID NO: 65, SEQ ID NO: 68. Alternatively or in addition (e.g., in addition), the humanized anti-TfR antibody of the present disclosure comprises a humanized VL comprising a CDR-L1 having the amino acid sequence of SEQ ID NO: 59 (according to the Chothia definition system), a CDR-L2 having the amino acid sequence of SEQ ID NO: 49 (according to the Chothia definition system), and a CDR-L3 having the amino acid sequence of SEQ ID NO: 60 (according to the Chothia definition system), and is at least 75% (e.g., 75%, 80%, 85%, 90%, 95%, 98%, or 99%) identical in the framework regions to the VL as set forth in SEQ ID NO: 62.

Examples of amino acid sequences of the humanized anti-TfR antibodies described herein are provided in Table 3.

TABLE 3

Variable Regions of Humanized Anti-TfR Antibodies

| Antibody | Variable Region Amino Acid Sequence** |
|---|---|
| 3A4<br>VH3 (N54T*)/Vκ4 | $V_H$:<br>EVQLVQSGSELKKPGASVKVSCTASGFNIKDDYMYWVRQPPGKGLEWIGWIDPETGDTEYASKFQDRVTVTADTSTNTAYMELSSLRSEDTAVYYCTLWLRRGLDYWGQGTLVTVSS (SEQ ID NO: 69)<br>$V_L$:<br>DIVMTQSPLSLPVTPGEPASISCRSSKSLLHSNGYTYLFWFQQRPGQSPRLLIYRMSNLASGVPDRFSGSGSGTDFTLKISRVEAEDVGVYYCMQHLEYPFTFGGGTK VEIK (SEQ ID NO: 70) |
| 3A4<br>VH3 (N54S*)/Vκ4 | $V_H$:<br>EVQLVQSGSELKKPGASVKVSCTASGFNIKDDYMYWVRQPPGKGLEWIGWIDPESGDTEYASKFQDRVTVTADTSTNTAYMELSSLRSEDTAVYYCTLWLRRGLDYWGQGTLVTVSS (SEQ ID NO: 71)<br>$V_L$:<br>DIVMTQSPLSLPVTPGEPASISCRSSKSLLHSNGYTYLFWFQQRPGQSPRLLIYRMSNLASGVPDRFSGSGSGTDFTLKISRVEAEDVGVYYCMQHLEYPFTFGGGTK VEIK (SEQ ID NO: 70) |

TABLE 3-continued

Variable Regions of Humanized Anti-TfR Antibodies

| Antibody | Variable Region Amino Acid Sequence** |
|---|---|
| 3A4<br>VH3/Vκ4 | $V_H$:<br>EVQLVQSGSELKKPGASVKVSCTASGFNIKDDYMYWVRQPPGKGLEWIGWIDP<br>ENGDTEYASKFQDRVTVTADTSTNTAYMELSSLRSEDTAVYYCTLWLRRGLD<br>YWGQGTLVTVSS (SEQ ID NO: 72)<br>$V_L$:<br>DIVMTQSPLSLPVTPGEPASISCRSSKSLLHSNGYTYLFWFQQRPGQSPRLLIYR<br>MSNLASGVPDRFSGSGSGTDFTLKISRVEAEDVGVYYCMQHLEYPFTFGGGTK<br>VEIK (SEQ ID NO: 70) |
| 3M12<br>VH3/Vκ2 | $V_H$:<br>QVQLQESGPGLVKPSQTLSLTCSVTGYSITSGYYWNWIRQPPGKGLEWMGYITF<br>DGANNYNPSLKNRVSISRDTSKNQFSLKLSSVTAEDTATYYCTRSSYDYDVLDY<br>WGQGTTVTVSS (SEQ ID NO: 73)<br>$V_L$:<br>DIQMTQSPSSLSASVGDRVTITCRASQDISNFLNWYQQKPGQPVKLLIYYTSRLH<br>SGVPSRFSGSGSGTDFTLTISSLQPEDFATYFCQQGHTLPYTFGQGTKLEIK (SEQ<br>ID NO: 74) |
| 3M12<br>VH3/Vκ3 | $V_H$:<br>QVQLQESGPGLVKPSQTLSLTCSVTGYSITSGYYWNWIRQPPGKGLEWMGYITF<br>DGANNYNPSLKNRVSISRDTSKNQFSLKLSSVTAEDTATYYCTRSSYDYDVLDY<br>WGQGTTVTVSS (SEQ ID NO: 73)<br>$V_L$:<br>DIQMTQSPSSLSASVGDRVTITCRASQDISNFLNWYQQKPGQPVKLLIYYTSRLH<br>SGVPSRFSGSGSGTDFTLTISSLQPEDFATYYCQQGHTLPYTFGQGTKLEIK (SEQ<br>ID NO: 75) |
| 3M12<br>VH4/Vκ2 | $V_H$:<br>QVQLQESGPGLVKPSQTLSLTCTVTGYSITSGYYWNWIRQPPGKGLEWIGYITFD<br>GANNYNPSLKNRVSISRDTSKNQFSLKLSSVTAEDTATYYCTRSSYDYDVLDYW<br>GQGTTVTVSS (SEQ ID NO: 76)<br>$V_L$:<br>DIQMTQSPSSLSASVGDRVTITCRASQDISNFLNWYQQKPGQPVKLLIYYTSRLH<br>SGVPSRFSGSGSGTDFTLTISSLQPEDFATYFCQQGHTLPYTFGQGTKLEIK (SEQ<br>ID NO: 74) |
| 3M12<br>VH4/Vκ3 | $V_H$:<br>QVQLQESGPGLVKPSQTLSLTCTVTGYSITSGYYWNWIRQPPGKGLEWIGYITFD<br>GANNYNPSLKNRVSISRDTSKNQFSLKLSSVTAEDTATYYCTRSSYDYDVLDYW<br>GQGTTVTVSS (SEQ ID NO: 76)<br>$V_L$:<br>DIQMTQSPSSLSASVGDRVTITCRASQDISNFLNWYQQKPGQPVKLLIYYTSRLH<br>SGVPSRFSGSGSGTDFTLTISSLQPEDFATYYCQQGHTLPYTFGQGTKLEIK (SEQ<br>ID NO: 75) |
| 5H12<br>VH5 (C33Y*)/Vκ3 | $V_H$:<br>QVQLVQSGAEVKKPGASVKVSCKASGYSFTDYYINWVRQAPGQGLEWMGWIY<br>PGSGNTRYSERFKGRVTITRDTSASTAYMELSSLRSEDTAVYYCAREDYYPYH<br>GMDYWGQGTLVTVSS (SEQ ID NO: 77)<br>$V_L$:<br>DIVLTQSPDSLAVSLGERATINCRASESVDGYDNSFMHWYQQKPGQPPKLLIFR<br>ASNLESGVPDRFSGSGSRTDFTLTISSLQAEDVAVYYCQQSSEDPWTFGQGTKL<br>EIK (SEQ ID NO: 78) |
| 5H12<br>VH5 (C33D*)/Vκ4 | $V_H$:<br>QVQLVQSGAEVKKPGASVKVSCKASGYSFTDYDINWVRQAPGQGLEWMGWIY<br>PGSGNTRYSERFKGRVTITRDTSASTAYMELSSLRSEDTAVYYCAREDYYPYH<br>GMDYWGQGTLVTVSS (SEQ ID NO: 79)<br>$V_L$:<br>DIVMTQSPDSLAVSLGERATINCRASESVDGYDNSFMHWYQQKPGQPPKLLIFR<br>ASNLESGVPDRFSGSGSGTDFTLTISSLQAEDVAVYYCQQSSEDPWTFGQGTKL<br>EIK (SEQ ID NO: 80) |
| 5H12<br>VH5 (C33Y*)/Vκ4 | $V_H$:<br>QVQLVQSGAEVKKPGASVKVSCKASGYSFTDYYINWVRQAPGQGLEWMGWIY<br>PGSGNTRYSERFKGRVTITRDTSASTAYMELSSLRSEDTAVYYCAREDYYPYH<br>GMDYWGQGTLVTVSS (SEQ ID NO: 77)<br>$V_L$:<br>DIVMTQSPDSLAVSLGERATINCRASESVDGYDNSFMHWYQQKPGQPPKLLIFR<br>ASNLESGVPDRFSGSGSGTDFTLTISSLQAEDVAVYYCQQSSEDPWTFGQGTKL<br>EIK (SEQ ID NO: 80) |

*mutation positions are according to Kabat numbering of the respective VH sequences containing the mutations
**CDRs according to the Kabat numbering system are bolded In some embodiments, the humanized anti-TfR antibody of the present disclosure comprises a humanized VH comprising the CDR-H1, CDR-H2, and CDR-H3 of any one of the anti-TfR antibodies provided in Table 2 and comprises one or more (e.g., 1, 2, 3, 4, 5, 6, 7, 8, 9, 10 or more) amino acid variations in the framework regions as compared with the respective humanized VH provided in Table 3. Alternatively or in addition (e.g., in addition), the humanized anti-TfR antibody of the present disclosure comprises a humanized VL comprising the CDR-L1, CDR-L2, and CDR-L3 of any one of the anti-TfR antibodies provided in Table 2 and comprises one or more (e.g., 1, 2, 3, 4, 5, 6, 7, 8, 9, 10 or more) amino acid variations in the framework regions as compared with the respective humanized VL provided in Table 3.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 69, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 69 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 71, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 71 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 72, and/or (e.g., and) a humanized VL comprising an amino acid sequence that is at least 80% identical (e.g., 80%, 85%, 90%, 95%, 98%, or 99%) to SEQ ID NO: 70. In some embodiments, the humanized anti-TfR antibody of the present disclosure comprises a humanized VH comprising the amino acid sequence of SEQ ID NO: 72 and a humanized VL comprising the amino acid sequence of SEQ ID NO: 70.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 73, and/or (e.g., and) a humanized VL comprising an amino acid sequence that is at least 80% identical (e.g., 80%, 85%, 90%, 95%, 98%, or 99%) to SEQ ID NO: 74. In some embodiments, the humanized anti-TfR antibody of the present disclosure comprises a humanized VH comprising the amino acid sequence of SEQ ID NO: 73 and a humanized VL comprising the amino acid sequence of SEQ ID NO: 74.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 73, and/or (e.g., and) a humanized VL comprising an amino acid sequence that is at least 80% identical (e.g., 80%, 85%, 90%, 95%, 98%, or 99%) to SEQ ID NO: 75. In some embodiments, the humanized anti-TfR antibody of the present disclosure comprises a humanized VH comprising the amino acid sequence of SEQ ID NO: 73 and a humanized VL comprising the amino acid sequence of SEQ ID NO: 75.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 76, and/or (e.g., and) a humanized VL comprising an amino acid sequence that is at least 80% identical (e.g., 80%, 85%, 90%, 95%, 98%, or 99%) to SEQ ID NO: 74. In some embodiments, the humanized anti-TfR antibody of the present disclosure comprises a humanized VH comprising the amino acid sequence of SEQ ID NO: 76 and a humanized VL comprising the amino acid sequence of SEQ ID NO: 74.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 76, and/or (e.g., and) a humanized VL comprising an amino acid sequence that is at least 80% identical (e.g., 80%, 85%, 90%, 95%, 98%, or 99%) to SEQ ID NO: 75. In some embodiments, the humanized anti-TfR antibody of the present disclosure comprises a humanized VH comprising the amino acid sequence of SEQ ID NO: 76 and a humanized VL comprising the amino acid sequence of SEQ ID NO: 75.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 77, and/or (e.g., and) a humanized VL comprising an amino acid sequence that is at least 80% identical (e.g., 80%, 85%, 90%, 95%, 98%, or 99%) to SEQ ID NO: 78. In some embodiments, the humanized anti-TfR antibody of the present disclosure comprises a humanized VH comprising the amino acid sequence of SEQ ID NO: 77 and a humanized VL comprising the amino acid sequence of SEQ ID NO: 78.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 79, and/or (e.g., and) a humanized VL comprising an amino acid sequence that is at least 80% identical (e.g., 80%, 85%, 90%, 95%, 98%, or 99%) to SEQ ID NO: 80. In some embodiments, the humanized anti-TfR antibody of the present disclosure comprises a humanized VH comprising the amino acid sequence of SEQ ID NO: 79 and a humanized VL comprising the amino acid sequence of SEQ ID NO: 80.

In some embodiments, the humanized anti-TfR antibody of the present disclosure comprises a humanized VH comprising an amino acid sequence that is at least 80% (e.g., 80%, 85%, 90%, 95%, 98%, or 99%) identical to SEQ ID NO: 77, and/or (e.g., and) a humanized VL comprising an amino acid sequence that is at least 80% identical (e.g., 80%, 85%, 90%, 95%, 98%, or 99%) to SEQ ID NO: 80. In some embodiments, the humanized anti-TfR antibody of the present disclosure comprises a humanized VH comprising the amino acid sequence of SEQ ID NO: 77 and a humanized VL comprising the amino acid sequence of SEQ ID NO: 80.

In some embodiments, the humanized anti-TfR antibody described herein is a full-length IgG, which can include a heavy constant region and a light constant region from a human antibody. In some embodiments, the heavy chain of any of the anti-TfR antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An example of a human IgG1 constant region is given below:

(SEQ ID NO: 81)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In some embodiments, the heavy chain of any of the anti-TfR antibodies described herein comprises a mutant human IgG1 constant region. For example, the introduction of LALA mutations (a mutant derived from mAb b12 that has been mutated to replace the lower hinge residues Leu234 Leu235 with Ala234 and Ala235) in the CH2 domain of human IgG1 is known to reduce Fcg receptor binding (Bruhns, P., et al. (2009) and Xu, D. et al. (2000)). The mutant human IgG1 constant region is provided below (mutations bonded and underlined):

(SEQ ID NO: 82)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPEAAGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

In some embodiments, the light chain of any of the anti-TfR antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

(SEQ ID NO: 83)
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC

Other antibody heavy and light chain constant regions are well known in the art, e.g., those provided in the IMGT database (www.imgt.org) or at www.vbase2.org/vbstat.php., both of which are incorporated by reference herein.

In some embodiments, the humanized anti-TfR antibody described herein comprises a heavy chain comprising any one of the VH as listed in Table 3 or any variants thereof and a heavy chain constant region that is at least 80%, at least 85%, at least 90%, at least 95%, or at least 99% identical to SEQ ID NO: 81 or SEQ ID NO: 82. In some embodiments, the humanized anti-TfR antibody described herein comprises a heavy chain comprising any one of the VH as listed in Table 3 or any variants thereof and a heavy chain constant region that contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 81 or SEQ ID NO: 82. In some embodiments, the humanized anti-TfR antibody described herein comprises a heavy chain comprising any one of the VH as listed in Table 3 or any variants thereof and a heavy chain constant region as set forth in SEQ ID NO: 81. In some embodiments, the humanized anti-TfR antibody described herein comprises heavy chain comprising any one of the VH as listed in Table 3 or any variants thereof and a heavy chain constant region as set forth in SEQ ID NO: 82.

In some embodiments, the humanized anti-TfR antibody described herein comprises a light chain comprising any one of the VL as listed in Table 3 or any variants thereof and a light chain constant region that is at least 80%, at least 85%, at least 90%, at least 95%, or at least 99% identical to SEQ ID NO: 83. In some embodiments, the humanized anti-TfR antibody described herein comprises a light chain comprising any one of the VL as listed in Table 3 or any variants thereof and a light chain constant region contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 83. In some embodiments, the humanized anti-TfR antibody described herein comprises a light chain comprising any one of the VL as listed in Table 3 or any variants thereof and a light chain constant region set forth in SEQ ID NO: 83.

Examples of IgG heavy chain and light chain amino acid sequences of the anti-TfR antibodies described are provided in Table 4 below.

TABLE 4

Heavy chain and light chain sequences of examples of humanized anti-TfR IgGs

| Antibody | IgG Heavy Chain/Light Chain Sequences** |
|---|---|
| 3A4<br>VH3 (N54T*)/Vκ4 | Heavy Chain (with wild type human IgG1 constant region)<br>EVQLVQSGSELKKPGASVKVSCTASGFNIKDDYMYWVRQPPGKGLEWIGWIDPE<br>TGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 84)<br>Light Chain (with kappa light chain constant region)<br>DIVMTQSPLSLPVTGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK |

TABLE 4-continued

Heavy chain and light chain sequences of examples of humanized anti-TfR IgGs

| Antibody | IgG Heavy Chain/Light Chain Sequences** |
|---|---|
| | RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NQ: 85) |
| 3A4<br>VH3 (N54S*)/Vκ4 | Heavy Chain (with wild type human IgG1 constant region)<br>EVQLVQSGSELKKPGASVKVSCTASGFNIKDDYMYWVRQPPGKGLEWIGWIDPE<br>SGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 86)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NQ: 85) |
| 3A4<br>VH3/Vκ4 | Heavy Chain (with wild type human IgG1 constant region)<br>EVQLVQSGSELKKPGASVKVSCTASGFNIKDDYMYWVRQPPGKGLEWIGWIDPE<br>NGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 87)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NQ: 85) |
| 3M12<br>VH3/Vκ2 | Heavy Chain (with wild type human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 88)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYT**FGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH3/Vκ3 | Heavy Chain (with wild type human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPGK (SEQ ID NO: 88)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYT**FGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 3M12<br>VH4/Vκ2 | Heavy Chain (with wild type human IgG1 constant region)<br>QVQLQESGPGLVKPSQTLSLTCSVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD |

TABLE 4-continued

Heavy chain and light chain sequences of examples of humanized anti-TfR IgGs

| Antibody | IgG Heavy Chain/Light Chain Sequences** |
|---|---|
| | KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPGK(SEQ ID NO: 91)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH4/Vκ3 | Heavy Chain (with wild type human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLS<br>LSPGK(SEQ ID NO: 91)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYYCQQGHTLPYTFGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO: 90) |
| 5H12<br>VH5 (C33Y*)/Vκ3 | Heavy Chain (with wild type human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 92)<br>Light Chain (with kappa light chain constant region)<br>DIVLTQSPDSLAVSLGERATINCRASESVDGYDNSFMHWYQQKPGQPPKLLIFRAS<br>NLESGVPDRFSGSGSRTDFTLTISSLQAEDVAVYYCQQSSEDPWTFGQGTKLEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC (SEQ ID NQ: 93) |
| 5H12<br>VH5 (C33D*)/Vκ4 | Heavy Chain (with wild type human IgG1 constant region)<br>QVQLVQSGAEVKKPGASVKVSCKASGYSFTDYDINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 94)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ ID NO: 95) |
| 5H12<br>VH5 (C33Y*)/Vκ4 | Heavy Chain (with wild type human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK (SEQ ID NO: 92)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK |

TABLE 4-continued

Heavy chain and light chain sequences of examples of humanized anti-TfR IgGs

| Antibody | IgG Heavy Chain/Light Chain Sequences** |
|---|---|
| | RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 95) |

*mutation positions are according to Kabat numbering of the respective VH sequences containing the mutations
**CDRs according to the Kabat numbering system are bolded; VH/VL sequences underlined In some embodiments, the humanized anti-TfR antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 84, 86, 87, 88, 91, 92, and 94. Alternatively or in addition (e.g., in addition), the humanized anti-TfR antibody of the present disclosure comprises a light chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the light chain as set forth in any one of SEQ ID NOs: 85, 89, 90, 93, and 95.

In some embodiments, the humanized anti-TfR antibody described herein comprises a heavy chain comprising an amino acid sequence that is at least 75% (e.g., 75%, 80%, 85%, 90%, 95%, 98%, or 99%) identical to any one of SEQ ID NOs: 84, 86, 87, 88, 91, 92, and 94. Alternatively or in addition (e.g., in addition), the humanized anti-TfR antibody described herein comprises a light chain comprising an amino acid sequence that is at least 75% (e.g., 75%, 80%, 85%, 90%, 95%, 98%, or 99%) identical to any one of SEQ ID NOs: 85, 89, 90, 93, and 95. In some embodiments, the anti-TfR antibody described herein comprises a heavy chain comprising the amino acid sequence of any one of SEQ ID NOs: 84, 86, 87, 88, 91, 92, and 94. Alternatively or in addition (e.g., in addition), the anti-TfR antibody described herein comprises a light chain comprising the amino acid sequence of any one of SEQ ID NOs: 85, 89, 90, 93, and 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 84, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 84 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 86, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 86 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 87, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 87 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 88, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 88 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 88, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 88 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 91, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 91 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 91, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 91 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 92, and/or (e.g., and) a light chain comprising an amino acid sequence that is at least 80% identical (e.g., 80%, 85%, 90%, 95%, 98%, or 99%) to SEQ ID NO: 93. In some embodiments, the humanized anti-TfR antibody of the present disclosure comprises a heavy chain comprising the amino acid sequence of SEQ ID NO: 92 and a light chain comprising the amino acid sequence of SEQ ID NO: 93.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 94, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 94 and a light chain comprising the amino acid sequence of SEQ ID NO: 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 92, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 92 and a light chain comprising the amino acid sequence of SEQ ID NO: 95.

In some embodiments, the anti-TfR antibody is a Fab fragment, Fab' fragment, or F(ab')₂ fragment of an intact antibody (full-length antibody). Antigen binding fragment of an intact antibody (full-length antibody) can be prepared via routine methods (e.g., recombinantly or by digesting the heavy chain constant region of a full length IgG using an enzyme such as papain). For example, F(ab')2 fragments can be produced by pepsin or papain digestion of an antibody molecule, and Fab' fragments that can be generated by reducing the disulfide bridges of F(ab')₂ fragments. In some embodiments, a heavy chain constant region in a Fab fragment of the anti-TfR1 antibody described herein comprises the amino acid sequence of:

```
                                           (SEQ ID NO: 96)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHT
```

In some embodiments, the humanized anti-TfR antibody described herein comprises a heavy chain comprising any one of the VH as listed in Table 3 or any variants thereof and a heavy chain constant region that is at least 80%, at least 85%, at least 90%, at least 95%, or at least 99% identical to SEQ ID NO: 96. In some embodiments, the humanized anti-TfR antibody described herein comprises a heavy chain comprising any one of the VH as listed in Table 3 or any variants thereof and a heavy chain constant region that contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 96. In some embodiments, the humanized anti-TfR antibody described herein comprises a heavy chain comprising any one of the VH as listed in Table 3 or any variants thereof and a heavy chain constant region as set forth in SEQ ID NO: 96.

In some embodiments, the humanized anti-TfR antibody described herein comprises a light chain comprising any one of the VL as listed in Table 3 or any variants thereof and a light chain constant region that is at least 80%, at least 85%, at least 90%, at least 95%, or at least 99% identical to SEQ ID NO: 83. In some embodiments, the humanized anti-TfR antibody described herein comprises a light chain comprising any one of the VL as listed in Table 3 or any variants thereof and a light chain constant region contains no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with SEQ ID NO: 83. In some embodiments, the humanized anti-TfR antibody described herein comprises a light chain comprising any one of the VL as listed in Table 3 or any variants thereof and a light chain constant region set forth in SEQ ID NO: 83.

Examples of Fab heavy chain and light chain amino acid sequences of the anti-TfR antibodies described are provided in Table 5 below.

TABLE 5

Heavy chain and light chain sequences of examples of humanized anti-TfR Fabs

| Antibody | Fab Heavy Chain/Light Chain Sequences** |
|---|---|
| 3A4<br>VH3 (N54T*)/Vκ4 | Heavy Chain (with partial human IgG1 constant region)<br>EVQLVQSGSELKKPGASVKVSCTASGFNIKDDYMYWVRQPPGKGLEWIGWIDPE<br>TGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 97)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3A4<br>VH3 (N54S*)/Vκ4 | Heavy Chain (with partial human IgG1 constant region)<br>EVQLVQSGSELKKPGASVKVSCTASGFNIKDDYMYWVRQPPGKGLEWIGWIDPE<br>SGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 98) |

TABLE 5-continued

Heavy chain and light chain sequences of examples of humanized anti-TfR Fabs

| Antibody | Fab Heavy Chain/Light Chain Sequences** |
|---|---|
| | Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3A4<br>VH3/Vκ4 | Heavy Chain (with partial human IgG1 constant region)<br>EVQLVQSGSELKKPGASVKVSCTASGFNIKDDYMYWVRQPPGKGLEWIGWIDPE<br>NGDTEYASKFQDRVTVTADTSTNTAYMELSSLRSEDTAVYYCTLWLRRGLDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKS<br>CDKTHT (SEQ ID NO: 99)<br>Light Chain (with kappa light chain constant region)<br>DIVMTQSPLSLPVTPGEPASISCRSSKSLLHSNGYTYLFWFQQRPGQSPRLLIYRMS<br>NLASGVPDRFSGSGSGTDFTLKISRVEAEDVGVYYCMQHLEYPFTFGGGTKVEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 85) |
| 3M12<br>VH3/Vκ2 | Heavy Chain (with partial human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHT (SEQ ID NO: 100)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH3/Vκ3 | Heavy Chain (with partial human IgG1 constant region)<br>QVQLQESGPGLVKPSQTLSLTCSVTGYSITSGYYWNWIRQPPGKGLEWMGYITFD<br>GANNYNPSLKNRVSISRDTSKNQFSLKLSSVTAEDTATYYCTRSSYDYDVLDYWG<br>QGTTVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSC<br>DKTHT (SEQ ID NO: 100)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO:<br>90) |
| 3M12<br>VH4/Vκ2 | Heavy Chain (with partial human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHT (SEQ ID NO: 101)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 89) |
| 3M12<br>VH4/Vκ3 | Heavy Chain (with partial human IgG1 constant region)<br>QVQLQESGPGLVKPSQTLSLTCTVTGYSITSGYYWNWIRQPPGKGLEWIGYITFDG<br>ANNYNPSLKNRVSISRDTSKNQFSLKLSSVTAEDTATYYCTRSSYDYDVLDYWGQ<br>GTTVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKKVEPKSCD<br>KTHT (SEQ ID NO: 101)<br>Light Chain (with kappa light chain constant region)<br>DIQMTQSPSSLSASVGDRVTITCRASQDISNFLNWYQQKPGQPVKLLIYYTSRLHS<br>GVPSRFSGSGSGTDFTLTISSLQPEDFATYFCQQGHTLPYTFGQGTKLEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC (SEQ ID NO:<br>90) |
| 5H12<br>VH5 (C33Y*)/Vκ3 | Heavy Chain (with partial human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 102) |

TABLE 5-continued

Heavy chain and light chain sequences of examples of humanized anti-TfR Fabs

| Antibody | Fab Heavy Chain/Light Chain Sequences** |
|---|---|
| | Light Chain (with kappa light chain constant region)<br>DIVLTQSPDSLAVSLGERATINCRASESVDGYDNSFMHWYQQKPGQPPKLLIFRAS<br>NLESGVPDRFSGSGSRTDFTLTISSLQAEDVAVYYCQQSSEDPWTFGQGTKLEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC (SEQ ID<br>NO: 93) |
| 5H12<br>VH5 (C33D*)/Vκ4 | Heavy Chain (with partial human IgG1 constant region)<br>QVQLVQSGAEVKKPGASVKVSCKASGYSFTDYDINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 103)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 95) |
| 5H12<br>VH5 (C33Y*)/Vκ4 | Heavy Chain (with partial human IgG1 constant region)<br>QVQLVQSGAEVKKPGASVKVSCKASGYSFTDYYINWVRQAPGQGLEWMGWIYP<br>GSGNTRYSERFKGRVTITRDTSASTAYMELSSLRSEDTAVYYCAREDYYPYHGM<br>DYWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKV<br>EPKSCDKTHT (SEQ ID NO: 102)<br>Light Chain (with kappa light chain constant region)<br>DIVMTQSPDSLAVSLGERATINCRASESVDGYDNSFMHWYQQKPGQPPKLLIFRA<br>SNLESGVPDRFSGSGSGTDFTLTISSLQAEDVAVYYCQQSSEDPWTFGQGTKLEIK<br>RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC (SEQ<br>ID NO: 95) |

*mutation positions are according to Kabat numbering of the respective VH sequences containing the mutations
**CDRs according to the Kabat numbering system are bolded; VH/VL sequences underlined In some embodiments, the humanized anti-TfR antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in any one of SEQ ID NOs: 97-103. Alternatively or in addition (e.g., in addition), the humanized anti-TfR antibody of the present disclosure comprises a light chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the light chain as set forth in any one of SEQ ID NOs: 85, 89, 90, 93, and 95.

In some embodiments, the humanized anti-TfR antibody described herein comprises a heavy chain comprising an amino acid sequence that is at least 75% (e.g., 75%, 80%, 85%, 90%, 95%, 98%, or 99%) identical to any one of SEQ ID NOs: 97-103. Alternatively or in addition (e.g., in addition), the humanized anti-TfR antibody described herein comprises a light chain comprising an amino acid sequence that is at least 75% (e.g., 75%, 80%, 85%, 90%, 95%, 98%, or 99%) identical to any one of SEQ ID NOs: 85, 89, 90, 93, and 95. In some embodiments, the anti-TfR antibody described herein comprises a heavy chain comprising the amino acid sequence of any one of SEQ ID NOs: 97-103. Alternatively or in addition (e.g., in addition), the anti-TfR antibody described herein comprises a light chain comprising the amino acid sequence of any one of SEQ ID NOs: 85, 89, 90, 93, and 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 97, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 97 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 98, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 98 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 99, and/or (e.g., and) a light chain comprising an amino acid sequence that is at least 80% identical (e.g., 80%, 85%, 90%, 95%, 98%, or 99%) to SEQ ID NO: 85. In some embodiments, the humanized anti-TfR antibody of the present disclosure comprises a heavy chain comprising the amino acid sequence of SEQ ID NO: 99 and a light chain comprising the amino acid sequence of SEQ ID NO: 85.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 100, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 100 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 100, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 100 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 101, and/or (e.g., and) a light chain comprising an amino acid sequence that is at least 80% identical (e.g., 80%, 85%, 90%, 95%, 98%, or 99%) to SEQ ID NO: 89. In some embodiments, the humanized anti-TfR antibody of the present disclosure comprises a heavy chain comprising the amino acid sequence of SEQ ID NO: 101 and a light chain comprising the amino acid sequence of SEQ ID NO: 89.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 101, and/or (e.g., and) a light chain comprising an amino acid sequence that is at least 80% identical (e.g., 80%, 85%, 90%, 95%, 98%, or 99%) to SEQ ID NO: 90. In some embodiments, the humanized anti-TfR antibody of the present disclosure comprises a heavy chain comprising the amino acid sequence of SEQ ID NO: 101 and a light chain comprising the amino acid sequence of SEQ ID NO: 90.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 102, and/or (e.g., and) a light chain comprising an amino acid sequence that is at least 80% identical (e.g., 80%, 85%, 90%, 95%, 98%, or 99%) to SEQ ID NO: 93. In some embodiments, the humanized anti-TfR antibody of the present disclosure comprises a heavy chain comprising the amino acid sequence of SEQ ID NO: 102 and a light chain comprising the amino acid sequence of SEQ ID NO: 93.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 103, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 103 and a light chain comprising the amino acid sequence of SEQ ID NO: 95.

In some embodiments, the humanized anti-TfR antibody of the present disclosure comprises a heavy chain comprising an amino acid sequence that is at least 80% (e.g., 80%, 85%, 90%, 95%, 98%, or 99%) identical to SEQ ID NO: 102, and/or (e.g., and) a light chain comprising an amino acid sequence that is at least 80% identical (e.g., 80%, 85%, 90%, 95%, 98%, or 99%) to SEQ ID NO: 95. In some embodiments, the humanized anti-TfR antibody of the present disclosure comprises a heavy chain comprising the amino acid sequence of SEQ ID NO: 102 and a light chain comprising the amino acid sequence of SEQ ID NO: 95.

In some embodiments, the humanized anti-TfR receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, humanized the anti-TfR antibody described herein is a scFv. In some embodiments, the humanized anti-TfR antibody described herein is a scFv-Fab (e.g., scFv fused to a portion of a constant region). In some embodiments, the anti-TfR receptor antibody described herein is a scFv fused to a constant region (e.g., human IgG1 constant region as set forth in SEQ ID NO: 81 or SEQ ID NO: 82, or a portion thereof such as the Fc portion) at either the N-terminus of C-terminus.

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of an anti-TfR antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to alter one or more functional properties of the antibody, such as serum half-life, complement fixation, Fc receptor binding and/or (e.g., and) antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-anti-TfR antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or (e.g., and) the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-anti-TfR antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of an anti-TfR antibody described herein can be replaced with a different amino acid residue such that the antibody has altered C1q binding and/or (e.g., and) reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or (e.g., and) to increase the affinity of the antibody for an Fcγ receptor. This approach is described further in International Publication No. WO 00/42072.

In some embodiments, the heavy and/or (e.g., and) light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

In some embodiments, any one of the anti-TfR1 antibodies described herein may comprise a signal peptide in the heavy and/or (e.g., and) light chain sequence (e.g., a N-terminal signal peptide). In some embodiments, the anti-TfR1 antibody described herein comprises any one of the VH and VL sequences, any one of the IgG heavy chain and light chain sequences, or any one of the Fab heavy chain and light chain sequences described herein, and further comprises a signal peptide (e.g., a N-terminal signal peptide). In some embodiments, the signal peptide comprises the amino acid sequence of MGWSCIILFLVATATGVHS (SEQ ID NO: 104).

Other Known Anti-Transferrin Receptor Antibodies

Any other appropriate anti-transferrin receptor antibodies known in the art may be used as the muscle-targeting agent in the complexes disclosed herein. Examples of known anti-transferrin receptor antibodies, including associated references and binding epitopes, are listed in Table 8. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 8.

TABLE 8

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |
| (From Genentech) 7A4, 8A2, 15D2, 10D11, 7B10, 15G11, 16G5, 13C3, 16G4, 16F6, 7G7, 4C2, 1B12, and 13D4 | WO 2016/081643, filed May 26, 2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. patent application 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A Streptococcus invasion. Cellular microbiology. 16:1806-21. | |
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | U.S. patent application 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I.S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 (BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K.C. et al. "Transferrin receptors in human tissues: their distribution and possible clinical relevance." J Clin Pathol. 1983 May; 36(5):539-45. | |

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 8. In some embodiments, transferrin receptor antibodies include the CDR-H1, CDR-H2, and CDR-H3 as provided for any one of the anti-transferrin receptor antibodies selected from Table 8. In some embodiments, anti-transferrin receptor antibodies include the CDR-L1, CDR-L2, and CDR-L3 as provided for any one of the anti-transferrin receptor antibodies selected from Table 8. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 8. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 8. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or (e.g., and) light chain CDR3s of any one of the anti-transferrin receptor antibodies selected from Table 8.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/or (e.g., and) CDR-L3 sequences from one of the anti-transferrin receptor antibodies selected from Table 8. In some embodiments, the position of one or more CDRs along the VH (e.g., CDR-H1, CDR-H2, or CDR-H3) and/or (e.g., and) VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or (e.g., and) C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or (e.g., and) VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or (e.g., and) CDR-H3 described herein may be one, two, three, four, five or more amino acids shorter than one or more of the CDRs described herein (e.g., CDRS from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or (e.g., and) CDR-H3 described herein may be one, two, three, four, five or more amino acids longer than one or more of the CDRs described herein (e.g., CDRS from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or (e.g., and) CDR-H3 described herein can be extended by one, two, three, four, five or more amino acids compared to one or more of the CDRs described herein (e.g., CDRS from any of the anti-transferrin receptor antibodies selected from Table 8) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or (e.g., and) CDR-H3 described herein can be extended by one, two, three, four, five or more amino acids compared to one or more of the CDRs described herein (e.g., CDRS from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or (e.g., and) CDR-H3 described herein can be shortened by one, two, three, four, five or more amino acids compared to one or more of the CDRs described herein (e.g., CDRS from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or (e.g., and) CDR-H3 described herein can be shortened by one, two, three, four, five or more amino acids compared to one or more of the CDRs described herein (e.g., CDRS from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 8. For example, the antibodies may include one or more CDR sequence(s) from any of the anti-transferrin receptor antibodies selected from Table 8 containing up to 5, 4, 3, 2, or 1 amino acid residue variations as compared to the corresponding CDR region in any one of the CDRs provided herein (e.g., CDRs from any of the anti-transferrin receptor antibodies selected from Table 8) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or (e.g., and) light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 8. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 8.

In some embodiments, anti-transferrin receptor antibodies of the disclosure include any antibody that includes a heavy chain variable domain and/or (e.g., and) a light chain variable domain of any anti-transferrin receptor antibody, such as any one of the anti-transferrin receptor antibodies selected from Table 8. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 8.

Aspects of the disclosure provide anti-transferrin receptor antibodies having a heavy chain variable (VH) and/or (e.g., and) a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 8. In some embodiments, the homologous heavy chain variable and/or (e.g., and) a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or (e.g., and) a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 8.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 8. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 8. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 8. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 8. In some embodiments, the light chain variable framework region that is derived from said amino acid sequence consists of said amino acid sequence but for the presence of up to 10 amino acid substitutions, deletions, and/or (e.g., and) insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 8. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 8. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 8. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 8.

In some embodiments, the anti-transferrin receptor antibody is any anti-transferrin receptor antibody, such as any one of the anti-transferrin receptor antibodies selected from Table 8.

In some embodiments, an anti-transferrin receptor antibody comprises a VL domain comprising the amino acid sequence of any anti-transferrin receptor antibody, such as any one of the anti-transferrin receptor antibodies selected from Table 8, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, the muscle-targeting agent is a transferrin receptor antibody (e.g., the antibody and variants thereof as described in International Application Publication WO 2016/081643, incorporated herein by reference).

The heavy chain and light chain CDRs of the antibody according to different definition systems are provided in Table 9. The different definition systems, e.g., the Kabat definition, the Chothia definition, and/or (e.g., and) the contact definition have been described. See, e.g., (e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

TABLE 9

Heavy chain and light chain CDRs of a mouse transferrin receptor antibody

| CDRs | Kabat | Chothia | Contact |
|---|---|---|---|
| CDR-H1 | SYWMH (SEQ ID NO: 110) | GYTFTSY (SEQ ID NO: 116) | TSYWMH (SEQ ID NO: 118) |
| CDR-H2 | EINPTNGRTNYIEKFKS (SEQ ID NO: 111) | NPTNGR (SEQ ID NO: 117) | WIGEINPTNGRTN (SEQ ID NO: 119) |
| CDR-H3 | GTRAYHY (SEQ ID NO: 112) | GTRAYHY (SEQ ID NO: 112) | ARGTRA (SEQ ID NO: 120) |
| CDR-L1 | RASDNLYSNLA (SEQ ID NO: 113) | RASDNLYSNLA (SEQ ID NO: 113) | YSNLAWY (SEQ ID NO: 121) |
| CDR-L2 | DATNLAD (SEQ ID NO: 114) | DATNLAD (SEQ ID NO: 114) | LLVYDATNLA (SEQ ID NO: 122) |
| CDR-L3 | QHFWGTPLT (SEQ ID NO: 115) | QHFWGTPLT (SEQ ID NO: 115) | QHFWGTPL (SEQ ID NO: 123) |

The heavy chain variable domain (VH) and light chain variable domain sequences are also provided:

VH
(SEQ ID NO: 124)
QVQLQQPGAELVKPGASVKLSCKASGYTFTSYWMHWVKQRPGQGLEWIG
EINPTNGRTNYIEKFKSKATLTVDKSSSTAYMQLSSLTSEDSAVYYCAR
GTRAYHYWGQGTSVTVSS

VL
(SEQ ID NO: 125)
DIQMTQSPASLSVSVGETVTITCRASDNLYSNLAWYQQKQGKSPQLLVY
DATNLADGVPSRFSGSGSGTQYSLKINSLQSEDFGTYYCQHFWGTPLTF
GAGTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 9. Alternatively or in addition (e.g., in addition), the transferrin receptor antibody of the present disclosure comprises a CDR-L1, a CDR-L2, and a CDR-L3 that are the same as the CDR-L1, CDR-L2, and CDR-L3 shown in Table 9.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 9. "Collectively" means that the total number of amino acid variations in all of the three heavy chain CDRs is within the defined range. Alternatively or in addition (e.g., in addition), the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 9.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 9. Alternatively or in addition (e.g., in addition), the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 9.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 9. In some embodiments, the transferrin receptor antibody of the present disclosure comprises a CDR-L3 containing one amino acid variation as compared with the CDR-L3 as shown in Table 9. In some embodiments, the transferrin receptor antibody of the present disclosure comprises a CDR-L3 of QHFAGTPLT (SEQ ID NO: 126) according to the Kabat and Chothia definition system) or QHFAGTPL (SEQ ID NO: 127) according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 9, and comprises a CDR-L3 of QHFAGTPLT (SEQ ID NO: 126) according to the Kabat and Chothia definition system) or QHFAGTPL (SEQ ID NO: 127) according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 9. Alternatively or in addition (e.g., in addition), the transferrin receptor antibody of the present disclosure comprises light chain CDRs that collectively are at least 80% (e.g., 80%, 85%, 90%, 95%, or 98%) identical to the light chain CDRs as shown in Table 9.

In some embodiments, the transferrin receptor antibody of the present disclosure comprises a VH comprising the amino acid sequence of SEQ ID NO: 124. Alternatively or in addition (e.g., in addition), the transferrin receptor antibody of the present disclosure comprises a VL comprising the amino acid sequence of SEQ ID NO: 125.

In some embodiments, the transferrin receptor antibody of the present disclosure comprises a VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 124. Alternatively or in addition (e.g., in addition), the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 125.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 124. Alternatively or in addition (e.g., in addition), the transferrin receptor antibody of the present disclosure comprises a VL comprising an amino acid sequence that is at least 80% (e.g., 80%, 85%, 90%, 95%, or 98%) identical to the VL as set forth in SEQ ID NO: 125.

In some embodiments, the transferrin receptor antibody of the present disclosure is a humanized antibody (e.g., a humanized variant of an antibody). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 9, and comprises a humanized heavy chain variable region and/or (e.g., and) a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 9) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 125, and/or (e.g., and) one or more amino acid substitutions at positions 1, 5, 7, 11, 12, 20, 38, 40, 44, 66, 75, 81, 83, 87, and 108 as compared with the VH as set forth in SEQ ID NO: 124. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 125, and/or (e.g., and) amino acid substitutions at all of positions 1, 5, 7, 11, 12, 20, 38, 40, 44, 66, 75, 81, 83, 87, and 108 as compared with the VH as set forth in SEQ ID NO: 124.

In some embodiments, the transferrin receptor antibody of the present disclosure is a humanized antibody and contains the residues at positions 43 and 48 of the VL as set forth in SEQ ID NO: 125. Alternatively or in addition (e.g., in addition), the transferrin receptor antibody of the present disclosure is a humanized antibody and contains the residues at positions 48, 67, 69, 71, and 73 of the VH as set forth in SEQ ID NO: 124.

The VH and VL amino acid sequences of an example humanized antibody that may be used in accordance with the present disclosure are provided:

```
Humanized VH
                                        (SEQ ID NO: 128)
EVQLVQSGAEVKKPGASVKVSCKASGYTFTSYWMHWVRQAPGQRLEWIG
EINPTNGRTNYIEKFKSRATLTVDKSASTAYMELSSLRSEDTAVYYCAR
GTRAYHYWGQGTMVTVSS Humanized VL
                                        (SEQ ID NO: 129)
DIQMTQSPSSLSASVGDRVTITCRASDNLYSNLAWYQQKPGKSPKLLVY
DATNLADGVPSRFSGSGSGTDYTLTISSLQPEDFATYYCQHFWGTPLTF
GQGTKVEIK
```

In some embodiments, the transferrin receptor antibody of the present disclosure comprises a VH comprising the amino acid sequence of SEQ ID NO: 128. Alternatively or in addition (e.g., in addition), the transferrin receptor antibody of the present disclosure comprises a VL comprising the amino acid sequence of SEQ ID NO: 129.

In some embodiments, the transferrin receptor antibody of the present disclosure comprises a VH containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 128. Alternatively or in addition (e.g., in addition), the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 129.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 128. Alternatively or in addition (e.g., in addition), the transferrin receptor antibody of the present disclosure comprises a VL comprising an amino acid sequence that is at least 80% (e.g., 80%, 85%, 90%, 95%, or 98%) identical to the VL as set forth in SEQ ID NO: 129.

In some embodiments, the transferrin receptor antibody of the present disclosure is a humanized variant comprising amino acid substitutions at one or more of positions 43 and 48 as compared with the VL as set forth in SEQ ID NO: 125, and/or (e.g., and) amino acid substitutions at one or more of positions 48, 67, 69, 71, and 73 as compared with the VH as set forth in SEQ ID NO: 124. In some embodiments, the transferrin receptor antibody of the present disclosure is a humanized variant comprising a S43A and/or (e.g., and) a V48L mutation as compared with the VL as set forth in SEQ ID NO: 125, and/or (e.g., and) one or more of A67V, L69I, V71R, and K73T mutations as compared with the VH as set forth in SEQ ID NO: 124.

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 125, and/or (e.g., and) amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 124.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or (e.g., and) the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or (e.g., and) the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An example of a human IgG1 constant region is given below:

```
                                        (SEQ ID NO: 130)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                        (SEQ ID NO: 83)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC
```

Other antibody heavy and light chain constant regions are well known in the art, e.g., those provided in the IMGT database (www.imgt.org) or at www.vbase2.org/vbstat.php., both of which are incorporated by reference herein.

Examples of heavy chain and light chain amino acid sequences of the transferrin receptor antibodies described are provided below:

```
Heavy Chain (VH + human IgG1 constant region)
                                                (SEQ ID NO: 132)
QVQLQQPGAELVKPGASVKLSCKASGYTFTSYWMHWVKQRPGQGLEWIGEINPTNGR

TNYIEKFKSKATLTVDKSSSTAYMQLSSLTSEDSAVYYCARGTRAYHYWGQGTSVTVS

SASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPGK

Light Chain (VL + kappa light chain)
                                                (SEQ ID NO: 133)
DIQMTQSPASLSVSVGETVTITCRASDNLYSNLAWYQQKQGKSPQLLVYDATNLADGV

PSRFSGSGSGTQYSLKINSLQSEDFGTYYCQHFWGTPLTFGAGTKLELKRTVAAPSVFIF

PPSDEQLKS GTASVVCLLNNFYPREAKVQWKVDNALQSGNSQESVTEQDSKDSTYSLS

STLTLSKADYEKHKVYACEVTHQGLSSPVTKSFNRGEC

Heavy Chain (humanized VH + human IgG1 constant region)
                                                (SEQ ID NO: 134)
EVQLVQSGAEVKKPGASVKVSCKASGYTFTSYWMHWVRQAPGQRLEWIGEINPTNGR

TNYIEKFKSRATLTVDKSASTAYMELSSLRSEDTAVYYCARGTRAYHYWGQGTMVTV

SSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGK

Light Chain (humanized VL + kappa light chain)
                                                (SEQ ID NO: 135)
DIQMTQSPSSLSASVGDRVTITCRASDNLYSNLAWYQQKPGKSPKLLVYDATNLADGV

PSRFSGSGSGTDYTLTISSLQPEDFATYYCQHFWGTPLTFGQGTKVEIKRTVAAPSVFIFP

PSDEQLKSGTASVVCLLNNFYPREAKVQWKVDNALQSGNSQESVTEQDSKDSTYSLSS

TLTLSKADYEKHKVYACEVTHQGLSSPVTKSFNRGEC
```

In some embodiments, the transferrin receptor antibody described herein comprises a heavy chain comprising an amino acid sequence that is at least 80% (e.g., 80%, 85%, 90%, 95%, or 98%) identical to SEQ ID NO: 132. Alternatively or in addition (e.g., in addition), the transferrin receptor antibody described herein comprises a light chain comprising an amino acid sequence that is at least 80% (e.g., 80%, 85%, 90%, 95%, or 98%) identical to SEQ ID NO: 133. In some embodiments, the transferrin receptor antibody described herein comprises a heavy chain comprising the amino acid sequence of SEQ ID NO: 132. Alternatively or in addition (e.g., in addition), the transferrin receptor antibody described herein comprises a light chain comprising the amino acid sequence of SEQ ID NO: 133.

In some embodiments, the transferrin receptor antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 132. Alternatively or in addition (e.g., in addition), the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 133.

In some embodiments, the transferrin receptor antibody described herein comprises a heavy chain comprising an amino acid sequence that is at least 80% (e.g., 80%, 85%, 90%, 95%, or 98%) identical to SEQ ID NO: 134. Alternatively or in addition (e.g., in addition), the transferrin receptor antibody described herein comprises a light chain comprising an amino acid sequence that is at least 80% (e.g., 80%, 85%, 90%, 95%, or 98%) identical to SEQ ID NO:

135. In some embodiments, the transferrin receptor antibody described herein comprises a heavy chain comprising the amino acid sequence of SEQ ID NO: 134. Alternatively or in addition (e.g., in addition), the transferrin receptor antibody described herein comprises a light chain comprising the amino acid sequence of SEQ ID NO: 135.

In some embodiments, the transferrin receptor antibody of the present disclosure comprises a heavy chain containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) as compared with the heavy chain of humanized antibody as set forth in SEQ ID NO: 134. Alternatively or in addition (e.g., in addition), the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 135.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')2 fragments can be produced by pepsin digestion of an antibody molecule, and Fab' fragments that can be generated by reducing the disulfide bridges of F(ab')2 fragments. Examples of Fab amino acid sequences of the transferrin receptor antibodies described herein are provided below:

```
Heavy Chain Fab (VH + a portion of human IgG1
constant region)
                                    (SEQ ID NO: 136)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain Fab (humanized VH + a portion of human
IgG1 constant region)
                                    (SEQ ID NO: 137)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP
```

In some embodiments, the transferrin receptor antibody described herein comprises a heavy chain comprising the amino acid sequence of SEQ ID NO: 136. Alternatively or in addition (e.g., in addition), the transferrin receptor antibody described herein comprises a light chain comprising the amino acid sequence of SEQ ID NO: 133.

In some embodiments, the transferrin receptor antibody described herein comprises a heavy chain comprising the amino acid sequence of SEQ ID NO: 137. Alternatively or in addition (e.g., in addition), the transferrin receptor antibody described herein comprises a light chain comprising the amino acid sequence of SEQ ID NO: 135.

The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 130).

In some embodiments, any one of the anti-TfR antibodies described herein is produced by recombinant DNA technology in Chinese hamster ovary (CHO) cell suspension culture, optionally in CHO-K1 cell (e.g., CHO-K1 cells derived from European Collection of Animal Cell Culture, Cat. No. 85051005) suspension culture.

In some embodiments, an antibody provided herein may have one or more post-translational modifications. In some embodiments, N-terminal cyclization, also called pyroglutamate formation (pyro-Glu), may occur in the antibody at N-terminal Glutamate (Glu) and/or Glutamine (Gln) residues during production. As such, it should be appreciated that an antibody specified as having a sequence comprising an N-terminal glutamate or glutamine residue encompasses antibodies that have undergone pyroglutamate formation resulting from a post-translational modification. In some embodiments, pyroglutamate formation occurs in a heavy chain sequence. In some embodiments, pyroglutamate formation occurs in a light chain sequence.

b. Other Muscle-Targeting Antibodies

In some embodiments, the muscle-targeting antibody is an antibody that specifically binds hemojuvelin, caveolin-3, Duchenne muscular dystrophy peptide, myosin IIb, or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to alter one or more functional properties of the antibody, such as serum half-life, complement fixation, Fc receptor binding and/or (e.g., and) antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or (e.g., and) CH3 domain (residues 341-447 of human IgG1) and/or (e.g., and) the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or (e.g., and) the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered Clq binding and/or (e.g., and) reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or (e.g., and) to increase the affinity of the antibody for an Fcγ receptor. This approach is described further in International Publication No. WO 00/42072.

In some embodiments, the heavy and/or (e.g., and) light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" *Biochim Biophys Acta* 2008, 1786: 126-38; Jarver P., et al., "In vivo biodistribution and efficacy of peptide mediated delivery" *Trends Pharmacol Sci* 2010; 31: 528-35; Samoylova T. I., et al., "Elucidation of muscle-binding peptides by phage display screening" *Muscle Nerve* 1999; 22: 460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." *Biomol Eng* 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 138) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 138). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." *Int J Pharm* 2002; 231: 177-84; the entire contents of which are hereby incorporated by reference. Here, a 12 amino acid peptide having the sequence SKTFNTHPQSTP (SEQ ID NO: 139) was identified and this muscle-targeting peptide showed improved binding to C2C12 cells relative to the ASSLNIA (SEQ ID NO: 138) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" *J Virol* 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEHKEEELI (SEQ ID NO: 140) appeared most frequently. Accordingly, in some embodiments, the muscle-targeting agent comprises the amino acid sequence TARGEHKEEELI (SEQ ID NO: 140).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or (e.g., and) derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cai, D. "BDNF-mediated enhancement of inflammation and injury in the aging heart." Physiol Genomics. 2006, 24:3, 191-7.; Zhang, L. "Molecular profiling of heart endothelial cells." Circulation, 2005, 112:11, 1601-11.; McGuire, M. J. et al. "In vitro selection of a peptide with high selectivity for cardiomyocytes in vivo." J Mol Biol. 2004, 342:1, 171-82.). Exemplary muscle-targeting peptides comprise an amino acid sequence of the following group: CQAQGQLVC (SEQ ID NO: 141), CSERSMNFC (SEQ ID NO: 142), CPKTRRVPC (SEQ ID NO: 143), WLSEAGPVVTVRALRGTGSW (SEQ ID NO: 144), ASSLNIA (SEQ ID NO: 138), CMQHSMRVC (SEQ ID NO: 145), and DDTRHWG (SEQ ID NO: 146). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include R-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147.).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or (e.g., and) derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20.; Germer, K. et al. "RNA aptamers and their therapeutic and diagnostic applications." Int. J. Biochem. Mol. Biol. 2013; 4: 27-40.). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214.; Thiel, W. H. et al. "Smooth Muscle Cell-targeted RNA Aptamer Inhibits Neointimal Formation." Mol Ther. 2016, 24:4, 779-87.). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or (e.g., and) lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a DUX4. In some embodiments, the molecular payload is a DNA decoy, e.g., of a DUX4 nucleic acid. Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to cause degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Any suitable oligonucleotide may be used as a molecular payload, as described herein. Examples of oligonucleotides useful for targeting DUX4 are provided in U.S. Pat. No. 9,988,628, published on Feb. 2, 2017, entitled "AGENTS USEFUL IN TREATING FACIOSCAPULOHUMERAL MUSCULAR DYSTROPHY"; U.S. Pat. No. 9,469,851, published Oct. 30, 2014, entitled "RECOMBINANT VIRUS PRODUCTS AND METHODS FOR INHIBITING EXPRESSION OF DUX4"; US Patent Application Publication 20120225034, published on Sep. 6, 2012, entitled "AGENTS USEFUL IN TREATING FACIOSCAPULOHUMERAL MUSCULAR DYSTROPHY"; PCT Patent Application Publication Number WO 2013/120038, published on Aug. 15, 2013, entitled "MORPHOLINO TARGETING DUX4 FOR TREATING FSHD"; Chen et al., "Morpholino-mediated Knockdown of DUX4 Toward Facioscapulohumeral Muscular Dystrophy Therapeutics," Molecular Therapy, 2016, 24:8, 1405-1411.; and Ansseau et al., "Antisense Oligonucleotides Used to Target the DUX4 mRNA as Therapeutic Approaches in Facioscapulohumeral Muscular Dystrophy (FSHD)," Genes, 2017, 8, 93; the contents of each of which are incorporated herein in their entireties. In some embodiments, the oligonucleotide is an antisense oligonucleotide, a morpholino, a siRNA, a shRNA, or another oligonucleotide which hybridizes with the target DUX4 gene or mRNA.

In some embodiments, oligonucleotides may have a region of complementarity to a sequence as set forth as: Human DUX4, corresponding to NCBI sequence NM_001293798.1 (SEQ ID NO: 147), NM_001293798.2 (SEQ ID NO: 157), and/or (e.g., and) NM_001306068.3 (SEQ ID NO: 158): as below and/or (e.g., and) Mouse DUX4, corresponding to NCBI sequence NM_001081954.1 (SEQ ID NO: 148), as below. In some embodiments, the oligonucleotide may have a region of complementarity to a hypomethylated, contracted D4Z4 repeat, as in Daxinger, et al., "Genetic and Epigenetic Contributors to FSHD," published in Curr Opin Genet Dev in 2015, Lim J-W, et al., DICER/AGO-dependent epigenetic silencing of D4Z4 repeats enhanced by exogenous siRNA suggests mechanisms and therapies for FSHD Hum Mol Genet. 2015 Sep. 1; 24(17): 4817-4828, the contents of each of which are incorporated in their entireties.

In some embodiments, oligonucleotides may have a region of complementarity to a sequence set forth as follows, which is an example human DUX4 gene sequence (NM_001293798.1) (SEQ ID NO: 147):
ATGGCCCTCCCGACACCCTCGGACAGCACCCTCCCCGCGGAAGCCCGGGG

ACGAGGACGGCGACGGAGACTCGTTTGGACCCCGAGCCAAAGCGAGGCCC

TGCGAGCCTGCTTTGAGCGGAACCCGTACCCGGGCATCGCCACCAGAGAA

-continued
CGGCTGGCCCAGGCCATCGGCATTCCGGAGCCCAGGGTCCAGATTTGGTT
TCAGAATGAGAGGTCACGCCAGCTGAGGCAGCACCGGCGGGAATCTCGGC
CCTGGCCCGGGAGACGCGGCCCGCCAGAAGGCCGGCGAAAGCGGACCGCC
GTCACCGGATCCCAGACCGCCCTGCTCCTCCGAGCCTTTGAGAAGGATCG
CTTTCCAGGCATCGCCGCCCGGGAGGAGCTGGCCAGAGAGACGGGCCTCC
CGGAGTCCAGGATTCAGATCTGGTTTCAGAATCGAAGGGCCAGGCACCCG
GGACAGGGTGGCAGGGCGCCCGCGCAGGCAGGCGGCCTGTGCAGCGCGGC
CCCCGGCGGGGTCACCCTGCTCCCTCGTGGGTCGCCTTCGCCCACACCG
GCGCGTGGGGAACGGGGCTTCCCGCACCCCACGTGCCCTGCGCGCCTGGG
GCTCTCCCACAGGGGGCTTTCGTGAGCCAGGCAGCGAGGGCCGCCCCCGC
GCTGCAGCCCAGCCAGGCCGCGCCGGCAGAGGGGATCTCCCAACCTGCCC
CGGCGCGCGGGGATTTCGCCTACGCCGCCCCGGCTCCTCCGGACGGGGCG
CTCTCCCACCCTCAGGCTCCTCGGTGGCCTCCGCACCCGGGCAAAAGCCG
GGAGGACCGGGACCCGCAGCGCGACGGCCTGCCGGGCCCCTGCGCGGTGG
CACAGCCTGGGCCCGCTCAAGCGGGGCCGCAGGGCCAAGGGGTGCTTGCG
CCACCCACGTCCCAGGGGAGTCCGTGGTGGGGCTGGGGCCGGGGTCCCCA
GGTCGCCGGGGCGGCGTGGGAACCCCAAGCCGGGGCAGCTCCACCTCCCC
AGCCCGCGCCCCGGACGCCTCCGCCTCCGCGCGGCAGGGGCAGATGCAA
GGCATCCCGGCGCCCTCCCAGGCGCTCCAGGAGCCGGCGCCCTGGTCTGC
ACTCCCCTGCGGCCTGCTGCTGGATGAGCTCCTGGCGAGCCCGGAGTTTC
TGCAGCAGGCGCAACCTCTCCTAGAAACGGAGGCCCCGGGGGAGCTGGAG
GCCTCGGAAGAGGCCGCCTCGCTGGAAGCACCCCTCAGCGAGGAAGAATA
CCGGGCTCTGCTGGAGGAGCTTTAG In some embodiments, oligonucleotides may have a region of complementarity to a sequence set forth as follows, which is an example human DUX4 gene sequence (NM_001293798.2) (SEQ ID NO: 157):
ATGGCCCTCCCGACACCCTCGGACAGCACCCTCCCCGCGGAAGCCCGGGG
ACGAGGACGGCGACGGAGACTCGTTTGGACCCCGAGCCAAAGCGAGGCCC
TGCGAGCCTGCTTTGAGCGGAACCCGTACCCGGGCATCGCCACCAGAGAA
CGGCTGGCCCAGGCCATCGGCATTCCGGAGCCCAGGGTCCAGATTTGGTT
TCAGAATGAGAGGTCACGCCAGCTGAGGCAGCACCGGCGGGAATCTCGGC
CCTGGCCCGGGAGACGCGGCCCGCCAGAAGGCCGGCGAAAGCGGACCGCC
GTCACCGGATCCCAGACCGCCCTGCTCCTCCGAGCCTTTGAGAAGGATCG
CTTTCCAGGCATCGCCGCCCGGGAGGAGCTGGCCAGAGAGACGGGCCTCC
CGGAGTCCAGGATTCAGATCTGGTTTCAGAATCGAAGGGCCAGGCACCCG
GGACAGGGTGGCAGGGCGCCCGCGCAGGCAGGCGGCCTGTGCAGCGCGGC
CCCCGGCGGGGTCACCCTGCTCCCTCGTGGGTCGCCTTCGCCCACACCG
GCGCGTGGGGAACGGGGCTTCCCGCACCCCACGTGCCCTGCGCGCCTGGG
GCTCTCCCACAGGGGGCTTTCGTGAGCCAGGCAGCGAGGGCCGCCCCCGC
GCTGCAGCCCAGCCAGGCCGCGCCGGCAGAGGGGATCTCCCAACCTGCCC
CGGCGCGCGGGGATTTCGCCTACGCCGCCCCGGCTCCTCCGGACGGGGCG
CTCTCCCACCCTCAGGCTCCTCGCTGGCCTCCGCACCCGGGCAAAAGCCG
GGAGGACCGGGACCCGCAGCGCGACGGCCTGCCGGGCCCCTGCGCGGTGG
CACAGCCTGGGCCCGCTCAAGCGGGGCCGCAGGGCCAAGGGGTGCTTGCG
CCACCCACGTCCCAGGGGAGTCCGTGGTGGGGCTGGGCCGGGGTCCCCA
GGTCGCCGGGGCGGCGTGGGAACCCCAAGCCGGGGCAGCTCCACCTCCCC
AGCCCGCGCCCCGGACGCCTCCGCCTCCGCGCGGCAGGGGCAGATGCAA
GGCATCCCGGCGCCCTCCCAGGCGCTCCAGGAGCCGGCGCCCTGGTCTGC
ACTCCCCTGCGGCCTGCTGCTGGATGAGCTCCTGGCGAGCCCGGAGTTTC
TGCAGCAGGCGCAACCTCTCCTAGAAACGGAGGCCCCGGGGGAGCTGGAG
GCCTCGGAAGAGGCCGCCTCGCTGGAAGCACCCCTCAGCGAGGAAGAATA
CCGGGCTCTGCTGGAGGAGCTTTAGGACGCGGGGTCTAGGCCCGGTGAGA
GACTCCACACCGCGGAGAACTGCCATTCTTTCCTGGGCATCCCGGGGATC
CCAGAGCCGGCCCAGGTACCAGCAGACCTGCGCGCAGTGCGCACCCCGGC
TGACGTGCAAGGGAGCTCGCTGGCCTCTCTGTGCCCTTGTTCTTCCGTGA
AATTCTGGCTGAATGTCTCCCCCCACCTTCCGACGCTGTCTAGGCAAACC
TGGATTAGAGTTACATCTCCTGGATGATTAGTTCAGAGATATATTAAAAT
GCCCCCTCCCTGTGGATCCTATAG.

In some embodiments, oligonucleotides may have a region of complementarity to a sequence set forth as follows, which is an example human DUX4 gene sequence (NM_001306068.3) (SEQ ID NO: 158):
ATGGCCCTCCCGACACCCTCGGACAGCACCCT-CCCCGCGGAAGCCCG GGGACGAGGACGGCGACG-GAGACTCGTTTGGACCCCGAGCCAAAGCGAG-GCCCTG CGAGCCTGCTTTGAGCGGAACCCGTA-CCCGGGCATCGCCACCAGAGAACGGCTGGC CCAGGCCATCGGCATTCCGGAGCCCAGGGTCCA-GATTTGGTTTCAGAATGAGAGGT CACGCCAGCT-GAGGCAGCACCGGCGGGAATCTCGGCCCTGG-CCCGGGAGACGCGG CCCGCCAGAAGGCCGGCG-AAAGCGGACCGCCGTCACCGGATCCCAGACCG-CCCTGC TCCTCCGAGCCTTTGAGAAGGATCGCT-TTCCAGGCATCGCCGCCCGGGAGGAGCTG GCC-AGAGAGACGGGCCTCCCGGAGTCCAGGATTCA-GATCTGGTTTCAGAATCGAAG GGCCAGGCAC-CCGGGACAGGGTGGCAGGGCGCCCGCGCAGGCA-GGCGGCCTGTGC AGCGCGGCCCCGGCGGGGT-CACCCTGCTCCCTCGTGGGTCGCCTTCGCCCACA-CC GGCGCGTGGGGAACGGGGCTTCCCGCACCC-CACGTGCCCTGCGCGCCTGGGGCTCT CCCACAG-GGGGCTTTCGTGAGCCAGGCAGCGAGGGCCGCCC-CCGCGCTGCAGCCCA GCCAGGCCGCGCCGGCA-GAGGGGATCTCCCAACCTGCCCCGGCGCGCGGG-GATTTC GCCTACGCCGCCCCGGCTCCTCCGGAC-GGGGCGCTCTCCCACCCTCAGGCTCCTCGG TGG-CCTCCGCACCCGGGCAAAAGCCGGGAGGACCG-GGACCCGCAGCGCGACGGCC TGCCGGGCCCCT-GCGCGGTGGCACAGCCTGGGCCCGCTCAAGCGG-GGCCGCAGGGC CAAGGGGTGCTTGCGCCACC-CACGTCCCAGGGGAGTCCGTGGTGGGGCGGCGTGG-GAACCCCAAGCCGGGGCAGCTCCACCTC CCCA-GCCCGCGCCCCGGACGCCTCCGCCTCCGCGCGG-CAGGGGCAGATGCAAGGC ATCCCGGCGCCC- TCCCAGGCGCTCCAGGAGCCGGCGCCCTGGTCTGCACTCCCCTGC GGCCTGCTGCTGGATGAGCTCCTGGCGAGCCCGGAGTTTCTGCAGCAGGCGCAACC TCTCCTAGAAACGGAGGCCCCGGGGGAGCTGGAGGCCTCGGAAGAGGCCGCCTCGCTGGAAGCACCCCTCAGCGAGGAAGAATACCGGGCTCTGCTGGAGGAGCTTTAGGAC GCGGGGTTGGGACGGGGTCGGGTGGTTCGGGGCAGGGCGGTGGCCTCTCTTTCGCG GGGAACACCTGGCTGGCTACGGAGGGGCGTGTCTCCGCCCCGCCCCTCCACCGGG CTGACCGGCCTGGGATTCCTGCCTTCTAGGTCTAGGCCCGGTGAGAGACTCCACTCC GCGGAGAACTGCCTTTCTTTCCTGGGCATCCCGGGGATCCCAGAGCCGGCCCAGGT ACCAGCAGACCTGCGCGCAGTGCGCACCCCGGCTGACGTGCAAGGGAGCTCGCTGG CCTCTCTGTGCCCTTGTTCTTCCGTGAAATTCTGGCTGAATGTCTCCCCCCACCTTCC GACGCTGTCTAGGCAAACCTGGATTAGAGTTACATCTCCTGGATGATTAGTTCAGAG ATATATTAAAATGCCCCTCCCTGTGGATCCTATAG. In some embodiments, oligonucleotides may have a region of complementarity to a sequence set forth as follows, which is an example mouse DUX4 gene sequence (SEQ ID NO: 148) (NM_001081954.1): ATGGCAGAAGCTGGCAGCCCTGTTGGTGGCAGTGGTGTGGCACGGGAATCCCGGCG GCGCAGGAAGACGGTTTGGCAGGCCTGGCAAGAGCAGGCCCTGCTATCAACTTTCA AGAAGAAGAGATACCTGAGCTTCAAGGAGAGGAAGGAGCTGGCCAAGCGAATGGG GGTCTCAGATTGCCGCATCCGCGTGTGGTTTCAGAACCGCAGGAATCGCAGTGGAG AGGAGGGGCATGCCTCAAAGAGGTCCATCAGAGGCTCCAGGCGGCTAGCCTCGCCA CAGCTCCAGGAAGAGCTTGGATCCAGGCCACAGGGTAGAGGCATGCGCTCATCTGG CAGAAGGCCTCGCACTCGACTCACCTCGCTACAGCTCAGGATCCTAGGGCAAGCCT TTGAGAGGAACCCACGACCAGGCTTTGCTACCAGGGAGGAGCTGGCGCGTGACACA GGGTTGCCCGAGGACACGATCCACATATGGTTTCAAAACCGAAGAGCTCGGCGGCG CCACAGGAGGGGCAGGCCCACAGCTCAAGATCAAGACTTGCTGGCGTCACAAGGGT CGGATGGGGCCCCTGCAGGTCCGGAAGGCAGAGAGCGTGAAGGTGCCCAGGAGAA CTTGTTGCCACAGGAAGAAGCAGGAAGTACGGGCATGGATACCTCGAGCCCTAGCG ACTTGCCCTCCTTCTGCGGAGAGTCCCAGCCTTTCCAAGTGGCACAGCCCCGTGGAG CAGGCCAACAAGAGGCCCCCACTCGAGCAGGCAACGCAGGCTCTCTGGAACCCCTC CTTGATCAGCTGCTGGATGAAGTCCAAGTAGAAGAGCCTGCTCCAGCCCCTCTGAA TTTGGATGGAGACCCTGGTGGCAGGGTGCATGAAGGTTCCCAGGAGAGCTTTGGC CACAGGAAGAAGCAGGAAGTACAGGCATGGATACTTCTAGCCCCAGCGACTCAAA CTCCTTCTGCAGAGAGTCCAGCCTTCCCAAGTGGCACAGCCCTGTGGAGCGGGCC AAGAAGATGCCCGCACTCAAGCAGACAGCACAGGCCCTCTGGAACTCCTCCTCCTT GATCAACTGCTGGACGAAGTCCAAAAGGAAGAGCATGTGCCAGTCCCACTGGATTG GGGTAGAAATCCTGGCAGCAGGGAGCATGAAGGTTCCCAGGACAGCTTACTGCCCC TGGAGGAAGCAGTAAATTCGGGCATGGATACCTCGATCCCTAGCATCTGGCCAACC TTCTGCAGAGAATCCCAGCCTCCCCAAGTGGCACAGCCCTCTGGACCAGGCCAAGC ACAGGCCCCCACTCAAGGTGGGAACACGGACCCCCTGGAGCTCTTCCTCTATCAAC TGTTGGATGAAGTCCAAGTAGAAGAGCATGCTCCAGCCCCTCTGAATTGGGATGTA GATCCTGGTGGCAGGGTGCATGAAGGTTCGTGGGAGAGCTTTTGGCCACAGGAAGA AGCAGGAAGTACAGGCCTGGATACTTCAAGCCCCAGCGACTCAAACTCCTTCTTCA GAGAGTCCAAGCCTTCCCAAGTGGCACAGCGCCGTGGAGCGGGCCAAGAAGATGC CCGCACTCAAGCAGACAGCACAGGCCCTCTGGAACTCCTCCTCTTTGATCAACTGCT GGACGAAGTCCAAAAGGAAGAGCATGTGCCAGCCCCACTGGATTGGGGTAGAAAT CCTGGCAGCATGGAGCATGAAGGTTCCCAGGACAGCTTACTGCCCCTGGAGGAAGC AGCAAATTCGGGCAGGGATACCTCGATCCCTAGCATCTGGCCAGCCTTCTGCAGAA AATCCCAGCCTCCCCAAGTGGCACAGCCCTCTGGACCAGGCCAAGCACAGGCCCCC ATTCAAGGTGGGAACACGGACCCCCTGGAGCTCTTCCTTGATCAACTGCTGACCGA AGTCCAACTTGAGGAGCAGGGGCCTGCCCCTGTGAATGTGGAGGAAACATGGGAGC AAATGGACACAACACCTATCTGCCTCTCACTTCAGAAGAATATCAGACTCTTCTAGA TATGCTCTGA.

In some embodiments, an oligonucleotide may have a region of complementarity to DUX4 gene sequences of multiple species, e.g., selected from human, mouse and non-human species.

In some embodiments, an oligonucleotide that targets DUX4 is a FM10 sequence. In some embodiments, an oligonucleotide that targets DUX4 is a phosphorodiamidate morpholino version of a FM10 sequence. In some embodiments, an oligonucleotide that targets DUX4 comprises the sequence GGGCATTTTAATATATCTCTGAACT (SEQ ID NO: 151). In some embodiments, an oligonucleotide that targets DUX4 comprises a sequence that is complementary to at least 15 consecutive nucleotides of AGTTCAGAGATATATTAAAATGCCC (SEQ ID NO: 150).

In some embodiments, muscle specific E3 ubiquitin ligases are overexpressed in FSHD and function in muscle atrophy (see, e.g., Vanderplanck, C. et al. "The FSHD Atrophic Myotube Phenotype Is Caused by DUX4 Expression" PLoS One 6,10:e26820, 2011). In some embodiments, downregulation of these ligases presents a viable therapeutic strategy. In some embodiments, an oligonucleotide may target, e.g., inhibit the expression of, a muscle specific E3 ubiquitin ligase implicated in FSHD, such as MuRFI (also known as TRIM63) and MAFbx (also known as Fbx032). In some embodiments, an oligonucleotide may have a region of complementarity to at least one MuRFI gene sequence, e.g. human MuRFI (NCBI Gene ID 84676). In some embodiments, an oligonucleotide may have a region of complementarity to at least one MAFbx gene sequence, e.g. human MAFbx (NCBI Gene ID 114907).

In some embodiments, any one of the oligonucleotides can be in salt form, e.g., as sodium, potassium, or magnesium salts.

In some embodiments, the 5' or 3' nucleoside (e.g., terminal nucleoside) of any one of the oligonucleotides described herein is conjugated to an amine group, optionally via a spacer. In some embodiments, the spacer comprises an aliphatic moiety. In some embodiments, the spacer comprises a polyethylene glycol moiety. In some embodiments, a phosphodiester linkage is present between the spacer and the 5' or 3' nucleoside of the oligonucleotide. In some embodiments, the 5' or 3' nucleoside (e.g., terminal nucleoside) of any of the oligonucleotides described herein is conjugated to a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof; each R$^A$ is independently hydrogen or substituted or unsubstituted alkyl. In certain embodiments, the spacer is a substituted or unsubstituted alkylene, substituted or unsubstituted heterocyclylene, substituted or unsubstituted heteroarylene, —O—, —N(R$^A$)—, or —C(=O)N(R$^A$)$_2$, or a combination thereof.

In some embodiments, the 5' or 3' nucleoside of any one of the oligonucleotides described herein is conjugated to a compound of the formula —NH$_2$—(CH$_2$)$_n$—, wherein n is an integer from 1 to 12. In some embodiments, n is 6, 7, 8, 9, 10, 11, or 12. In some embodiments, a phosphodiester linkage is present between the compound of the formula NH$_2$—(CH$_2$)$_n$— and the 5' or 3' nucleoside of the oligonucleotide. In some embodiments, a compound of the formula NH$_2$—(CH$_2$)$_6$— is conjugated to the oligonucleotide via a reaction between 6-amino-1-hexanol (NH$_2$—(CH$_2$)$_6$—OH) and the 5' phosphate of the oligonucleotide.

In some embodiments, the oligonucleotide is conjugated to a targeting agent, e.g., a muscle targeting agent such as an anti-TfR antibody, e.g., via the amine group.

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In a some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

In some embodiments, the oligonucleotide is complementary (e.g., at least 85% at least 90%, at least 95%, or 100%) to a target sequence of any one of the oligonucleotides provided herein. In some embodiments, such target sequence is 100% complementary to the oligonucleotide provided herein.

In some embodiments, any one or more of the thymine bases (T's) in any one of the oligonucleotides provided herein may optionally be uracil bases (U's), and/or any one or more of the U's may optionally be T's.

b. Oligonucleotide Modifications:

The oligonucleotides described herein may be modified, e.g., comprise a modified sugar moiety, a modified internucleoside linkage, a modified nucleotide and/or (e.g., and) combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleosides

In some embodiments, the oligonucleotide described herein comprises at least one nucleoside modified at the 2' position of the sugar. In some embodiments, an oligonucleotide comprises at least one 2-modified nucleoside. In some embodiments, all of the nucleosides in the oligonucleotide are 2'-modified nucleosides.

In some embodiments, the oligonucleotide described herein comprises one or more non-bicyclic 2'-modified nucleosides, e.g., 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleoside.

In some embodiments, the oligonucleotide described herein comprises one or more 2'-4' bicyclic nucleosides in which the ribose ring comprises a bridge moiety connecting two atoms in the ring, e.g., connecting the 2'-O atom to the 4'-C atom via a methylene (LNA) bridge, an ethylene (ENA) bridge, or a (S)-constrained ethyl (cEt) bridge. Examples of LNAs are described in International Patent Application Publication WO/2008/043753, published on Apr. 17, 2008, and entitled "RNA Antagonist Compounds For The Modulation Of PCSK9", the contents of which are incorporated herein by reference in its entirety. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties. Examples of cEt are provided in U.S. Pat. Nos. 7,101,993; 7,399,845 and 7,569,686, each of which is herein incorporated by reference in its entirety.

In some embodiments, the oligonucleotide comprises a modified nucleoside disclosed in one of the following United States Patent or Patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-Modified Bicyclic Nucleic Acid Analogs"; U.S. Pat. No. 7,569,686, issued on Aug. 4, 2009, and entitled "Compounds And Methods For Synthesis Of Bicyclic Nucleic Acid Analogs"; U.S. Pat. No. 7,335,765, issued on Feb. 26, 2008, and entitled "Novel Nucleoside And Oligonucleotide Analogues"; U.S. Pat. No. 7,314,923, issued on Jan. 1, 2008, and entitled "Novel Nucleoside And Oligonucleotide Analogues"; U.S. Pat. No. 7,816,333, issued on Oct. 19, 2010, and entitled "Oligonucleotide Analogues And Methods Utilizing The Same" and US Publication Number 2011/0009471 now U.S. Pat. No. 8,957,201, issued on Feb. 17, 2015, and entitled "Oligonucleotide Analogues And Methods Utilizing The Same", the entire contents of each of which are incorporated herein by reference for all purposes.

In some embodiments, the oligonucleotide comprises at least one modified nucleoside that results in an increase in Tm of the oligonucleotide in a range of 1° C., 2° C., 3° C., 4° C., or 5° C. compared with an oligonucleotide that does not have the at least one modified nucleoside. The oligonucleotide may have a plurality of modified nucleosides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleoside.

The oligonucleotide may comprise a mix of nucleosides of different kinds. For example, an oligonucleotide may comprise a mix of 2'-deoxyribonucleosides or ribonucleosides and 2'-fluoro modified nucleosides. An oligonucleotide may comprise a mix of deoxyribonucleosides or ribonucleosides and 2'-O-Me modified nucleosides. An oligonucleotide may comprise a mix of 2'-fluoro modified nucleosides and 2'-O-Me modified nucleosides. An oligonucleotide may comprise a mix of 2'-4' bicyclic nucleosides and 2'-MOE, 2'-fluoro, or 2'-O-Me modified nucleosides. An oligonucleotide may comprise a mix of non-bicyclic 2'-modified nucleosides (e.g., 2'-MOE, 2'-fluoro, or 2'-O-Me) and 2'-4' bicyclic nucleosides (e.g., LNA, ENA, cEt).

The oligonucleotide may comprise alternating nucleosides of different kinds. For example, an oligonucleotide may comprise alternating 2'-deoxyribonucleosides or ribonucleosides and 2'-fluoro modified nucleosides. An oligonucleotide may comprise alternating deoxyribonucleosides or ribonucleosides and 2'-O-Me modified nucleosides. An oligonucleotide may comprise alternating 2'-fluoro modified nucleosides and 2'-O-Me modified nucleosides. An oligonucleotide may comprise alternating 2'-4' bicyclic nucleosides and 2'-MOE, 2'-fluoro, or 2'-O-Me modified nucleosides. An oligonucleotide may comprise alternating non-bicyclic 2'-modified nucleosides (e.g., 2'-MOE, 2'-fluoro, or 2'-O-Me) and 2'-4' bicyclic nucleosides (e.g., LNA, ENA, cEt).

In some embodiments, an oligonucleotide described herein comprises a 5'-vinylphosphonate modification, one or more abasic residues, and/or one or more inverted abasic residues.

d. Internucleoside Linkages/Backbones

In some embodiments, oligonucleotide may contain a phosphorothioate or other modified internucleoside linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleoside linkages at the first, second, and/or (e.g., and) third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563, 253; 5,571,799; 5,587,361; and 5,625,050.

In some embodiments, oligonucleotides may have heteroatom backbones, such as methylene(methylimino) or MMI backbones; amide backbones (see De Mesmaeker et al. Acc. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides are adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides are provided that comprise nucleoside units that are joined together by either substantially all Sp or substantially all Rp phosphorothioate intersugar linkages. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, an oligonucleotide described herein is a gapmer. A gapmer oligonucleotide generally has the formula 5'-X-Y-Z-3', with X and Z as flanking regions around a gap region Y. In some embodiments, flanking region X of formula 5'-X-Y-Z-3' is also referred to as X region, flanking sequence X, 5' wing region X, or 5' wing segment. In some embodiments, flanking region Z of formula 5'-X-Y-Z-3' is also referred to as Z region, flanking sequence Z, 3' wing region Z, or 3' wing segment. In some embodiments, gap region Y of formula 5'-X-Y-Z-3' is also referred to as Y region, Y segment, or gap-segment Y. In some embodiments, each nucleoside in the gap region Y is a 2'-deoxyribonucleoside, and neither the 5' wing region X or the 3' wing region Z contains any 2'-deoxyribonucleosides.

In some embodiments, the Y region is a contiguous stretch of nucleotides, e.g., a region of 6 or more DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleosides, e.g., one to six high-affinity modified nucleosides. Examples of high affinity modified nucleosides include, but are not limited to, 2'-modified nucleosides (e.g., 2'-MOE, 2'0-Me, 2'-F) or 2'-4' bicyclic nucleosides (e.g., LNA, cEt, ENA). In some embodiments, the flanking sequences X and Z may be of 1-20 nucleotides, 1-8 nucleotides, or 1-5 nucleotides in length. The flanking sequences X and Z may be of similar length or of dissimilar lengths. In some embodiments, the gap-segment Y may be a nucleotide sequence of 5-20 nucleotides, 5-15 twelve nucleotides, or 6-10 nucleotides in length.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleoside linkages. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,015,315; 7,101,993; 7,399,845; 7,432,250; 7,569,686; 7,683,036; 7,750,131; 8,580,756; 9,045,754; 9,428,534; 9,695,418; 10,017,764; 10,260,069; 9,428,534; 8,580,756; U.S. patent publication Nos. US20050074801, US20090221685; US20090286969, US20100197762, and US20110112170; PCT publication Nos. WO2004069991; WO2005023825; WO2008049085 and WO2009090182; and EP Patent No. EP2,149,605, each of which is herein incorporated by reference in its entirety.

In some embodiments, a gapmer is 10-40 nucleosides in length. For example, a gapmer may be 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40 nucleosides in length. In some embodiments, a gapmer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleosides in length.

In some embodiments, the gap region Y in a gapmer is 5-20 nucleosides in length. For example, the gap region Y may be 5-20, 5-15, 5-10, 10-20, 10-15, or 15-20 nucleosides in length. In some embodiments, the gap region Y is 5, 6, 7, 8, 9, 10, 11, 12, 13, 14, 15, 16, 17, 18, 19, or 20 nucleosides in length. In some embodiments, each nucleoside in the gap region Y is a 2'-deoxyribonucleoside. In some embodiments, all nucleosides in the gap region Y are 2'-deoxyribonucleosides. In some embodiments, one or more of the nucleosides in the gap region Y is a modified nucleoside (e.g., a 2' modified nucleoside such as those described herein). In some embodiments, one or more cytosines in the gap region Y are optionally 5-methyl-cytosines. In some embodiments, each cytosine in the gap region Y is a 5-methyl-cytosines.

In some embodiments, the 5'wing region of a gapmer (X in the 5'-X-Y-Z-3' formula) and the 3'wing region of a gapmer (Z in the 5'-X-Y-Z-3' formula) are independently 1-20 nucleosides long. For example, the 5'wing region of a gapmer (X in the 5'-X-Y-Z-3' formula) and the 3'wing region of the gapmer (Z in the 5'-X-Y-Z-3' formula) may be independently 1-20, 1-15, 1-10, 1-7, 1-5, 1-3, 1-2, 2-5, 2-7, 3-5, 3-7, 5-20, 5-15, 5-10, 10-20, 10-15, or 15-20 nucleosides long. In some embodiments, the 5'wing region of the gapmer (X in the 5'-X-Y-Z-3' formula) and the 3'wing region of the gapmer (Z in the 5'-X-Y-Z-3' formula) are independently 1, 2, 3, 4, 5, 6, 7, 8, 9, 10, 11, 12, 13, 14, 15, 16, 17, 18, 19, or 20 nucleosides long. In some embodiments, the 5'wing region of the gapmer (X in the 5'-X-Y-Z-3' formula) and the 3'wing region of the gapmer (Z in the 5'-X-Y-Z-3' formula) are of the same length. In some embodiments, the 5'wing region of the gapmer (X in the 5'-X-Y-Z-3' formula) and the 3'wing region of the gapmer (Z in the 5'-X-Y-Z-3' formula) are of different lengths. In some embodiments, the 5'wing region of the gapmer (X in the 5'-X-Y-Z-3' formula) is longer than the 3'wing region of the gapmer (Z in the 5'-X-Y-Z-3' formula). In some embodiments, the 5'wing region of the gapmer (X in the 5'-X-Y-Z-3' formula) is shorter than the 3'wing region of the gapmer (Z in the 5'-X-Y-Z-3' formula).

In some embodiments, a gapmer comprises a 5'-X-Y-Z-3' of 5-10-5, 4-12-4, 3-14-3, 2-16-2, 1-18-1, 3-10-3, 2-10-2, 1-10-1, 2-8-2, 4-6-4, 3-6-3, 2-6-2, 4-7-4, 3-7-3, 2-7-2, 4-8-4, 3-8-3, 2-8-2, 1-8-1, 2-9-2, 1-9-1, 2-10-2, 1-10-1, 1-12-1, 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6- 11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. The numbers indicate the number of nucleosides in X, Y, and Z regions in the 5'-X-Y-Z-3' gapmer.

In some embodiments, one or more nucleosides in the 5'wing region of a gapmer (X in the 5'-X-Y-Z-3' formula) or the 3'wing region of a gapmer (Z in the 5'-X-Y-Z-3' formula) are modified nucleotides (e.g., high-affinity modified nucleosides). In some embodiments, the modified nuclsoside (e.g., high-affinity modified nucleosides) is a 2'-modified nucleoside. In some embodiments, the 2'-modified nucleoside is a 2'-4' bicyclic nucleoside or a non-bicyclic 2'-modified nucleoside. In some embodiments, the high-affinity modified nucleoside is a 2'-4' bicyclic nucleoside (e.g., LNA, cEt, or ENA) or a non-bicyclic 2'-modified nucleoside (e.g., 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-0-dimethylaminoethyloxyethyl (2'-O-DMAEOE), or 2'-O—N-methylacetamido (2'-O-NMA)).

In some embodiments, one or more nucleosides in the 5'wing region of a gapmer (X in the 5'-X-Y-Z-3' formula) are high-affinity modified nucleosides. In some embodiments, each nucleoside in the 5'wing region of the gapmer (X in the 5'-X-Y-Z-3' formula) is a high-affinity modified nucleoside. In some embodiments, one or more nucleosides in the 3'wing region of a gapmer (Z in the 5'-X-Y-Z-3' formula) are high-affinity modified nucleosides. In some embodiments, each nucleoside in the 3'wing region of the gapmer (Z in the 5'-X-Y-Z-3' formula) is a high-affinity modified nucleoside. In some embodiments, one or more nucleosides in the 5'wing region of the gapmer (X in the 5'-X-Y-Z-3' formula) are high-affinity modified nucleosides and one or more nucleosides in the 3'wing region of the gapmer (Z in the 5'-X-Y-Z-3' formula) are high-affinity modified nucleosides. In some embodiments, each nucleoside in the 5'wing region of the gapmer (X in the 5'-X-Y-Z-3' formula) is a high-affinity modified nucleoside and each nucleoside in the 3'wing region of the gapmer (Z in the 5'-X-Y-Z-3' formula) is high-affinity modified nucleoside.

In some embodiments, the 5'wing region of a gapmer (X in the 5'-X-Y-Z-3' formula) comprises the same high affinity nucleosides as the 3'wing region of the gapmer (Z in the 5'-X-Y-Z-3' formula). For example, the 5'wing region of the gapmer (X in the 5'-X-Y-Z-3' formula) and the 3'wing region of the gapmer (Z in the 5'-X-Y-Z-3' formula) may comprise one or more non-bicyclic 2'-modified nucleosides (e.g., 2'-MOE or 2'-O-Me). In another example, the 5'wing region of the gapmer (X in the 5'-X-Y-Z-3' formula) and the 3'wing region of the gapmer (Z in the 5'-X-Y-Z-3' formula) may comprise one or more 2'-4' bicyclic nucleosides (e.g., LNA or cEt). In some embodiments, each nucleoside in the 5'wing region of the gapmer (X in the 5'-X-Y-Z-3' formula) and the 3'wing region of the gapmer (Z in the 5'-X-Y-Z-3' formula) is a non-bicyclic 2'-modified nucleosides (e.g., 2'-MOE or 2'-O-Me). In some embodiments, each nucleoside in the 5'wing region of the gapmer (X in the 5'-X-Y-Z-3' formula) and the 3'wing region of the gapmer (Z in the 5'-X-Y-Z-3' formula) is a 2'-4' bicyclic nucleosides (e.g., LNA or cEt).

In some embodiments, a gapmer comprises a 5'-X-Y-Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X and Z is a non-bicyclic 2'-modified nucleosides (e.g., 2'-MOE or 2'-O-Me) and each nucleoside in Y is a 2'-deoxyribonucleoside. In some embodiments, the gapmer comprises a 5'-X-Y-Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X and Z is a 2'-4' bicyclic nucleosides (e.g., LNA or cEt) and each nucleoside in Y is a 2'-deoxyribonucleoside. In some embodiments, the 5'wing region of the gapmer (X in the 5'-X-Y-Z-3' formula) comprises different high affinity nucleosides as the 3'wing region of the gapmer (Z in the 5'-X-Y-Z-3' formula). For example, the 5'wing region of the gapmer (X in the 5'-X-Y-Z-3' formula) may comprise one or more non-bicyclic 2'-modified nucleosides (e.g., 2'-MOE or 2'-O-Me) and the 3'wing region of the gapmer (Z in the 5'-X-Y-Z-3' formula) may comprise one or more 2'-4' bicyclic nucleosides (e.g., LNA or cEt). In another example, the 3'wing region of the gapmer (Z in the 5'-X-Y-Z-3' formula) may comprise one or more non-bicyclic 2'-modified nucleosides (e.g., 2'-MOE or 2'-O-Me) and the 5'wing region of the gapmer (X in the 5'-X-Y-Z-3' formula) may comprise one or more 2'-4' bicyclic nucleosides (e.g., LNA or cEt).

In some embodiments, a gapmer comprises a 5'-X-Y-Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X is a non-bicyclic 2'-modified nucleosides (e.g., 2'-MOE or 2'-O-Me), each nucleoside in Z is a 2'-4' bicyclic nucleosides (e.g., LNA or cEt), and each nucleoside in Y is a 2'-deoxyribonucleoside. In some embodiments, the gapmer comprises a 5'-X-Y-Z-3' configuration, wherein X and Z is independently 1-7 (e.g., 1, 2, 3, 4, 5, 6, or 7) nucleosides in length and Y is 6-10 (e.g., 6, 7, 8, 9, or 10) nucleosides in length, wherein each nucleoside in X is a 2'-4' bicyclic nucleosides (e.g., LNA or cEt), each nucleoside in Z is a non-bicyclic 2'-modified nucleosides (e.g., 2'-MOE or 2'-O-Me) and each nucleoside in Y is a 2'-deoxyribonucleoside.

In some embodiments, the 5'wing region of a gapmer (X in the 5'-X-Y-Z-3' formula) comprises one or more non-bicyclic 2'-modified nucleosides (e.g., 2'-MOE or 2'-O-Me) and one or more 2'-4' bicyclic nucleosides (e.g., LNA or cEt). In some embodiments, the 3'wing region of the gapmer (Z in the 5'-X-Y-Z-3' formula) comprises one or more non-bicyclic 2'-modified nucleosides (e.g., 2'-MOE or 2'-O-Me) and one or more 2'-4' bicyclic nucleosides (e.g., LNA or cEt). In some embodiments, both the 5'wing region of the gapmer (X in the 5'-X-Y-Z-3' formula) and the 3'wing region of the gapmer (Z in the 5'-X-Y-Z-3' formula) comprise one or more non-bicyclic 2'-modified nucleosides (e.g., 2'-MOE or 2'-O-Me) and one or more 2'-4' bicyclic nucleosides (e.g., LNA or cEt).

In some embodiments, a gapmer comprises a 5'-X-Y-Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside. In some embodiments, the gapmer comprises a 5'-X-Y-Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in Z (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside. In some embodiments, the gapmer comprises a 5'-X-Y-Z-3' configuration, wherein X and Z is independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X and at least one of positions but not all (e.g., 1, 2, 3, 4, 5, or 6) 1, 2, 3, 4, 5, 6, or 7 in Z (the 5' most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2'deoxyribonucleoside.

Non-limiting examples of gapmers configurations with a mix of non-bicyclic 2'-modified nucleoside (e.g., 2'-MOE or 2'-O-Me) and 2'-4' bicyclic nucleosides (e.g., LNA or cEt) in the 5'wing region of the gapmer (X in the 5'-X-Y-Z-3' formula) and/or the 3'wing region of the gapmer (Z in the 5'-X-Y-Z-3' formula) include: BBB-(D)n-BBBAA; KKK-(D)n-KKKAA; LLL-(D)n-LLLAA; BBB-(D)n-BBBEE; KKK-(D)n-KKKEE; LLL-(D)n-LLLEE; BBB-(D)n-BBAA; KKK-(D)n-KKKAA; LLL-(D)n-LLLAA; BBB-(D)n-BBBEE; KKK-(D)n-KKKEE; LLL-(D)n-LLLEE; BBB-(D)n-BBBAAA; KKK-(D)n-KKKAAA; LLL-(D)n-LLLAAA; BBB-(D)n-BBBEEE; KKK-(D)n-KKKEEE; LLL-(D)n-LLLEEE; BBB-(D)n-BBBAAA; KKK-(D)n-KKKAAA; LLL-(D)n-LLLAAA; BBB-(D)n-BBBEEE; KKK-(D)n-KKKEEE; LLL-(D)n-LLLEEE; BABA-(D)n-ABAB; KAKA-(D)n-AKAK; LALA-(D)n-ALAL; BEBE-(D)n-EBEB; KEKE-(D)n-EKEK; LELE-(D)n-ELEL; BABA-(D)n-ABAB; KAKA-(D)n-AKAK; LALA-(D)n-ALAL; BEBE-(D)n-EBEB; KEKE-(D)n-EKEK; LELE-(D)n-ELEL; ABAB-(D)n-ABAB; AKAK-(D)n-AKAK; ALAL-(D)n-ALAL; EBEB-(D)n-EBEB; EKEK-(D)n-EKEK; ELEL-(D)n-ELEL; ABAB-(D)n-ABAB; AKAK-(D)n-AKAK; ALAL-(D)n-ALAL; EBEB-(D)n-EBEB; EKEK-(D)n-EKEK; ELEL-(D)n-ELEL; AABB-(D)n-BBAA; BBAA-(D)n-AABB; AAKK-(D)n-KKAA; AALL-(D)n-

LLAA; EEBB-(D)n-BBEE; EEKK-(D)n-KKEE; EELL-(D)n-LLEE; AABB-(D)n-BBAA; AAKK-(D)n-KKAA; AALL-(D)n-LLAA; EEBB-(D)n-BBEE; EEKK-(D)n-KKEE; EELL-(D)n-LLEE; BBB-(D)n-BBA; KKK-(D)n-KKA; LLL-(D)n-LLA; BBB-(D)n-BBE; KKK-(D)n-KKE; LLL-(D)n-LLE; BBB-(D)n-BBA; KKK-(D)n-KKA; LLL-(D)n-LLA; BBB-(D)n-BBE; KKK-(D)n-KKE; LLL-(D)n-LLE; BBB-(D)n-BBA; KKK-(D)n-KKA; LLL-(D)n-LLA; BBB-(D)n-BBE; KKK-(D)n-KKE; LLL-(D)n-LLE; ABBB-(D)n-BBBA; AKKK-(D)n-KKKA; ALLL-(D)n-LLLA; EBBB-(D)n-BBBE; EKKK-(D)n-KKKE; ELLL-(D)n-LLLE; ABBB-(D)n-BBBA; AKKK-(D)n-KKKA; ALLL-(D)n-LLLA; EBBB-(D)n-BBBE; EKKK-(D)n-KKKE; ELLL-(D)n-LLLE; ABBB-(D)n-BBBAA; AKKK-(D)n-KKKAA; ALLL-(D)n-LLLAA; EBBB-(D)n-BBBEE; EKKK-(D)n-KKKEE; ELLL-(D)n-LLLEE; ABBB-(D)n-BBBAA; AKKK-(D)n-KKKAA; ALLL-(D)n-LLLAA; EBBB-(D)n-BBBEE; EKKK-(D)n-KKKEE; ELLL-(D)n-LLLEE; AABBB-(D)n-BBB; AAKKK-(D)n-KKK; AALLL-(D)n-LLL; EEBBB-(D)n-BBB; EEKKK-(D)n-KKK; EELLL-(D)n-LLL; AABBB-(D)n-BBB; AAKKK-(D)n-KKK; AALLL-(D)n-LLL; EEBBB-(D)n-BBB; EEKKK-(D)n-KKK; EELLL-(D)n-LLL; AABBB-(D)n-BBBA; AAKKK-(D)n-KKKA; AALLL-(D)n-LLLA; EEBBB-(D)n-BBBE; EEKKK-(D)n-KKKE; EELLL-(D)n-LLLE; AABBB-(D)n-BBBA; AAKKK-(D)n-KKKA; AALLL-(D)n-LLLA; EEBBB-(D)n-BBBE; EEKKK-(D)n-KKKE; EELLL-(D)n-LLLE; ABBAABB-(D)n-BB; AKKAAKK-(D)n-KK; ALLAALLL-(D)n-LL; EBBEEBB-(D)n-BB; EKKEEKK-(D)n-KK; ELLEELL-(D)n-LL; ABBAABB-(D)n-BB; AKKAAKK-(D)n-KK; ALLAALL-(D)n-LL; EBBEEBB-(D)n-BB; EKKEEKK-(D)n-KK; ELLEELL-(D)n-LL; ABBABB-(D)n-BBB; AKKAKK-(D)n-KKK; ALLALLL-(D)n-LLL; EBBEBB-(D)n-BBB; EKKEKK-(D)n-KKK; ELLELL-(D)n-LLL; ABBABB-(D)n-BBB; AKKAKK-(D)n-KKK; ALLALL-(D)n-LLL; EBBEBB-(D)n-BBB; EKKEKK-(D)n-KKK; ELLELL-(D)n-LLL; EEEK-(D)n-EEEEEEEE; EEK-(D)n-EEEEEEEE; EK-(D)n-EEEEEEEE; EK-(D)n-EEEKK; K-(D)n-EEEKEKE; K-(D)n-EEEKEKEE; K-(D)n-EEKEK; EK-(D)n-EEEEKEKE; EK-(D)n-EEEKEK; EEK-(D)n-KEEKE; EK-(D)n-EEKEK; EK-(D)n-KEEK; EEK-(D)n-EEEKEK; EK-(D)n-KEEE-KEE; EK-(D)n-EEKEKE; EK-(D)n-EEEKEKE; and EK-(D)n-EEEEKEK; "A" nucleosides comprise a 2'-modified nucleoside; "B" represents a 2'-4' bicyclic nucleoside; "K" represents a constrained ethyl nucleoside (cEt); "L" represents an LNA nucleoside; and "E" represents a 2'-MOE modified ribonucleoside; "D" represents a 2'-deoxyribonucleoside; "n" represents the length of the gap segment (Y in the 5'-X-Y-Z-3' configuration) and is an integer between 1-20.

In some embodiments, any one of the gapmers described herein comprises one or more modified nucleoside linkages (e.g., a phosphorothioate linkage) in each of the X, Y, and Z regions. In some embodiments, each internucleoside linkage in the any one of the gapmers described herein is a phosphorothioate linkage. In some embodiments, each of the X, Y, and Z regions independently comprises a mix of phosphorothioate linkages and phosphodiester linkages. In some embodiments, each internucleoside linkage in the gap region Y is a phosphorothioate linkage, the 5'wing region X comprises a mix of phosphorothioate linkages and phosphodiester linkages, and the 3'wing region Z comprises a mix of phosphorothioate linkages and phosphodiester linkages.

i. Mixmers

In some embodiments, an oligonucleotide described herein may be a mixmer or comprise a mixmer sequence pattern. In general, mixmers are oligonucleotides that comprise both naturally and non-naturally occurring nucleosides or comprise two different types of non-naturally occurring nucleosides typically in an alternating pattern. Mixmers generally have higher binding affinity than unmodified oligonucleotides and may be used to specifically bind a target molecule, e.g., to block a binding site on the target molecule. Generally, mixmers do not recruit an RNase to the target molecule and thus do not promote cleavage of the target molecule. Such oligonucleotides that are incapable of recruiting RNase H have been described, for example, see WO2007/112754 or WO2007/112753.

In some embodiments, the mixmer comprises or consists of a repeating pattern of nucleoside analogues and naturally occurring nucleosides, or one type of nucleoside analogue and a second type of nucleoside analogue. However, a mixmer need not comprise a repeating pattern and may instead comprise any arrangement of modified nucleosides and naturally occurring nucleoside s or any arrangement of one type of modified nucleoside and a second type of modified nucleoside. The repeating pattern, may, for instance be every second or every third nucleoside is a modified nucleoside, such as LNA, and the remaining nucleosides are naturally occurring nucleosides, such as DNA, or are a 2' substituted nucleoside analogue such as 2'-MOE or 2' fluoro analogues, or any other modified nucleoside described herein. It is recognized that the repeating pattern of modified nucleoside, such as LNA units, may be combined with modified nucleoside at fixed positions—e.g. at the 5' or 3' termini.

In some embodiments, a mixmer does not comprise a region of more than 5, more than 4, more than 3, or more than 2 consecutive naturally occurring nucleosides, such as DNA nucleosides. In some embodiments, the mixmer comprises at least a region consisting of at least two consecutive modified nucleosides, such as at least two consecutive LNAs. In some embodiments, the mixmer comprises at least a region consisting of at least three consecutive modified nucleoside units, such as at least three consecutive LNAs.

In some embodiments, the mixmer does not comprise a region of more than 7, more than 6, more than 5, more than 4, more than 3, or more than 2 consecutive nucleoside analogues, such as LNAs. In some embodiments, LNA units may be replaced with other nucleoside analogues, such as those referred to herein.

Mixmers may be designed to comprise a mixture of affinity enhancing modified nucleosides, such as in non-limiting example LNA nucleosides and 2'-O-Me nucleosides. In some embodiments, a mixmer comprises modified internucleoside linkages (e.g., phosphorothioate internucleoside linkages or other linkages) between at least two, at least three, at least four, at least five or more nucleosides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleosides. For example, in some embodiments, a mixmer may comprise morpholino nucleosides mixed (e.g., in an alternating manner) with one or more other nucleosides (e.g., DNA, RNA nucleosides) or modified nucleosides (e.g., LNA, 2'-O-Me nucleosides).

In some embodiments, mixmers are useful for splice correcting or exon skipping, for example, as reported in Touznik A., et al., *LNA/DNA mixmer-based antisense oli-* gonucleotides correct alternative splicing of the SMN2 gene and restore SMN protein expression in type 1 SMA fibroblasts *Scientific Reports*, volume 7, Article number: 3672 (2017), Chen S. et al., *Synthesis of a Morpholino Nucleic Acid (MNA)-Uridine Phosphoramidite, and Exon Skipping Using MNA/2'-O-Methyl Mixmer Antisense Oligonucleotide*, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective. In some embodiments, the siRNA molecules are 7, 8, 9, 10, 11, 12, 13, 14, 15, 16, 17, 18, 19, 20, 21, 22, 23, 24, 25, 26, 27, 28, 29, 30, 35, 40, 45, 50, or more base pairs in length. In some embodiments, the siRNA molecules are 8 to 30 base pairs in length, 10 to 15 base pairs in length, 10 to 20 base pairs in length, 15 to 25 base pairs in length, 19 to 21 base pairs in length, 21 to 23 base pairs in length.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791). The siRNA molecule can be double stranded (i.e. a dsRNA molecule comprising an antisense strand and a complementary sense strand that hybridizes to form the dsRNA) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

In some embodiments, the antisense strand of the siRNA molecule is 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides in length. In some embodiments, the antisense strand is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 19 to 21 nucleotides in length, 21 to 23 nucleotides in lengths.

In some embodiments, the sense strand of the siRNA molecule is 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides in length. In some embodiments, the sense strand is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 19 to 21 nucleotides in length, 21 to 23 nucleotides in lengths.

In some embodiments, siRNA molecules comprise an antisense strand comprising a region of complementarity to a target region in a target mRNA. In some embodiments, the region of complementarity is at least 80%, at least 85%, at least 90%, at least 91%, at least 92%, at least 93%, at least 94%, at least 95%, at least 96%, at least 97%, at least 98%, at least 99% or 100% complementary to a target region in a target mRNA. In some embodiments, the target region is a region of consecutive nucleotides in the target mRNA. In some embodiments, a complementary nucleotide sequence need not be 100% complementary to that of its target to be specifically hybridizable or specific for a target RNA sequence.

In some embodiments, siRNA molecules comprise an antisense strand that comprises a region of complementarity to a target RNA sequence and the region of complementarity is in the range of 8 to 15, 8 to 30, 8 to 40, or 10 to 50, or 5 to 50, or 5 to 40 nucleotides in length. In some embodiments, a region of complementarity is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more consecutive nucleotides of a target RNA sequence. In some embodiments, siRNA molecules comprise a nucleotide sequence that contains no more than 1, 2, 3, 4, or 5 base mismatches compared to the portion of the consecutive nucleotides of target RNA sequence. In some embodiments, siRNA molecules comprise a nucleotide sequence that has up to 3 mismatches over 15 bases, or up to 2 mismatches over 10 bases.

In some embodiments, siRNA molecules comprise an antisense strand comprising a nucleotide sequence that is complementary (e.g., at least 85%, at least 90%, at least 95%, or 100%) to the target RNA sequence of the oligonucleotides provided herein. In some embodiments, siRNA molecules comprise an antisense strand comprising a nucleotide sequence that is at least 85%, at least 90%, at least 95%, or 100% identical to the oligonucleotides provided herein. In some embodiments, siRNA molecules comprise an antisense strand comprising at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more consecutive nucleotides of the oligonucleotides provided herein.

Double-stranded siRNA may comprise sense and antisense RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or (e.g., and) the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or (e.g., and) the 5' end of either or both strands). A spacer sequence may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule. The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule. In some embodiments, the siRNA molecule comprises 3' overhangs of about 1 to about 3 nucleotides on the sense strand. In some embodiments, the siRNA molecule comprises 3' overhangs of about 1 to about 3 nucleotides on the antisense strand. In some embodiments, the siRNA molecule comprises 3' overhangs of about 1 to about 3 nucleotides on both the sense strand and the antisense strand.

In some embodiments, the siRNA molecule comprises one or more modified nucleotides (e.g. 1, 2, 3, 4, 5, 6, 7, 8, 9, 10 or more). In some embodiments, the siRNA molecule comprises one or more modified nucleotides and/or (e.g., and) one or more modified internucleotide linkages. In some embodiments, the modified nucleotide comprises a modified sugar moiety (e.g. a 2' modified nucleotide). In some embodiments, the siRNA molecule comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). In some embodiments, each nucleotide of the siRNA molecule is a modified nucleotide (e.g., a 2'-modified nucleotide). In some embodiments, the siRNA molecule comprises one or more phosphorodiamidate morpholinos. In some embodiments, each nucleotide of the siRNA molecule is a phosphorodiamidate morpholino.

In some embodiments, the siRNA molecule contains a phosphorothioate or other modified internucleotide linkage. In some embodiments, the siRNA molecule comprises phosphorothioate internucleoside linkages. In some embodiments, the siRNA molecule comprises phosphorothioate internucleoside linkages between at least two nucleotides. In some embodiments, the siRNA molecule comprises phosphorothioate internucleoside linkages between all nucleotides. For example, in some embodiments, the siRNA molecule comprises modified internucleotide linkages at the first, second, and/or (e.g., and) third internucleoside linkage at the 5' or 3' end of the siRNA molecule.

In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of siRNA molecules described herein can be combined with each other. For example, one, two, three, four, five, or more different types of modifications can be included within the same siRNA molecule.

In some embodiments, the antisense strand comprises one or more modified nucleotides (e.g. 1, 2, 3, 4, 5, 6, 7, 8, 9, 10 or more). In some embodiments, the antisense strand comprises one or more modified nucleotides and/or (e.g., and) one or more modified internucleotide linkages. In some embodiments, the modified nucleotide comprises a modified sugar moiety (e.g. a 2' modified nucleotide). In some embodiments, the antisense strand comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). In some embodiments, each nucleotide of the antisense strand is a modified nucleotide (e.g., a 2'-modified nucleotide). In some embodiments, the antisense strand comprises one or more phosphorodiamidate morpholinos. In some embodiments, the antisense strand is a phosphorodiamidate morpholino oligomer (PMO).

In some embodiments, antisense strand contains a phosphorothioate or other modified internucleotide linkage. In some embodiments, the antisense strand comprises phosphorothioate internucleoside linkages. In some embodiments, the antisense strand comprises phosphorothioate internucleoside linkages between at least two nucleotides. In some embodiments, the antisense strand comprises phosphorothioate internucleoside linkages between all nucleotides. For example, in some embodiments, the antisense strand comprises modified internucleotide linkages at the first, second, and/or (e.g., and) third internucleoside linkage at the 5' or 3' end of the siRNA molecule. In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of the antisense strand described herein can be combined with each other. For example, one, two, three, four, five, or more different types of modifications can be included within the same antisense strand.

In some embodiments, the sense strand comprises one or more modified nucleotides (e.g. 1, 2, 3, 4, 5, 6, 7, 8, 9, 10 or more). In some embodiments, the sense strand comprises one or more modified nucleotides and/or (e.g., and) one or more modified internucleotide linkages. In some embodiments, the modified nucleotide comprises a modified sugar moiety (e.g. a 2' modified nucleotide). In some embodiments, the sense strand comprises one or more 2' modified nucleotides, e.g., a 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). In some embodiments, each nucleotide of the sense strand is a modified nucleotide (e.g., a 2'-modified nucleotide). In some embodiments, the sense strand comprises one or more phosphorodiamidate morpholinos. In some embodiments, the antisense strand is a phosphorodiamidate morpholino oligomer (PMO). In some embodiments, the sense strand contains a phosphorothioate or other modified internucleotide linkage. In some embodiments, the sense strand comprises phosphorothioate internucleoside linkages. In some embodiments, the sense strand comprises phosphorothioate internucleoside linkages between at least two nucleotides. In some embodiments, the sense strand comprises phosphorothioate internucleoside linkages between all nucleotides. For example, in some embodiments, the sense strand comprises modified internucleotide linkages at the first, second, and/or (e.g., and) third internucleoside linkage at the 5' or 3' end of the sense strand.

In some embodiments, the modified internucleotide linkages are phosphorus-containing linkages. In some embodiments, phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Any of the modified chemistries or formats of the sense strand described herein can be combined with each other. For example, one, two, three, four, five, or more different types of modifications can be included within the same sense strand.

In some embodiments, the antisense or sense strand of the siRNA molecule comprises modifications that enhance or reduce RNA-induced silencing complex (RISC) loading. In some embodiments, the antisense strand of the siRNA molecule comprises modifications that enhance RISC loading. In some embodiments, the sense strand of the siRNA molecule comprises modifications that reduce RISC loading and reduce off-target effects. In some embodiments, the antisense strand of the siRNA molecule comprises a 2'-O-methoxyethyl (2'-MOE) modification. The addition of the 2'-O-methoxyethyl (2'-MOE) group at the cleavage site improves both the specificity and silencing activity of siRNAs by facilitating the oriented RNA-induced silencing complex (RISC) loading of the modified strand, as described in Song et al., (2017) Mol Ther Nucleic Acids 9:242-250, incorporated herein by reference in its entirety. In some embodiments, the antisense strand of the siRNA molecule comprises a 2'-OMe-phosphorodithioate modification, which increases RISC loading as described in Wu et al., (2014) Nat Commun 5:3459, incorporated herein by reference in its entirety.

In some embodiments, the sense strand of the siRNA molecule comprises a 5'-morpholino, which reduces RISC loading of the sense strand and improves antisense strand selection and RNAi activity, as described in Kumar et al., (2019) Chem Commun (Camb) 55(35):5139-5142, incorporated herein by reference in its entirety. In some embodiments, the sense strand of the siRNA molecule is modified with a synthetic RNA-like high affinity nucleotide analogue, Locked Nucleic Acid (LNA), which reduces RISC loading of the sense strand and further enhances antisense strand incorporation into RISC, as described in Elman et al., (2005) Nucleic Acids Res. 33(1): 439-447, incorporated herein by reference in its entirety. In some embodiments, the sense strand of the siRNA molecule comprises a 5' unlocked nucleic acid (UNA) modification, which reduce RISC loading of the sense strand and improve silencing potency of the antisense strand, as described in Snead et al., (2013) Mol Ther Nucleic Acids 2(7):e103, incorporated herein by reference in its entirety. In some embodiments, the sense strand of the siRNA molecule comprises a 5-nitroindole modification, which decreased the RNAi potency of the sense strand and reduces off-target effects as described in Zhang et al., (2012) Chembiochem 13(13):1940-1945, incorporated herein by reference in its entirety. In some embodiments, the sense strand comprises a 2'-O'methyl (2'-O-Me) modification, which reduces RISC loading and the off-target effects of the sense strand, as described in Zheng et al., FASEB (2013) 27(10): 4017-4026, incorporated herein by reference in its entirety. In some embodiments, the sense strand of the siRNA molecule is fully substituted with morpholino, 2'-MOE or 2'-O-Me residues, and are not recognized by RISC as described in Kole et al., (2012) Nature reviews. Drug Discovery 11(2):125-140, incorporated herein by reference in its entirety. In some embodiments the antisense strand of the siRNA molecule comprises a 2'-MOE modification and the sense strand comprises a 2'-O-Me modification (see e.g., Song et al., (2017) Mol Ther Nucleic Acids 9:242-250). In some embodiments at least one (e.g., at least 2, at least 3, at least 4, at least 5, at least 10) siRNA molecule is linked (e.g., covalently) to a muscle-targeting agent. In some embodiments, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). In some embodiments, the muscle-targeting agent is an antibody. In some embodiments, the muscle-targeting agent is an anti-transferrin receptor antibody (e.g., any one of the anti-TfR antibodies provided herein). In some embodiments, the muscle-targeting agent may be linked to the 5' end of the sense strand of the siRNA molecule. In some embodiments, the muscle-targeting agent may be linked to the 3' end of the sense strand of the siRNA molecule. In some embodiments, the muscle-targeting agent may be linked internally to the sense strand of the siRNA molecule. In some embodiments, the muscle-targeting agent may be linked to the 5' end of the antisense strand of the siRNA molecule. In some embodiments, the muscle-targeting agent may be linked to the 3' end of the antisense strand of the siRNA molecule. In some embodiments, the muscle-targeting agent may be linked internally to the antisense strand of the siRNA molecule.

k. microRNA (miRNAs)

In some embodiments, an oligonucleotide may be a microRNA (miRNA). MicroRNAs (referred to as "miRNAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or (e.g., and) loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via an oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled Methods of delivering multiple targeting oligonucleotides to a cell using cleavable linkers, which was published on Nov. 5, 2015; US Patent Application Number 2015/0247141 A1, entitled Multimeric Oligonucleotide Compounds, which was published on Sep. 3, 2015, US Patent Application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules:

Any suitable small molecule may be used as a molecular payload, as described herein. In some embodiments, the small molecule is as described in US Patent Application Publication 20170340606, published on Nov. 30, 2017, entitled "METHODS OF TREATING MUSCULAR DYSTROPHY" or as described in US Patent Application Publication 20180050043, published on Feb. 22, 2018, entitled "INHIBITION OF DUX4 EXPRESSION USING BROMODOMAIN AND EXTRA-TERMINAL DOMAIN PROTEIN INHIBITORS (BETi). Further examples of small molecule payloads are provided in Bosnakovski, D., et al., High-throughput screening identifies inhibitors of DUX4-induced myoblast toxicity, Skelet Muscle, February 2014, and Choi. S., et al., "Transcriptional Inhibitors Identified in a 160,000-Compound Small-Molecule DUX4 Viability Screen," Journal of Biomolecular Screening, 2016. For example, in some embodiments, the small molecule is a transcriptional inhibitor, such as SHC351, SHC540, SHC572. In some embodiments, the small molecule is STR00316 increases production or activity of another protein, such as integrin. In some embodiments, the small molecule is a bromodomain inhibitor (BETi), such as JQ1, PF1-1, I-BET-762, I-BET-151, RVX-208, or CPI-0610.

iii. Peptides

Any suitable peptide or protein may be used as a molecular payload, as described herein. In some embodiments, a protein is an enzyme. These peptides or proteins may be produced, synthesized, and/or (e.g., and) derivatized using several methodologies, e.g. phage displayed peptide libraries, one-bead one-compound peptide libraries, or positional scanning synthetic peptide combinatorial libraries. In some embodiments, the peptide or protein may bind a DME1 or DME2 enhancer to inhibit DUX4 expression, e.g., by blocking binding of an activator.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5' methyl cap. In some embodiments, a mRNA may comprise a polyA tail, optionally of up to 160 nucleotides in length. In some embodiments, the gene expression construct may be expressed, e.g., overexpressed, within the nucleus of a muscle cell. In some embodiments, the gene expression construct encodes a oligonucleotide (e.g., an shRNA targeting DUX4) or a protein that downregulates the expression of DUX4 (e.g., a peptide or protein that binds to DME1 or DME2 enhancer to inhibit DUX4 expression, e.g., by blocking binding of an activator). In some embodiments, the gene expression construct encodes a oligonucleotide (e.g., an shRNA targeting MuRFI or MAFbx) that downregulates the expression of MuRFI or MAFbx, respectively. In some embodiments, the gene expression constructs encode a protein that comprises at least one zinc finger. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "CLOSED-ENDED LINEAR DUPLEX DNA FOR NON-VIRAL GENE TRANSFER"; U.S. Pat. No. 8,853,377B2, issued on Oct. 7, 2014, entitled, "MRNA FOR USE IN TREATMENT OF HUMAN GENETIC DISEASES"; and US Patent U.S. Pat. No. 8,822,663B2, issued on Sep. 2, 2014, ENGINEERED NUCLEIC ACIDS AND METHODS OF USE THEREOF," the contents of each of which are incorporated herein by reference in their entireties.

C. Linkers

Complexes described herein generally comprise a linker that connects any one of the anti-TfR antibodies described herein to a molecular payload. A linker comprises at least one covalent bond. In some embodiments, a linker may be a single bond, e.g., a disulfide bond or disulfide bridge, that connects an anti-TfR antibody to a molecular payload. However, in some embodiments, a linker may connect any one of the anti-TfR antibodies described herein to a molecular payload through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the anti-TfR antibody or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493.; Jain, N. et al. "Current ADC Linker Chemistry" Pharm Res. 2015, 32:11, 3526-3540.; McCombs, J. R. and Owen, S. C. "Antibody Drug Conjugates: Design and Selection of Linker, Payload and Conjugation Chemistry" AAPS J. 2015, 17:2, 339-351.).

A precursor to a linker typically will contain two different reactive species that allow for attachment to both the anti-TfR antibody and a molecular payload. In some embodiments, the two different reactive species may be a nucleophile and/or (e.g., and) an electrophile. In some embodiments, a linker is connected to an anti-TfR antibody via conjugation to a lysine residue or a cysteine residue of the anti-TfR antibody. In some embodiments, a linker is connected to a cysteine residue of an anti-TfR antibody via a maleimide-containing linker, wherein optionally the maleimide-containing linker comprises a maleimidocaproyl or maleimidomethyl cyclohexane-1-carboxylate group. In some embodiments, a linker is connected to a cysteine residue of an anti-TfR antibody or thiol functionalized molecular payload via a 3-arylpropionitrile functional group. In some embodiments, a linker is connected to a lysine residue of an anti-TfR antibody. In some embodiments, a linker is connected to an anti-TfR antibody and/or (e.g., and) a molecular payload via an amide bond, a carbamate bond, a hydrazide, a trizaole, a thioether, or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or (e.g., and) an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by a disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

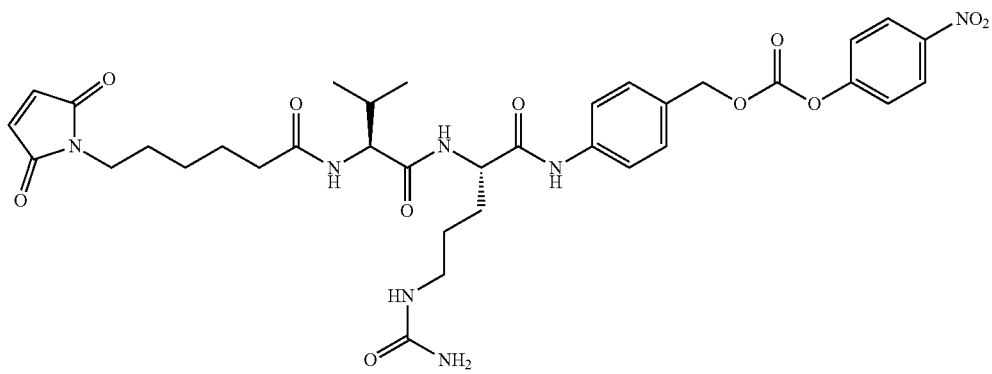 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of:

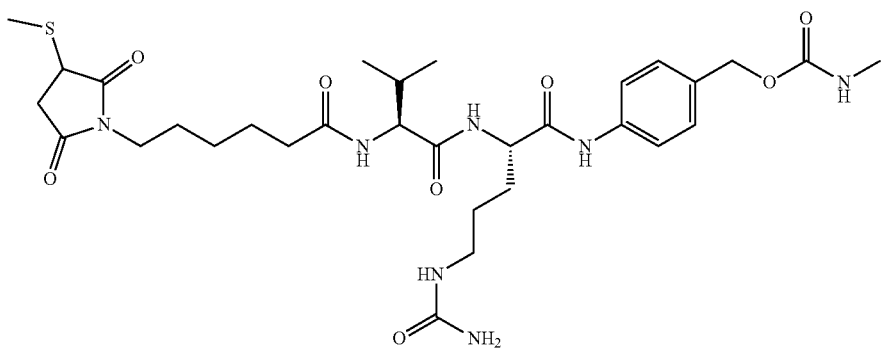

In some embodiments, the Val-cit linker is attached to a reactive chemical moiety (e.g., SPAAC for click chemistry conjugation). In some embodiments, before click chemistry conjugation, the val-cit linker attached to a reactive chemical moiety (e.g., SPAAC for click chemistry conjugation) has the structure of:

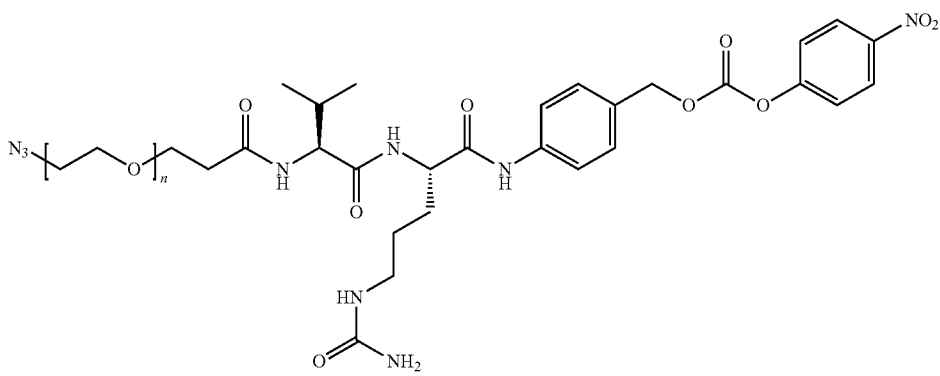

wherein n is any number from 0-10. In some embodiments, n is 3.

In some embodiments, the val-cit linker attached to a reactive chemical moiety (e.g., SPAAC for click chemistry conjugation) is conjugated (e.g., via a different chemical moiety) to a molecular payload (e.g., an oligonucleotide). In some embodiments, the val-cit linker attached to a reactive chemical moiety (e.g., SPAAC for click chemistry conjugation) and conjugated to a molecular payload (e.g., an oligonucleotide) has the structure of (before click chemistry conjugation):

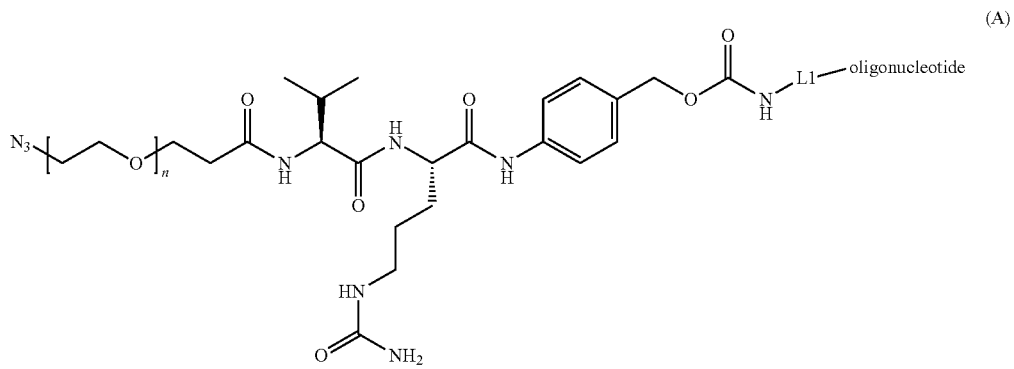

(A)

wherein n is any number from 0-10. In some embodiments, n is 3.

In some embodiments, after conjugation to a molecular payload (e.g., an oligonucleotide), the val-cit linker has a structure of:

amides, sulfamides, and/or (e.g., and) an alkoxy-amine linker. In some embodiments, sortase-mediated ligation will be utilized to covalently link an anti-TfR antibody comprising a LPXT sequence to a molecular payload comprising a $(G)_n$ sequence (see, e.g. Proft T. Sortase-mediated protein ligation: an emerging biotechnology tool for protein modification and immobilization. Biotechnol Lett. 2010, 32(1): 1-10.).

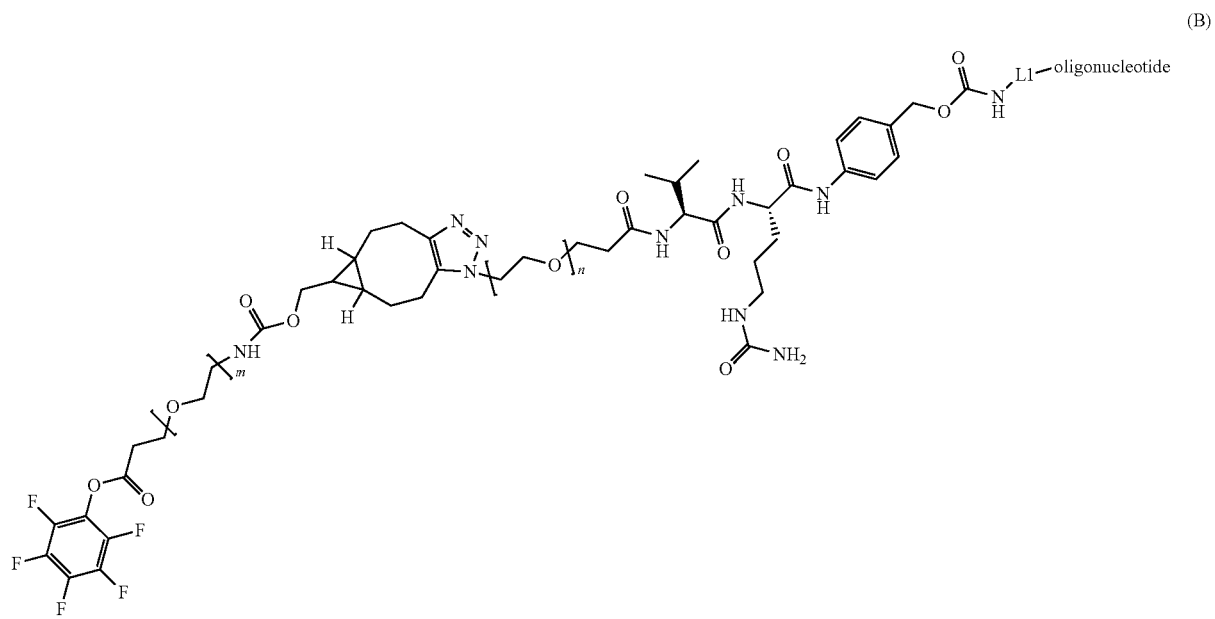

(B)

wherein n is any number from 0-10, and wherein m is any number from 0-10. In some embodiments, n is 3 and m is 4.

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or (e.g., and) an alkoxy-amine linker.

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S; an optionally substituted heterocyclylene further comprising at least one heteroatom selected from N, O, and S; an imino, an optionally substituted nitrogen species, an optionally substituted oxygen species O, an optionally substituted sulfur species, or a poly(alkylene oxide), e.g. polyethylene oxide or polypropylene oxide.

iii. Linker Conjugation

In some embodiments, a linker is connected to an anti-TfR antibody and/or (e.g., and) molecular payload via a phosphate, thioether, ether, carbon-carbon, carbamate, or amide bond. In some embodiments, a linker is connected to an oligonucleotide through a phosphate or phosphorothioate group, e.g. a terminal phosphate of an oligonucleotide backbone. In some embodiments, a linker is connected to an anti-TfR antibody, through a lysine or cysteine residue present on the anti-TfR antibody.

In some embodiments, a linker is connected to an anti-TfR antibody and/or (e.g., and) molecular payload by a cycloaddition reaction between an azide and an alkyne to form a triazole, wherein the azide and the alkyne may be located on the anti-TfR antibody, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "Fused Cyclooctyne Compounds And Their Use In Metal-free Click Reactions". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase". In some embodiments, a cycloaddition reaction between an azide and an alkyne to form a triazole, wherein the azide and the alkyne may be located on the anti-TfR antibody, molecular payload, or the linker is as described in International Patent Application Publication WO2014065661, published on May 1, 2014, entitled, "Modified antibody, antibody-conjugate and process for the preparation thereof"; or International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase".

In some embodiments, a linker further comprises a spacer, e.g., a polyethylene glycol spacer or an acyl/carbomoyl sulfamide spacer, e.g., a HydraSpace™ spacer. In some embodiments, a spacer is as described in Verkade, J. M. M. et al., "*A Polar Sulfamide Spacer Significantly Enhances the Manufacturability, Stability, and Therapeutic Index of Antibody-Drug Conjugates*", Antibodies, 2018, 7, 12.

In some embodiments, a linker is connected to an anti-TfR antibody and/or (e.g., and) molecular payload by the Diels-Alder reaction between a dienophile and a diene/hetero-diene, wherein the dienophile and the diene/hetero-diene may be located on the anti-TfR antibody, molecular payload, or the linker. In some embodiments a linker is connected to an anti-TfR antibody and/or (e.g., and) molecular payload by other pericyclic reactions, e.g. ene reaction. In some embodiments, a linker is connected to an anti-TfR antibody and/or (e.g., and) molecular payload by an amide, thioamide, or sulfonamide bond reaction. In some embodiments, a linker is connected to an anti-TfR antibody and/or (e.g., and) molecular payload by a condensation reaction to form an oxime, hydrazone, or semicarbazide group existing between the linker and the anti-TfR antibody and/or (e.g., and) molecular payload.

In some embodiments, a linker is connected to an anti-TfR antibody and/or (e.g., and) molecular payload by a conjugate addition reactions between a nucleophile, e.g. an amine or a hydroxyl group, and an electrophile, e.g. a carboxylic acid, carbonate, or an aldehyde. In some embodiments, a nucleophile may exist on a linker and an electrophile may exist on an anti-TfR antibody or molecular payload prior to a reaction between a linker and an anti-TfR antibody or molecular payload. In some embodiments, an electrophile may exist on a linker and a nucleophile may exist on an anti-TfR antibody or molecular payload prior to a reaction between a linker and an anti-TfR antibody or molecular payload. In some embodiments, an electrophile may be an azide, pentafluorophenyl, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or (e.g., and) an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

In some embodiments, the val-cit linker attached to a reactive chemical moiety (e.g., SPAAC for click chemistry conjugation) is conjugated to the anti-TfR antibody by a structure of:

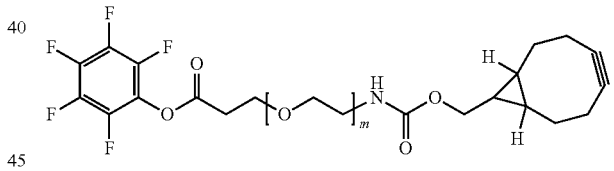

wherein m is any number from 0-10. In some embodiments, m is 4.

In some embodiments, the val-cit linker attached to a reactive chemical moiety (e.g., SPAAC for click chemistry conjugation) is conjugated to an anti-TfR antibody having a structure of:

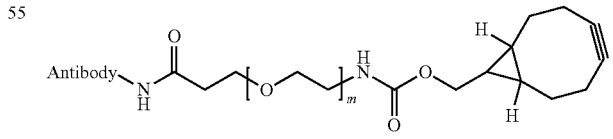

wherein m is any number from 0-10. In some embodiments, m is 4.

In some embodiments, the val-cit linker attached to a reactive chemical moiety (e.g., SPAAC for click chemistry conjugation) and conjugated to an anti-TfR antibody has a structure of:

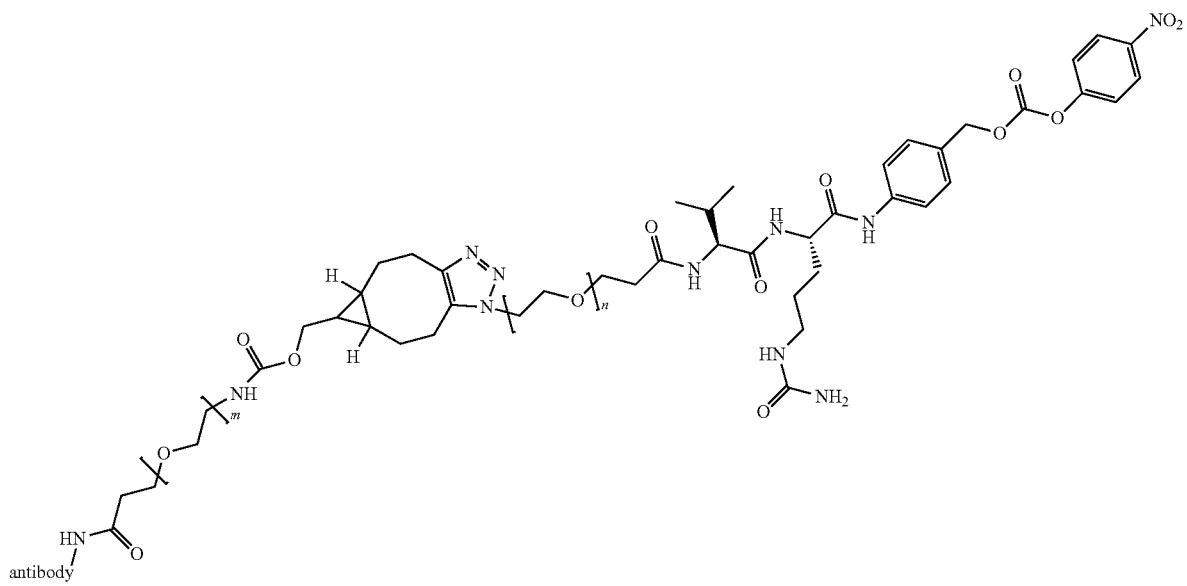

wherein n is any number from 0-10, wherein m is any number from 0-10. In some embodiments, n is 3 and/or (e.g., and) m is 4.

In some embodiments, the val-cit linker that links the antibody and the molecular payload has a structure of:

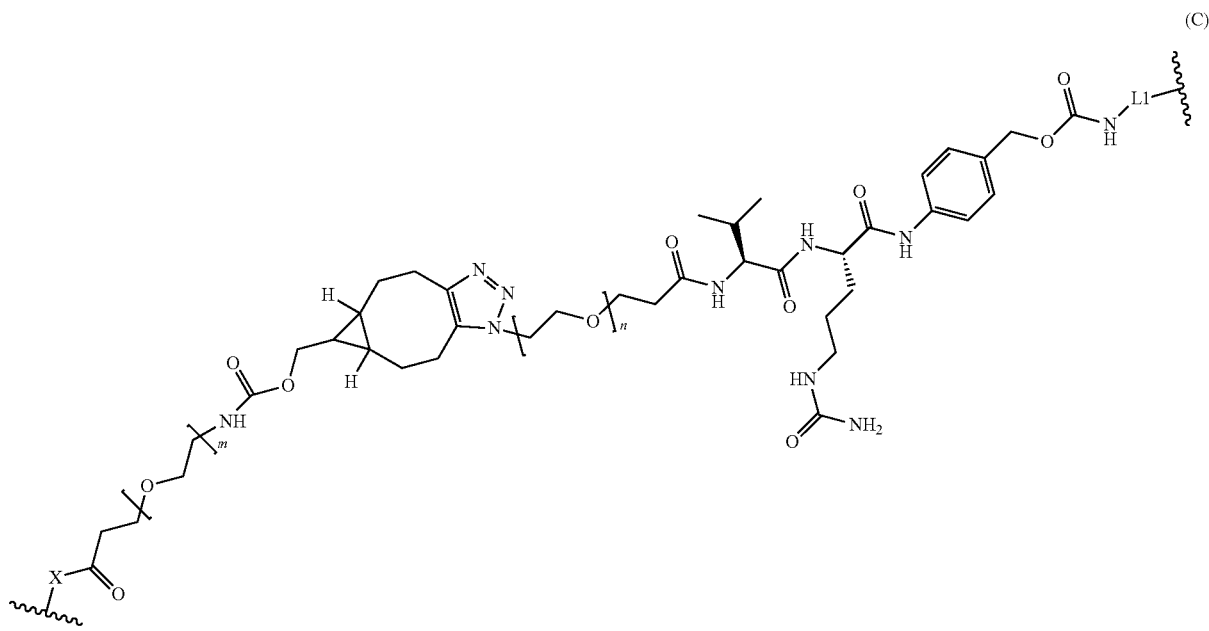

(C)

wherein n is any number from 0-10, wherein m is any number from 0-10. In some embodiments, n is 3 and/or (e.g., and) m is 4. In some embodiments, n is 3 and/or (e.g., and) m is 4. In some embodiments, X is NH (e.g., NH from an amine group of a lysine), S (e.g., S from a thiol group of a cysteine), or O (e.g., O from a hydroxyl group of a serine, threonine, or tyrosine) of the antibody.

In some embodiments, the complex described herein has a structure of:

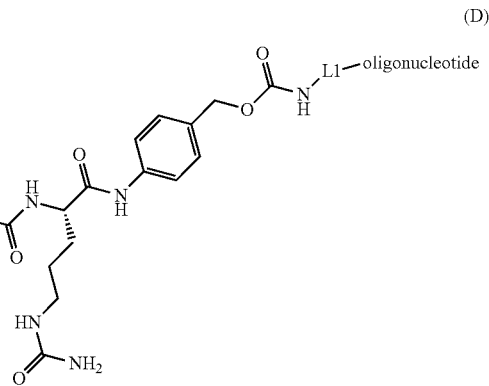
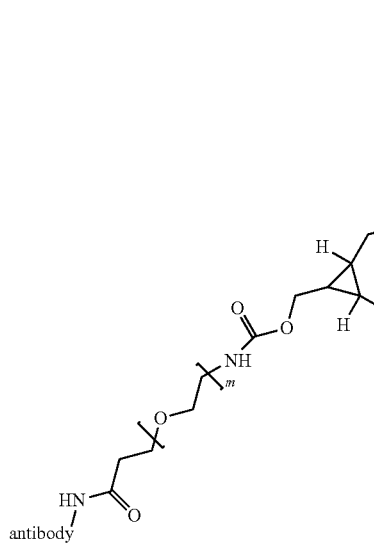

(D)

wherein n is any number from 0-10, wherein m is any number from 0-10. In some embodiments, n is 3 and/or (e.g., and) m is 4.

In structures formula (A), (B), (C), and (D), L1, in some embodiments, is a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof. In some embodiments, L1 is

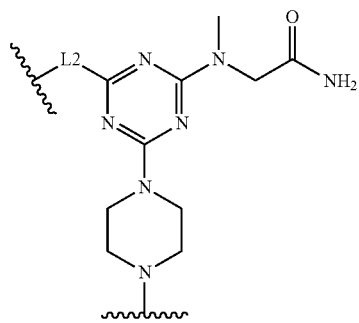

wherein the piperazine moiety links to the oligonucleotide, wherein L2 is

-continued

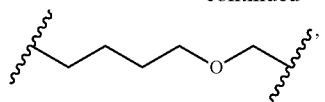

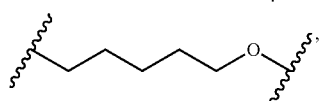,

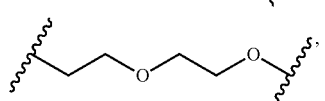,

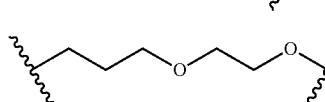,

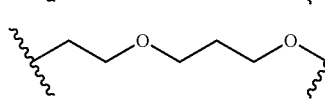,

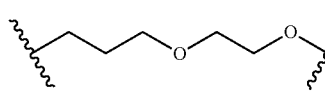,

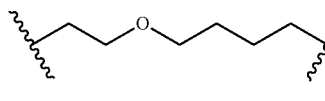,

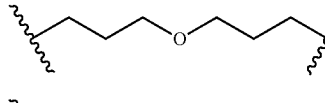, or

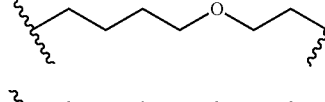.

In some embodiments, L1 is:

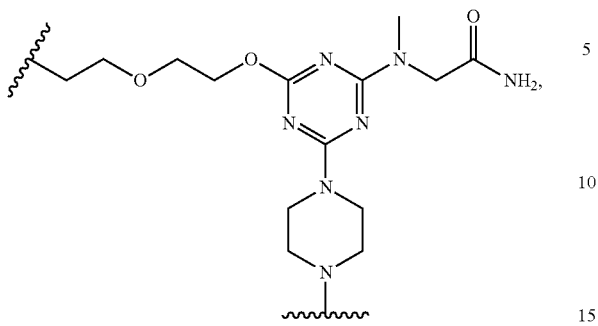

wherein the piperazine moiety links to the oligonucleotide.

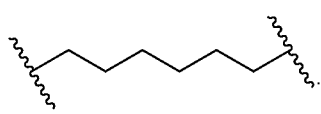 [SMILES: *CCCCCC*]

In some embodiments, L1 is

In some embodiments, L1 is linked to a 5' phosphate of the oligonucleotide.

In some embodiments, L1 is optional (e.g., need not be present).

In some embodiments, any one of the complexes described herein has a structure of:

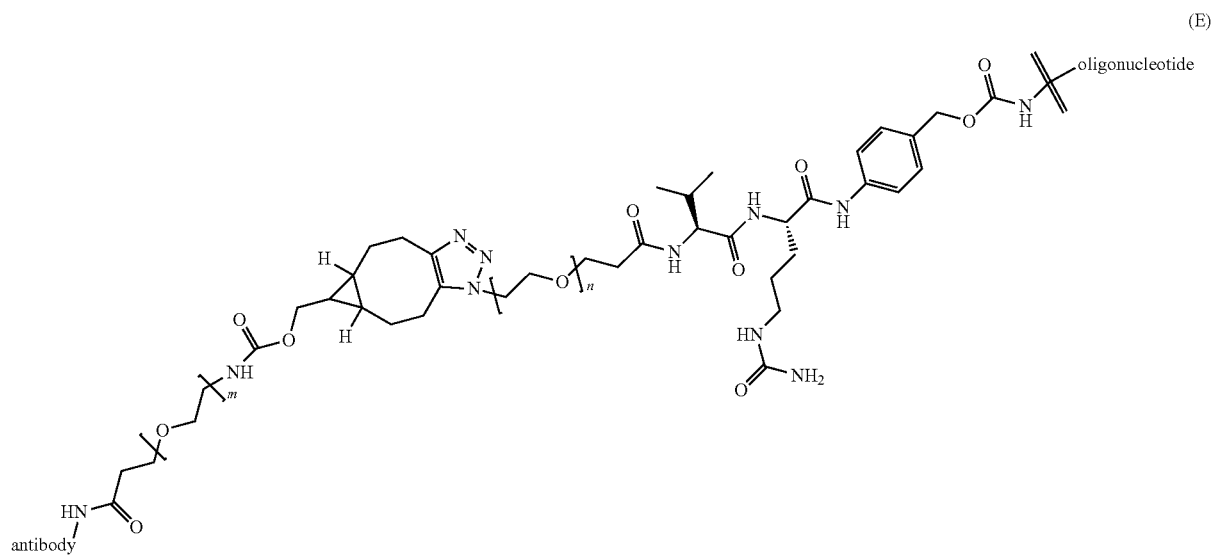

(E)

wherein n is 0-15 (e.g., 3) and m is 0-15 (e.g., 4).

C. Examples of Antibody-Molecular Payload Complexes

Further provided herein are non-limiting examples of complexes comprising any one the anti-TfR antibodies described herein covalently linked to any of the molecular payloads (e.g., an oligonucleotide) described herein. In some embodiments, the anti-TfR antibody (e.g., any one of the anti-TfR antibodies provided in Table 2) is covalently linked to a molecular payload (e.g., an oligonucleotide) via a linker. Any of the linkers described herein may be used. In some embodiments, if the molecular payload is an oligonucleotide, the linker is linked to the 5' end, the 3' end, or internally of the oligonucleotide. In some embodiments, the linker is linked to the anti-TfR antibody via a thiol-reactive linkage (e.g., via a cysteine in the anti-TfR antibody). In some embodiments, the linker (e.g., a Val-cit linker) is linked to the antibody (e.g., an anti-TfR antibody described herein) via an amine group (e.g., via a lysine in the antibody). In some embodiments, the molecular payload is a DUX4-targeting oligonucleotide (e.g., an oligonucleotide comprising the nucleotide sequence of SEQ ID NO: 151).

An example of a structure of a complex comprising an anti-TfR antibody covalently linked to a molecular payload via a Val-cit linker is provided below:

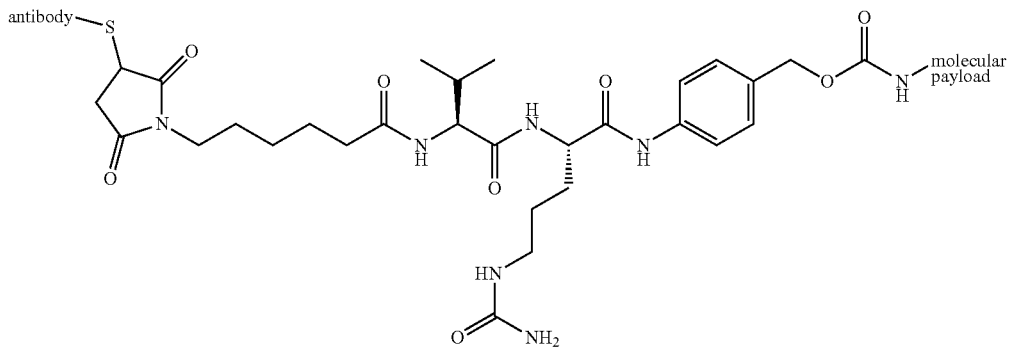

wherein the linker is linked to the antibody via a thiol-reactive linkage (e.g., via a cysteine in the antibody). In some embodiments, the molecular payload is a DUX4-targeting oligonucleotide (e.g., an oligonucleotide comprising the nucleotide sequence of SEQ ID NO: 151).

Another example of a structure of a complex comprising an anti-TfR antibody covalently linked to a molecular payload via a Val-cit linker is provided below:

embodiments, one molecular payload is linked to an antibody (DAR=1). In some embodiments, two molecular payloads are linked to an antibody (DAR=2). In some embodiments, three molecular payloads are linked to an antibody (DAR=3). In some embodiments, four molecular payloads are linked to an antibody (DAR=4). In some embodiments, a mixture of different complexes, each having a different DAR, is provided. In some embodiments, an average DAR (D)

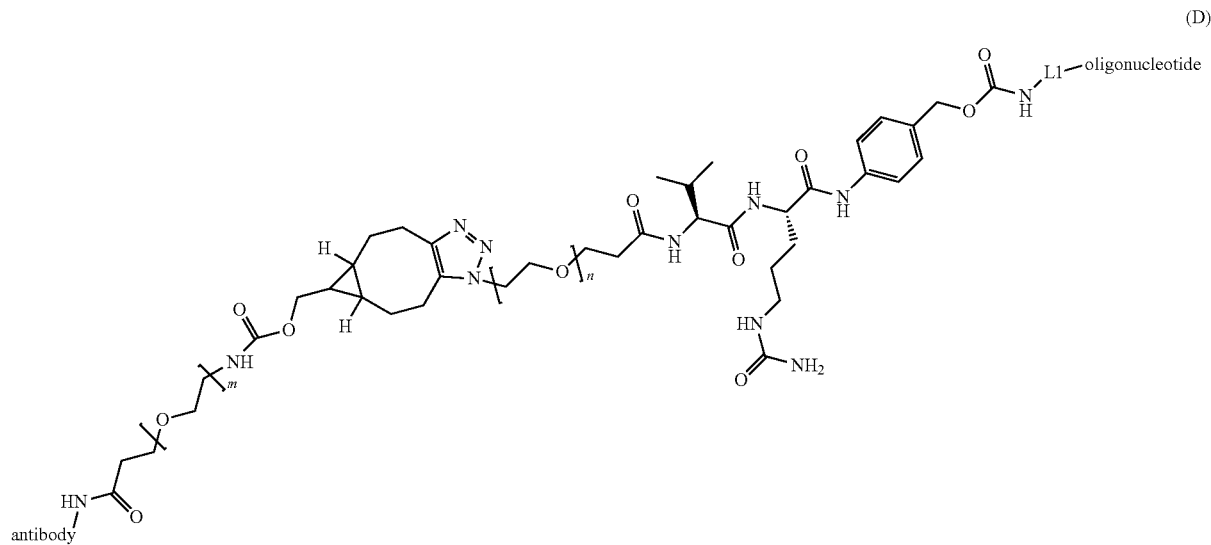

wherein n is a number between 0-10, wherein m is a number between 0-10, wherein the linker is linked to the antibody via an amine group (e.g., on a lysine residue), and/or (e.g., and) wherein the linker is linked to the oligonucleotide (e.g., at the 5' end, 3' end, or internally). In some embodiments, the linker is linked to the antibody via a lysine, the linker is linked to the oligonucleotide at the 5' end, n is 3, and m is 4. In some embodiments, the molecular payload is an oligonucleotide comprising a sense strand and an antisense strand, and, the linker is linked to the sense strand or the antisense strand at the 5' end or the 3' end. In some embodiments, the molecular payload is a DUX4-targeting oligonucleotide (e.g., an oligonucleotide comprising the nucleotide sequence of SEQ ID NO: 151).

It should be appreciated that antibodies can be linked to molecular payloads with different stochiometries, a property that may be referred to as a drug to antibody ratios (DAR) with the "drug" being the molecular payload. In some of complexes in such a mixture may be in a range of 1 to 3, 1 to 4, 1 to 5 or more. DAR may be increased by conjugating molecular payloads to different sites on an antibody and/or (e.g., and) by conjugating multimers to one or more sites on antibody. For example, a DAR of 2 may be achieved by conjugating a single molecular payload to two different sites on an antibody or by conjugating a dimer molecular payload to a single site of an antibody.

In some embodiments, the complex described herein comprises an anti-TfR antibody described herein (e.g., the 3-A4, 3-M12, and 5-H12 antibodies provided in Table 2 in a IgG or Fab form) covalently linked to a molecular payload. In some embodiments, the complex described herein comprises an anti-TfR antibody described herein (e.g., the 3-A4, 3-M12, and 5-H12 antibodies provided in Table 2 in a IgG or Fab form) covalently linked to molecular payload via a linker (e.g., a Val-cit linker). In some embodiments, the linker (e.g., a Val-cit linker) is linked to the antibody (e.g., an anti-TfR antibody described herein) via a thiol-reactive linkage (e.g., via a cysteine in the antibody). In some embodiments, the linker (e.g., a Val-cit linker) is linked to the antibody (e.g., an anti-TfR antibody described herein) via an amine group (e.g., via a lysine in the antibody). In some embodiments, the molecular payload is a DUX4-targeting oligonucleotide (e.g., an oligonucleotide comprising the nucleotide sequence of SEQ ID NO: 151).

In some embodiments, in any one of the examples of complexes described herein, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a CDR-H1, a CDR-H2, and a CDR-H3 that are the same as the CDR-H1, CDR-H2, and CDR-H3 shown in Table 2; and a CDR-L1, a CDR-L2, and a CDR-L3 that are the same as the CDR-L1, CDR-L2, and CDR-L3 shown in Table 2. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a VH comprising the amino acid sequence of SEQ ID NO: 69, SEQ ID NO: 71, or SEQ ID NO: 72, and a VL comprising the amino acid sequence of SEQ ID NO: 70. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a VH comprising the amino acid sequence of SEQ ID NO: 73 or SEQ ID NO: 76, and a VL comprising the amino acid sequence of SEQ ID NO: 74. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a VH comprising the amino acid sequence of SEQ ID NO: 73 or SEQ ID NO: 76, and a VL comprising the amino acid sequence of SEQ ID NO: 75. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a VH comprising the amino acid sequence of SEQ ID NO: 77, and a VL comprising the amino acid sequence of SEQ ID NO: 78. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a VH comprising the amino acid sequence of SEQ ID NO: 77 or SEQ ID NO: 79, and a VL comprising the amino acid sequence of SEQ ID NO: 80. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 84, SEQ ID NO: 86 or SEQ ID NO: 87 and a light chain comprising the amino acid sequence of SEQ ID NO: 85. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 88 or SEQ ID NO: 91, and a light chain comprising the amino acid sequence of SEQ ID NO: 89. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 88 or SEQ ID NO: 91, and a light chain comprising the amino acid sequence of SEQ ID NO: 90. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 92 or SEQ ID NO: 94, and a light chain comprising the amino acid sequence of SEQ ID NO: 95. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 92, and a light chain comprising the amino acid sequence of SEQ ID NO: 93. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 97, SEQ ID NO: 98, or SEQ ID NO: 99 and a VL comprising the amino acid sequence of SEQ ID NO: 85. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 100 or SEQ ID NO: 101 and a light chain comprising the amino acid sequence of SEQ ID NO: 89. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 100 or SEQ ID NO: 101 and a light chain comprising the amino acid sequence of SEQ ID NO: 90. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 102 and a light chain comprising the amino acid sequence of SEQ ID NO: 93. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked to a molecular payload, wherein the anti-TfR antibody comprises a heavy chain comprising the amino acid sequence of SEQ ID NO: 102 or SEQ ID NO: 103 and a light chain comprising the amino acid sequence of SEQ ID NO: 95. In some embodiments, the molecular payload is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 84 and a light chain comprising the amino acid sequence of in SEQ ID NO: 85; wherein the complex has the structure of:

(D)

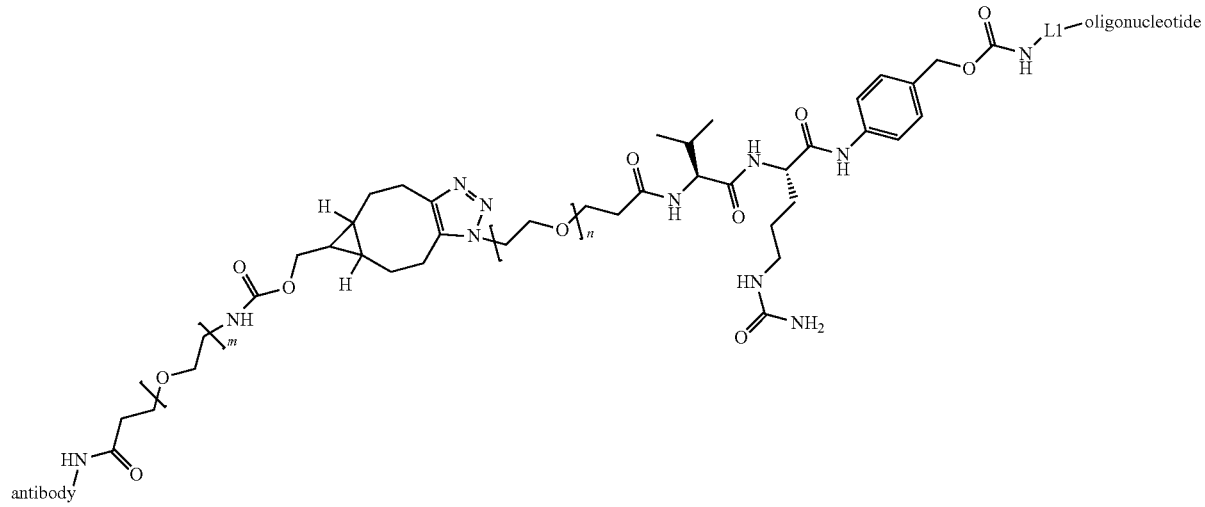

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 86 and a light chain comprising the amino acid sequence of in SEQ ID NO: 85; wherein the complex has the structure of:

(D)

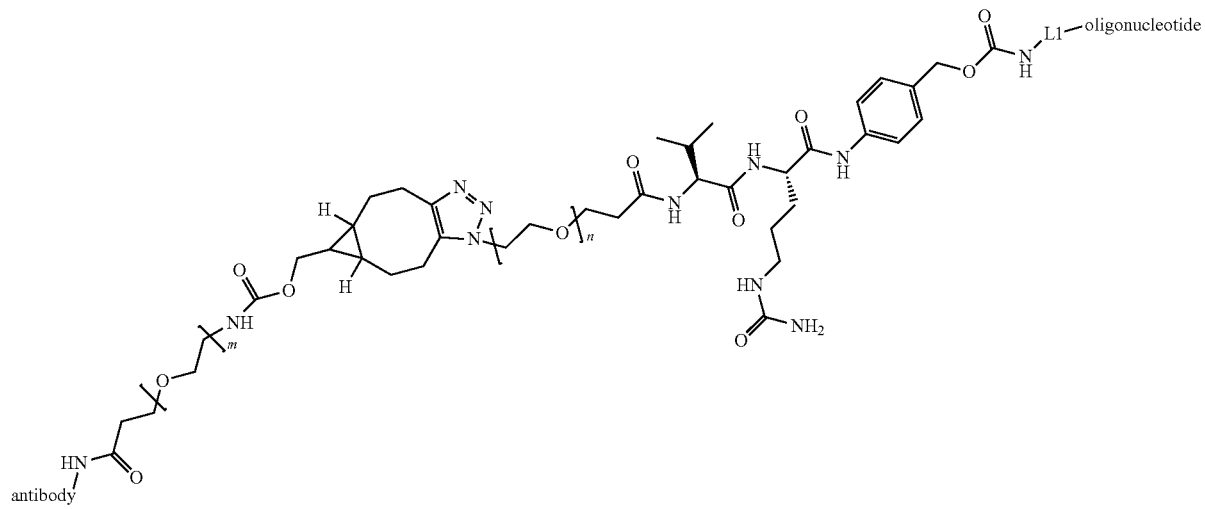

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 87 and a light chain comprising the amino acid sequence of in SEQ ID NO: 85; wherein the complex has the structure of:

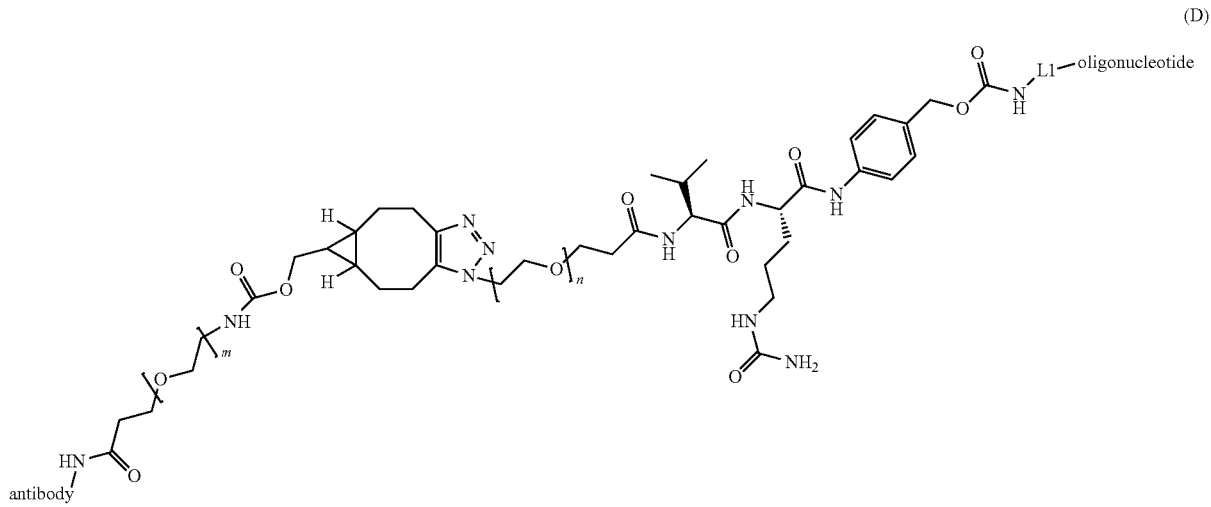

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 88 and a light chain comprising the amino acid sequence of in SEQ ID NO: 89; wherein the complex has the structure of:

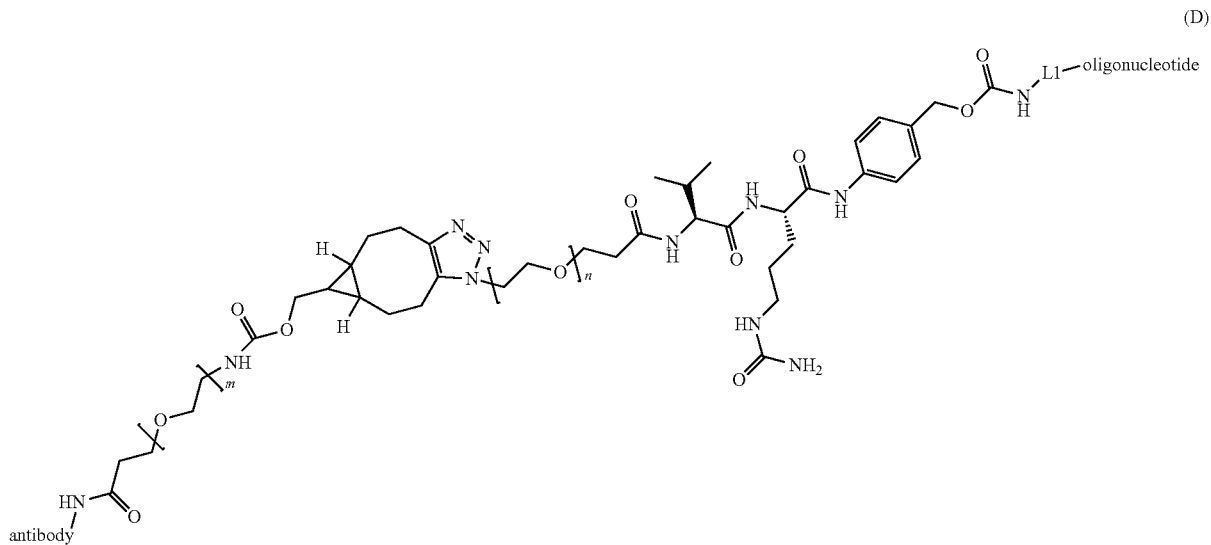

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 88 and a light chain comprising the amino acid sequence of in SEQ ID NO: 90; wherein the complex has the structure of:

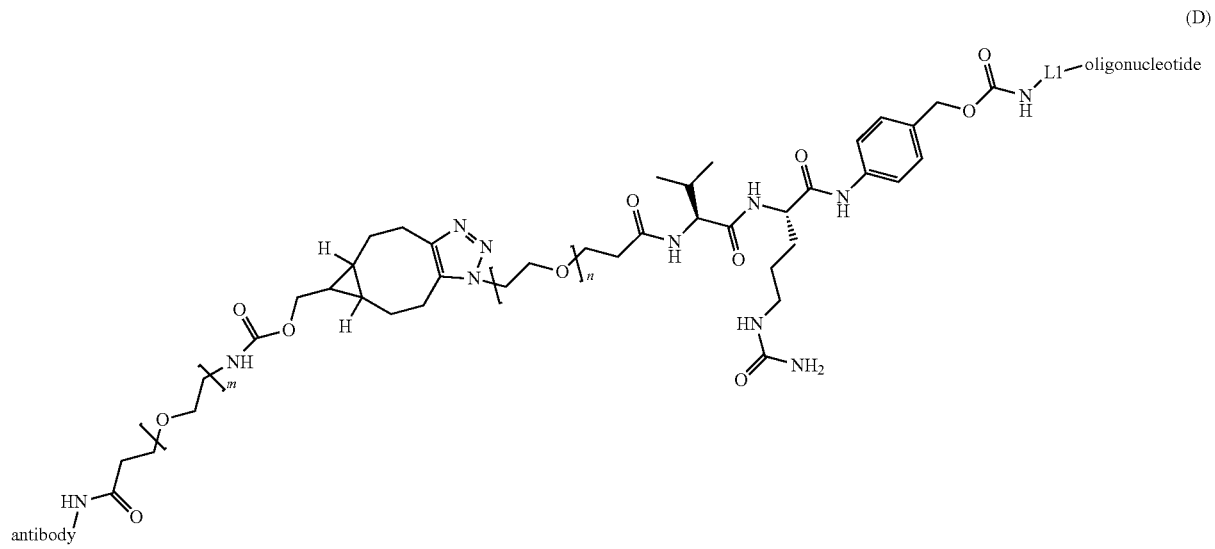

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 91 and a light chain comprising the amino acid sequence of in SEQ ID NO: 89; wherein the complex has the structure of:

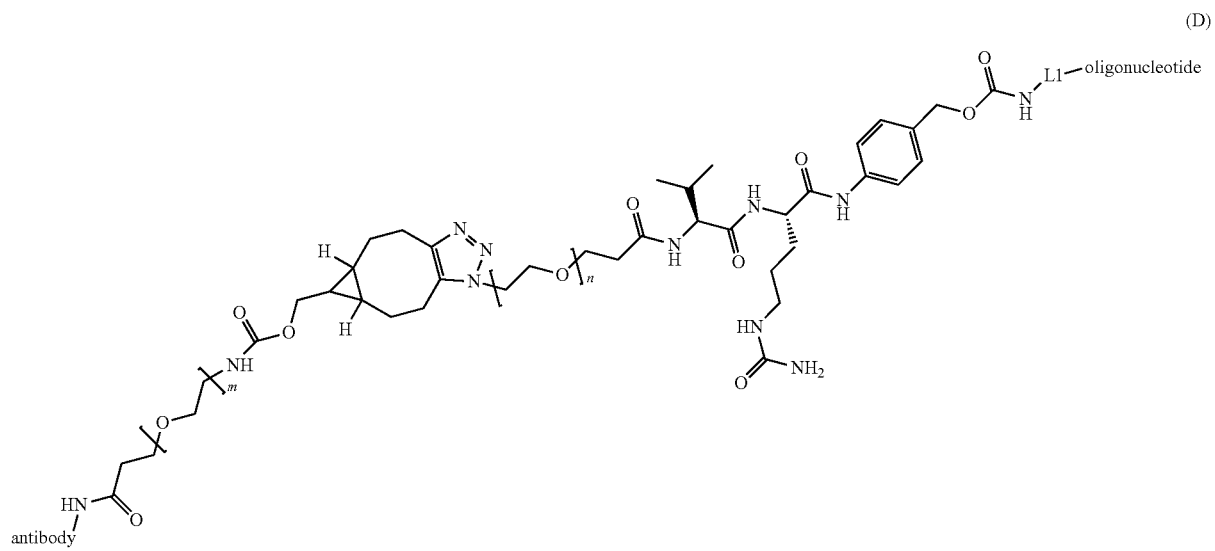

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 91 and a light chain comprising the amino acid sequence of in SEQ ID NO: 90; wherein the complex has the structure of:

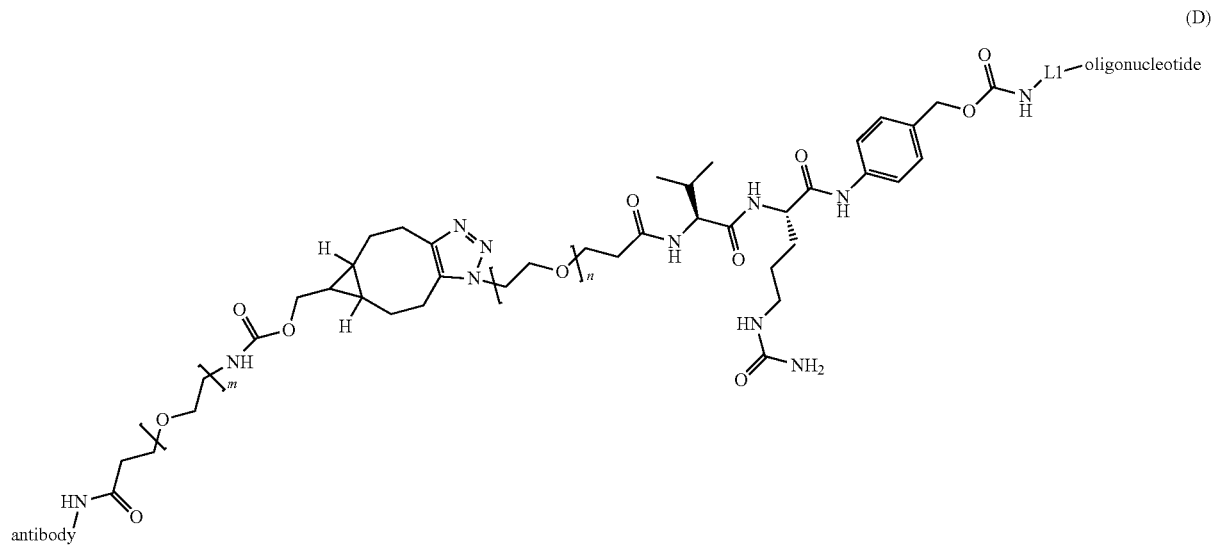

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 92 and a light chain comprising the amino acid sequence of in SEQ ID NO: 93; wherein the complex has the structure of:

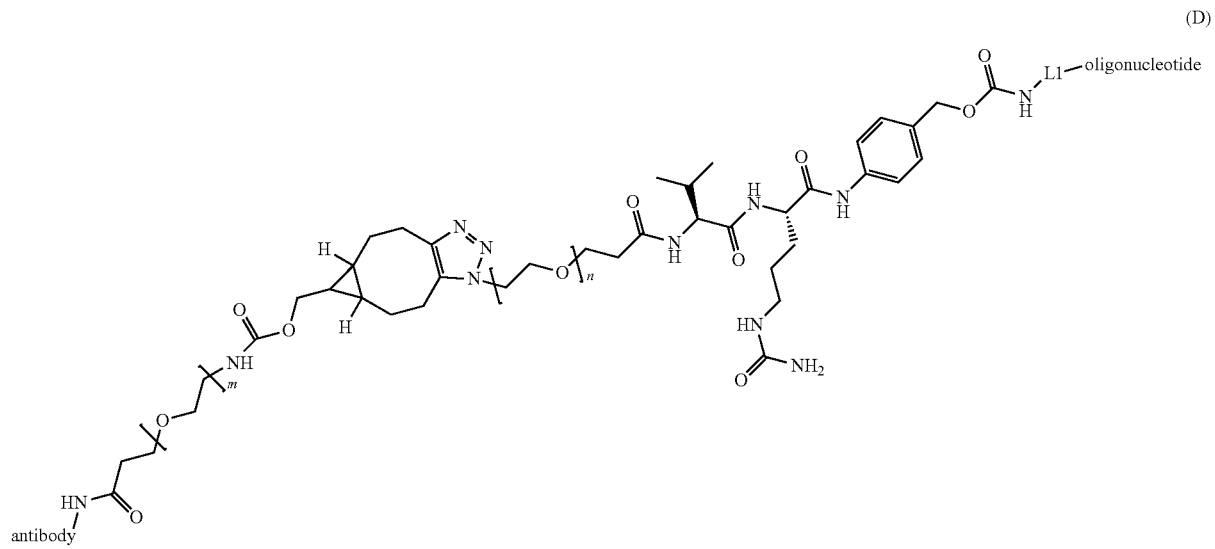

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 94 and a light chain comprising the amino acid sequence of in SEQ ID NO: 95; wherein the complex has the structure of:

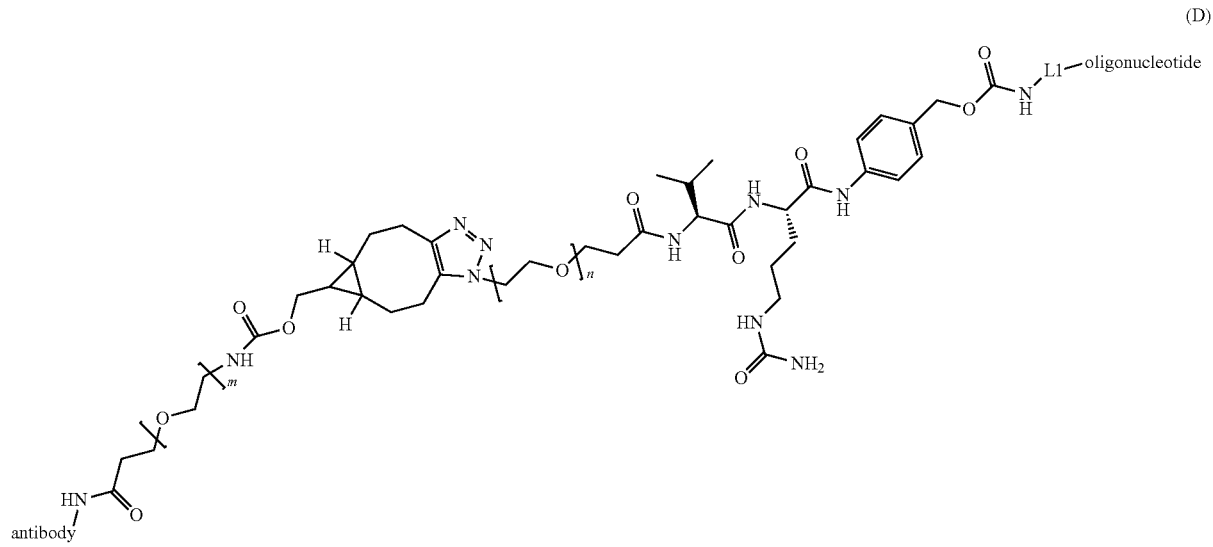

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR antibody covalently linked via a lysine to the 5' end of an oligonucleotide, wherein the anti-TfR antibody comprises a heavy chain comprising the amino acid sequence of SEQ ID NO: 92 and a light chain comprising the amino acid sequence of in SEQ ID NO: 95; wherein the complex has the structure of:

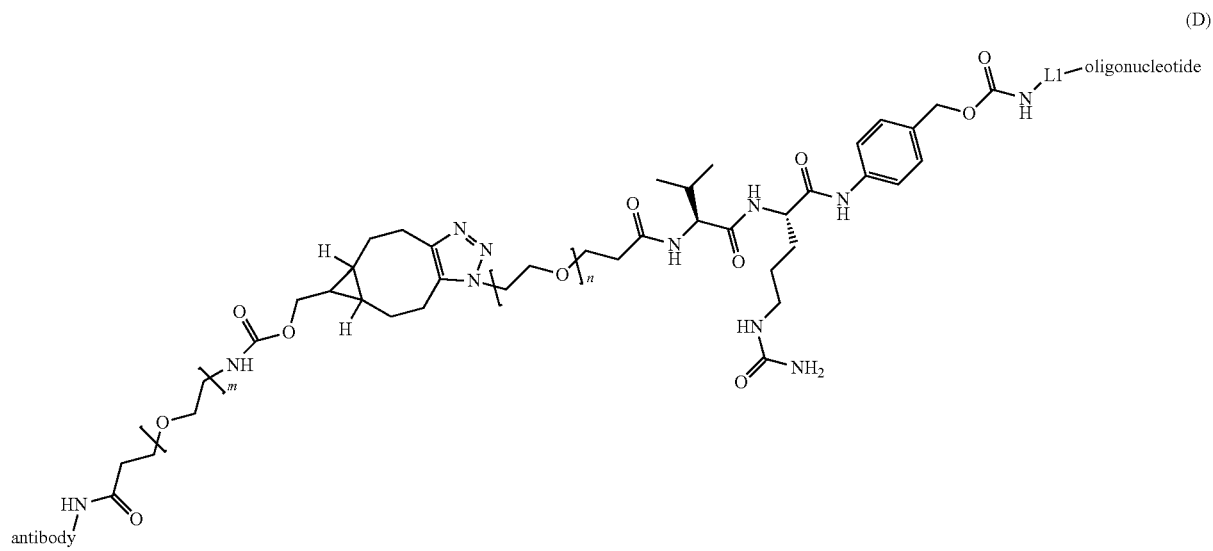

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 69 and a VL comprising the amino acid sequence of in SEQ ID NO: 70; wherein the complex has the structure of:

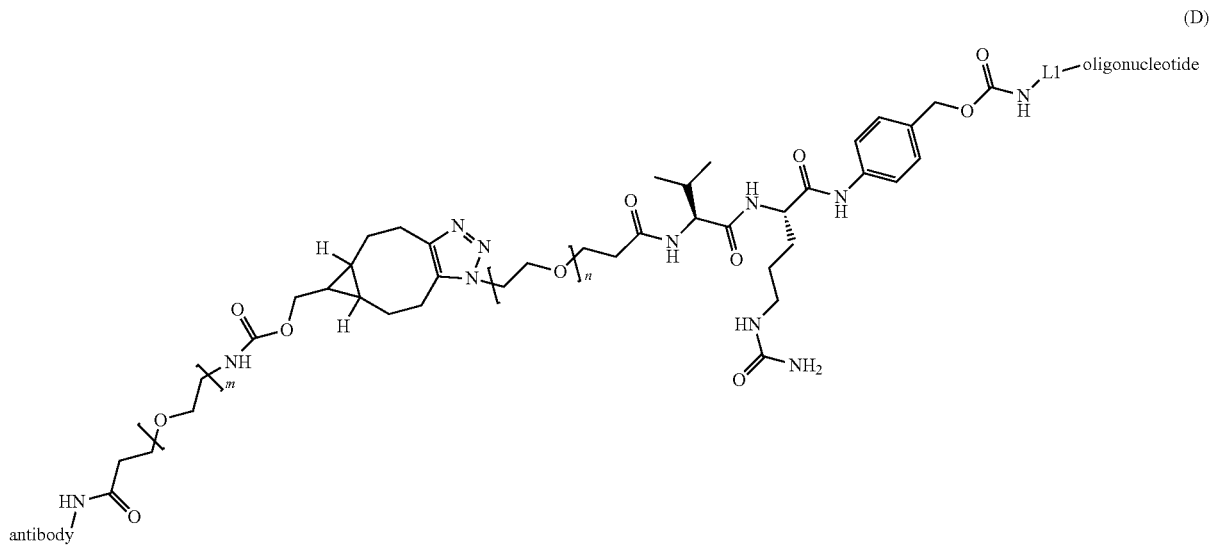

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 71 and a VL comprising the amino acid sequence of in SEQ ID NO: 70; wherein the complex has the structure of:

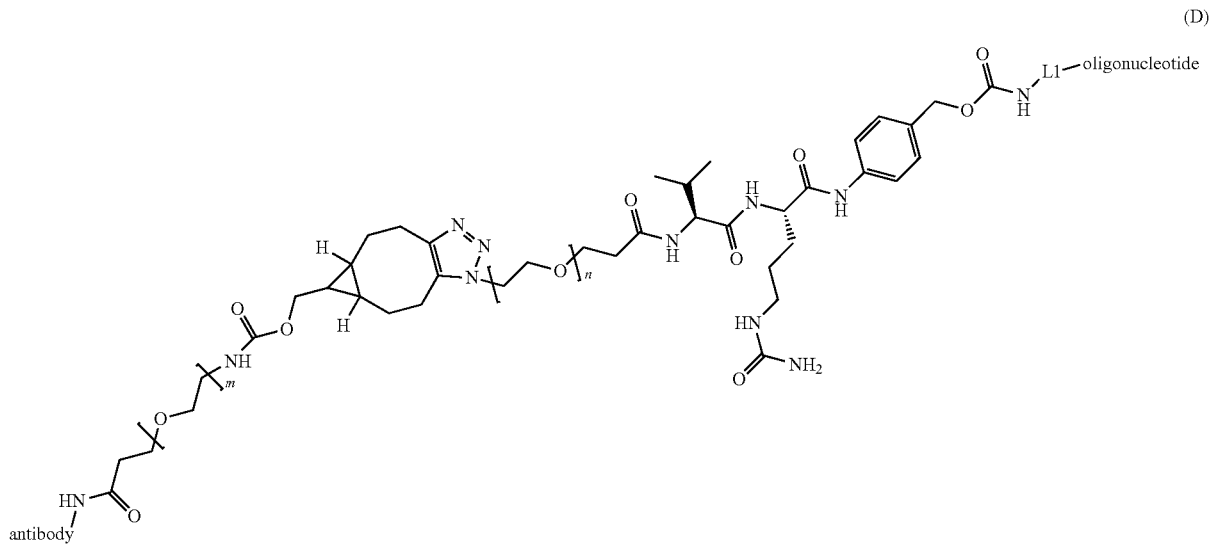

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 72 and a VL comprising the amino acid sequence of in SEQ ID NO: 70; wherein the complex has the structure of:

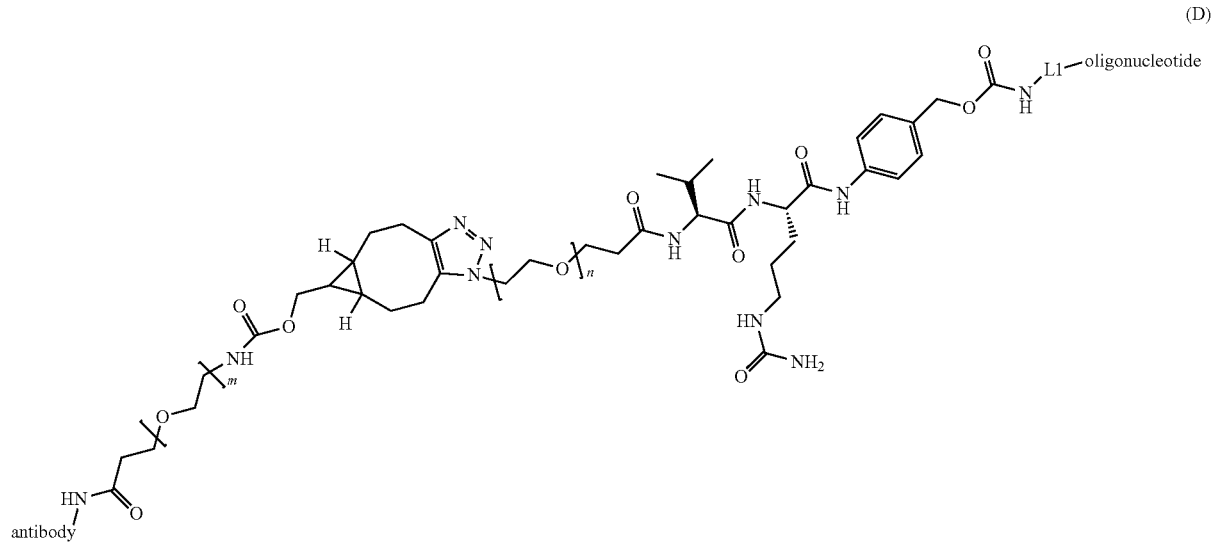

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 73 and a VL comprising the amino acid sequence of in SEQ ID NO: 74; wherein the complex has the structure of:

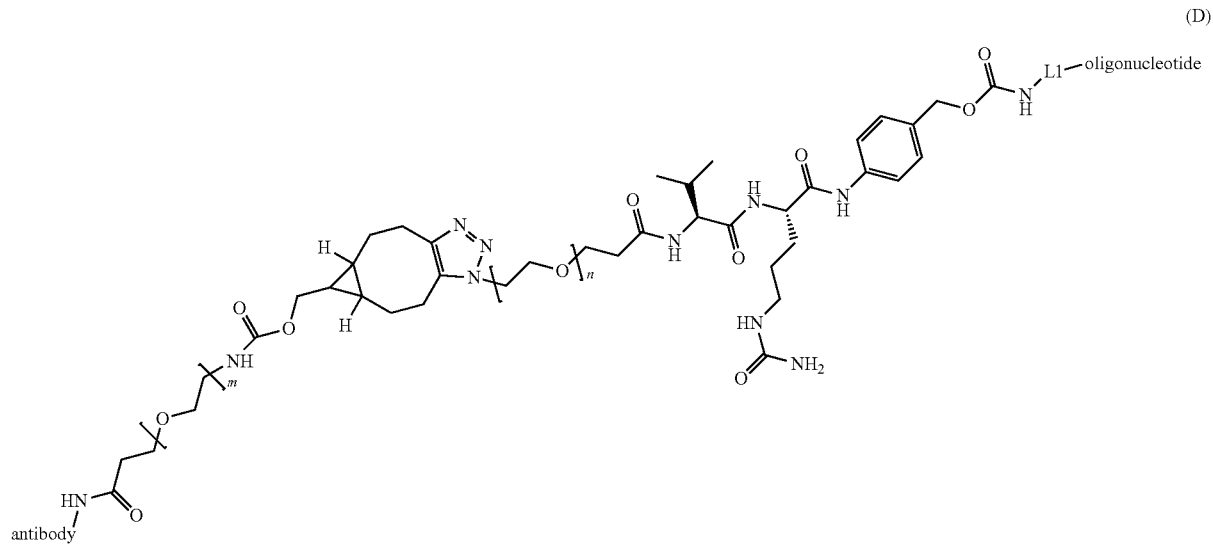

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 73 and a VL comprising the amino acid sequence of in SEQ ID NO: 75; wherein the complex has the structure of:

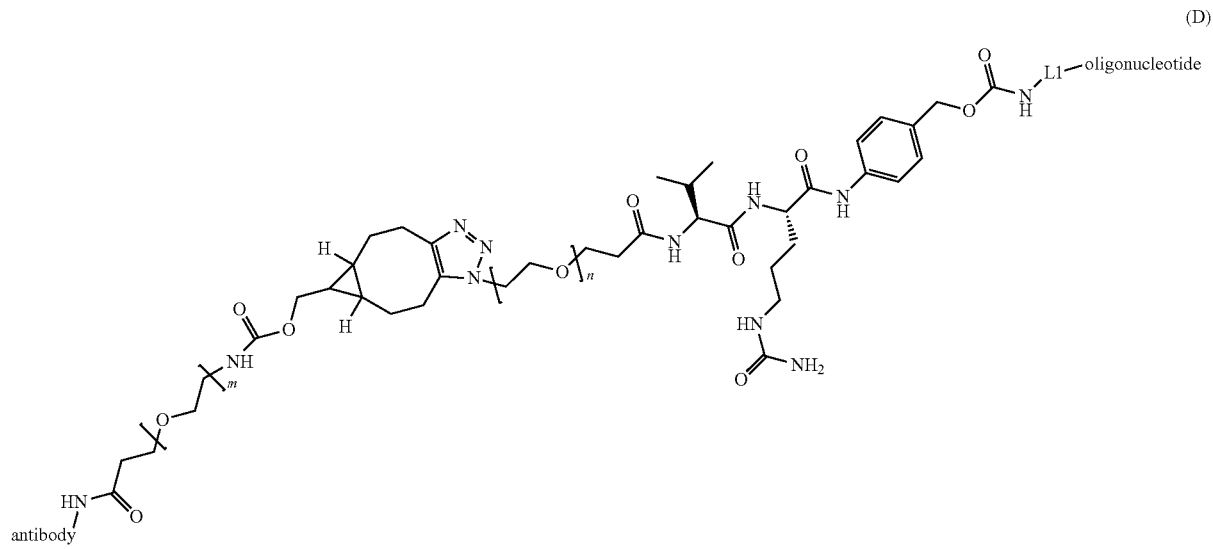

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 76 and a VL comprising the amino acid sequence of in SEQ ID NO: 74; wherein the complex has the structure of:

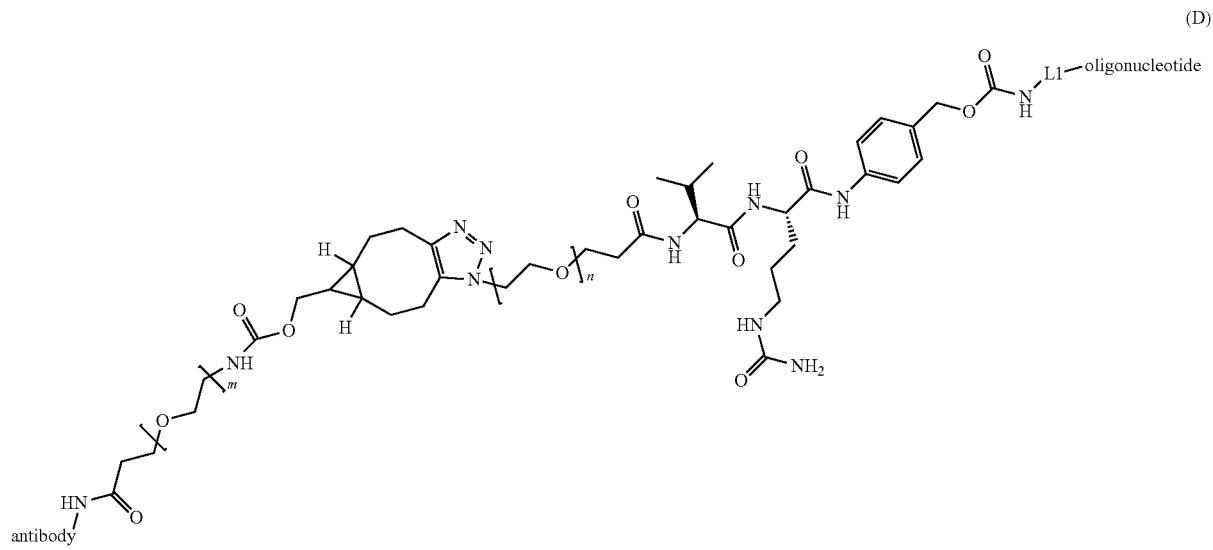

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 76 and a VL comprising the amino acid sequence of in SEQ ID NO: 75; wherein the complex has the structure of:

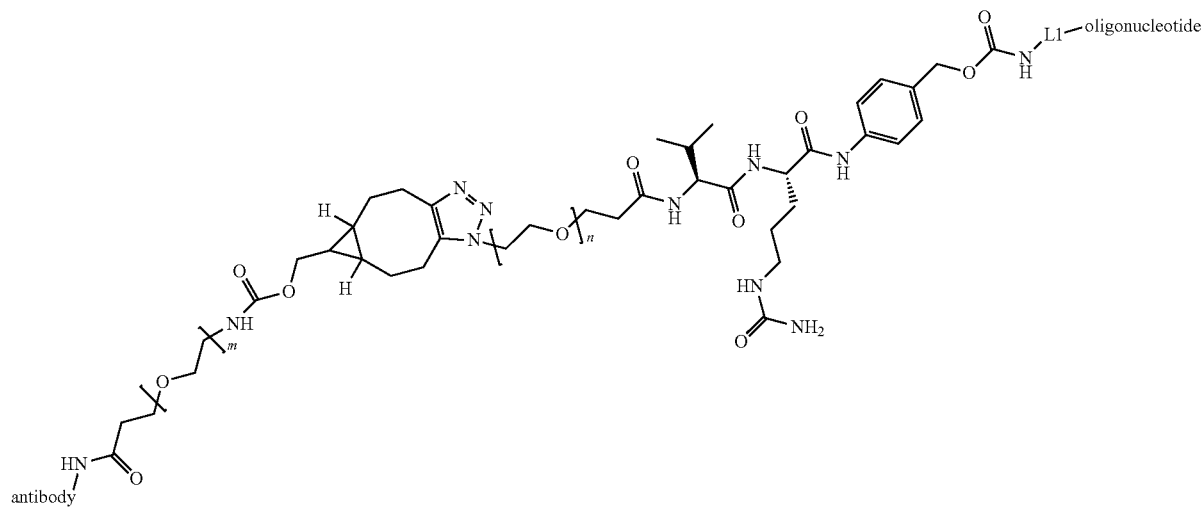

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 77 and a VL comprising the amino acid sequence of in SEQ ID NO: 78; wherein the complex has the structure of:

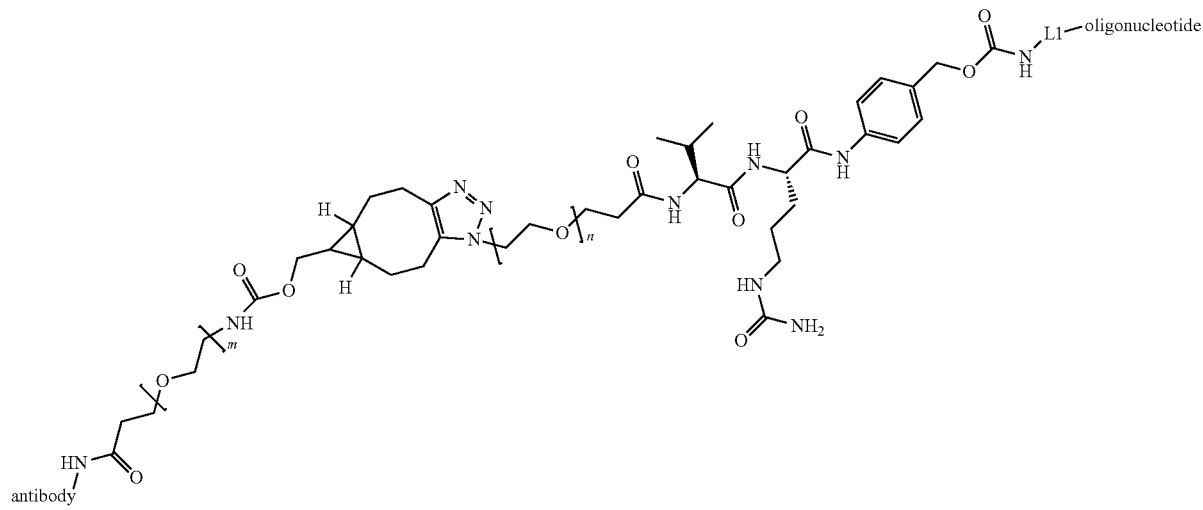

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 79 and a VL comprising the amino acid sequence of in SEQ ID NO: 80; wherein the complex has the structure of:

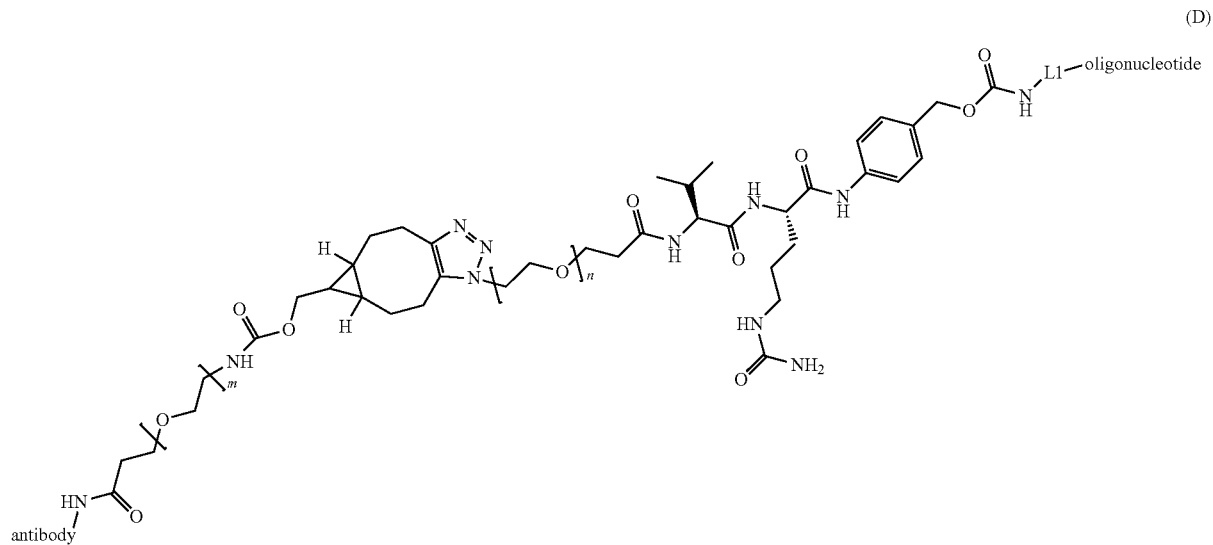

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a VH comprising the amino acid sequence of SEQ ID NO: 77 and a VL comprising the amino acid sequence of in SEQ ID NO: 80; wherein the complex has the structure of:

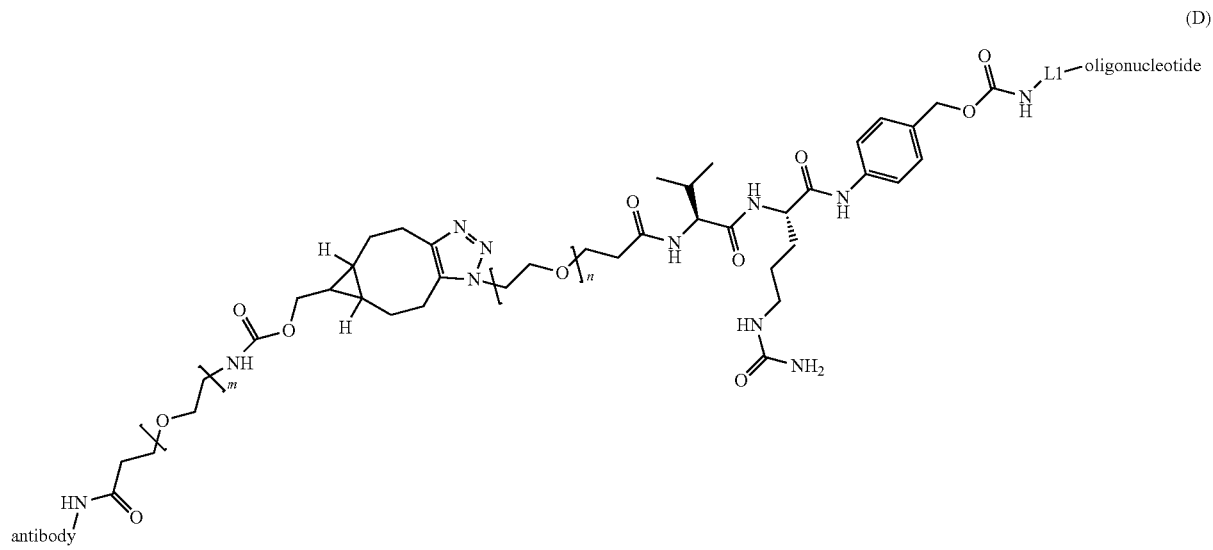

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 97 and a light chain comprising the amino acid sequence of in SEQ ID NO: 85; wherein the complex has the structure of:

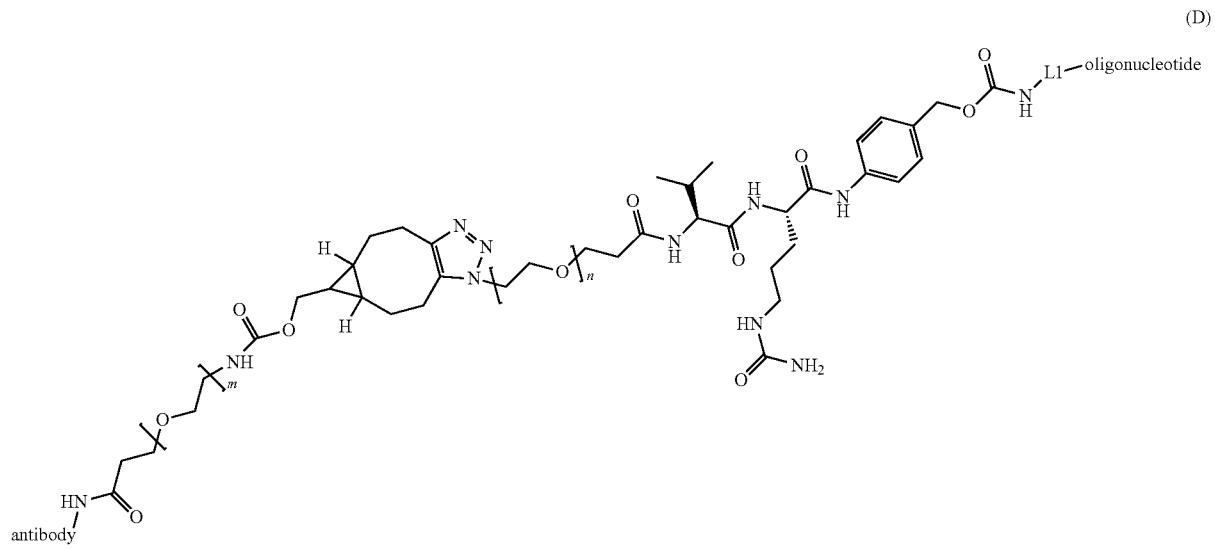

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 98 and a light chain comprising the amino acid sequence of in SEQ ID NO: 85; wherein the complex has the structure of:

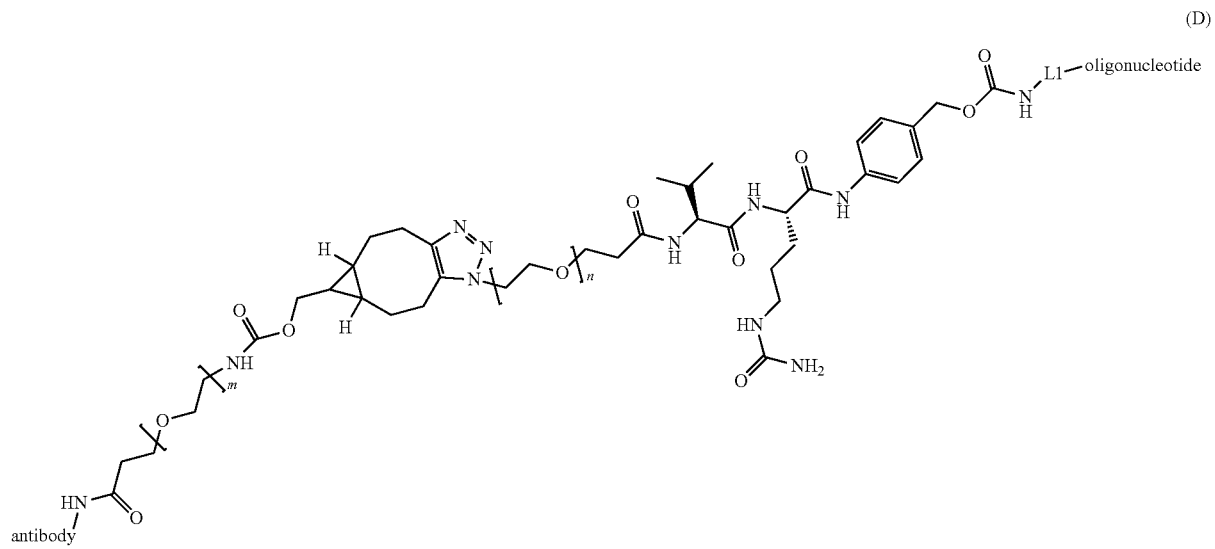

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 99 and a light chain comprising the amino acid sequence of in SEQ ID NO: 85; wherein the complex has the structure of:

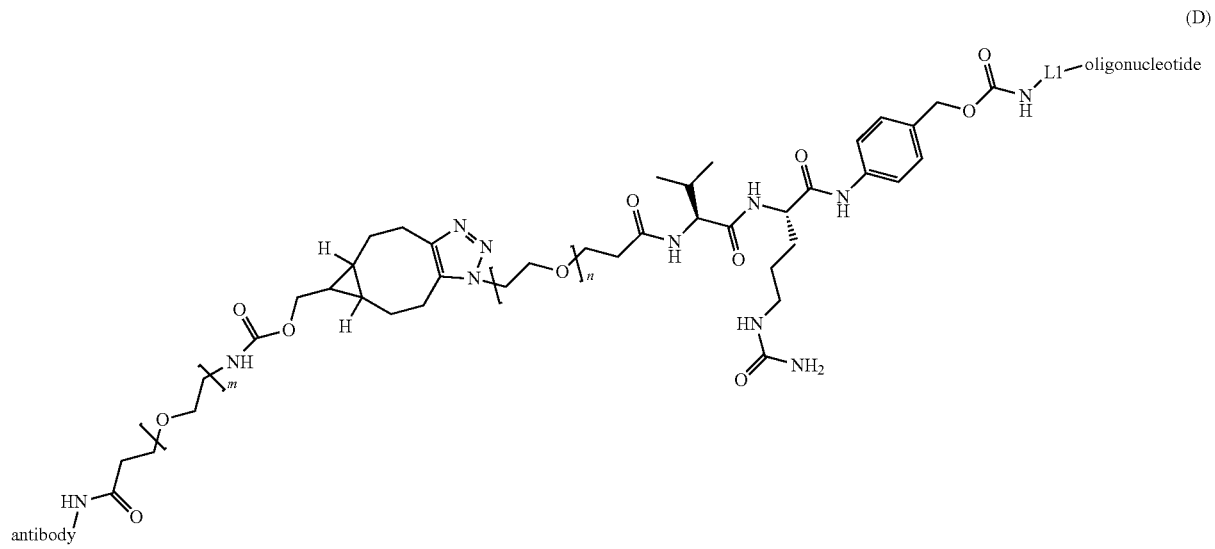

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 100 and a light chain comprising the amino acid sequence of in SEQ ID NO: 89; wherein the complex has the structure of:

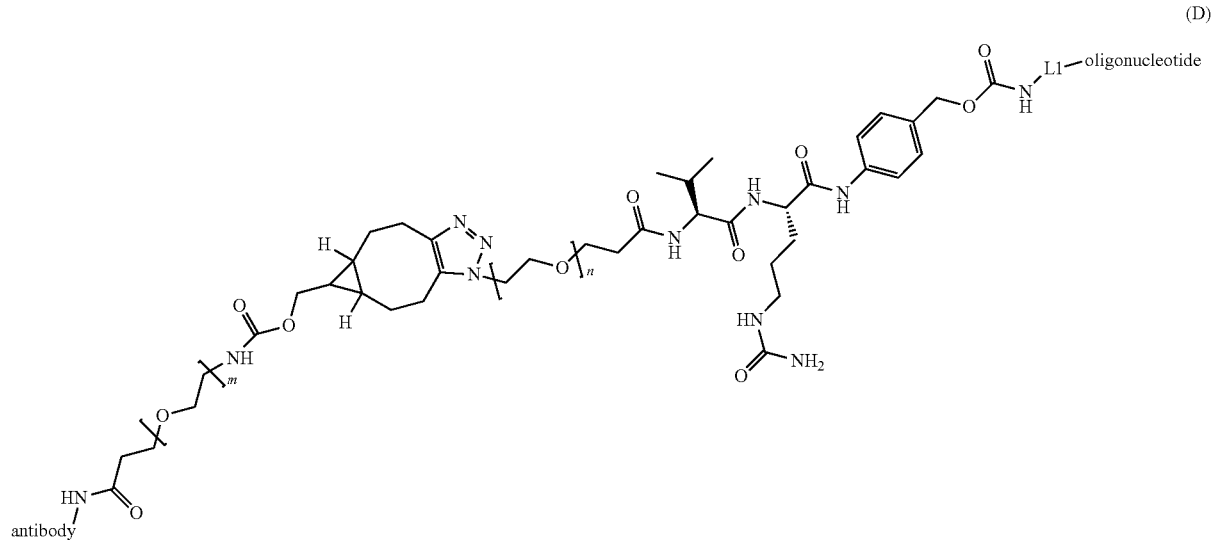

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 100 and a light chain comprising the amino acid sequence of in SEQ ID NO: 90; wherein the complex has the structure of:

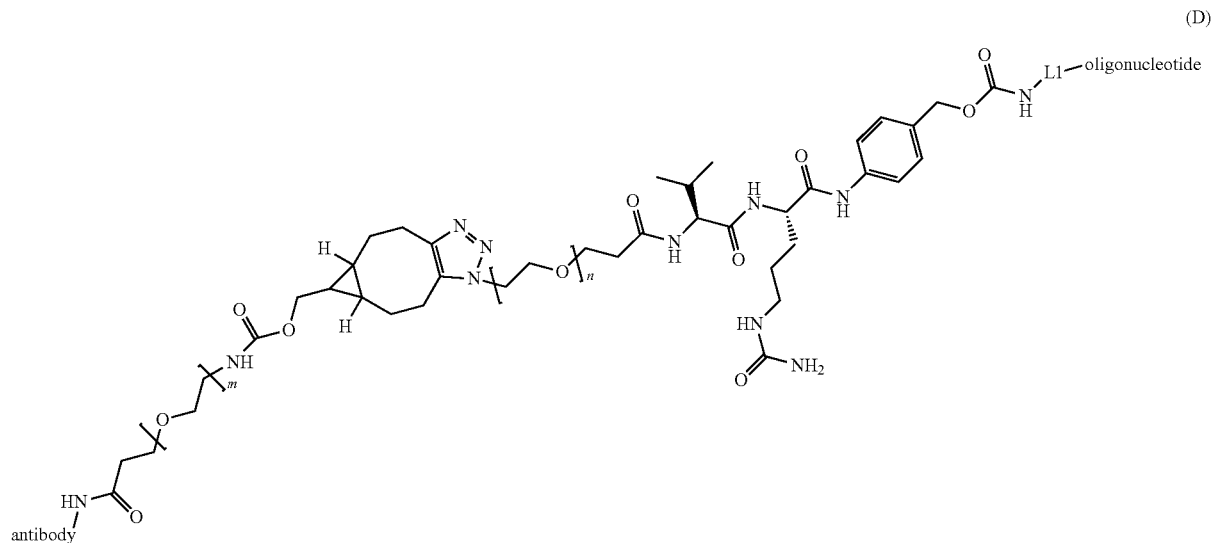

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 101 and a light chain comprising the amino acid sequence of in SEQ ID NO: 89; wherein the complex has the structure of:

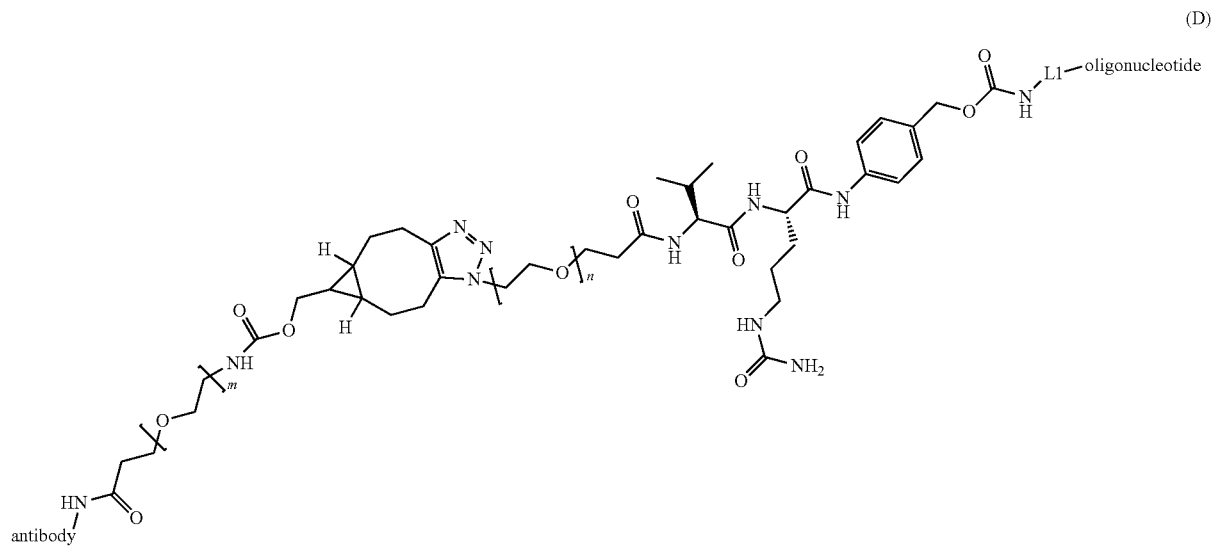

(D)

wherein n is 3 and m is 4. In some embodiments, the oligonucleotide is a DUX4-targeting oligonucleotide (e.g., an oligonucleotide comprising the nucleotide sequence of SEQ ID NO:151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 101 and a light chain comprising the amino acid sequence of in SEQ ID NO: 90; wherein the complex has the structure of:

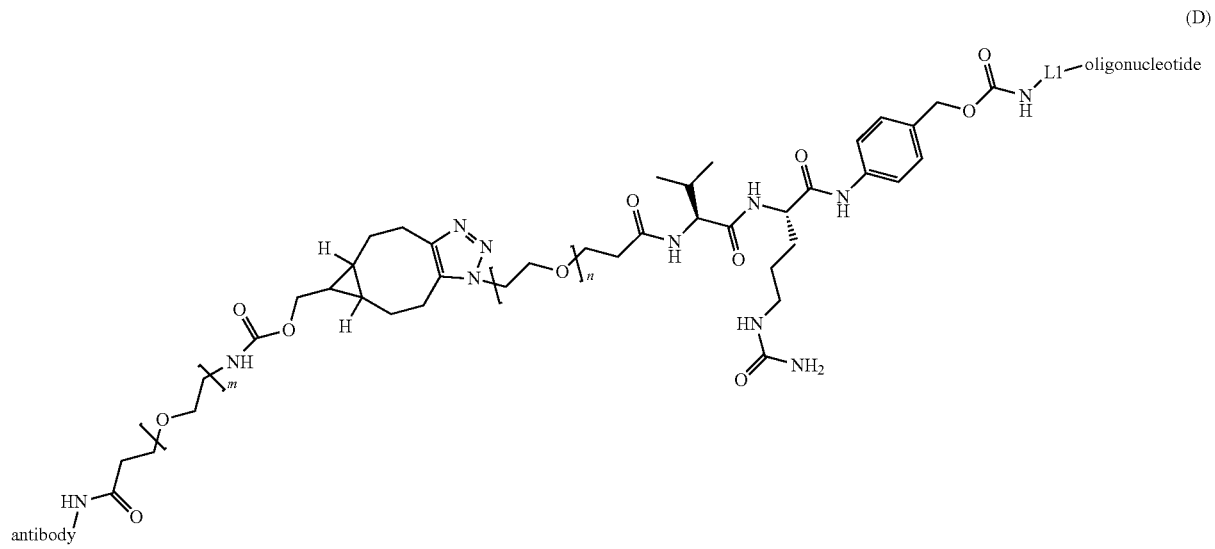

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 102 and a light chain comprising the amino acid sequence of in SEQ ID NO: 93; wherein the complex has the structure of:

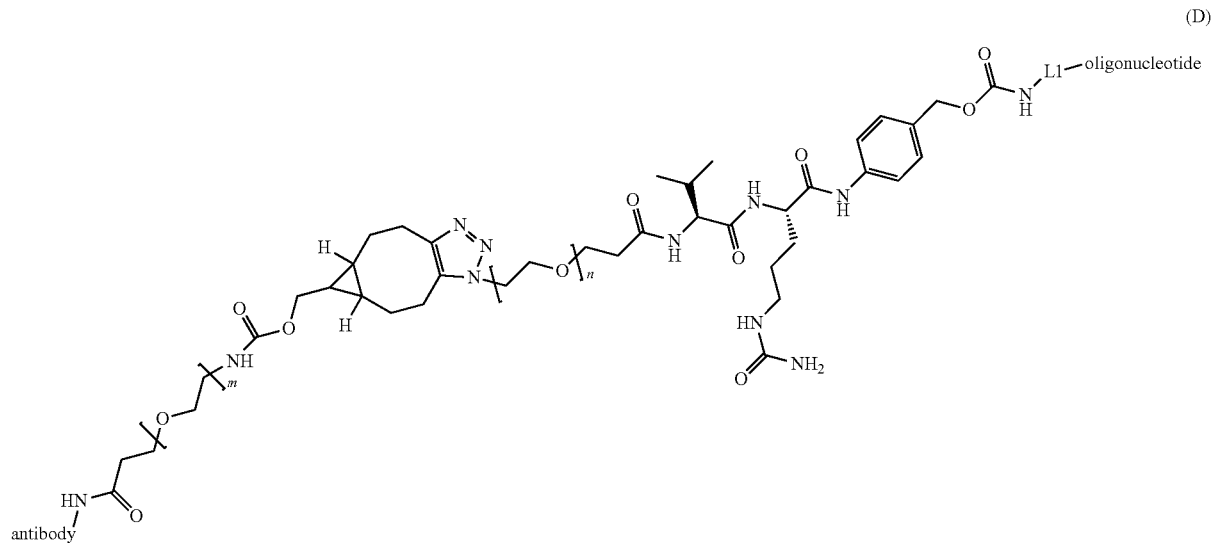

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 103 and a light chain comprising the amino acid sequence of in SEQ ID NO: 95; wherein the complex has the structure of:

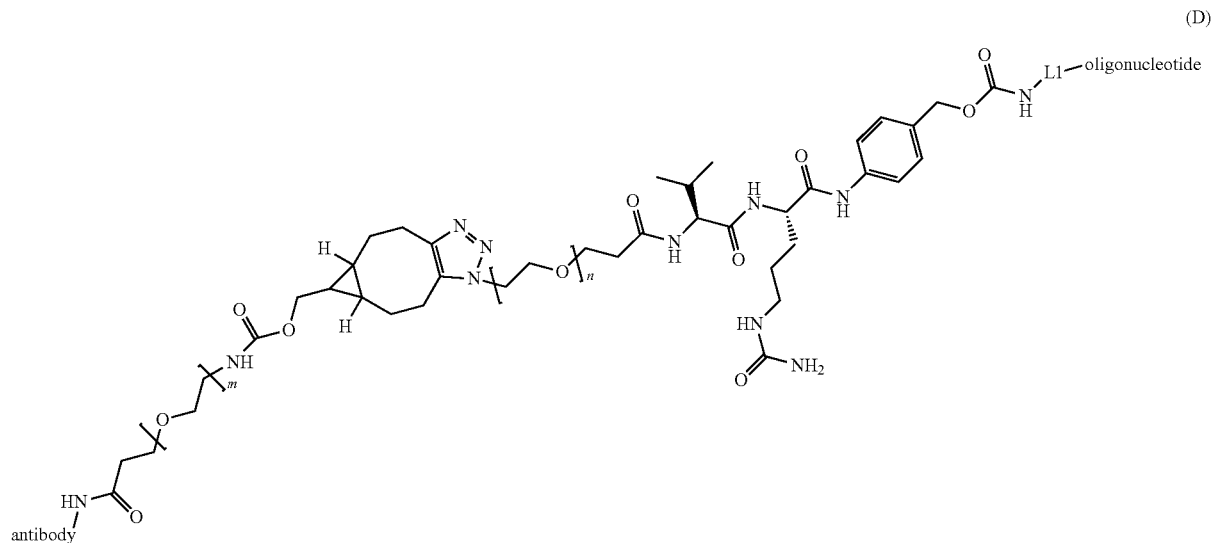

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, the complex described herein comprises an anti-TfR Fab covalently linked via a lysine to the 5' end of an oligonucleotide, wherein the anti-TfR Fab comprises a heavy chain comprising the amino acid sequence of SEQ ID NO: 102 and a light chain comprising the amino acid sequence of in SEQ ID NO: 95; wherein the complex has the structure of:

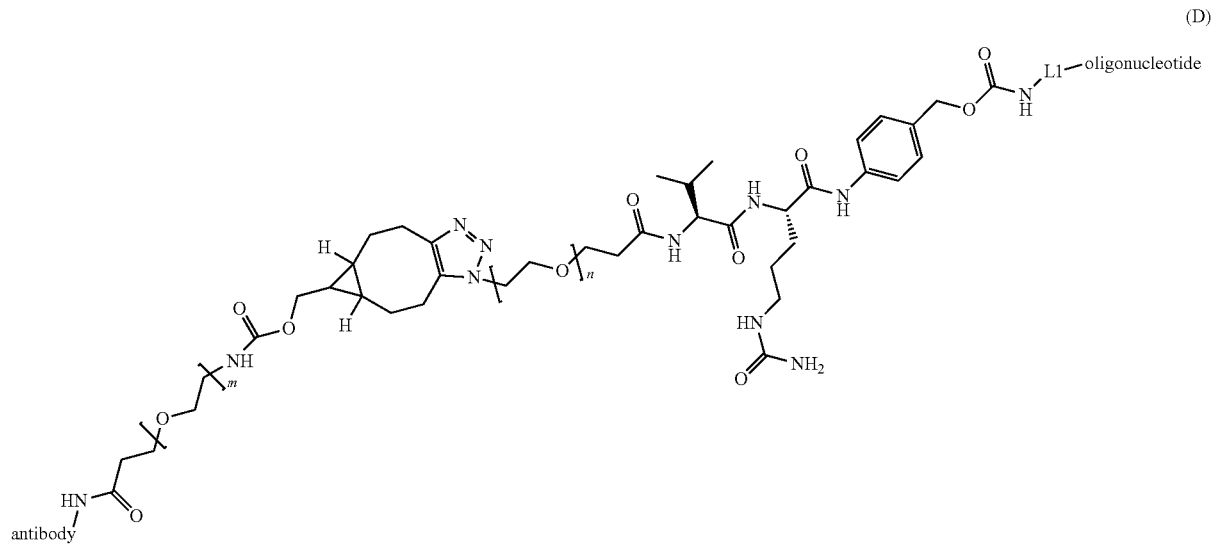

(D)

wherein n is 3 and m is 4. In some embodiments, the oligonucleotide is a DUX4-targeting oligonucleotide (e.g., an oligonucleotide comprising the nucleotide sequence of SEQ ID NO: 151).

In some embodiments, in any one of the examples of complexes described herein, L1 is any one of the spacers described herein.

In some embodiments, L1 is:

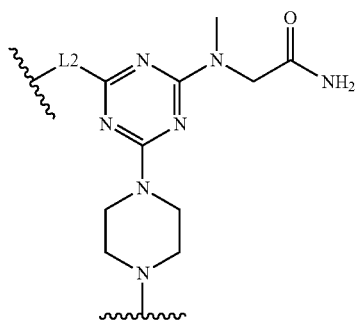

wherein the piperazine moiety links to the oligonucleotide, wherein L2 is

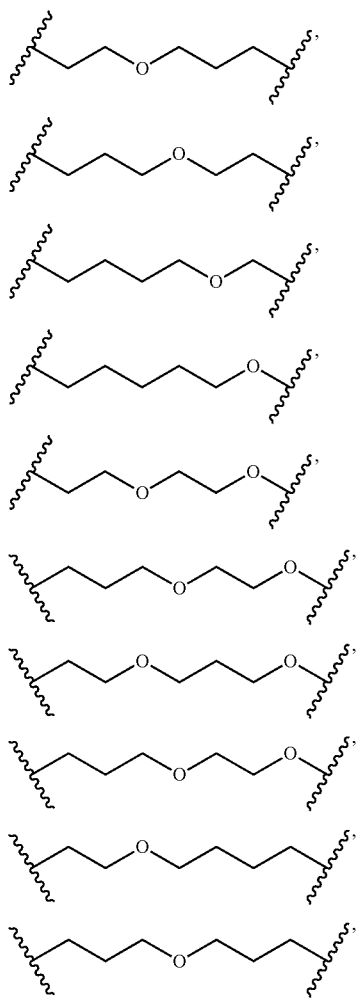

-continued

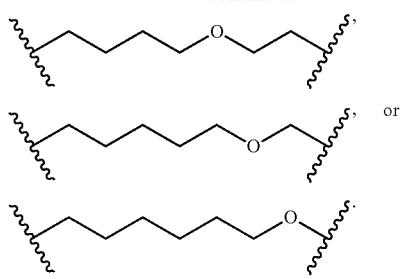

In some embodiments, L1 is:

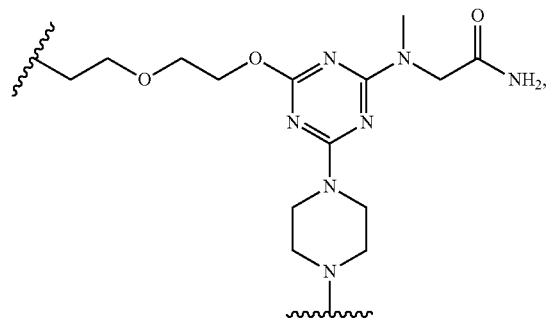 [SMILES: *CCOCCOc1nc(N(C)CC(N)=O)nc(N2CCN(*)CC2)n1]

wherein the piperazine moiety links to the oligonucleotide.

In some embodiments, L1 is

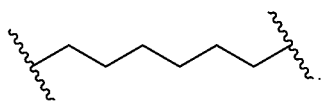 [SMILES: *CCCCCC*]

In some embodiments, L1 is linked to a 5' phosphate of the oligonucleotide.

In some embodiments, L1 is optional (e.g., need not be present).

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or (e.g., and) uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or (e.g., and) therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the complexes in a required amount in a selected solvent with one or a combination of ingredients enumerated above, as required, followed by filtered sterilization.

In some embodiments, a composition may contain at least about 0.1% of the complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently linked to a molecular payload as described herein are effective in treating FSHD. In some embodiments, complexes are effective in treating Type 1 FSHD. In some embodiments, complexes are effective in treating Type 2 FSHD. In some embodiments, FSHD is associated with deletions in D4Z4 repeat regions on chromosome 4 which contain the DUX4 gene. In some embodiments, FSHD is associated with mutations in the SMCHD1 gene.

In some embodiments, a subject may be a human subject, a non-human primate subject, a rodent subject, or any suitable mammalian subject. In some embodiments, a subject may have myotonic dystrophy. In some embodiments, a subject has elevated expression of the DUX4 gene outside of fetal development and the testes. In some embodiments, the subject has facioscapulohumeral muscular dystrophy of Type 1 or Type 2. In some embodiments, the subject having FSHD has mutations in the SMCHD1 gene. In some embodiments, the subject having FSHD has deletion mutations in D4Z4 repeat regions on chromosome 4.

An aspect of the disclosure includes methods involving administering to a subject an effective amount of a complex as described herein. In some embodiments, an effective amount of a pharmaceutical composition that comprises a complex comprising a muscle-targeting agent covalently linked to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently linked to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently linked to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment.

The efficacy of treatment may be assessed using any suitable methods. In some embodiments, the efficacy of treatment may be assessed by evaluation of observation of symptoms associated with FSHD including muscle mass loss and muscle atrophy, primarily in the muscles of the face, shoulder blades, and upper arms.

In some embodiments, a pharmaceutical composition that comprises a complex comprising a muscle-targeting agent covalently linked to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently linked to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently linked to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently linked to a molecular payload described herein to a subject is sufficient to inhibit activity or expression of a target gene for at least 1, 2, 3, 4, 5, or 6 months.

In some embodiments, a pharmaceutical composition may comprise more than one complex comprising a muscle-targeting agent covalently linked to a molecular payload. In some embodiments, a pharmaceutical composition may further comprise any other suitable therapeutic agent for treatment of a subject, e.g. a human subject having FSHD. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting Gene Expression with Transfected Antisense Oligonucleotides A siRNA that targets hypoxanthine phosphoribosyltransferase (HPRT) was tested in vitro for its ability to reduce expression levels of HPRT in an immortalized cell line. Briefly, Hepa 1-6 cells were transfected with either a control siRNA (siCTRL; 100 nM) or the siRNA that targets HPRT (siHPRT; 100 nM), formulated with lipofectamine 2000. HPRT expression levels were evaluated 48 hours following transfection. A control experiment was also performed in which vehicle (phosphate-buffered saline) was delivered to Hepa 1-6 cells in culture and the cells were maintained for 48 hours. As shown in FIG. 1, it was found that the HPRT siRNA reduced HPRT expression levels by about 90% compared with controls. Sequences of the siRNAs used are provided in Table 6.

TABLE 6

Sequences of siHPRT and siCTRL

| | Sequence | SEQ ID NO: |
|---|---|---|
| siHPRT sense strand | 5'-UcCuAuGaCuGuAgAuUuUaU-(CH$_2$)$_6$NH$_2$-3' | 152 |
| siHPRT antisense strand | 5'-aUaAaAuCuAcAgUcAuAgGasAsu-3' | 153 |
| siCTRL sense strand | 5'-UgUaAuAaCcAuAuCuAcCuU-(CH$_2$)$_6$NH$_2$-3' | 154 |
| siCTRL antisense strand | 5'-aAgGuAgAuAuGgUuAuUaCasAsa-3' | 155 |

*Lower case-2'-O-Me ribonucleosides; Capital letter-2'-Fluoro ribonucleosides; s-phosphorothioate linkage Example 2: Targeting HPRT with a Muscle-Targeting Complex A muscle-targeting complex was generated comprising the HPRT siRNA used in Example 1 (siHPRT) covalently linked, via a non-cleavable N-gamma-maleimidobutyryl-oxysuccinimide ester (GMBS) linker, to RI7 217 anti-TfR1 Fab (DTX-A-002), an anti-transferrin receptor antibody.

Briefly, the GMBS linker was dissolved in dry DMSO and coupled to the 3' end of the sense strand of siHPRT through amide bond formation under aqueous conditions. Completion of the reaction was verified by Kaiser test. Excess linker and organic solvents were removed by gel permeation chromatography. The purified, maleimide functionalized sense strand of siHPRT was then coupled to DTX-A-002 antibody using a Michael addition reaction.

The product of the antibody coupling reaction was then subjected to size exclusion chromatography (SEC) purification. antiTfR-siHPRT complexes comprising one or two siHPRT molecules covalently attached to DTX-A-002 antibody were purified. Densitometry confirmed that the purified sample of complexes had an average siHPRT to antibody ratio of 1.46. SDS-PAGE analysis demonstrated that >90% of the purified sample of complexes comprised DTX-A-002 linked to either one or two siHPRT molecules.

Using the same methods as described above, a control IgG2a-siHPRT complex was generated comprising the HPRT siRNA used in Example 1 (siHPRT) covalently linked via the GMBS linker to an IgG2a (Fab) antibody (DTX-A-003). Densitometry confirmed that DTX-C-001 (the IgG2a-siHPRT complex) had an average siHPRT to antibody ratio of 1.46 and SDS-PAGE demonstrated that >90% of the purified sample of control complexes comprised DTX-A-003 linked to either one or two siHPRT molecules.

Figure 2:
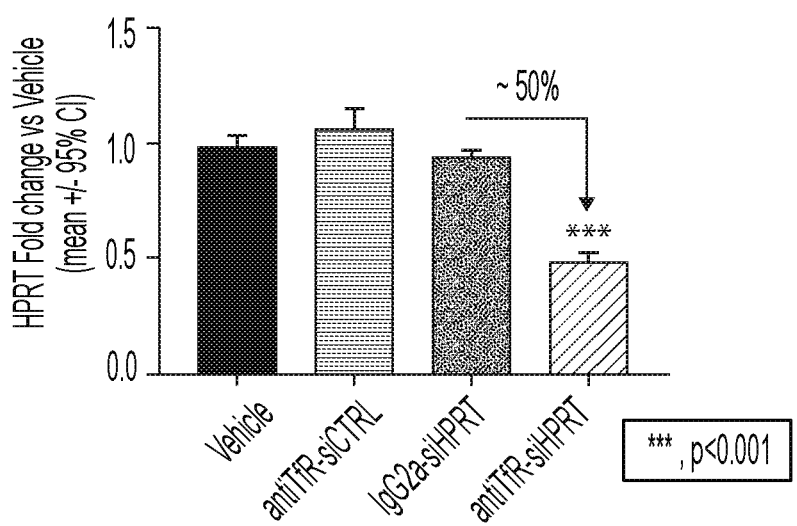
FIG. 2 depicts a non-limiting schematic showing the activity of a muscle targeting complex comprising an siRNA.

The antiTfR-siHPRT complex was then tested for cellular internalization and inhibition of HPRT in cellulo. Hepa 1-6 cells, which have relatively high expression levels of transferrin receptor, were incubated in the presence of vehicle (phosphate-buffered saline), IgG2a-siHPRT (100 nM), anti-TfR-siCTRL (100 nM), or antiTfR-siHPRT (100 nM), for 72 hours. After the 72 hour incubation, the cells were isolated and assayed for expression levels of HPRT (FIG. 2). Cells treated with the antiTfR-siHPRT demonstrated a reduction in HPRT expression by ~50% relative to the cells treated with the vehicle control and to those treated with the IgG2a-siHPRT complex. Meanwhile, cells treated with either of the IgG2a-siHPRT or antiTfR-siCTRL had HPRT expression levels comparable to the vehicle control (no reduction in HPRT expression). These data indicate that the anti-transferrin receptor antibody of the antiTfR-siHPRT enabled cellular internalization of the complex, thereby allowing the siHPRT to inhibit expression of HPRT.

Example 3: Targeting HPRT in Mouse Muscle Tissues with a Muscle-Targeting Complex The muscle-targeting complex described in Example 2, antiTfR-siHPRT, was tested for inhibition of HPRT in mouse tissues. C57BL/6 wild-type mice were intravenously injected with a single dose of a vehicle control (phosphate-buffered saline); siHPRT (2 mg/kg of siRNA); IgG2a-siHPRT (2 mg/kg of siRNA, corresponding to 9 mg/kg antibody complex); or antiTfR-siHPRT (2 mg/kg of siRNA, corresponding to 9 mg/kg antibody complex). Each experimental condition was replicated in four individual C57BL/6 wild-type mice. Following a three-day period after injection, the mice were euthanized and segmented into isolated tissue types. Individual tissue samples were subsequently assayed for expression levels of HPRT (FIGS. 3A-3B and 4A-4E).

Figure 3A:
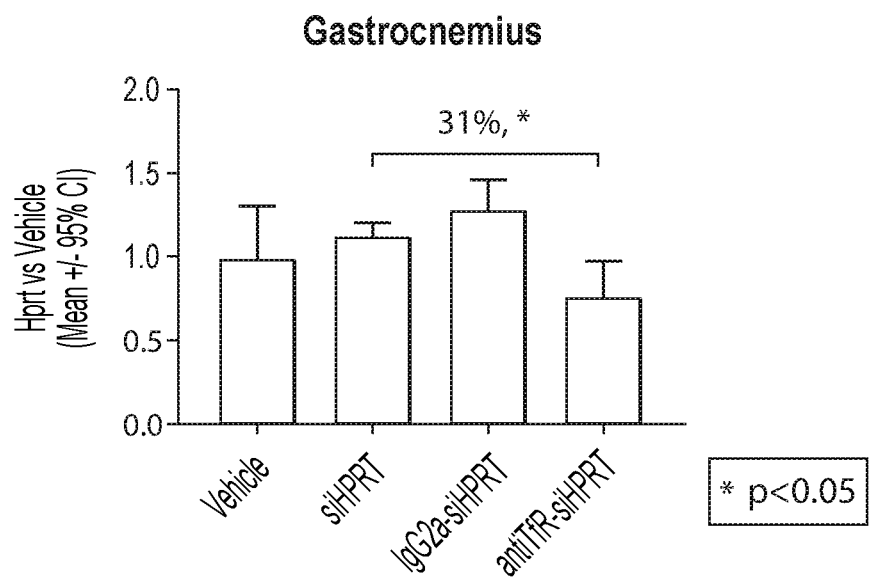
FIGS. 3A-3B depict non-limiting schematics showing the activity of a muscle targeting complex comprising an siRNA in mouse muscle tissues (gastrocnemius and heart) in vivo, relative to vehicle-treated controls. (N=4 C57BL/6 WT mice)
Figure 3B:
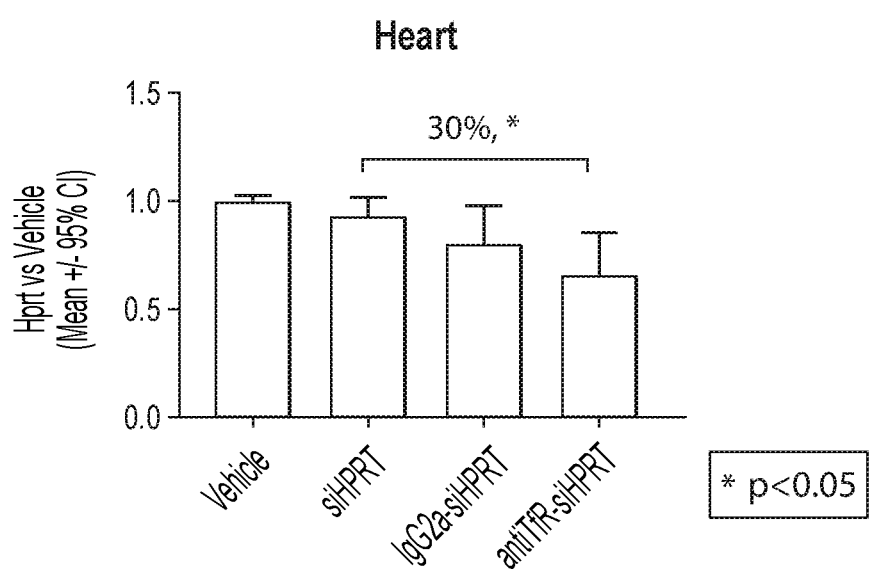
Figure 4A:
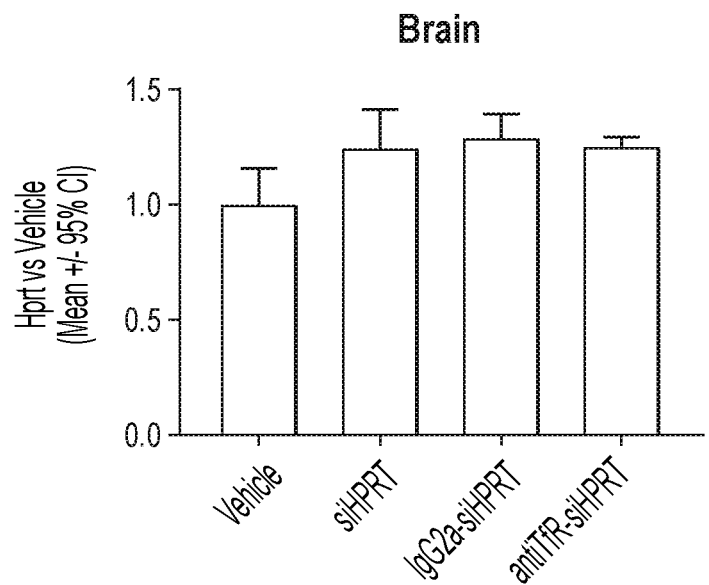
FIGS. 4A-4E depict non-limiting schematics showing the tissue selectivity of a muscle targeting complex comprising an siRNA.
Figure 4B:
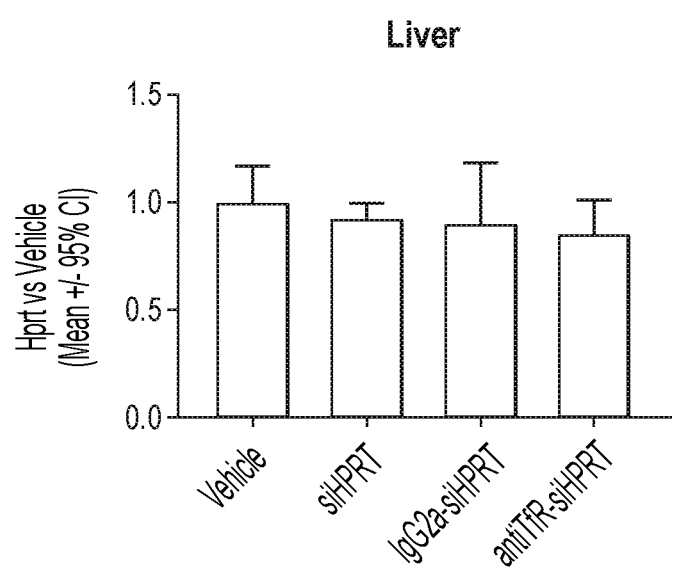
Figure 4C:
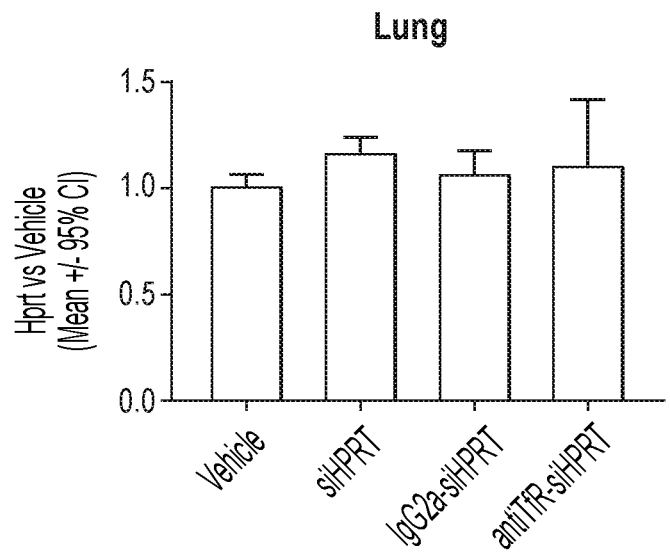
Figure 4D:
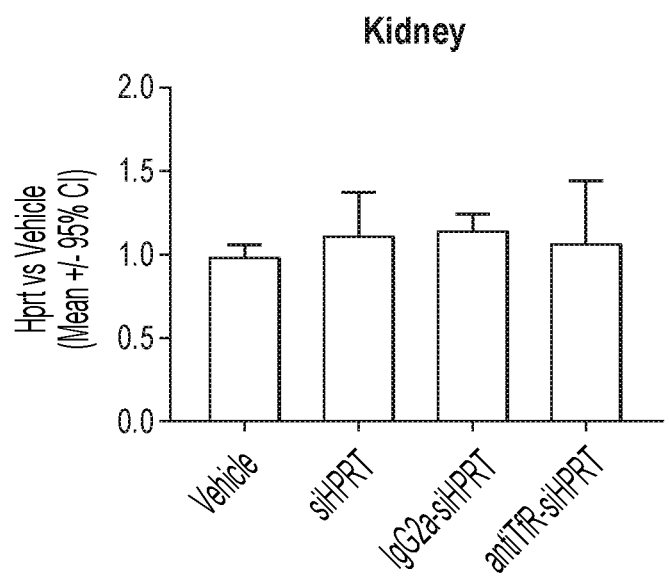
Figure 4E:
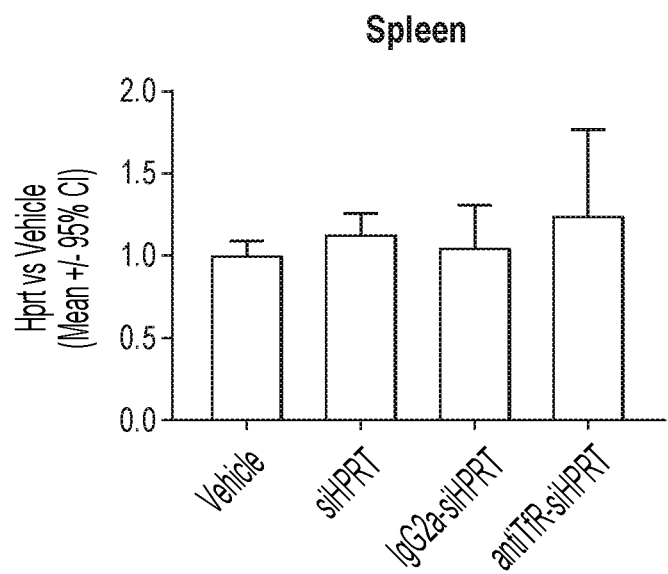

Mice treated with the antiTfR-siHPRT complex demonstrated a reduction in HPRT expression in gastrocnemius (31% reduction; p<0.05) and heart (30% reduction; p<0.05), relative to the mice treated with the siHPRT control (FIGS. 3A-3B). Meanwhile, the mice treated with the IgG2a-siHPRT complex had HPRT expression levels comparable to the siHPRT control (little or no reduction in HPRT expression) for all assayed muscle tissue types.

Mice treated with the antiTfR-siHPRT complex demonstrated no change in HPRT expression in non-muscle tissues such as brain, liver, lung, kidney, and spleen tissues (FIGS. 4A-4E).

These data indicate that the anti-transferrin receptor antibody of the antiTfR-siHPRT complex enabled cellular internalization of the complex into muscle-specific tissues in an in vivo mouse model, thereby allowing the siHPRT to inhibit expression of HPRT. These data further demonstrate that the antiTfR-oligonucleotide complexes of the current disclosure are capable of specifically targeting muscle tissues.

Example 4: Targeting DUX4 with Transfected Antisense Oligonucleotides

Figure 5:
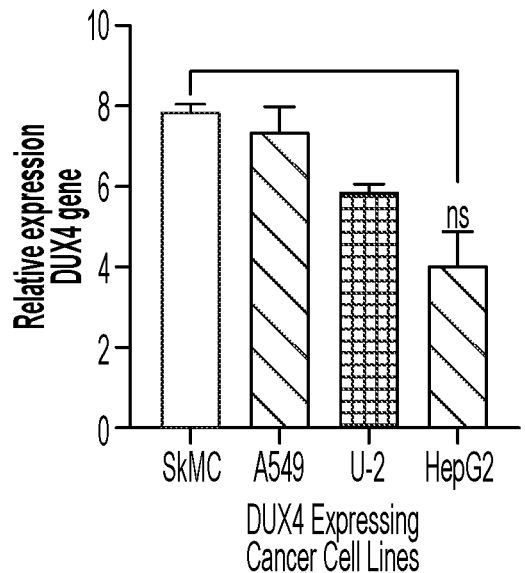
FIG. 5 depicts a non-limiting schematic showing the expression levels of DUX4 in three DUX4-expressing cell lines (A549, U-2 OS, and HepG2 cell lines) and immortalized skeletal muscle myoblasts (SkMC).

Three DUX4-expressing cell lines (A549, U-2 OS, and HepG2 cell lines) and immortalized skeletal muscle myoblasts (SkMC) were screened for expression of DUX4 mRNA (FIG. 5). Cells were seeded at a density of 10,000 cells/well and harvested for total RNA. cDNA was synthesized from the total RNA extracts and qPCR was performed to determine concentration of DUX4 relative to a control gene (PPIB) in technical quadruplicate. These data were used to aid in the selection of the U-2 OS cell line for downstream development of DUX4-targeting oligonucleotides.

Following selection of U-2 OS cells for development of DUX4-targeting oligonucleotides, a phosphorodiamidate morpholino oligomer (PMO) version of an antisense oligonucleotide that targets DUX4 (FM10 PMO) was evaluated for its ability to target DUX4 in vitro. FM10 PMO comprises the sequence GGGCATTTTAATATATCTCTGAACT (SEQ ID NO: 151). A control phosphorodiamidate morpholino oligomer (PMO), that comprises the sequence CCTCTTACCTCAGTTACAATTTATA (SEQ ID NO: 149), was utilized as a negative control.

Briefly, U-2 OS cells were seeded at a density of 10 k cells/well before being allowed to recover overnight. Cells were then treated with either a control PMO (10 µM) or with the FM10 PMO (10 µM). Cells were incubated for 72 hours before being harvested for total RNA. cDNA was then synthesized from the total RNA extracts and qPCR was performed to determine expression of downstream DUX4 genes (ZSCAN4, MBD3L2, TRIM43) in technical quadruplicate. All qPCR data were analyzed using a standard ΔΔCT method and were normalized to a plate-based negative control comprised of untreated cells (i.e., without any oligonucleotide). Results were then converted to fold change to evaluate efficacy.

Figure 6:
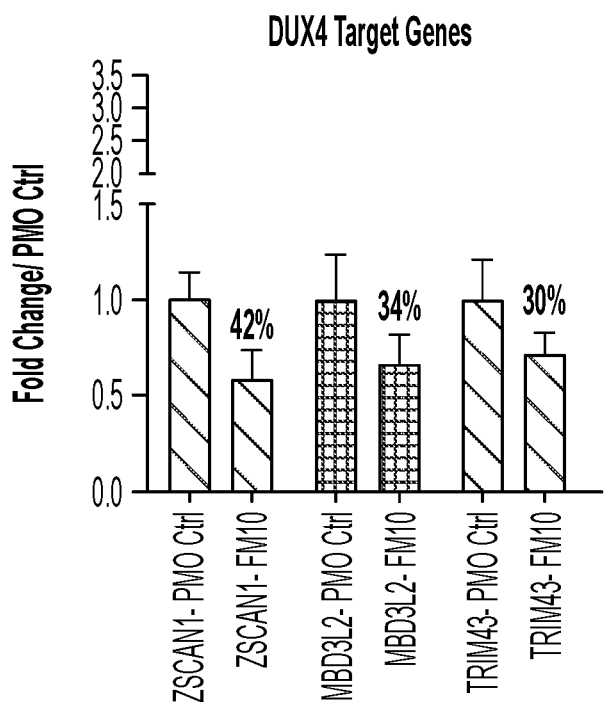
FIG. 6 depicts non-limiting schematics showing the ability of a phosphorodiamidate morpholino oligomer (PMO) version of an antisense oligonucleotide that targets DUX4 (FM10 PMO) to reduce expression levels of downstream DUX4 genes (ZSCAN4, MBD3L2, TRIM43).

As shown in FIG. 6, all of ZSCAN4, MBD3L2, and TRIM43 showed decreased expression in the presence of the FM10 PMO compared to the control PMO (42%, 34%, and 32%; respectively). These data demonstrate that the FM10 PMO is capable of targeting DUX4 in vitro.

Example 5: Targeting DUX4 with a Muscle-Targeting Complex

A muscle-targeting complex is generated comprising an antisense oligonucleotide that targets a mutant allele of DUX4 (DUX4 ASO) covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule is coupled to NH$_2$—C$_6$-DUX4 ASO using an amide coupling reaction. Excess linker and organic solvents are removed by gel permeation chromatography. The purified Val-Cit-linker-DUX4 ASO is then coupled to a thiol on the anti-transferrin receptor antibody (DTX-A-002).

The product of the antibody coupling reaction is then subjected to hydrophobic interaction chromatography (HIC-HPLC) to purify the muscle-targeting complex. Densitometry and SDS-PAGE analysis of the purified complex allow for determination of the average ratio of ASO-to-antibody and total purity, respectively.

Using the same methods as described above, a control complex is generated comprising DUX4 ASO covalently linked via a Val-Cit linker to an IgG2a (Fab) antibody.

The purified muscle-targeting complex comprising DTX-A-002 covalently linked to DUX4 ASO is then tested for cellular internalization and inhibition of DUX4. Disease-relevant muscle cells that have relatively high expression levels of transferrin receptor, are incubated in the presence of vehicle control (saline), muscle-targeting complex (100 nM), or control complex (100 nM) for 72 hours. After the 72 hour incubation, the cells are isolated and assayed for expression levels of DUX4.

Example 6: A Muscle-Targeting Complex Enables Cellular Internalization and Targeting of DUX4

A muscle-targeting complex (anti-TfR antibody-FM10) was generated comprising the FM10 PMO covalently linked to an anti-transferrin receptor antibody.

Briefly, purified Val-Cit-linker-FM10 was coupled to a functionalized 15G11 antibody generated through modifying ε-amine on lysine of the antibody.

The product of the antibody coupling reaction was then purified. Ultrafiltration was then used to concentrate the conjugate and densitometry confirmed that this sample of anti-TfR antibody-FM10 complexes had an average ASO to antibody ratio of 1.9.

FM10 PMO comprises the sequence GGGCATTT-TAATATATCTCTGAACT (SEQ ID NO: 151).

Human U-2 OS cells were dosed with the complex. Briefly, U-2 OS cells were seeded at a density of 10 k cells/well before being allowed to recover overnight. Cells were then treated with one of the following treatments—vehicle control (PBS), a siRNA that targets DUX4, naked FM10 PMO (1 μM), naked FM10 PMO (10 μM), or anti-TfR antibody-FM10 (1 μM; equivalent to 800 nM naked PMO). Cells were incubated for 72 hours before being harvested for total RNA. cDNA was then synthesized from the total RNA extracts and qPCR was performed to determine expression of downstream DUX4 genes (ZSCAN4, MBD3L2, TRIM43) in technical quadruplicate. All qPCR data were analyzed using a standard ΔΔCT method and were normalized to a plate-based negative control comprised of untreated cells (i.e., without any oligonucleotide). Results were then converted to fold change to evaluate efficacy.

Figure 7:
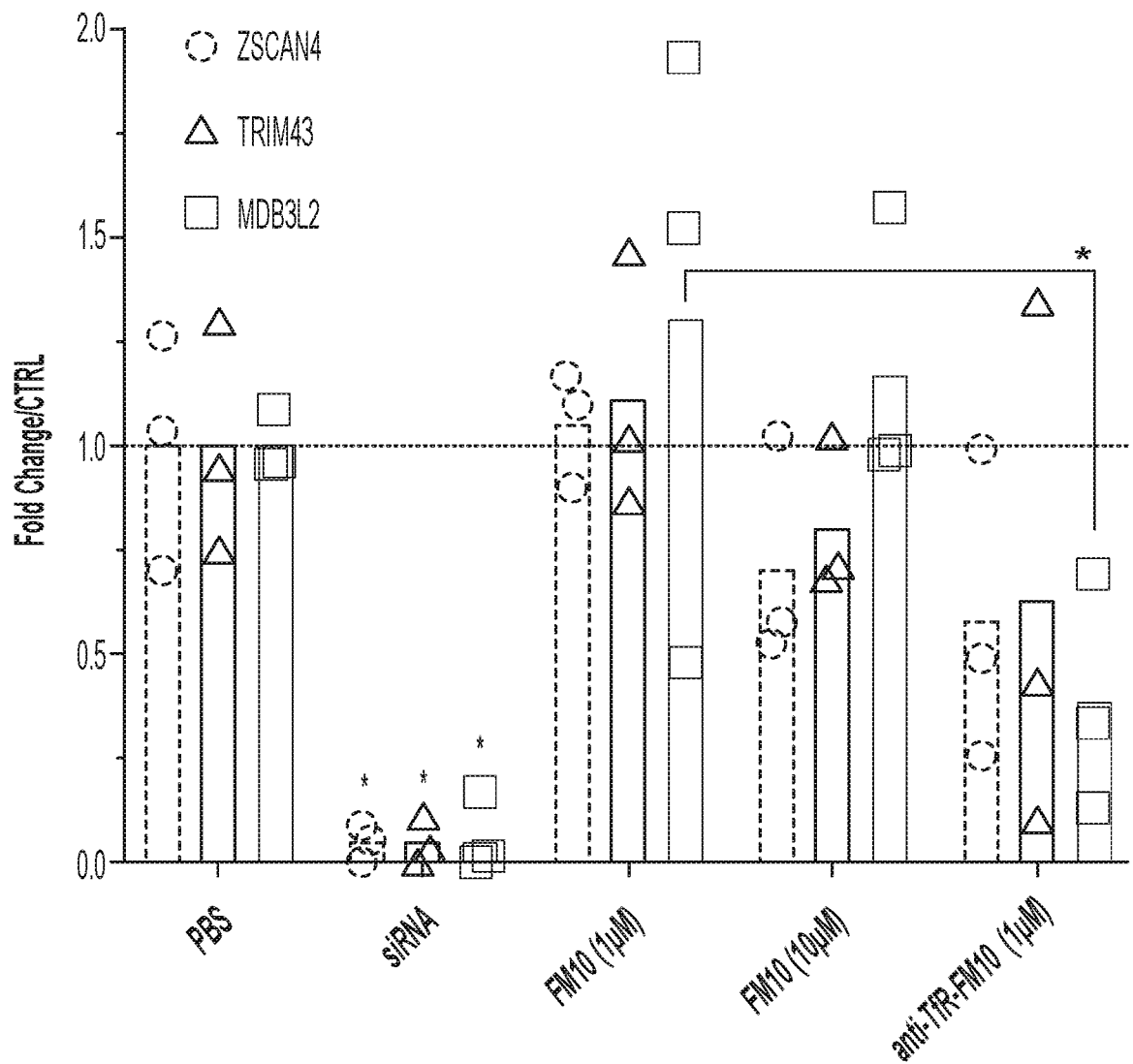
FIG. 7 depicts a non-limiting schematic showing the ability of a muscle-targeting complex (anti-TfR antibody-FM10) comprising an anti-TfR1 Fab (RI7 217) conjugated to FM10 antisense oligonucleotide to reduce expression levels of downstream DUX4 genes (ZSCAN4, MBD3L2, TRIM43) in human U-2 OS cells, relative to naked FM10 antisense oligonucleotide.

As shown in FIG. 7, upregulation of DUX4 in FSHD leads to the upregulation of disease characteristic genes including ZSCAN4, MBD3L2, and TRIM43. In U-2 OS cells that express DUX4 and have elevated levels of ZSCAN4, MDB3L2 and TRIM43, mirroring pathologically relevant events in FSHD patient cells, treatment with naked FM10 at 1 μM fails to reduce ZSCAN4, MBD3L2, and TRIM43 expression. Increased concentration of naked FM10 (to 10 μM) leads to a modest reduction in ZSCAN4 and TRIM43 expression, but has no effect on MDB3L2 expression. In contrast, treatment with anti-TfR antibody-FM10 (1 μM concentration; equivalent to 800 nM of naked FM10) significantly reduced expression of MBD3L2, ZSCAN4 and TRIM43.

These data indicate that the anti-transferrin receptor antibody of the anti-TfR antibody-FM10 complex enabled cellular internalization of the complex into U-2 OS cells, thereby allowing the FM10 PMO to inhibit expression of DUX4.

Example 7: Binding Affinity of Selected Anti-TfR1 Antibodies to Human TfR1

Selected anti-TfR1 antibodies were tested for their binding affinity to human TfR1 for measurement of Ka (association rate constant), Kd (dissociation rate constant), and $K_D$(affinity). Two known anti-TfR1 antibodies were used as control, 15G11 and OKT9. The binding experiment was performed on Carterra LSA at 25° C. An anti-mouse IgG and anti-human IgG antibody "lawn" was prepared on a HC30M chip by amine coupling. The IgGs were captured on the chip. Dilution series of hTfR1, cyTfR1, and hTfR2 were injected to the chip for binding (starting from 1000 nM, 1:3 dilution, 8 concentrations).

Binding data were referenced by subtracting the responses from a buffer analyte injection and globally fitting to a 1:1 Langmuir binding model for estimate of Ka (association rate constant), Kd (dissociation rate constant), and $K_D$ (affinity) using the Carterra™ Kinetics software. 5-6 concentrations were used for curve fitting.

The result showed that the mouse mAbs demonstrated binding to hTfR1 with $K_D$ values ranging from 13 μM to 50 nM. A majority of the mouse mAbs had $K_D$ values in the single digit nanomolar to sub-nanomolar range. The tested mouse mAbs showed cross-reactive binding to cyTfR1 with $K_D$ values ranging from 16 μM to 22 nM.

Ka, Kd, and $K_D$ values of anti-TfR1 antibodies are provided in Table 10.

TABLE 10

Ka, Kd, and $K_D$ values of anti-TfR1 antibodies

| Name | $K_D$ (M) | Ka (M) | Kd (M) |
|---|---|---|---|
| ctrl-15G11 | 2.83E−10 | 3.70E+05 | 1.04E−04 |
| ctrl-OKT9 mIgG | 5.36E−10 | 7.74E+05 | 4.15E−04 |
| 3-A04 | 4.36E−10 | 4.47E+05 | 1.95E−04 |
| 3-M12 | 7.68E−10 | 1.66E+05 | 1.27E−04 |
| 5-H12 | 2.08E−07 | 6.67E+04 | 1.39E−02 |

Example 8: Conjugation of Anti-TfR1 Antibodies with Oligonucleotides

Complexes containing an anti-TfR1 antibody covalently conjugated to a tool oligo (ASO300) were generated. First, Fab fragments of anti-TfR antibody clones 3-A4, 3-M12, and 5-H12 were prepared by cutting the mouse monoclonal antibodies with an enzyme in or below the hinge region of the full IgG followed by partial reduction. The Fabs were confirmed to be comparable to mAbs in avidity or affinity.

Muscle-targeting complexes were generated by covalently linking the anti-TfR mAbs to the ASO300 via a cathepsin cleavable linker. Briefly, a Bicyclo[6.1.0]nonyne-PEG3-L-valine-L-citrulline-pentafluorophenyl ester (BCN-PEG3-Val-Cit-PFP) linker molecule was coupled to ASO300 through a carbamate bond. Excess linker and organic solvents were removed by tangential flow filtration (TFF). The purified Val-Cit-linker-ASO was then coupled to an azide functionalized anti-transferrin receptor antibody generated through modifying F-amine on lysine with Azide-PEG4-PFP. A positive control muscle-targeting complex was also generated using 15G11.

The product of the antibody coupling reaction was then subjected to two purification methods to remove free antibody and free payload. Concentrations of the conjugates were determined by either Nanodrop A280 or BCA protein assay (for antibody) and Quant-It Ribogreen assay (for payload). Corresponding drug-antibody ratios (DARs) were calculated. DARs ranged between 0.8 and 2.0, and were standardized so that all samples receive equal amounts of payload.

The purified complexes were then tested for cellular internalization and inhibition of the target gene, DMPK. Non-human primate (NHP) or DM1 (donated by DM1 patients) cells were grown in 96-well plates and differentiated into myotubes for 7 days. Cells were then treated with escalating concentrations (0.5 nM, 5 nM, 50 nM) of each complex for 72 hours. Cells were harvested, RNA was isolated, and reverse transcription was performed to generate cDNA. qPCR was performed using TaqMan kits specific for Ppib (control) and DMPK on the QuantStudio 7. The relative amounts of remaining DMPK transcript in treated vs non-treated cells were calculated and the results are shown in Table 11.

The results demonstrated that the anti-TfR1 antibodies are able to target muscle cells, be internalized by the muscle cells with the molecular payload (the tool oligo ASO300), and that the molecular payload (DMPK ASO) is able to target and knockdown the target gene (DMPK). Knockdown activity of a complex comprising the anti-TfR1 antibody conjugated to a molecular payload (e.g., an oligonucleotide) targeting DUX4 can be tested in the same assay using an oligonucleotide targeting DUX4 such as the FM10 oligonucleotide.

TABLE 11

Binding Affinity of anti-TfR1 Antibodies and Efficacy of Conjugates

| Clone Name | huTfR1 Avg $K_D$ (M) (antibody alone) | cyTfR1 Avg $K_d$ (M) (antibody alone) | % knockdown of DMPK in NHP cells using Antibody-DMPK ASO conjugate | % knockdown of DMPK in cells from human DM1 patients using Antibody-DMPK ASO conjugate |
|---|---|---|---|---|
| 15G11 (control) | 8.0E−10 | 1.0E−09 | 36 | 46 |
| 3-A4 | 4.36E−10 | 2.32E−09 | 77 | 70 |
| 3-M12 | 7.68E−10 | 5.18E−09 | 77 | 52 |
| 5-H12 | 2.02316E−07 | 1.20E−08 | 88 | 57 |

Interestingly, the DMPK knockdown results showed a lack of correlation between the binding affinity of the anti-TfR to transferrin receptor and efficacy in delivering a DMPK ASO to cells for DMPK knockdown. Surprisingly, the anti-TfR antibodies provided herein (e.g., at least 3-A4, 3-M12, and 5-H12) demonstrated superior activity in delivering a payload (e.g., DMPK ASO) to the target cells and achieving the biological effect of the molecular payload (e.g., DMPK knockdown) in either cyno cells or human DM1 patient cells, compared to the control antibody 15G11, despite the comparable binding affinity (or, in certain instances, such as 5-H12, lower binding affinity) to human or cyno transferrin receptor between these antibodies and the control antibody 15G11.

Top attributes such as high huTfR1 affinity, >50% knockdown of DMPK in NHP and DM1 patient cell line, identified epitope binding with 3 unique sequences, low/no predicted PTM sites, and good expression and conjugation efficiency led to the selection of the top 3 clones for humanization, 3-A4, 3-M12, and 5-H12.

Example 9: Humanized Anti-TfR1 Antibodies

The anti-TfR antibodies shown in Table 2 were subjected to humanization and mutagenesis to reduce manufacturability liabilities. The humanized variants were screened and tested for their binding properties and biological actives. Humanized variants of anti-TfR1 heavy and light chain variable regions (5 variants each) were designed using Composite Human Technology. Genes encoding Fabs having these heavy and light chain variable regions were synthesized, and vectors were constructed to express each humanized heavy and light chain variant. Subsequently, each vector was expressed on a small scale and the resultant humanized anti-TfR1 Fabs were analyzed. Humanized Fabs were selected for further testing based upon several criteria including Biocore assays of antibody affinity for the target antigen, relative expression, percent homology to human germline sequence, and the number of MHC class II predicted T cell epitopes (determined using iTope™ MCH class II in silico analysis).

Potential liabilities were identified within the parental sequence of some antibodies by introducing amino acid substitutions in the heavy chain and light chain variable regions. These substitutions were chosen based on relative expression levels, iTope™ score and relative $K_D$ from Biacore single cycle kinetics analysis. The humanized variants were tested and variants were selected initially based upon affinity for the target antigen. Subsequently, the selected humanized Fabs were further screened based on a series of biophysical assessments of stability and susceptibility to aggregation and degradation of each analyzed variant, shown in Table 13 and Table 14. The selected Fabs were analyzed for their properties binding to TfR1 by kinetic analysis. The results of these analyses are shown in Table 7. For conjugates shown in Table 13 and Table 14, the selected humanized Fabs were conjugated to a DMPK-targeting oligonucleotide ASO300. The selected Fabs are thermally stable, as indicated by the comparable binding affinity to human and cyno TfR1 after been exposed to high temperature (40° C.) for 9 days, compared to before the exposure (see Table 7).

TABLE 13

Biophysical assessment data for humanized anti-TfR Fabs

| | Variant | | | | |
|---|---|---|---|---|---|
| Criteria | 3M12 (VH3/Vk2) | 3M12 (VH3/Vk3) | 3M12 (VH4/Vk2) | 3M12 (VH4/Vk3) | 3A4 (VH3-N54T/Vk4) |
| Binding Affinity (Biacore d0) | 395 pM | 345 pM | 396 pM | 341 pM | 3.09 nM |
| Binding Affinity (Biacore d25) | 567 pM | 515 pM | 510 pM | 486 pM | 3.01 nM |
| Fab binding affinity ELISA (human/cyno TfR1) | 0.8 nM/ 9.9 nM | 0.6 nM/ 4.7 nM | 0.4 nM/ 1.4 nM | 0.5 nM/ 2.2 nM | 2.6 nM/ 156 nM* |
| Conjugate binding affinity ELISA (human/cyno TfR1) | 2.2 nM/ 2.9 nM | N/A | N/A | 1.7 nM/ 2.1 nM | 2.8 nM/ 4.7 nM |

TABLE 13-continued

Biophysical assessment data for humanized anti-TfR Fabs

...

| Criteria | Variant | | | | |
|---|---|---|---|---|---|
| | 3A4 (VH3-N54S/Vk4) | 3A4 (VH3/Vk4) | 5H12 (VH5-C33Y/Vk3) | 5H12 (VH5-C33D/Vk4) | 5H12 (VH4-C33Y/Vk4) |
| Binding Affinity (Biacore d0) | 1.34 nM | 1.5 nM | 627 pM | 991 pM | 626 pM |
| Binding Affinity (Biacore d25) | 1.39 nM | 1.35 nM | 1.07 nM | 3.01 nM | 1.33 nM |
| Fab binding affinity ELISA (human/cyno TfR1) | 1.6 nM/ 398 nM* | 1.5 nM/ 122 nM* | 6.3 nM/ 2.1 nM | 6.0 nM/ 3.5 nM | 2.8 nM/ 3.3 nM |
| Conjugate binding affinity ELISA (human/cyno TfR1) | 2.9 nM/ 7.8 nM | 2.8 nM/ 7.6 nM | 33.4 nM/ 2.3 nM | 110 nM/ 10.2 nM | 23.7 nM/ 3.3 nM |

*Regains cyno binding after conjugation;

TABLE 14

Thermal Stability for humanized anti-TfR Fabs and conjugates

| Criteria | Variant | | | | |
|---|---|---|---|---|---|
| | 3M12 (VH3/Vk2) | 3M12 (VH3/Vk3) | 3M12 (VH4/Vk2) | 3M12 (VH4/Vk3) | 3A4 (VH3-N54T/Vk4) |
| Binding affinity hTfR1 d0 (nM) | 0.8 | 0.6 | 0.4 | 0.5 | 2.6 |
| Binding affinity hTfR1 d9 (nM) | 0.98 | 1.49 | 0.50 | 0.28 | 0.40 |
| Binding affinity cyno TfR1 d0 (nM) | 9.9 | 4.7 | 1.4 | 2.2 | 156 |
| Binding affinity cyno TfR1 d9 (nM) | 19.51 | 15.58 | 5.01 | 16.40 | 127.50 |
| DMPK oligo conjugate binding to hTfR1 (nM) | 1.14 | N/A | N/A | 1.18 | 2.22 |
| DMPK oligo conjugate binding to cyno TfR1 (nM) | 2.26 | N/A | N/A | 1.85 | 5.12 |

...

| Criteria | Variant | | | | |
|---|---|---|---|---|---|
| | 3A4 (VH3-N54S/Vk4) | 3A4 (VH3/Vk4) | 5H12 (VH5-C33Y/Vk3) | 5H12 (VH5-C33D/Vk4) | 5H12 (VH4-C33Y/Vk4) |
| Binding affinity hTfR1 d0 (nM) | 1.6 | 1.5 | 6.3 | 6 | 2.8 |
| Binding affinity hTfR1 d9 (nM) | 0.65 | 0.46 | 71.90 | 92.34 | 1731.00 |
| Binding affinity cyno TfR1 d0 (nM) | 398 | 122 | 2.1 | 3.5 | 3.3 |
| Binding affinity cyno TfR1 d9 (nM) | 248.30 | 878.40 | 0.69 | 0.63 | 0.26 |
| DMPK oligo conjugate binding to hTfR1 (nM) | 2.71 | 2.837 | N/A | 110.5 | 13.9 |
| DMPK oligo conjugate binding to cyno TfR1 (nM) | 4.1 | 7.594 | N/A | 10.18 | 13.9 |

TABLE 7

Kinetic analysis of humanized anti-TfR Fabs binding to TfR1

| Humanized anti-TfR Fabs | $k_a$ (1/Ms) | $k_d$ (1/s) | $K_D$ (M) | $R_{MAX}$ | $Chi^2$ ($RU^2$) |
|---|---|---|---|---|---|
| 3A4 (VH3/Vk4) | 7.65E+10 | 1.15E+02 | 1.50E−09 | 48.0 | 0.776 |
| 3A4 (VH3-N54S/Vk4) | 4.90E+10 | 6.56E+01 | 1.34E−09 | 49.4 | 0.622 |
| 3A4 (VH3-N54T/Vk4) | 2.28E+05 | 7.05E−04 | 3.09E−09 | 61.1 | 1.650 |
| 3M12 (VH3/Vk2) | 2.64E+05 | 1.04E−04 | 3.95E−10 | 78.4 | 0.037 |

TABLE 7-continued

Kinetic analysis of humanized anti-TfR Fabs binding to TfR1

| Humanized anti-TfR Fabs | $k_a$ (1/Ms) | $k_d$ (1/s) | $K_D$ (M) | $R_{MAX}$ | Chi² (RU²) |
|---|---|---|---|---|---|
| 3M12 (VH3/Vk3) | 2.42E+05 | 8.34E−05 | 3.45E−10 | 91.1 | 0.025 |
| 3M12 (VH4/Vk2) | 2.52E+05 | 9.98E−05 | 3.96E−10 | 74.8 | 0.024 |
| 3M12 (VH4/Vk3) | 2.52E+05 | 8.61E−05 | 3.41E−10 | 82.4 | 0.030 |
| 5H12 (VH5-C33D/Vk4) | 6.78E+05 | 6.72E−04 | 9.91E−10 | 49.3 | 0.093 |
| 5H12 (VH5-C33Y/Vk3) | 1.95E+05 | 1.22E−04 | 6.27E−10 | 68.5 | 0.021 |
| 5H12 (VH5-C33Y/Vk4) | 1.86E+05 | 1.17E−04 | 6.26E−10 | 75.2 | 0.026 |

Binding of Humanized Anti-TfR1 Fabs to TfR1 (ELISA)

To measure binding of humanized anti-TfR antibodies to TfR1, ELISAs were conducted. High binding, black, flat bottom, 96 well plates (Corning #3925) were first coated with 100 µL/well of recombinant huTfR1 at 1 µg/mL in PBS and incubated at 4° C. overnight. Wells were emptied and residual liquid was removed. Blocking was conducted by adding 200 µL of 1% BSA (w/w) in PBS to each well. Blocking was allowed to proceed for 2 hours at room temperature on a shaker at 300 rpm. After blocking, liquid was removed and wells were washed three times with 300 µL of TBST. Anti-TfR1 antibodies were then added in 0.5% BSA/TBST in triplicate in an 8 point serial dilution (dilution range 5 µg/mL-5 ng/mL). A positive control and isotype controls were also included on the ELISA plate. The plate was incubated at room temperature on an orbital shaker for 60 minutes at 300 rpm, and the plate was washed three times with 300 µL of TBST. Anti-(H+L)IgG-A488 (1:500) (Invitrogen #A11013) was diluted in 0.5% BSA in TBST, and 100 µL was added to each well. The plate was then allowed to incubate at room temperature for 60 minutes at 300 rpm on orbital shaker. The liquid was removed and the plate was washed four times with 300 µL of TBST. Absorbance was then measured at 495 nm excitation and 50 nm emission (with a 15 nm bandwidth) on a plate reader. Data was recorded and analyzed for $EC_{50}$. The data for binding to human TfR1 (hTfR1) for the humanized 3M12, 3A4 and 5H12 Fabs are shown in FIGS. 9A, 9C, and 9E, respectively. ELISA measurements were conducted using cynomolgus monkey (*Macaca fascicularis*) TfR1 (cTfR1) according to the same protocol described above for hTfR1, and results are shown in FIGS. 9B, 9D, and 9F.

Results of these two sets of ELISA analyses for binding of the humanized anti-TfR Fabs to hTfR1 and cTfR1 demonstrate that humanized 3M12 Fabs show consistent binding to both hTfR1 and cTfR1, and that humanized 3A4 Fabs show decreased binding to cTfR1 relative to hTfR1.

Antibody-oligonucleotide conjugates were prepared using six humanized anti-TfR Fabs, each of which were conjugated to a DMPK targeting oligonucleotide ASO300. Conjugation efficiency and down-stream purification were characterized, and various properties of the product conjugates were measured. The results demonstrate that conjugation efficiency was robust across all 10 variants tested, and that the purification process (hydrophobic interaction chromatography followed by hydroxyapatite resin chromatography) were effective. The purified conjugates showed a >97% purity as analyzed by size exclusion chromatography.

Figure 10:
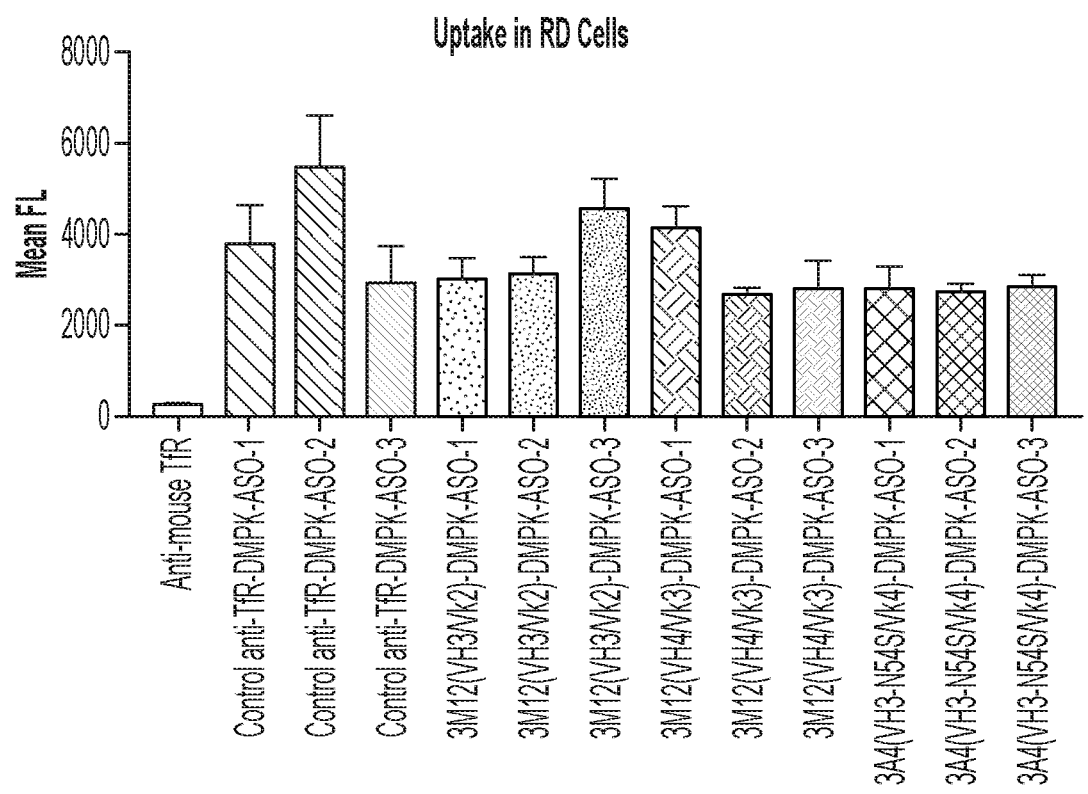
FIG. 10 shows the quantified cellular uptake of anti-TfR Fab conjugates into rhabdomyosarcoma (RD) cells. The molecular payload in the tested conjugates are DMPK-targeting oligonucleotides and the uptake of the conjugates were facilitated by indicated anti-TfR Fabs. Conjugates having a negative control Fab (anti-mouse TfR) or a positive control Fab (anti-human TfR1) are also included this assay. Cells were incubated with indicated conjugate at a concentration of 100 nM for 4 hours. Cellular uptake was measured by mean Cypher5e fluorescence.

Several humanized Fabs were tested in cellular uptake experiments to evaluate TfR1-mediated internalization. To measure such cellular uptake mediated by antibodies, humanized anti-TfR Fab conjugates were labeled with Cypher5e, a pH-sensitive dye. Rhabdomyosarcoma (RD) cells were treated for 4 hours with 100 nM of the conjugates, trypsinized, washed twice, and analyzed by flow cytometry. Mean Cypher5e fluorescence (representing uptake) was calculated using Attune NxT software. As shown in FIG. 10, the humanized anti-TfR Fabs show similar or greater endosomal uptake compared to a positive control anti-TfR1 Fab. Similar internalization efficiencies were observed for different oligonucleotide payloads. An anti-mouse TfR antibody was used as the negative control. Cold (non-internalizing) conditions abrogated the fluorescence signal of the positive control antibody-conjugate (data not shown), indicating that the positive signal in the positive control and humanized anti-TfR Fab-conjugates is due to internalization of the Fab-conjugates. Similarly, oligonucleotides targeting DUX4 can also be conjugated to the humanized anti-TfR Fabs and be internalized to muscle cells.

Figure 11A:
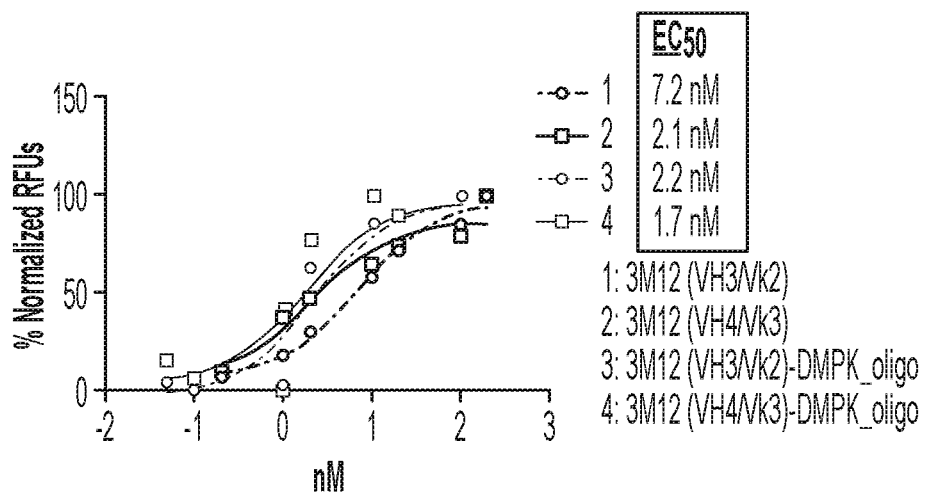
FIGS. 11A-11F show binding of oligonucleotide-conjugated or unconjugated humanized anti-TfR Fabs to human TfR1 (hTfR1) and cynomolgus monkey TfR1 (cTfR1), as measured by ELISA.
Figure 11B:
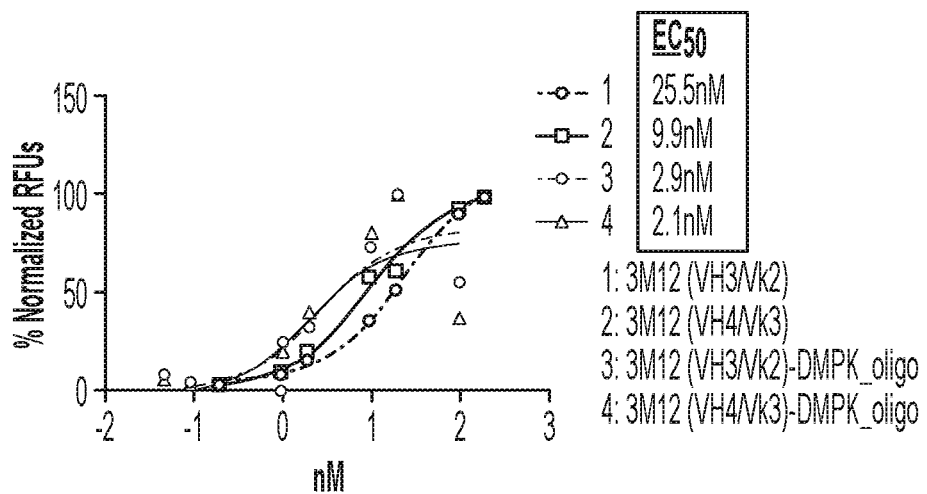
Figure 11C:
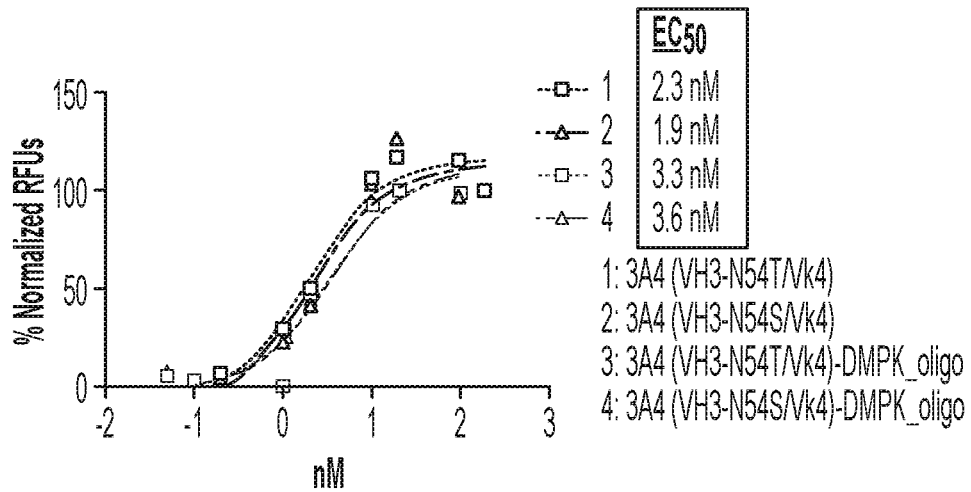
Figure 11D:
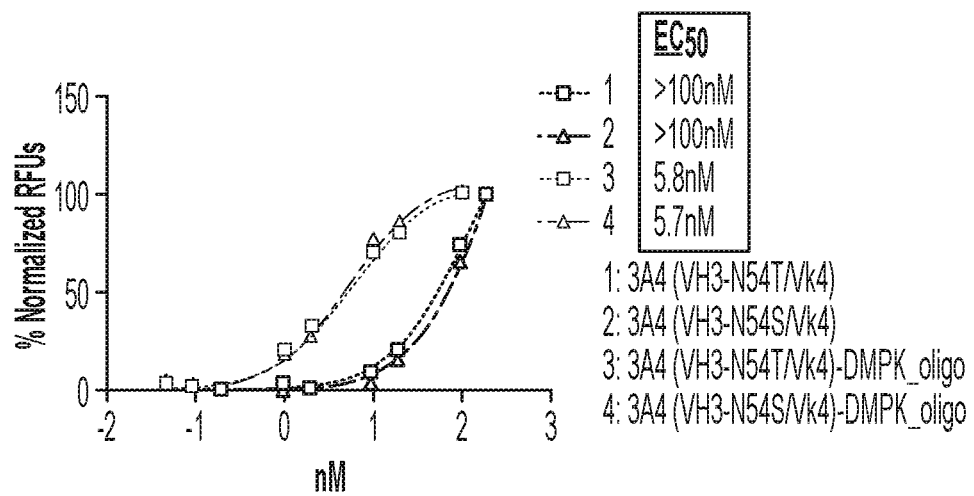
Figure 11E:
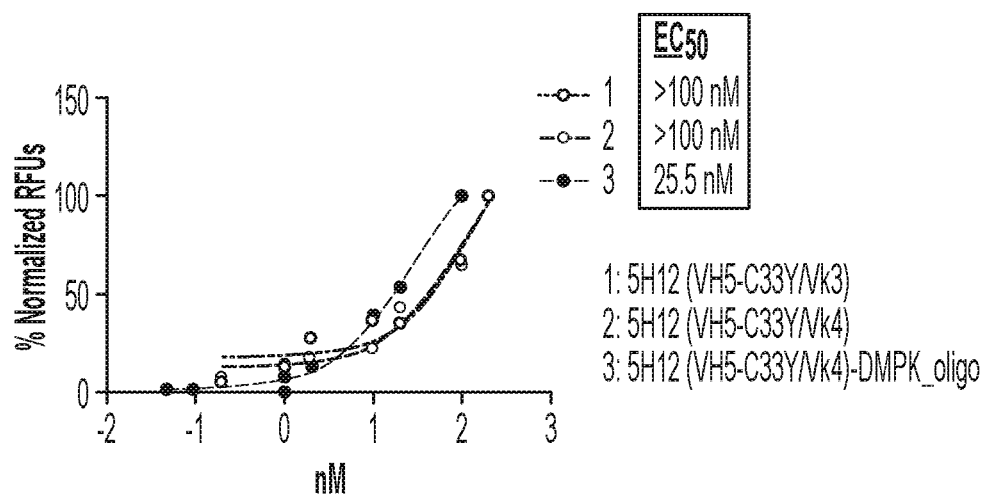
Figure 11F:
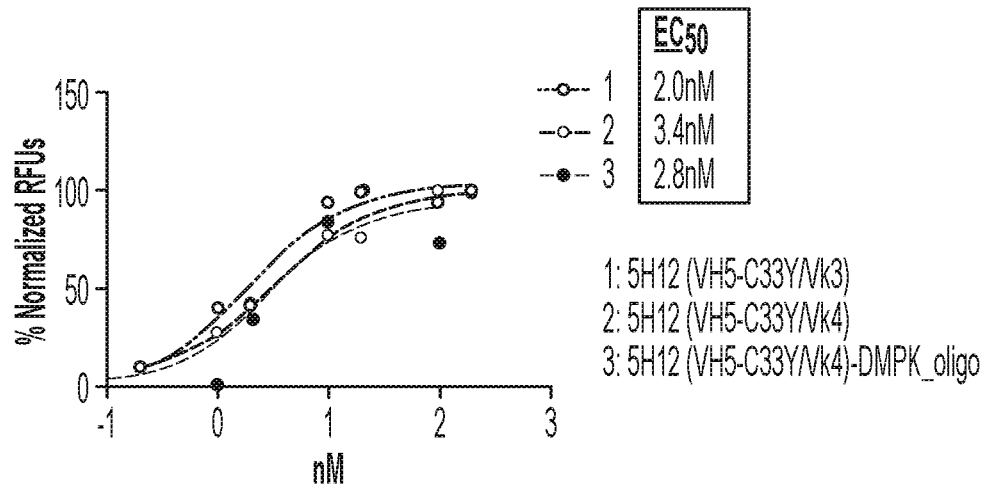

Conjugates of six humanized anti-TfR Fabs of were also tested for binding to hTfR1 and cTfR1 by ELISA, and compared to the unconjugated forms of the humanized Fabs. Results demonstrate that humanized 3M12 and 5H12 Fabs maintain similar levels of hTfR1 and cTfR1 binding after conjugation relative to their unconjugated forms (3M12, FIGS. 11A and 11B; 5H12, FIGS. 11E and 11F). Interestingly, 3A4 clones show improved binding to cTfR1 after conjugation relative to their unconjugated forms (FIGS. 11C and 11D).

As used in this Example, the term 'unconjugated' indicates that the antibody was not conjugated to an oligonucleotide.

Example 10. Knockdown of DMPK mRNA Level Facilitated by Antibody-Oligonucleotide Conjugates In Vitro Conjugates containing humanized anti-TfR Fabs 3M12 (VH3/Vk2), 3M-12 (VH4/Vk3), and 3A4(VH2-N54S/Vk4) were conjugated to a DMPK-targeting oligonucleotide ASO300 and were tested in rhabdomyosarcoma (RD) cells for knockdown of DMPK transcript expression. Antibodies were conjugated to ASO300 via the linker shown in Formula (C).

RD cells were cultured in a growth medium of DMEM with glutamine, supplemented with 10% FBS and penicillin/streptomycin until nearly confluent. Cells were then seeded into a 96 well plate at 20K cells per well and were allowed to recover for 24 hours. Cells were then treated with the conjugates for 3 days. Total RNA was collected from cells, cDNA was synthesized and DMPK expression was measured by qPCR.

Figure 12:
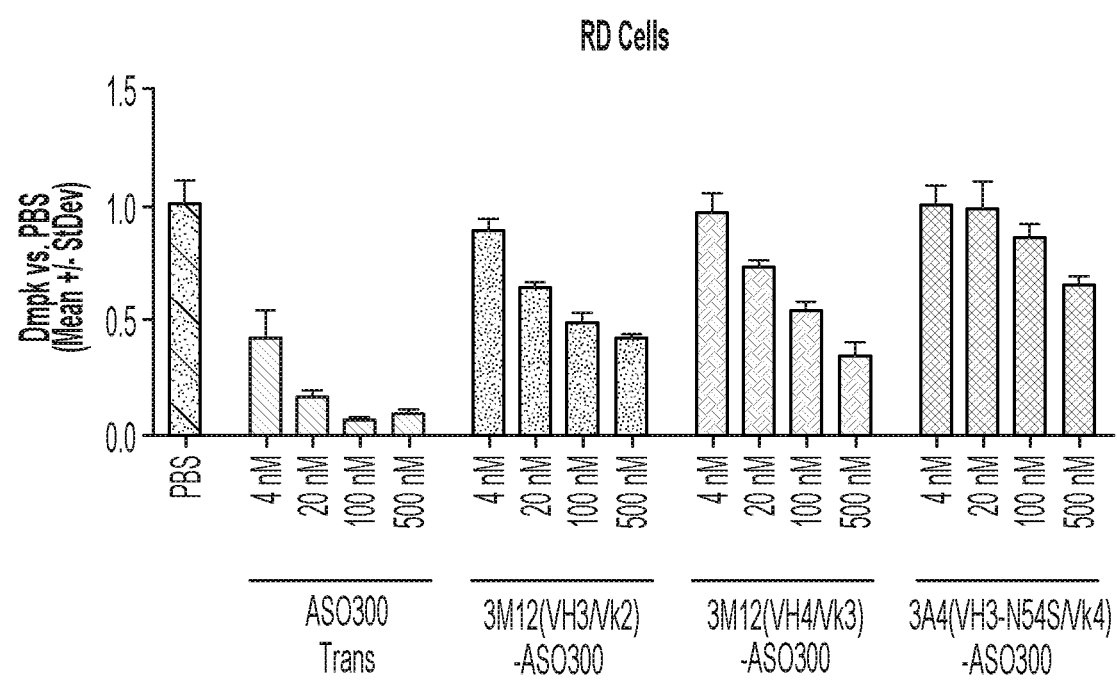
FIG. 12 shows DMPK expression in RD cells treated with various concentrations of conjugates containing the indicated humanized anti-TfR antibodies conjugated to a DMPK-targeting oligonucleotide ASO300. The duration of treatment was 3 days. The ASO300 was delivered using transfection agents were used as control.

Results in FIG. 12 show that DMPK expression level was reduced in cells treated with each indicated conjugate, relative to expression in PBS-treated cells, indicating that the humanized anti-TfR Fabs are able to mediate the uptake of the DMPK-targeting oligonucleotide by the RD cells and that the internalized DMPK-targeting oligonucleotide are effective in knocking down DMPK mRNA level. Similarly, the humanized anti-TfR Fabs can also facilitate the delivery of DUX4 targeting oligonucleotides to muscle cells for knocking down DUX4 expression.

Figure 13A:
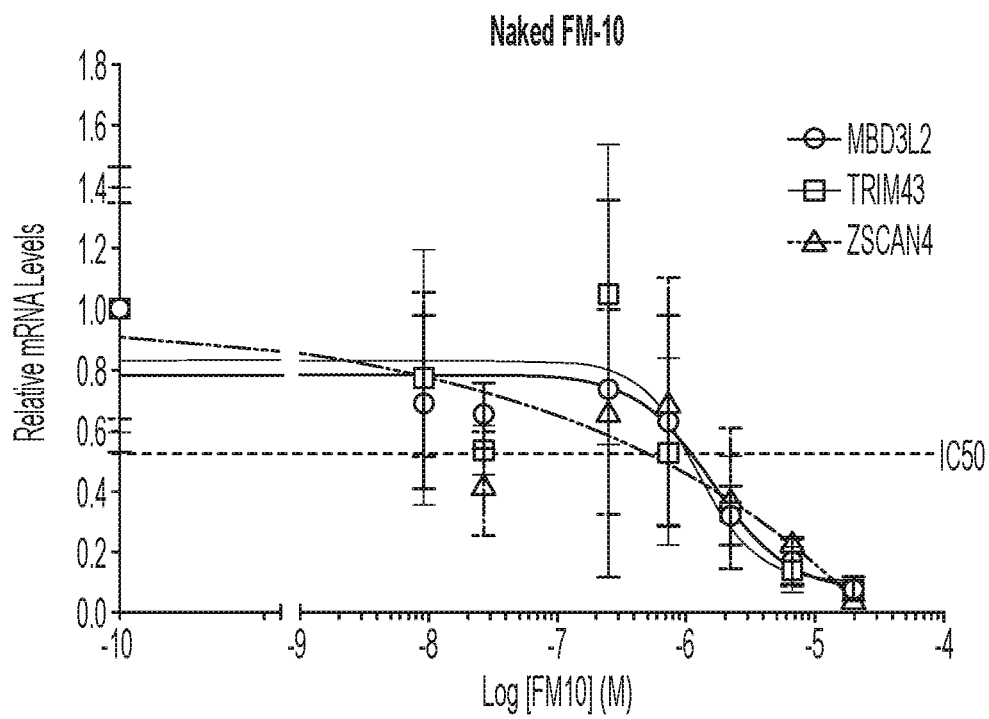
FIGS. 13A-13B show expression of MBD3L2, TRIM43, and ZSCAN4 transcripts in FSHD patient-derived myotubes treated with naked FM10 (FIG. 13A) or FM10 conjugated to anti-TfR1 (FIG. 13B) over a range of concentrations.
Figure 13B:
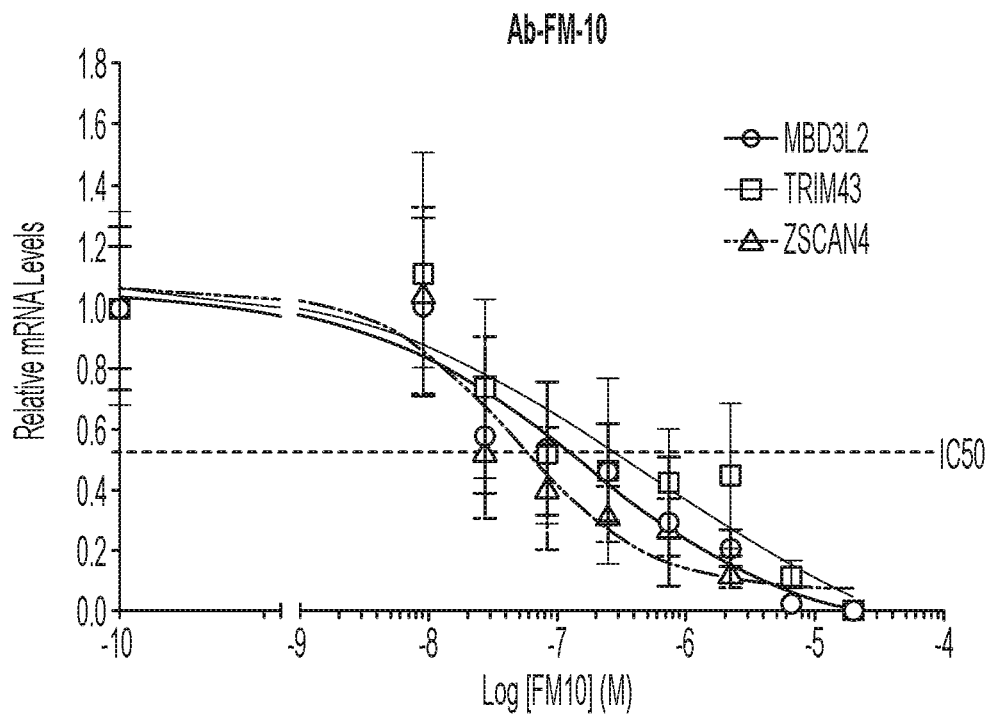

Example 11. Functional Activity of Antibody-Conjugated Oligonucleotides Targeting DUX4 for Treating FSHD FSHD patient-derived myotubes were treated with FM10 conjugated to an anti-TfR1 Fab or with naked FM10. FM10 has the sequence 5'-GGGCATTTTAATATATCTCT-GAACT-3' (SEQ ID NO: 151). Expression of mRNA transcribed from three genes known to be only expressed following DUX4 activation was subsequently measured in the myotubes. Expression of these three DUX4-associated genes was reduced, as shown in FIG. 13A (naked oligonucleotide) and 13B (Ab-oligonucleotide). In addition, the half maximal concentration required to inhibit ($IC_{50}$) values for the conjugate were up to 9.6 times lower than those observed for naked FM-10, as shown in Table 12 below, demonstrating that the conjugates were up to 9.6 times more potent than naked FM10 in suppressing DUX4-associated gene expression.

Additional DUX4-targeting oligonucleotides that may also be used to suppress DUX4-associated genes are ACUGCGCGCAGGUCUAGCCAGGAAG (SEQ ID NO: 131) and UGCGCACUGCGCGCAGGUCUAGCCAGGAAG (SEQ ID NO: 156).

TABLE 12

$IC_{50}$ values for inhibition of DUX4-associated genes.

| Transcript | Ab-FM-10 $IC_{50}$ (nM) | Naked FM-10 $IC_{50}$ (nM) | Fold Improvement with Ab conjugation |
|---|---|---|---|
| ZSCAN4 | 67 | 643 | 9.6× |
| MBD3L2 | 144 | 1208 | 8.4× |
| TRIM43 | 352 | 1117 | 3.2× |

Example 12. Serum Stability of the Linker Linking the Anti-TfR Antibody and the Molecular Payload Oligonucleotides which were linked to antibodies in examples were conjugated via a cleavable linker shown in Formula (C). It is important that the linker maintain stability in serum and provide release kinetics that favor sufficient payload accumulation in the targeted muscle cell. This serum stability is important for systemic intravenous administration, stability of the conjugated oligonucleotide in the bloodstream, delivery to muscle tissue and internalization of the therapeutic payload in the muscle cells. The linker has been confirmed to facilitate precise conjugation of multiple types of payloads (including ASOs, siRNAs and PMOs) to Fabs. This flexibility enabled rational selection of the appropriate type of payload to address the genetic basis of each muscle disease. Additionally, the linker and conjugation chemistry allowed the optimization of the ratio of payload molecules attached to each Fab for each type of payload, and enabled rapid design, production and screening of molecules to enable use in various muscle disease applications.

Figure 8:
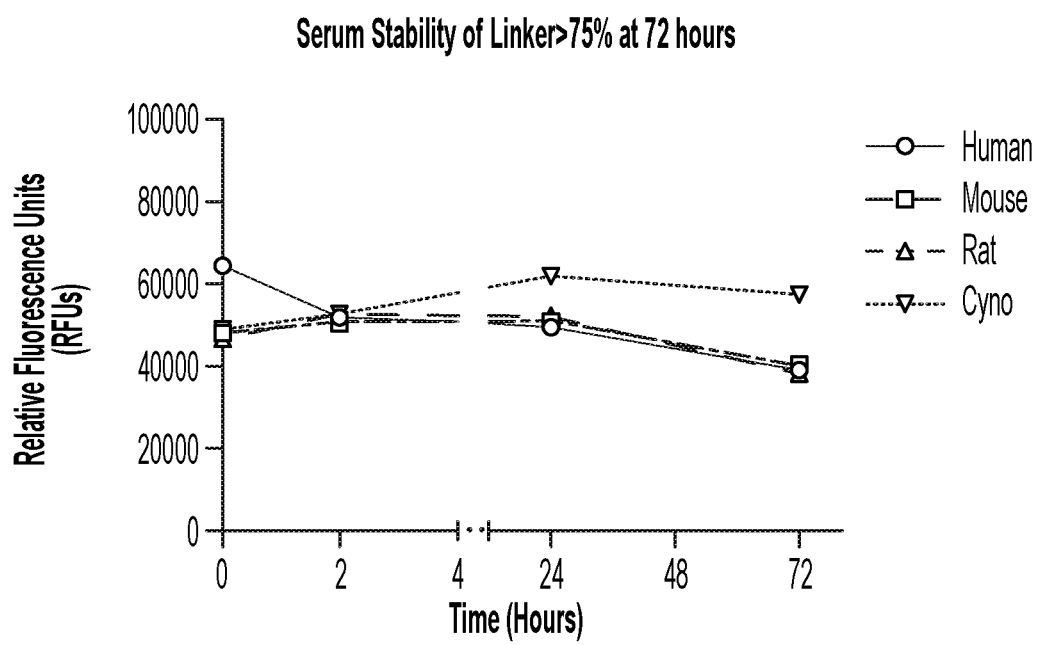
FIG. 8 shows the serum stability of the linker used for linking an anti-TfR antibody and a molecular payload (e.g., an oligonucleotide) in various species over time after intravenous administration.

FIG. 8 shows serum stability of the linker in vivo, which was comparable across multiple species over the course of 72 hours after intravenous dosing. At least 75% stability was measured in each case at 72 hours after dosing.

Example 13. Characterization of Binding Activities of Anti-TfR Fab 3M12 VH4/Vk3

Figure 14:
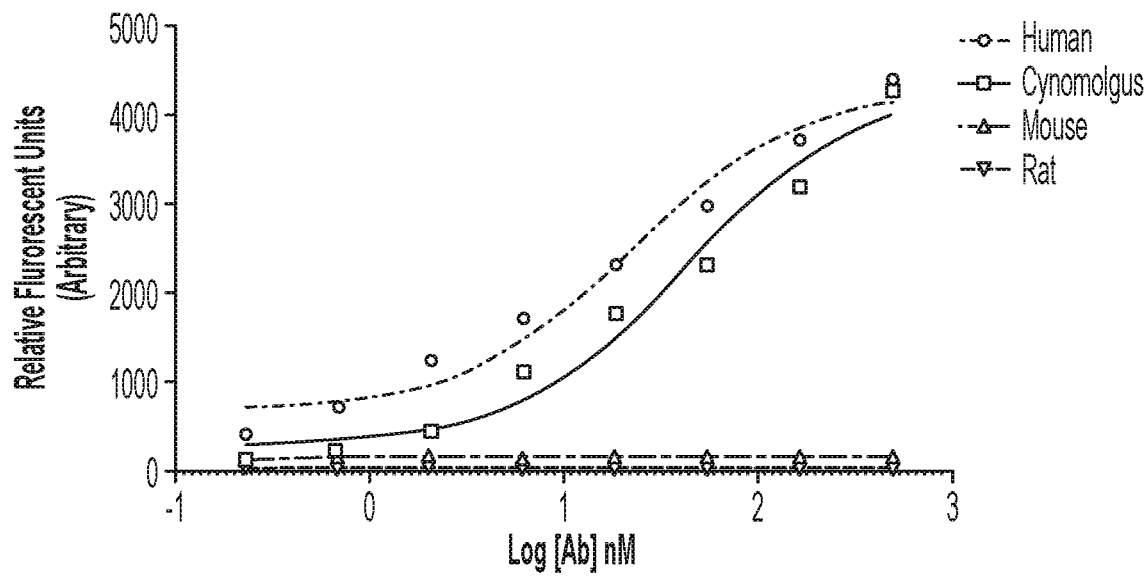
FIG. 14 shows ELISA measurements of binding of anti-TfR Fab 3M12 VH4/Vk3 to recombinant human (circles), cynomolgus monkey (squares), mouse (upward triangles), or rat (downward triangles) TfR1 protein, at a range of concentrations from 230 pM to 500 nM of the Fab. Measurement results show that the anti-TfR Fab is reactive with human and cynomolgus monkey TfR1. Binding was not observed to mouse or rat recombinant TfR1. Data is shown as relative fluorescent units normalized to baseline.

In vitro studies were performed to test the specificity of anti-TfR Fab 3M12 VH4/Vk3 for human and cynomolgus monkey TfR1 binding and to confirm its selectivity for human TfR1 vs TfR2. The binding affinity of anti-TfR Fab 3M12 VH4/Vk3 to TfR1 from various species was determined using an enzyme-linked immunosorbent assay (ELISA). Serial dilutions of the Fab were added to plates precoated with recombinant human, cynomolgus monkey, mouse, or rat TfR1. After a short incubation, binding of the Fab was quantified by addition of a fluorescently tagged anti-(H+L) IgG secondary antibody and measurement of fluorescence intensity at 495 nm excitation and 520 nm emission. The Fab showed strong binding affinity to human and cynomolgus monkey TfR1, and no detectable binding of mouse or rat TfR1 was observed (FIG. 14). Surface plasmon resonance (SPR) measurements were also conducted, and results are shown in Table 15. The $K_d$ of the Fab against the human TfR1 receptor was calculated to be $7.68 \times 10^{-10}$ M and against the cynomolgus monkey TfR1 receptor was calculated to be $5.18 \times 10^{-9}$ M.

TABLE 15

Kinetic analysis of anti-TfR Fab 3M12 VH4/Vk3 binding to human and cynomolgus monkey TfR1 or human TfR2, measured using surface plasmon resonance

| | Anti-TfR Fab 3M12 VH4/Vk3 | | | | |
|---|---|---|---|---|---|
| Target | $K_d$ (M) | $k_a$ ($M^{-1} s^{-1}$) | $k_d$ ($s^{-1}$) | $R_{max}$ | $R_{es}$ SD |
| Human TfR1 | 7.68E−10 | 1.66E+05 | 1.27E−04 | 1.11E+02 | 3.45E+00 |
| Cyno TfR1 | 5.18E−09 | 9.19E+04 | 4.76E−04 | 1.87E+02 | 6.24E+00 |
| Human TfR2 | ND | ND | ND | ND | ND |

ND = No detectable binding by SPR (10 pM-100 uM)

Figure 15:
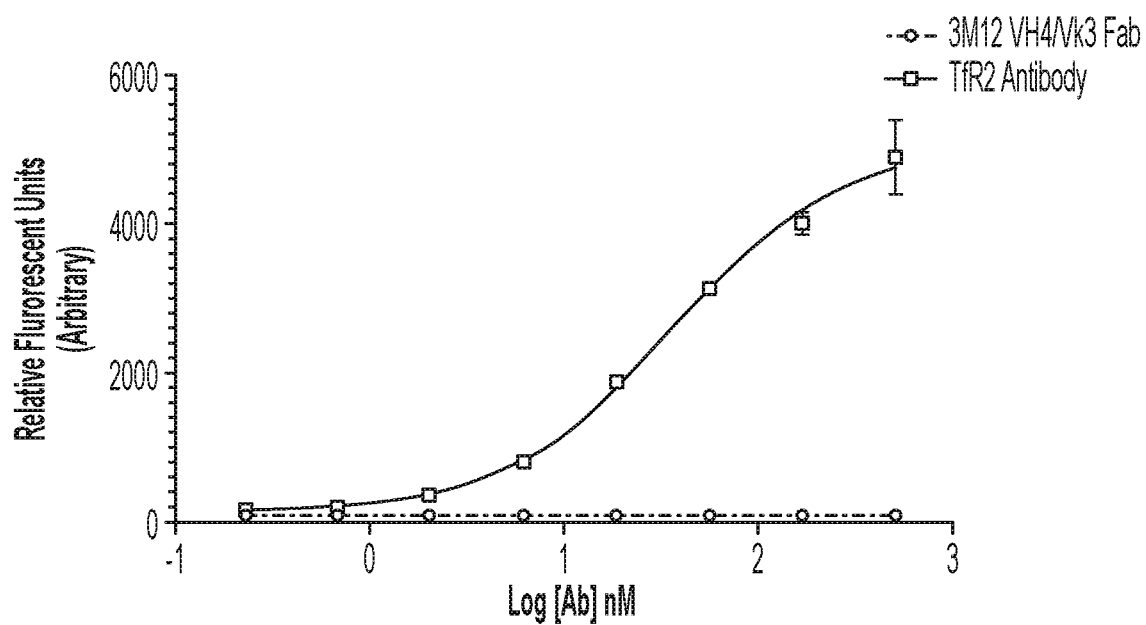
FIG. 15 shows results of an ELISA testing the affinity of anti-TfR Fab 3M12 VH4/Vk3 to recombinant human TfR1 or TfR2 over a range of concentrations from 230 pM to 500 nM of Fab. The data are presented as relative fluorescence units normalized to baseline. The results demonstrate that the Fab does not bind recombinant human TfR2.

To test for cross-reactivity of anti-TfR Fab 3M12 VH4/Vk3 to human TfR2, an ELISA was performed. Recombinant human TfR2 protein was plated overnight at 2 μg/mL and was blocked for 1 hour with 1% bovine serum albumin (BSA) in PBS. Serial dilutions of the Fab or a positive control anti-TfR2 antibody were added in 0.5% BSA/TBST for 1 hour. After washing, anti-(H+L) IgG-A488 (Invitrogen #MA5-25932) fluorescent secondary antibody was added at a 1:500 dilution in 0.5% BSA/TBST and the plate was incubated for 1 hour. Relative fluorescence was measured using a Biotek Synergy plate reader at 495 nm excitation and 520 nm emission. No binding of anti-TfR Fab 3M12 VH4/Vk3 to hTfR2 was observed (FIG. 15).

Example 14. Serum Stability of Anti-TfR Fab-ASO Conjugate

Figure 16:
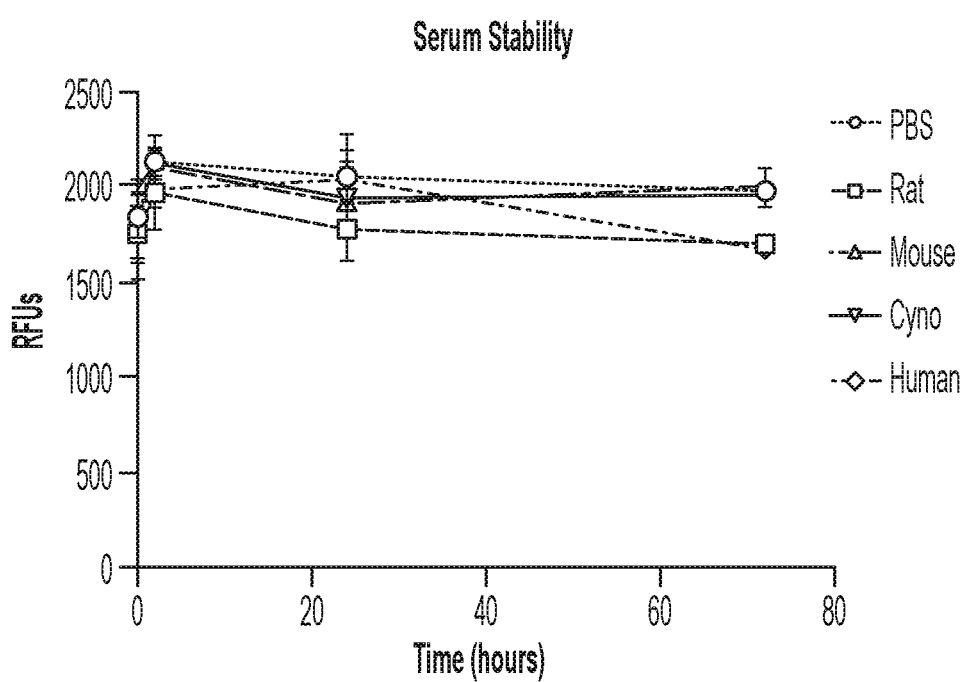
FIG. 16 shows the serum stability of the linker used for linking anti-TfR Fab 3M12 VH4/Vk3 to a control antisense oligonucleotide over 72 hours incubation in PBS or in rat, mouse, cynomolgus monkey or human serum.

Anti-TfR Fab VH4/Vk3 was conjugated to a control antisense oligonucleotide (ASO) via a linker as shown in Formula (C) and the resulting conjugate was tested for stability of the linker conjugating the Fab to the ASO. Serum stability was measured by incubating fluorescently labeled conjugate in PBS or in rat, mouse, cynomolgus monkey, or human serum and measuring relative fluorescence intensity over time, with higher fluorescence indicating more conjugate remaining intact. FIG. 16 shows serum stability was similar across multiple species and remained high after 72 hours.

Figure 17:
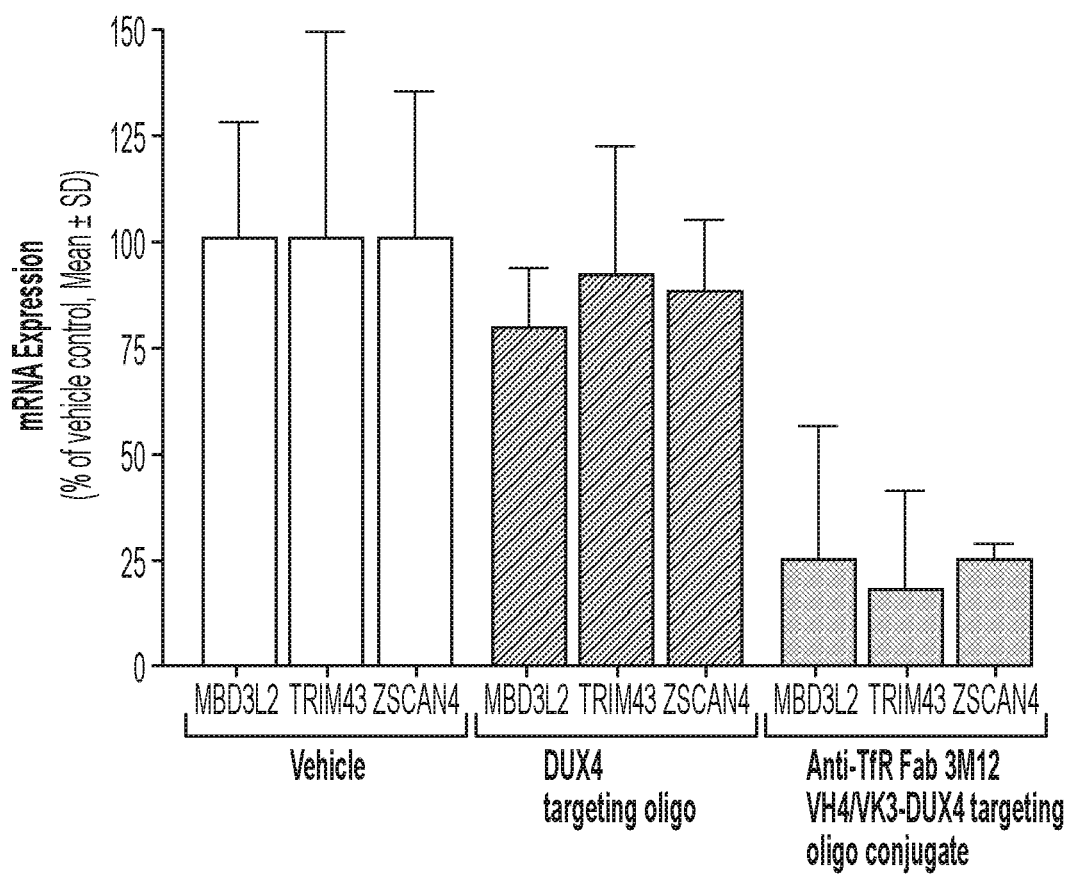
FIG. 17 shows that conjugates containing an anti-TfR Fab 3M12 VH4/Vk3 conjugated to a DUX4-targeting oligonucleotide (SEQ ID NO: 151) inhibited DUX4 transcriptome in C6 (AB1080) immortalized FSHD1 cells, as indicated by decreased mRNA expression of MDB3L2, TRIM43, and ZSCAN4. The conjugates showed superior activities relative to the unconjugated DUX4-targeting oligonucleotide in inhibiting DUX4 transcriptome.

Example 15. Effects of Conjugates Containing an Anti-TfR Fab Conjugated to a DUX4-Targeting Oligonucleotide in FSHD Patient-Derived Immortalized Myoblasts An anti-TfR Fab 3M12 VH4/VK3 was conjugated to a DUX4-targeting oligonucleotide (SEQ ID NO: 151) via a cleavable Val-Cit linker to achieve enhanced muscle delivery of the oligonucleotide. The oligonucleotide is a PMO and targets the polyadenylation signal of the DUX4 transcript. The activity of the conjugate was evaluated in the C6(AB1080) immortalized FSHD1 cell line, which has significant levels of surface TfR1 expression and activation of DUX4 transcriptome markers (MBD3L2, TRIM43, ZSCAN4). It is demonstrated that receptor-mediated delivery of the PMO (SEQ ID NO: 151) by the anti-TfR Fab into muscle cells resulted in ~75% reduction of DUX4 transcriptome biomarkers at an 8 nM PMO concentration, whereas equivalent unconjugated PMO shows no significant biomarker reduction compared to vehicle treated cells (FIG. 17). The results show that conjugating with anti-TfR Fab enhances delivery of therapeutic oligonucleotides to muscle cells for the treatment of FSHD.

As used in this Example, the term 'unconjugated' indicates that the oligonucleotide was not conjugated to an antibody.

Figure 18A:
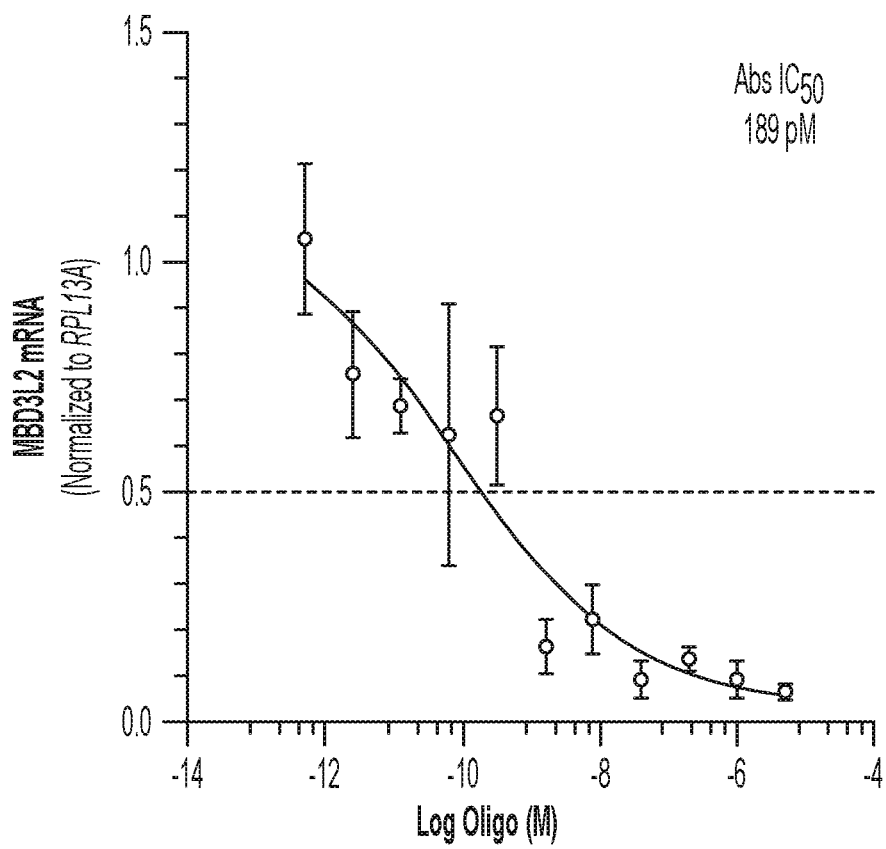
FIGS. 18A-18B show dose response curves for gene knockdown.
Figure 18B:
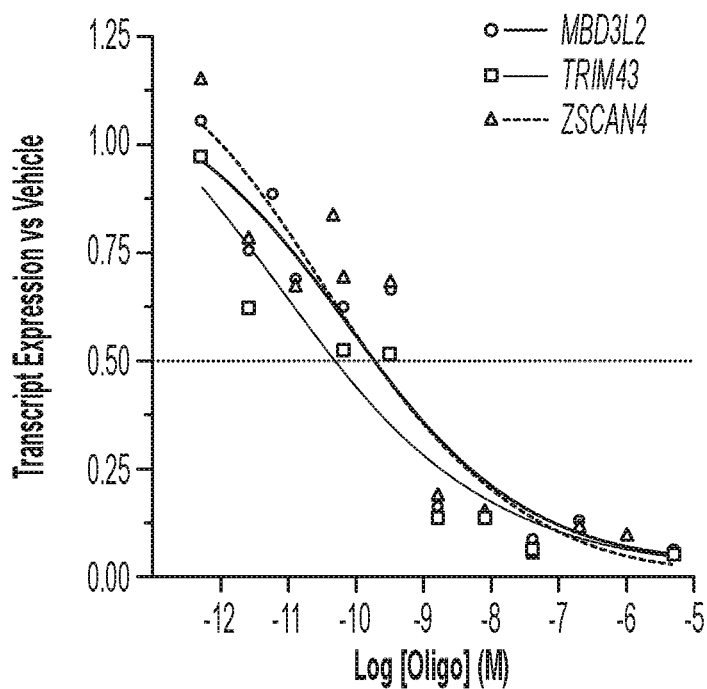

Additionally, a dose response curve for reduction of MBD3L2 mRNA is shown in FIG. 18A. The half maximal concentration required to inhibit (IC50) value for the conjugate was 189 µM. Dose response curves for reduction of MBD3L2, TRIM43, and ZSCAN4 mRNA are shown in FIG. 18B. The IC50 values for the conjugate inhibiting MBD3L2, TRIM43, and ZSCAN4 were 200 µM, 50 µM, and 200 µM, respectively.

Experimental Procedures for Example 15

Cell Culture and Test Article Treatment

C6 (AB1080) immortalized FSHD myoblasts were seeded to a density of 45,000 cells/well on a 96-well plate (ThermoFisher Scientific) in Skeletal Growth Media (CAT #C-23060, Promocell) with Supplementary mix (C-39365, Promocell) and 1% Penstrep (15140-122, Gibco). Growth media was replaced with differentiation media, NbActiv4 (Brainbits) and 1% Pen/Strep (Gibco), 24 hours later. The cells were treated with unconjugated DUX4-targeting oligonucleotide, the conjugate at a PMO concentration of 8 nM, vehicle in technical replicates for 4 hours prior to washout with 1×PBS (10010023, Gibco) one time. Conditioned differentiation media was immediately added back to wells and the cells were harvested 5 days later for downstream analyses.

For the dose response curves for MBD3L2, TRIM43, and ZSCAN4 knockdown, C6 (AB1080) immortalized FSHD myoblasts were treated as described above but with varying concentrations of the conjugates.

RNA Extraction and qPCR

Total RNA was extracted from cell monolayers with the RNeasy 96 Kit (Qiagen) in accordance with the manufacturer's instructions. The RNA was quantified with the Biotek Plate Reader and diluted to 50 ng per sample with Nuclease-Free Water (Qiagen) and reverse transcribed with qScript cDNA SuperMix (QuantaBio). Gene expression was analyzed by qPCR with specific TaqMan assays (ThermoFisher) by measuring levels of TRIM43 (Hs00299174_m1), MBD3L2 (Hs00544743_m1), ZSCAN4 (Hs00537549_m1) and RPL13A (Hs04194366_g1) transcripts. Two-step amplification reactions and fluorescence measurements for Ct determination were conducted on a QuantStudio 7 instrument (Thermo Scientific). Log fold changes in the expression of transcripts of interest were calculated according to the $2^{-\Delta\Delta C_T}$ method using RPL13A as the reference gene and cells exposed to vehicle as the control group. Data are expressed as means±S.D.

Figure 19:
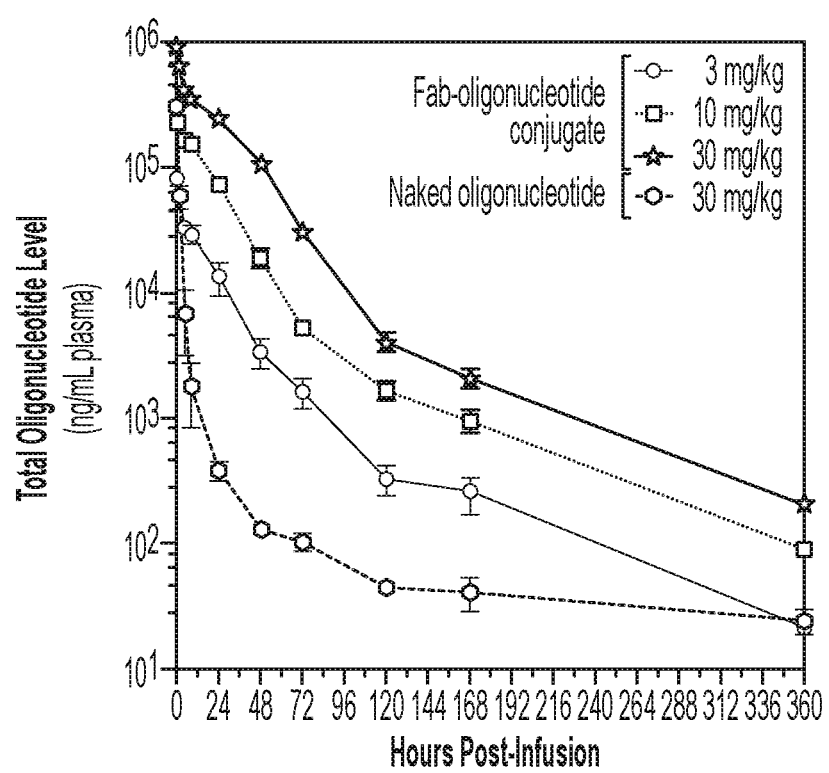
FIG. 19 shows non-human primate plasma levels of DUX4-targeting oligonucleotide (SEQ ID NO: 151) over time following administration of 30 mg/kg unconjugated ('naked') oligonucleotide or 3, 10, or 30 mg/kg oligonucleotide equivalent of conjugates comprising anti-TfR1 Fab 3M12 VH4/Vk3 covalently linked to the DUX4-targeting oligonucleotide ('Fab-oligonucleotide conjugate').

Example 16. Pharmacokinetic Properties of Antibody-Oligonucleotide Conjugate in Non-Human Primates A DUX4-targeting oligonucleotide (SEQ ID NO: 151) was administered intravenously to non-human primates, either naked or conjugated to an anti-TfR1 antibody (3M12 VH4/Vk3 Fab). The naked oligonucleotide was administered at a dose of 30 mg/kg, and the conjugate was administered at a dose of 3 mg/kg, 10 mg/kg, or 30 mg/kg oligonucleotide equivalent. Plasma levels of the oligonucleotide measured over time are shown in FIG. 19. The results demonstrate that systemic exposure of the antibody-oligonucleotide conjugate shows dose-dependent pharmacokinetic properties, and achieves higher exposure relative to the naked oligonucleotide. The plasma measurements also demonstrate the antibody-oligonucleotide conjugate has a long serum half-life of about 60 hours. Furthermore, the antibody-oligonucleotide conjugate demonstrates a 58-fold increase in area under the curve (AUC) and a 3-fold increase in $C_{max}$ compared to the naked oligonucleotide at an oligonucleotide equivalent dose of 30 mg/kg. These results are summarized in Table 16.

TABLE 16

Pharmacokinetic values calculated from plasma concentration measurements

| Dose (mg/kg) | Antibody-Oligonucleotide Conjugate | | | Oligonucleotide |
|---|---|---|---|---|
| | 3 | 10 | 30 | 30 |
| $C_{max}$ (ug/mL) | 84 | 242 | 893 | 305 |
| $AUC_t$ (h * µg/mL) | 969 | 4714 | 15191 | 260 |
| $T_{1/2}$ (h) | 61 | 58 | 56 | N/A |

Figure 20:
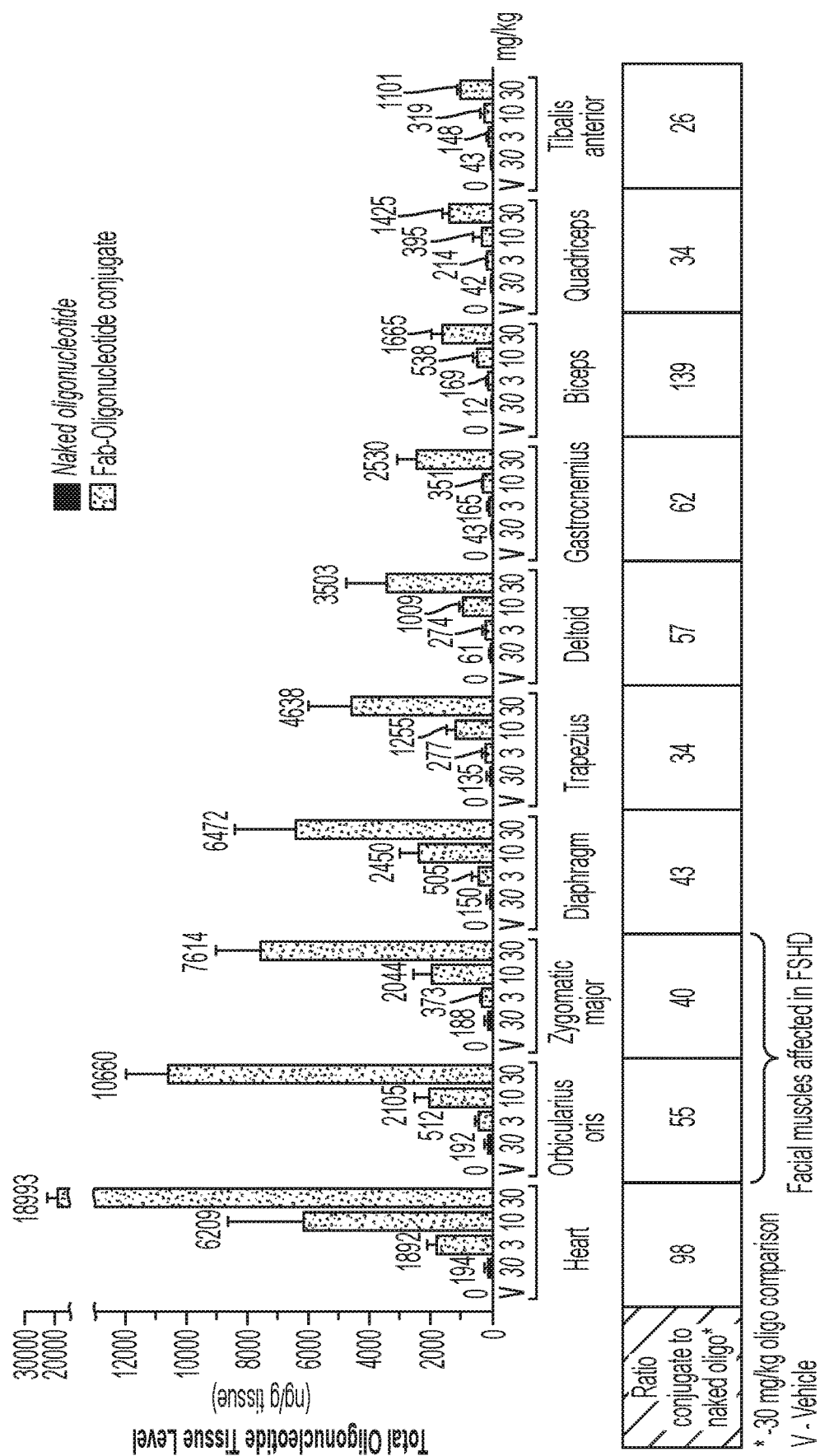
FIG. 20 shows tissue levels of DUX4-targeting oligonucleotide (SEQ ID NO: 151) measured in non-human primate muscle tissue samples two-weeks following administration of 30 mg/kg unconjugated ('naked') oligonucleotide or 3, 10, or 30 mg/kg oligonucleotide equivalent of conjugates comprising anti-TfR1 Fab 3M12 VH4/Vk3 covalently linked to the DUX4-targeting oligonucleotide ('Fab-Oligonucleotide conjugate').

Two-weeks following administration of the oligonucleotide or the antibody-oligonucleotide conjugate, necropsies were performed and muscle tissues from the non-human primates were collected and oligonucleotide levels were measured. In each muscle tissue tested (heart, orbicularius oris, zygomatic major, diaphragm, trapezius, deltoid, gastrocnemius, biceps, quadriceps, and tibialis anterior), tissue oligonucleotide levels were higher for each dose of antibody-oligonucleotide conjugate (3, 10, or 30 mg/kg oligonucleotide equivalent) compared to the naked oligonucleotide (30 mg/kg) (FIG. 20). As a control, tissue oligonucleotide levels were also measured in tissues collected from vehicle-treated animals, and no oligonucleotide was detected in any of the muscle tissues tested. These results demonstrate that the antibody-oligonucleotide conjugate achieves high exposure of the DUX4-targeting oligonucleotide to muscle tissue, and markedly higher than oligonucleotide administered naked. At an oligonucleotide equivalent dose of 30 mg/kg, oligonucleotide concentrations in each muscle tested were 26- to 139-fold higher in animals treated with antibody-oligonucleotide conjugates relative to naked oligonucleotide.

Figure 21:
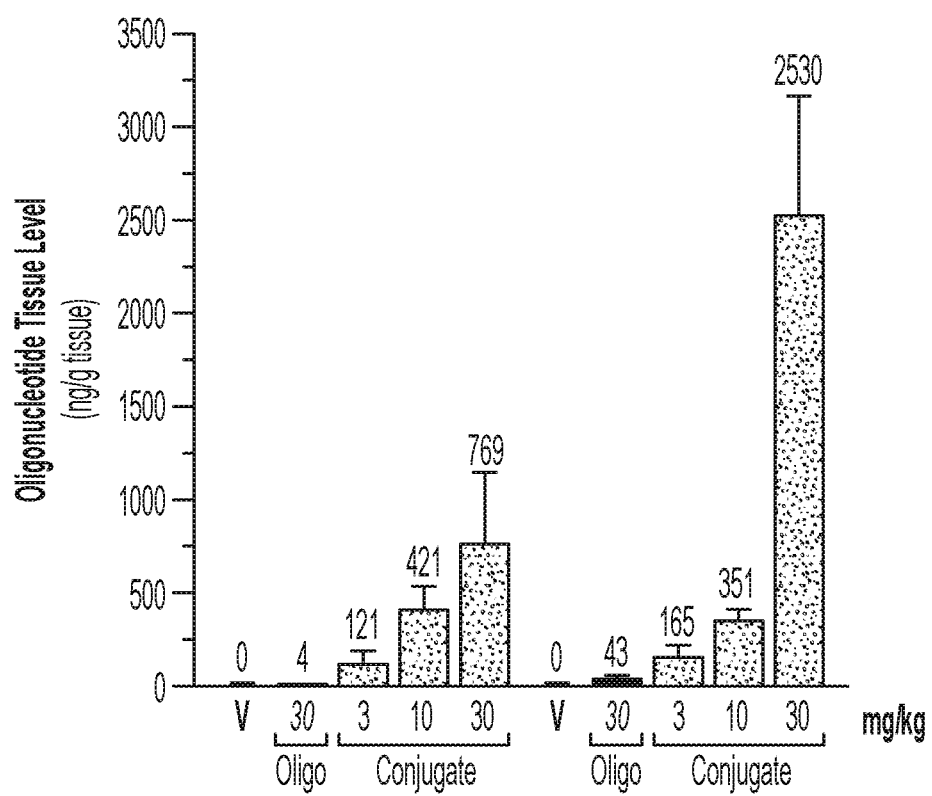
FIG. 21 shows tissue levels of DUX4-targeting oligonucleotide (SEQ ID NO: 151) measured in non-human primate muscle tissue samples collected by biopsy one-week following administration (left 5 bars) or by necropsy two-weeks following administration (right 5 bars) of 30 mg/kg unconjugated oligonucleotide ('Oligo') or 3, 10, or 30 mg/kg oligonucleotide equivalent of conjugates comprising anti-TfR1 Fab 3M12 VH4/Vk3 covalently linked to the DUX4-targeting oligonucleotide ('Conjugate').

To evaluate tissue accumulation of DUX4-targeting oligonucleotide over time, tissue oligonucleotide levels were measured in gastrocnemius biopsy samples collected one-week following administration and compared to the values measured in the necropsy samples collected two-weeks following administration. The oligonucleotide levels were markedly higher in the gastrocnemius biopsy samples collected from the animals administered 3, 10, or 30 mg/kg oligonucleotide equivalent of antibody-oligonucleotide conjugate than in the biopsy samples collected from the animals administered 30 mg/kg naked oligonucleotide, and the levels were even higher in the tissues collected two-weeks following administration (FIG. 21). No oligonucleotide was detected in tissue samples from vehicle-treated animals. These results demonstrate that the antibody-oligonucleotide conjugate achieves high exposure of the DUX4-targeting oligonucleotide to muscle tissue when compared to naked oligonucleotide, and that the conjugate continues to accumulate over time.

ADDITIONAL EMBODIMENTS

1. A complex comprising a muscle-targeting agent covalently linked to a molecular payload configured for inhibiting expression or activity of DUX4, wherein the muscle-targeting agent specifically binds to an internalizing cell surface receptor on muscle cells, wherein the muscle targeting agent is a humanized antibody that binds to a transferrin receptor wherein the antibody comprises:

(i) a heavy chain variable region (VH) comprising an amino acid sequence at least 85% identical to SEQ ID NO: 69; and/or a light chain variable region (VL) comprising an amino acid sequence at least 85% identical to SEQ ID NO: 70;

(ii) a heavy chain variable region (VH) comprising an amino acid sequence at least 85% identical to SEQ ID NO: 71; and/or a light chain variable region (VL) comprising an amino acid sequence at least 85% identical to SEQ ID NO: 70;

(iii) a heavy chain variable region (VH) comprising an amino acid sequence at least 85% identical to SEQ ID NO: 72; and/or a light chain variable region (VL) comprising an amino acid sequence at least 85% identical to SEQ ID NO: 70;

(iv) a heavy chain variable region (VH) comprising an amino acid sequence at least 85% identical to SEQ ID NO: 73; and/or a light chain variable region (VL) comprising an amino acid sequence at least 85% identical to SEQ ID NO: 74;

(v) a heavy chain variable region (VH) comprising an amino acid sequence at least 85% identical to SEQ ID NO: 73; and/or a light chain variable region (VL) comprising an amino acid sequence at least 85% identical to SEQ ID NO: 75;

(vi) a heavy chain variable region (VH) comprising an amino acid sequence at least 85% identical to SEQ ID NO: 76; and/or a light chain variable region (VL) comprising an amino acid sequence at least 85% identical to SEQ ID NO: 74;

(vii) a heavy chain variable region (VH) comprising an amino acid sequence at least 85% identical to SEQ ID NO: 76; and/or a light chain variable region (VL) comprising an amino acid sequence at least 85% identical to SEQ ID NO: 75;

(viii) a heavy chain variable region (VH) comprising an amino acid sequence at least 85% identical to SEQ ID NO: 77; and/or a light chain variable region (VL) comprising an amino acid sequence at least 85% identical to SEQ ID NO: 78;

(ix) a heavy chain variable region (VH) comprising an amino acid sequence at least 85% identical to SEQ ID NO: 79; and/or a light chain variable region (VL) comprising an amino acid sequence at least 85% identical to SEQ ID NO: 80; or (x) a heavy chain variable region (VH) comprising an amino acid sequence at least 85% identical to SEQ ID NO: 77; and/or a light chain variable region (VL) comprising an amino acid sequence at least 85% identical to SEQ ID NO: 80.

2. The complex of embodiment 1, wherein the antibody comprises:

(i) a VH comprising the amino acid sequence of SEQ ID NO: 69 and a VL comprising the amino acid sequence of SEQ ID NO: 70;

(ii) a VH comprising the amino acid sequence of SEQ ID NO: 71 and a VL comprising the amino acid sequence of SEQ ID NO: 70;

(iii) a VH comprising the amino acid sequence of SEQ ID NO: 72 and a VL comprising the amino acid sequence of SEQ ID NO: 70;

(iv) a VH comprising the amino acid sequence of SEQ ID NO: 73 and a VL comprising the amino acid sequence of SEQ ID NO: 74;

(v) a VH comprising the amino acid sequence of SEQ ID NO: 73 and a VL comprising the amino acid sequence of SEQ ID NO: 75;

(vi) a VH comprising the amino acid sequence of SEQ ID NO: 76 and a VL comprising the amino acid sequence of SEQ ID NO: 74;

(vii) a VH comprising the amino acid sequence of SEQ ID NO: 76 and a VL comprising the amino acid sequence of SEQ ID NO: 75;

(viii) a VH comprising the amino acid sequence of SEQ ID NO: 77 and a VL comprising the amino acid sequence of SEQ ID NO: 78;

(ix) a VH comprising the amino acid sequence of SEQ ID NO: 79 and a VL comprising the amino acid sequence of SEQ ID NO: 80; or (x) a VH comprising the amino acid sequence of SEQ ID NO: 77 and a VL comprising the amino acid sequence of SEQ ID NO: 80.

3. The complex of embodiment 1 or embodiment 2, wherein the antibody is selected from the group consisting of a full-length IgG, a Fab fragment, a Fab' fragment, a F(ab')$_2$ fragment, a scFv, and a Fv.

4. The complex of embodiment 3, wherein the antibody is a full-length IgG, optionally wherein the full-length IgG comprises a heavy chain constant region of the isotype IgG1, IgG2, IgG3, or IgG4.

5. The complex of embodiment 4, wherein the antibody comprises:

(i) a heavy chain comprising an amino acid sequence at least 85% identical to SEQ ID NO: 84; and/or a light chain comprising an amino acid sequence at least 85% identical to SEQ ID NO: 85;

(ii) a heavy chain comprising an amino acid sequence at least 85% identical to SEQ ID NO: 86; and/or a light chain comprising an amino acid sequence at least 85% identical to SEQ ID NO: 85;

(iii) a heavy chain comprising an amino acid sequence at least 85% identical to SEQ ID NO: 87; and/or a light chain comprising an amino acid sequence at least 85% identical to SEQ ID NO: 85;

(iv) a heavy chain comprising an amino acid sequence at least 85% identical to SEQ ID NO: 88; and/or a light chain comprising an amino acid sequence at least 85% identical to SEQ ID NO: 89;

(v) a heavy chain comprising an amino acid sequence at least 85% identical to SEQ ID NO: 88; and/or a light chain comprising an amino acid sequence at least 85% identical to SEQ ID NO: 90;

(vi) a heavy chain comprising an amino acid sequence at least 85% identical to SEQ ID NO: 91; and/or a light chain comprising an amino acid sequence at least 85% identical to SEQ ID NO: 89;

(vii) a heavy chain comprising an amino acid sequence at least 85% identical to SEQ ID NO: 91; and/or a light chain comprising an amino acid sequence at least 85% identical to SEQ ID NO: 90;

(viii) a heavy chain comprising an amino acid sequence at least 85% identical to SEQ ID NO: 92; and/or a light chain comprising an amino acid sequence at least 85% identical to SEQ ID NO: 93;

(ix) a heavy chain comprising an amino acid sequence at least 85% identical to SEQ ID NO: 94; and/or a light chain comprising an amino acid sequence at least 85% identical to SEQ ID NO: 95; or (x) a heavy chain comprising an amino acid sequence at least 85% identical to SEQ ID NO: 92; and/or a light chain comprising an amino acid sequence at least 85% identical to SEQ ID NO: 95.

6. The complex of embodiment 3, wherein the antibody is a Fab fragment.

7. The complex of embodiment 6, wherein the antibody comprises:

(i) a heavy chain comprising an amino acid sequence at least 85% identical to SEQ ID NO: 97; and/or a light chain comprising an amino acid sequence at least 85% identical to SEQ ID NO: 85;

(ii) a heavy chain comprising an amino acid sequence at least 85% identical to SEQ ID NO: 98; and/or a light chain comprising an amino acid sequence at least 85% identical to SEQ ID NO: 85;

(iii) a heavy chain comprising an amino acid sequence at least 85% identical to SEQ ID NO: 99; and/or a light chain comprising an amino acid sequence at least 85% identical to SEQ ID NO: 85;

(iv) a heavy chain comprising an amino acid sequence at least 85% identical to SEQ ID NO: 100; and/or a light chain comprising an amino acid sequence at least 85% identical to SEQ ID NO: 89;

(v) a heavy chain comprising an amino acid sequence at least 85% identical to SEQ ID NO: 100; and/or a light chain comprising an amino acid sequence at least 85% identical to SEQ ID NO: 90;

(vi) a heavy chain comprising an amino acid sequence at least 85% identical to SEQ ID NO: 101; and/or a light chain comprising an amino acid sequence at least 85% identical to SEQ ID NO: 89;

(vii) a heavy chain comprising an amino acid sequence at least 85% identical to SEQ ID NO: 101; and/or a light chain comprising an amino acid sequence at least 85% identical to SEQ ID NO: 90;

(viii) a heavy chain comprising an amino acid sequence at least 85% identical to SEQ ID NO: 102; and/or a light chain comprising an amino acid sequence at least 85% identical to SEQ ID NO: 93;

(ix) a heavy chain comprising an amino acid sequence at least 85% identical to SEQ ID NO: 103; and/or a light chain comprising an amino acid sequence at least 85% identical to SEQ ID NO: 95; or (x) a heavy chain comprising an amino acid sequence at least 85% identical to SEQ ID NO: 102; and/or a light chain comprising an amino acid sequence at least 85% identical to SEQ ID NO: 95.

8. The complex of embodiment 6 or embodiment 7, wherein the antibody comprises:

(i) a heavy chain comprising the amino acid sequence of SEQ ID NO: 97; and a light chain comprising the amino acid sequence of SEQ ID NO: 85;

(ii) a heavy chain comprising the amino acid sequence of SEQ ID NO: 98; and a light chain comprising the amino acid sequence of SEQ ID NO: 85;

(iii) a heavy chain comprising the amino acid sequence of SEQ ID NO: 99; and a light chain comprising the amino acid sequence of SEQ ID NO: 85;

(iv) a heavy chain comprising the amino acid sequence of SEQ ID NO: 100; and a light chain comprising the amino acid sequence of SEQ ID NO: 89;

(v) a heavy chain comprising the amino acid sequence of SEQ ID NO: 100; and a light chain comprising the amino acid sequence of SEQ ID NO: 90;

(vi) a heavy chain comprising the amino acid sequence of SEQ ID NO: 101; and a light chain comprising the amino acid sequence of SEQ ID NO: 89;

(vii) a heavy chain comprising the amino acid sequence of SEQ ID NO: 101; and a light chain comprising the amino acid sequence of SEQ ID NO: 90;

(viii) a heavy chain comprising the amino acid sequence of SEQ ID NO: 102; and a light chain comprising the amino acid sequence of SEQ ID NO: 93;

(ix) a heavy chain comprising the amino acid sequence of SEQ ID NO: 103; and a light chain comprising the amino acid sequence of SEQ ID NO: 95; or (x) a heavy chain comprising the amino acid sequence of SEQ ID NO: 102; and a light chain comprising the amino acid sequence of SEQ ID NO: 95.

9. The complex of any one of embodiments 1 to 5, wherein the equilibrium dissociation constant ($K_D$) of binding of the antibody to the transferrin receptor is in a range from $10^{-11}$ M to $10^{-6}$ M.

10. The complex of any one of embodiments 1 to 9, wherein the antibody does not specifically bind to the transferrin binding site of the transferrin receptor and/or wherein the antibody does not inhibit binding of transferrin to the transferrin receptor.

11. The complex of any one of embodiments 1 to 10, wherein the antibody is cross-reactive with extracellular epitopes of two or more of a human, non-human primate and rodent transferrin receptor.

12. The complex of any one of embodiments 1 to 11, wherein the complex is configured to promote transferrin receptor mediated internalization of the molecular payload into a muscle cell.

13. The complex of any one of embodiments 1 to 12, wherein the antibody is a chimeric antibody, wherein optionally the chimeric antibody is a humanized monoclonal antibody.

14. The complex of any one of embodiments 1 to 13, wherein the antibody is in the form of a ScFv, Fab fragment, Fab' fragment, F(ab')$_2$ fragment, or Fv fragment.

15. The complex of any one of embodiments 1 to 14, wherein the molecular payload is an oligonucleotide.

16. The complex of embodiment 15, wherein the oligonucleotide comprises at least 15 consecutive nucleotides of SEQ ID NO: 151 (GGGCATTTTAATATATCTCTGAACT).

17. The complex of embodiment 16, wherein the oligonucleotide comprises SEQ ID NO: 151 (GGGCATTTTAATATATCTCTGAACT).

18. The complex of any one of embodiments 15 to 17, wherein the oligonucleotide comprises a sequence that is complementary to at least 15 consecutive nucleotides of SEQ ID NO: 150 (AGTTCAGAGATATATTAAAATGCCC).

19. The complex of any one of embodiments 15 to 18, wherein the oligonucleotide comprises a region of complementarity to DUX4 gene.

20. The complex of any one of embodiments 1 to 14, wherein the molecular payload is a polypeptide that inhibits DUX4 expression.

21. The complex of embodiment 20, wherein the polypeptide binds to a DUX4 enhancer sequence, thereby blocking recruitment of one or more activators of DUX4 expression.

22. The complex of any one of embodiments 15 to 19, wherein the oligonucleotide comprises an antisense strand that hybridizes, in a cell, with a wild-type DUX4 mRNA transcript encoded by the allele.

23. The complex of any one of embodiments 15 to 19, wherein the oligonucleotide comprises an antisense strand that hybridizes, in a cell, with a mutant DUX4 mRNA transcript encoded by the allele.

24. The complex of embodiment 23, wherein the oligonucleotide comprises a strand complementary to the coding sequence of DUX4.

25. The complex of embodiment 23, wherein the oligonucleotide comprises a strand complementary to the non-coding sequence of DUX4.

26. The complex of embodiment 25, wherein the oligonucleotide comprises a strand complementary to a 5' or 3' UTR sequence of DUX4.

27. The complex of embodiment 23, wherein the oligonucleotide mediates epigenetic silencing of DUX4.

28. The complex of any one of embodiments 15 to 19 or 22 to 27, wherein the oligonucleotide comprises at least one modified internucleotide linkage.

29. The complex of embodiment 28, wherein the at least one modified internucleotide linkage is a phosphorothioate linkage.

30. The complex of embodiment 29, wherein the oligonucleotide comprises phosphorothioate linkages in the Rp stereochemical conformation and/or in the Sp stereochemical conformation.

31. The complex of embodiment 30, wherein the oligonucleotide comprises phosphorothioate linkages that are all in the Rp stereochemical conformation or that are all in the Sp stereochemical conformation.

32. The complex of any one of embodiments 15 to 19 or 22 to 31, wherein the oligonucleotide comprises one or more modified nucleotides.

33. The complex of embodiment 32, wherein the one or more modified nucleotides are 2'-modified nucleotides.

34. The complex of any one of embodiments 15 to 19, or 22 to 33, wherein the oligonucleotide is a gapmer oligonucleotide that directs RNAse H-mediated cleavage of the DUX4 mRNA transcript in a cell.

35. The complex of embodiment 34, wherein the gapmer oligonucleotide comprises a central portion of 5 to 15 deoxyribonucleotides flanked by wings of 2 to 8 modified nucleotides.

36. The complex of embodiment 35, wherein the modified nucleotides of the wings are 2'-modified nucleotides.

37. The complex of any one of embodiments 15 to 19 or 22 to 33, wherein the oligonucleotide is a mixmer oligonucleotide.

38. The complex of embodiment 37, wherein the mixmer oligonucleotide inhibits translation of a DUX4 mRNA transcript.

39. The complex of embodiment 37 or 38, wherein the mixmer oligonucleotide comprises two or more different 2' modified nucleotides.

40. The complex of any one of embodiments 15 to 19 or 22 to 33, wherein the oligonucleotide is an RNAi oligonucleotide that promotes RNAi-mediated cleavage of the DUX4 mRNA transcript.

41. The complex of embodiment 40, wherein the RNAi oligonucleotide is a double-stranded oligonucleotide of 19 to 25 nucleotides in length.

42. The complex of embodiment 40 or 41, wherein the RNAi oligonucleotide comprises at least one 2' modified nucleotide.

43. The complex of embodiment 33, 36, 39, or 42, wherein each 2' modified nucleotide is selected from the group consisting of: 2'-O-methyl, 2'-fluoro (2'-F), 2'-O-methoxyethyl (2'-MOE), and 2', 4'-bridged nucleotides.

44. The complex of embodiment 32, wherein the one or more modified nucleotides are bridged nucleotides.

45. The complex embodiment 33, 36, 39, or 42, wherein at least one 2' modified nucleotide is a 2',4'-bridged nucleotide selected from: 2',4'-constrained 2'-O-ethyl (cEt) and locked nucleic acid (LNA) nucleotides.

46. The complex of any one of embodiments 15 to 19 or 22 to 33, wherein the oligonucleotide comprises a guide sequence for a genome editing nuclease.

47. The complex of any one of embodiments 15 to 19 or 22 to 33, wherein the oligonucleotide is a phosphorodiamidite morpholino oligomer.

48. The complex of any one of embodiments 1 to 47, wherein the muscle-targeting agent is covalently linked to the molecular payload via a cleavable linker.

49. The complex of embodiment 48, wherein the cleavable linker is selected from: a protease-sensitive linker, pH-sensitive linker, and glutathione-sensitive linker.

50. The complex of embodiment 49, wherein the cleavable linker is a protease-sensitive linker.

51. The complex of embodiment 50, wherein the protease-sensitive linker comprises a sequence cleavable by a lysosomal protease and/or an endosomal protease.

52. The complex of embodiment 50, wherein the protease-sensitive linker comprises a valine-citrulline dipeptide sequence.

53. The complex of embodiment 49, wherein the linker is pH-sensitive linker that is cleaved at a pH in a range of 4 to 6.

54. The complex of any one of embodiments 1 to 47, wherein the muscle-targeting agent is covalently linked to the molecular payload via a non-cleavable linker.

55. The complex of embodiment 54, wherein the non-cleavable linker is an alkane linker.

56. The complex of any one of embodiments 1 to 55, wherein the antibody comprises a non-natural amino acid to which the oligonucleotide is covalently linked.

57. The complex of any one of embodiments 1 to 55, wherein the antibody is covalently linked to the oligonucleotide via conjugation to a lysine residue or a cysteine residue of the antibody.

58. The complex of embodiment 57, wherein the oligonucleotide is conjugated to the cysteine of the antibody via a maleimide-containing linker, optionally wherein the maleimide-containing linker comprises a maleimidocaproyl or maleimidomethyl cyclohexane-1-carboxylate group.

59. The complex of embodiments 1 to 58, wherein the antibody is a glycosylated antibody that comprises at least one sugar moiety to which the oligonucleotide is covalently linked.

60. The complex of embodiment 59, wherein the sugar moiety is a branched mannose.

61. The complex of embodiment 59 or 60, wherein the antibody is a glycosylated antibody that comprises one to four sugar moieties each of which is covalently linked to a separate oligonucleotide.

62. The complex of embodiment 59, wherein the antibody is a fully-glycosylated antibody.

63. The complex of embodiment 59, wherein the antibody is a partially-glycosylated antibody.

64. The complex of embodiment 63, wherein the partially-glycosylated antibody is produced via chemical or enzymatic means.

65. The complex of embodiment 63, wherein the partially-glycosylated antibody is produced in a cell that is deficient for an enzyme in the N- or O-glycosylation pathway.

66. A method of delivering a molecular payload to a cell expressing transferrin receptor, the method comprising contacting the cell with the complex of any one of embodiments 1 to 65.

67. A method of inhibiting expression or activity of DUX4 in a cell, the method comprising contacting the cell with the complex of any one of embodiments 1 to 65 in an amount effective for promoting internalization of the molecular payload to the cell.

68. The method of embodiment 67, wherein the cell is in vitro.

69. The method of embodiment 67, wherein the cell is in a subject.

70. The method of embodiment 69, wherein the subject is a human.

71. A method of treating a subject having one or more deletions of a D4Z4 repeat in chromosome 4 that is associated with facioscapulohumeral muscular dystrophy, the method comprising administering to the subject an effective amount of the complex of any one of embodiments 1 to 65.

72. The method of embodiment 71, wherein the subject has 10 or fewer D4Z4 repeats.

73. The method of embodiment 72, wherein the subject has 9, 8, 7, 6, 5, 4, 3, 2, or 1 D4Z4 repeats.

74. The method of embodiment 72, wherein the subject has no D4Z4 repeats.

75. A complex comprising an anti-transferrin receptor (TfR) antibody covalently linked to a molecular payload configured for reducing expression or activity of DUX4, wherein the antibody comprises:

(i) a heavy chain variable region (VH) comprising an amino acid sequence at least 85% identical to SEQ ID NO: 76; and/or a light chain variable region (VL) comprising an amino acid sequence at least 85% identical to SEQ ID NO: 75;

(ii) a heavy chain variable region (VH) comprising an amino acid sequence at least 85% identical to SEQ ID NO: 69; and/or a light chain variable region (VL) comprising an amino acid sequence at least 85% identical to SEQ ID NO: 70;

(iii) a heavy chain variable region (VH) comprising an amino acid sequence at least 85% identical to SEQ ID NO: 71; and/or a light chain variable region (VL) comprising an amino acid sequence at least 85% identical to SEQ ID NO: 70;

(iv) a heavy chain variable region (VH) comprising an amino acid sequence at least 85% identical to SEQ ID NO: 72; and/or a light chain variable region (VL) comprising an amino acid sequence at least 85% identical to SEQ ID NO: 70;

(v) a heavy chain variable region (VH) comprising an amino acid sequence at least 85% identical to SEQ ID NO: 73; and/or a light chain variable region (VL) comprising an amino acid sequence at least 85% identical to SEQ ID NO: 74;

(vi) a heavy chain variable region (VH) comprising an amino acid sequence at least 85% identical to SEQ ID NO: 73; and/or a light chain variable region (VL) comprising an amino acid sequence at least 85% identical to SEQ ID NO: 75;

(vii) a heavy chain variable region (VH) comprising an amino acid sequence at least 85% identical to SEQ ID NO: 76; and/or a light chain variable region (VL) comprising an amino acid sequence at least 85% identical to SEQ ID NO: 74;

(viii) a heavy chain variable region (VH) comprising an amino acid sequence at least 85% identical to SEQ ID NO: 77; and/or a light chain variable region (VL) comprising an amino acid sequence at least 85% identical to SEQ ID NO: 78;

(ix) a heavy chain variable region (VH) comprising an amino acid sequence at least 85% identical to SEQ ID NO: 79; and/or a light chain variable region (VL) comprising an amino acid sequence at least 85% identical to SEQ ID NO: 80; or (x) a heavy chain variable region (VH) comprising an amino acid sequence at least 85% identical to SEQ ID NO: 77; and/or a light chain variable region (VL) comprising an amino acid sequence at least 85% identical to SEQ ID NO: 80.

76. A complex comprising an anti-transferrin receptor (TfR) antibody covalently linked to a molecular payload configured for reducing expression or activity of DUX4, wherein the anti-TfR antibody has undergone pyroglutamate formation resulting from a post-translational modification.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or (e.g., and) one or more modified nucleotides and/or (e.g., and) one or more modified internucleotide linkages and/or (e.g., and) one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising complexes comprising an anti-transferrin receptor (TfR) antibody covalently linked to at least one oligonucleotide, wherein the antibody is a Fab comprising a heavy chain comprising the amino acid sequence of SEQ ID NO: 101 and a light chain comprising the amino acid sequence of SEQ ID NO: 90, and wherein each anti-TfR antibody of the complexes is on average covalently linked to 1 to 3 oligonucleotides.

2. The composition of claim 1, wherein the heavy chain of the antibody comprises an N-terminal pyroglutamate.

3. The composition of claim 1, wherein the equilibrium dissociation constant (KD) of binding of the antibody to the transferrin receptor is in a range from $10^{-11}$ M to $10^{-6}$ M.

4. The composition of claim 1, wherein the oligonucleotide is single stranded.

5. The composition of claim 1, wherein the oligonucleotide is double stranded.

6. The composition of claim 1, wherein the oligonucleotide is an siRNA.

7. The composition of claim 1, wherein the oligonucleotide comprises one or more modified nucleosides.

8. The composition of claim 7, wherein the one or more modified nucleosides comprise 2'-modified nucleosides.

9. The composition of claim 1, wherein the oligonucleotide comprises one or more modified internucleoside linkages.

10. The composition of claim 9, wherein the oligonucleotide comprises one or more phosphorothioate internucleoside linkages.

11. The composition of claim 1, wherein the antibody is covalently linked to each oligonucleotide via a linker.

12. The composition of claim 11, wherein the linker comprises a cleavable linker.

13. The composition of claim 12, wherein the linker comprises a valine-citrulline sequence.

14. The composition of claim 1, wherein each complex comprises a structure of:

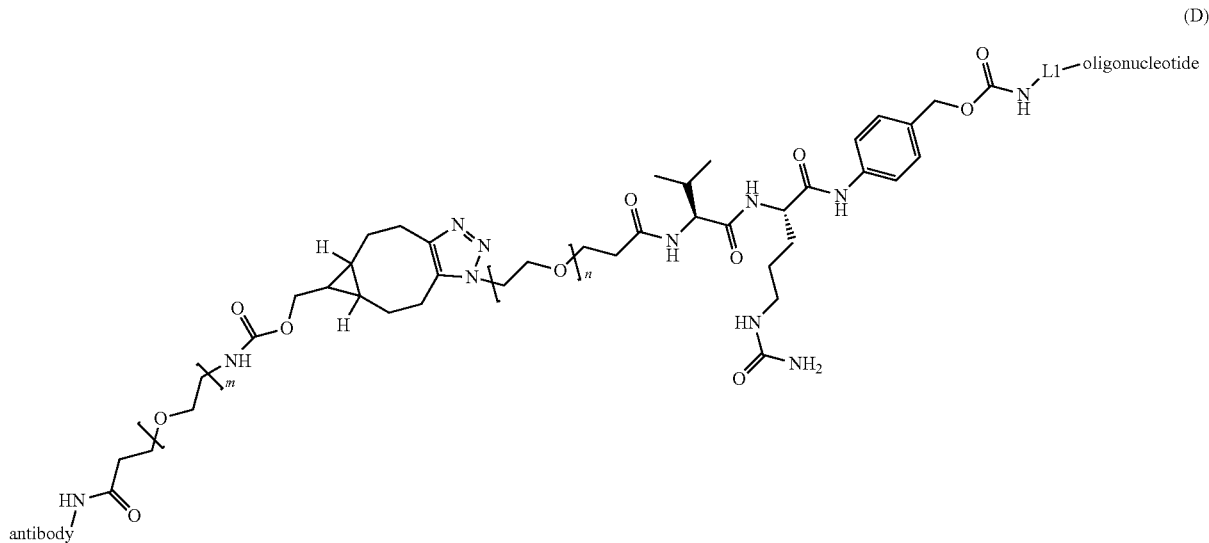

(D)

wherein n is 3 and m is 4, and wherein L1 comprises a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N($R^A$)—, —S—, —C(=O)—, —C(=O)O—, —C(=O)N$R^A$—, —N$R^A$C(=O)—, —N$R^A$C(=O)$R^A$—, —C(=O)$R^A$—, —N$R^A$C(=O)O—, —N$R^A$C(=O)N($R^A$)—, —OC(=O)—, —OC(=O)O—, —OC(=O)N($R^A$)—, —S(O)$_2$N$R^A$—, —N$R^A$S(O)$_2$—, or a combination thereof, wherein each $R^A$ is independently hydrogen or substituted or unsubstituted alkyl.

15. A method of delivering an oligonucleotide to a subject, comprising administering to the subject the composition of claim 8.

16. The method of claim 15, wherein the oligonucleotide is delivered to a muscle cell of the subject.

17. The method of claim 15, wherein the oligonucleotide is single stranded.

18. The method of claim 15, wherein the oligonucleotide is double stranded.

19. The method of claim 15, wherein the oligonucleotide is an siRNA.

20. The method of claim 15, wherein the subject is human.

21. The method of claim 15, wherein the subject has a muscle disorder.

22. The method of claim 21, wherein the muscle disorder is a muscular dystrophy.

23. The method of claim 22, wherein the muscular dystrophy is DMD.

24. The method of claim 22, wherein the muscular dystrophy is DM1.

25. The method of claim 22, wherein the muscular dystrophy is FSHD.

* * * * *

```
                              SEQUENCE LISTING

Sequence total quantity: 158
SEQ ID NO: 1           moltype = AA  length = 8
FEATURE                Location/Qualifiers
REGION                 1..8
                       note = Synthetic
source                 1..8
                       mol_type = protein
                       organism = synthetic construct
SEQUENCE: 1
GFNIKDDY                                                                    8

SEQ ID NO: 2           moltype = AA  length = 8
FEATURE                Location/Qualifiers
REGION                 1..8
                       note = Synthetic
source                 1..8
                       mol_type = protein
                       organism = synthetic construct
SEQUENCE: 2
IDPENGDT                                                                    8

SEQ ID NO: 3           moltype = AA  length = 10
FEATURE                Location/Qualifiers
REGION                 1..10
                       note = Synthetic
source                 1..10
                       mol_type = protein
                       organism = synthetic construct
SEQUENCE: 3
TLWLRRGLDY                                                                 10

SEQ ID NO: 4           moltype = AA  length = 11
FEATURE                Location/Qualifiers
REGION                 1..11
                       note = Synthetic
source                 1..11
                       mol_type = protein
                       organism = synthetic construct
SEQUENCE: 4
KSLLHSNGYT Y                                                               11

SEQ ID NO: 5           moltype =     length =
SEQUENCE: 5
000

SEQ ID NO: 6           moltype = AA  length = 9
FEATURE                Location/Qualifiers
REGION                 1..9
```

```
                        note = Synthetic
source                  1..9
                        mol_type = protein
                        organism = synthetic construct
SEQUENCE: 6
MQHLEYPFT                                                                    9

SEQ ID NO: 7            moltype = AA  length = 5
FEATURE                 Location/Qualifiers
REGION                  1..5
                        note = Synthetic
source                  1..5
                        mol_type = protein
                        organism = synthetic construct
SEQUENCE: 7
DDYMY                                                                        5

SEQ ID NO: 8            moltype = AA  length = 17
FEATURE                 Location/Qualifiers
REGION                  1..17
                        note = Synthetic
source                  1..17
                        mol_type = protein
                        organism = synthetic construct
SEQUENCE: 8
WIDPENGDTE YASKFQD                                                          17

SEQ ID NO: 9            moltype = AA  length = 8
FEATURE                 Location/Qualifiers
REGION                  1..8
                        note = Synthetic
source                  1..8
                        mol_type = protein
                        organism = synthetic construct
SEQUENCE: 9
WLRRGLDY                                                                     8

SEQ ID NO: 10           moltype = AA  length = 16
FEATURE                 Location/Qualifiers
REGION                  1..16
                        note = Synthetic
source                  1..16
                        mol_type = protein
                        organism = synthetic construct
SEQUENCE: 10
RSSKSLLHSN GYTYLF                                                           16

SEQ ID NO: 11           moltype = AA  length = 7
FEATURE                 Location/Qualifiers
REGION                  1..7
                        note = Synthetic
source                  1..7
                        mol_type = protein
                        organism = synthetic construct
SEQUENCE: 11
RMSNLAS                                                                      7

SEQ ID NO: 12           moltype = AA  length = 7
FEATURE                 Location/Qualifiers
REGION                  1..7
                        note = Synthetic
source                  1..7
                        mol_type = protein
                        organism = synthetic construct
SEQUENCE: 12
GFNIKDD                                                                      7

SEQ ID NO: 13           moltype =     length =
SEQUENCE: 13
000

SEQ ID NO: 14           moltype = AA  length = 6
FEATURE                 Location/Qualifiers
REGION                  1..6
                        note = Synthetic
source                  1..6
                        mol_type = protein
                        organism = synthetic construct
SEQUENCE: 14
```

```
LRRGLD                                                                          6

SEQ ID NO: 15           moltype = AA  length = 12
FEATURE                 Location/Qualifiers
REGION                  1..12
                        note = Synthetic
source                  1..12
                        mol_type = protein
                        organism = synthetic construct
SEQUENCE: 15
SKSLLHSNGY TY                                                                  12

SEQ ID NO: 16           moltype = AA  length = 6
FEATURE                 Location/Qualifiers
REGION                  1..6
                        note = Synthetic
source                  1..6
                        mol_type = protein
                        organism = synthetic construct
SEQUENCE: 16
HLEYPF                                                                          6

SEQ ID NO: 17           moltype = AA  length = 117
FEATURE                 Location/Qualifiers
REGION                  1..117
                        note = Synthetic
source                  1..117
                        mol_type = protein
                        organism = synthetic construct
SEQUENCE: 17
EVQLQQSGAE LVRPGASVKL SCTASGFNIK DDYMYWVKQR PEQGLEWIGW IDPENGDTEY              60
ASKFQDKATV TADTSSNTAY LQLSSLTSED TAVYYCTLWL RRGLDYWGQG TSVTVSS                117

SEQ ID NO: 18           moltype = AA  length = 112
FEATURE                 Location/Qualifiers
REGION                  1..112
                        note = Synthetic
source                  1..112
                        mol_type = protein
                        organism = synthetic construct
SEQUENCE: 18
DIVMTQAAPS VPVTPGESVS ISCRSSKSLL HSNGYTYLFW FLQRPGQSPQ LLIYRMSNLA              60
SGVPDRFSGS GSGTAFTLRI SRVEAEDVGV YYCMQHLEYP FTFGGGTKLE IK                     112

SEQ ID NO: 19           moltype = AA  length = 8
FEATURE                 Location/Qualifiers
REGION                  1..8
                        note = Synthetic
source                  1..8
                        mol_type = protein
                        organism = synthetic construct
SEQUENCE: 19
IDPETGDT                                                                        8

SEQ ID NO: 20           moltype = AA  length = 17
FEATURE                 Location/Qualifiers
REGION                  1..17
                        note = Synthetic
source                  1..17
                        mol_type = protein
                        organism = synthetic construct
SEQUENCE: 20
WIDPETGDTE YASKFQD                                                             17

SEQ ID NO: 21           moltype =     length =
SEQUENCE: 21
000

SEQ ID NO: 22           moltype = AA  length = 117
FEATURE                 Location/Qualifiers
REGION                  1..117
                        note = Synthetic
source                  1..117
                        mol_type = protein
                        organism = synthetic construct
SEQUENCE: 22
EVQLQQSGAE LVRPGASVKL SCTASGFNIK DDYMYWVKQR PEQGLEWIGW IDPETGDTEY              60
ASKFQDKATV TADTSSNTAY LQLSSLTSED TAVYYCTLWL RRGLDYWGQG TSVTVSS                117
```

```
SEQ ID NO: 23              moltype = AA  length = 8
FEATURE                    Location/Qualifiers
REGION                     1..8
                           note = Synthetic
source                     1..8
                           mol_type = protein
                           organism = synthetic construct
SEQUENCE: 23
IDPESGDT                                                                    8

SEQ ID NO: 24              moltype = AA  length = 17
FEATURE                    Location/Qualifiers
REGION                     1..17
                           note = Synthetic
source                     1..17
                           mol_type = protein
                           organism = synthetic construct
SEQUENCE: 24
WIDPESGDTE YASKFQD                                                         17

SEQ ID NO: 25              moltype =     length =
SEQUENCE: 25
000

SEQ ID NO: 26              moltype = AA  length = 117
FEATURE                    Location/Qualifiers
REGION                     1..117
                           note = Synthetic
source                     1..117
                           mol_type = protein
                           organism = synthetic construct
SEQUENCE: 26
EVQLQQSGAE LVRPGASVKL SCTASGFNIK DDYMYWVKQR PEQGLEWIGW IDPESGDTEY           60
ASKFQDKATV TADTSSNTAY LQLSSLTSED TAVYYCTLWL RRGLDYWGQG TSVTVSS             117

SEQ ID NO: 27              moltype = AA  length = 9
FEATURE                    Location/Qualifiers
REGION                     1..9
                           note = Synthetic
source                     1..9
                           mol_type = protein
                           organism = synthetic construct
SEQUENCE: 27
GYSITSGYY                                                                   9

SEQ ID NO: 28              moltype = AA  length = 7
FEATURE                    Location/Qualifiers
REGION                     1..7
                           note = Synthetic
source                     1..7
                           mol_type = protein
                           organism = synthetic construct
SEQUENCE: 28
ITFDGAN                                                                     7

SEQ ID NO: 29              moltype = AA  length = 12
FEATURE                    Location/Qualifiers
REGION                     1..12
                           note = Synthetic
source                     1..12
                           mol_type = protein
                           organism = synthetic construct
SEQUENCE: 29
TRSSYDYDVL DY                                                              12

SEQ ID NO: 30              moltype = AA  length = 6
FEATURE                    Location/Qualifiers
REGION                     1..6
                           note = Synthetic
source                     1..6
                           mol_type = protein
                           organism = synthetic construct
SEQUENCE: 30
QDISNF                                                                      6

SEQ ID NO: 31              moltype =     length =
SEQUENCE: 31
000
```

```
SEQ ID NO: 32            moltype = AA  length = 9
FEATURE                  Location/Qualifiers
REGION                   1..9
                         note = Synthetic
source                   1..9
                         mol_type = protein
                         organism = synthetic construct
SEQUENCE: 32
QQGHTLPYT                                                                9

SEQ ID NO: 33            moltype = AA  length = 6
FEATURE                  Location/Qualifiers
REGION                   1..6
                         note = Synthetic
source                   1..6
                         mol_type = protein
                         organism = synthetic construct
SEQUENCE: 33
SGYYWN                                                                   6

SEQ ID NO: 34            moltype = AA  length = 16
FEATURE                  Location/Qualifiers
REGION                   1..16
                         note = Synthetic
source                   1..16
                         mol_type = protein
                         organism = synthetic construct
SEQUENCE: 34
YITFDGANNY NPSLKN                                                       16

SEQ ID NO: 35            moltype = AA  length = 10
FEATURE                  Location/Qualifiers
REGION                   1..10
                         note = Synthetic
source                   1..10
                         mol_type = protein
                         organism = synthetic construct
SEQUENCE: 35
SSYDYDVLDY                                                              10

SEQ ID NO: 36            moltype = AA  length = 11
FEATURE                  Location/Qualifiers
REGION                   1..11
                         note = Synthetic
source                   1..11
                         mol_type = protein
                         organism = synthetic construct
SEQUENCE: 36
RASQDISNFL N                                                            11

SEQ ID NO: 37            moltype = AA  length = 7
FEATURE                  Location/Qualifiers
REGION                   1..7
                         note = Synthetic
source                   1..7
                         mol_type = protein
                         organism = synthetic construct
SEQUENCE: 37
YTSRLHS                                                                  7

SEQ ID NO: 38            moltype = AA  length = 8
FEATURE                  Location/Qualifiers
REGION                   1..8
                         note = Synthetic
source                   1..8
                         mol_type = protein
                         organism = synthetic construct
SEQUENCE: 38
GYSITSGY                                                                 8

SEQ ID NO: 39            moltype =     length =
SEQUENCE: 39
000

SEQ ID NO: 40            moltype = AA  length = 8
FEATURE                  Location/Qualifiers
REGION                   1..8
                         note = Synthetic
source                   1..8
```

```
                        mol_type = protein
                        organism = synthetic construct
SEQUENCE: 40
SYDYDVLD                                                                     8

SEQ ID NO: 41           moltype = AA   length = 7
FEATURE                 Location/Qualifiers
REGION                  1..7
                        note = Synthetic
source                  1..7
                        mol_type = protein
                        organism = synthetic construct
SEQUENCE: 41
SQDISNF                                                                      7

SEQ ID NO: 42           moltype = AA   length = 6
FEATURE                 Location/Qualifiers
REGION                  1..6
                        note = Synthetic
source                  1..6
                        mol_type = protein
                        organism = synthetic construct
SEQUENCE: 42
GHTLPY                                                                       6

SEQ ID NO: 43           moltype = AA   length = 119
FEATURE                 Location/Qualifiers
REGION                  1..119
                        note = Synthetic
source                  1..119
                        mol_type = protein
                        organism = synthetic construct
SEQUENCE: 43
DVQLQESGPG LVKPSQSLSL TCSVTGYSIT SGYYWNWIRQ FPGNKLEWMG YITFDGANNY            60
NPSLKNRISI TRDTSKNQFF LKLTSVTTED TATYYCTRSS YDYDVLDYWG QGTTLTVSS            119

SEQ ID NO: 44           moltype = AA   length = 107
FEATURE                 Location/Qualifiers
REGION                  1..107
                        note = Synthetic
source                  1..107
                        mol_type = protein
                        organism = synthetic construct
SEQUENCE: 44
DIQMTQTTSS LSASLGDRVT ISCRASQDIS NFLNWYQQRP DGTVKLLIYY TSRLHSGVPS            60
RFSGSGSGTD FSLTVSNLEQ EDIATYFCQQ GHTLPYTFGG GTKLEIK                        107

SEQ ID NO: 45           moltype = AA   length = 8
FEATURE                 Location/Qualifiers
REGION                  1..8
                        note = Synthetic
source                  1..8
                        mol_type = protein
                        organism = synthetic construct
SEQUENCE: 45
GYSFTDYC                                                                     8

SEQ ID NO: 46           moltype = AA   length = 8
FEATURE                 Location/Qualifiers
REGION                  1..8
                        note = Synthetic
source                  1..8
                        mol_type = protein
                        organism = synthetic construct
SEQUENCE: 46
IYPGSGNT                                                                     8

SEQ ID NO: 47           moltype = AA   length = 13
FEATURE                 Location/Qualifiers
REGION                  1..13
                        note = Synthetic
source                  1..13
                        mol_type = protein
                        organism = synthetic construct
SEQUENCE: 47
AREDYYPYHG MDY                                                              13

SEQ ID NO: 48           moltype = AA   length = 10
FEATURE                 Location/Qualifiers
```

```
REGION              1..10
                    note = Synthetic
source              1..10
                    mol_type = protein
                    organism = synthetic construct
SEQUENCE: 48
ESVDGYDNSF                                                              10

SEQ ID NO: 49       moltype =   length =
SEQUENCE: 49
000

SEQ ID NO: 50       moltype = AA  length = 9
FEATURE             Location/Qualifiers
REGION              1..9
                    note = Synthetic
source              1..9
                    mol_type = protein
                    organism = synthetic construct
SEQUENCE: 50
QQSSEDPWT                                                                9

SEQ ID NO: 51       moltype = AA  length = 5
FEATURE             Location/Qualifiers
REGION              1..5
                    note = Synthetic
source              1..5
                    mol_type = protein
                    organism = synthetic construct
SEQUENCE: 51
DYCIN                                                                    5

SEQ ID NO: 52       moltype = AA  length = 17
FEATURE             Location/Qualifiers
REGION              1..17
                    note = Synthetic
source              1..17
                    mol_type = protein
                    organism = synthetic construct
SEQUENCE: 52
WIYPGSGNTR YSERFKG                                                      17

SEQ ID NO: 53       moltype = AA  length = 11
FEATURE             Location/Qualifiers
REGION              1..11
                    note = Synthetic
source              1..11
                    mol_type = protein
                    organism = synthetic construct
SEQUENCE: 53
EDYYPYHGMD Y                                                            11

SEQ ID NO: 54       moltype = AA  length = 15
FEATURE             Location/Qualifiers
REGION              1..15
                    note = Synthetic
source              1..15
                    mol_type = protein
                    organism = synthetic construct
SEQUENCE: 54
RASESVDGYD NSFMH                                                        15

SEQ ID NO: 55       moltype = AA  length = 7
FEATURE             Location/Qualifiers
REGION              1..7
                    note = Synthetic
source              1..7
                    mol_type = protein
                    organism = synthetic construct
SEQUENCE: 55
RASNLES                                                                  7

SEQ ID NO: 56       moltype = AA  length = 7
FEATURE             Location/Qualifiers
REGION              1..7
                    note = Synthetic
source              1..7
                    mol_type = protein
                    organism = synthetic construct
```

```
SEQUENCE: 56
GYSFTDY                                                                 7

SEQ ID NO: 57           moltype =    length =
SEQUENCE: 57
000

SEQ ID NO: 58           moltype = AA   length = 9
FEATURE                 Location/Qualifiers
REGION                  1..9
                        note = Synthetic
source                  1..9
                        mol_type = protein
                        organism = synthetic construct
SEQUENCE: 58
DYYPYHGMD                                                               9

SEQ ID NO: 59           moltype = AA   length = 11
FEATURE                 Location/Qualifiers
REGION                  1..11
                        note = Synthetic
source                  1..11
                        mol_type = protein
                        organism = synthetic construct
SEQUENCE: 59
SESVDGYDNS F                                                           11

SEQ ID NO: 60           moltype = AA   length = 6
FEATURE                 Location/Qualifiers
REGION                  1..6
                        note = Synthetic
source                  1..6
                        mol_type = protein
                        organism = synthetic construct
SEQUENCE: 60
SSEDPW                                                                  6

SEQ ID NO: 61           moltype = AA   length = 120
FEATURE                 Location/Qualifiers
REGION                  1..120
                        note = Synthetic
source                  1..120
                        mol_type = protein
                        organism = synthetic construct
SEQUENCE: 61
QIQLQQSGPE LVRPGASVKI SCKASGYSFT DYCINWVNQR PGQGLEWIGW IYPGSGNTRY        60
SERFKGKATL TVDTSSNTAY MQLSSLTSED SAVYFCARED YYPYHGMDYW GQGTSVTVSS       120

SEQ ID NO: 62           moltype = AA   length = 111
FEATURE                 Location/Qualifiers
REGION                  1..111
                        note = Synthetic
source                  1..111
                        mol_type = protein
                        organism = synthetic construct
SEQUENCE: 62
DIVLTQSPTS LAVSLGQRAT ISCRASESVD GYDNSFMHWY QQKPGQPPKL LIFRASNLES        60
GIPARFSGSG SRTDFTLTIN PVEAADVATY YCQQSSEDPW TFGGGTKLEI K                111

SEQ ID NO: 63           moltype = AA   length = 8
FEATURE                 Location/Qualifiers
REGION                  1..8
                        note = Synthetic
source                  1..8
                        mol_type = protein
                        organism = synthetic construct
SEQUENCE: 63
GYSFTDYY                                                                8

SEQ ID NO: 64           moltype = AA   length = 5
FEATURE                 Location/Qualifiers
REGION                  1..5
                        note = Synthetic
source                  1..5
                        mol_type = protein
                        organism = synthetic construct
SEQUENCE: 64
DYYIN                                                                   5
```

```
SEQ ID NO: 65            moltype = AA   length = 120
FEATURE                  Location/Qualifiers
REGION                   1..120
                         note = Synthetic
source                   1..120
                         mol_type = protein
                         organism = synthetic construct
SEQUENCE: 65
QIQLQQSGPE LVRPGASVKI SCKASGYSFT DYYINWVNQR PGQGLEWIGW IYPGSGNTRY   60
SERFKGKATL TVDTSSNTAY MQLSSLTSED SAVYFCARED YYPYHGMDYW GQGTSVTVSS  120

SEQ ID NO: 66            moltype = AA   length = 8
FEATURE                  Location/Qualifiers
REGION                   1..8
                         note = Synthetic
source                   1..8
                         mol_type = protein
                         organism = synthetic construct
SEQUENCE: 66
GYSFTDYD                                                             8

SEQ ID NO: 67            moltype = AA   length = 5
FEATURE                  Location/Qualifiers
REGION                   1..5
                         note = Synthetic
source                   1..5
                         mol_type = protein
                         organism = synthetic construct
SEQUENCE: 67
DYDIN                                                                5

SEQ ID NO: 68            moltype = AA   length = 120
FEATURE                  Location/Qualifiers
REGION                   1..120
                         note = Synthetic
source                   1..120
                         mol_type = protein
                         organism = synthetic construct
SEQUENCE: 68
QIQLQQSGPE LVRPGASVKI SCKASGYSFT DYDINWVNQR PGQGLEWIGW IYPGSGNTRY   60
SERFKGKATL TVDTSSNTAY MQLSSLTSED SAVYFCARED YYPYHGMDYW GQGTSVTVSS  120

SEQ ID NO: 69            moltype = AA   length = 117
FEATURE                  Location/Qualifiers
REGION                   1..117
                         note = Synthetic
source                   1..117
                         mol_type = protein
                         organism = synthetic construct
SEQUENCE: 69
EVQLVQSGSE LKKPGASVKV SCTASGFNIK DDYMYWVRQP PGKGLEWIGW IDPETGDTEY   60
ASKFQDRVTV TADTSTNTAY MELSSLRSED TAVYYCTLWL RRGLDYWGQG TLVTVSS     117

SEQ ID NO: 70            moltype = AA   length = 112
FEATURE                  Location/Qualifiers
REGION                   1..112
                         note = Synthetic
source                   1..112
                         mol_type = protein
                         organism = synthetic construct
SEQUENCE: 70
DIVMTQSPLS LPVTPGEPAS ISCRSSKSLL HSNGYTYLFW FQQRPGQSPR LLIYRMSNLA   60
SGVPDRFSGS GSGTDFTLKI SRVEAEDVGV YYCMQHLEYP FTFGGGTKVE IK          112

SEQ ID NO: 71            moltype = AA   length = 117
FEATURE                  Location/Qualifiers
REGION                   1..117
                         note = Synthetic
source                   1..117
                         mol_type = protein
                         organism = synthetic construct
SEQUENCE: 71
EVQLVQSGSE LKKPGASVKV SCTASGFNIK DDYMYWVRQP PGKGLEWIGW IDPESGDTEY   60
ASKFQDRVTV TADTSTNTAY MELSSLRSED TAVYYCTLWL RRGLDYWGQG TLVTVSS     117

SEQ ID NO: 72            moltype = AA   length = 117
FEATURE                  Location/Qualifiers
REGION                   1..117
                         note = Synthetic
```

```
source                   1..117
                         mol_type = protein
                         organism = synthetic construct
SEQUENCE: 72
EVQLVQSGSE LKKPGASVKV SCTASGFNIK DDYMYWVRQP PGKGLEWIGW IDPENGDTEY    60
ASKFQDRVTV TADTSTNTAY MELSSLRSED TAVYYCTLWL RRGLDYWGQG TLVTVSS      117

SEQ ID NO: 73            moltype = AA  length = 119
FEATURE                  Location/Qualifiers
REGION                   1..119
                         note = Synthetic
source                   1..119
                         mol_type = protein
                         organism = synthetic construct
SEQUENCE: 73
QVQLQESGPG LVKPSQTLSL TCSVTGYSIT SGYYWNWIRQ PPGKGLEWMG YITFDGANNY    60
NPSLKNRVSI SRDTSKNQFS LKLSSVTAED TATYYCTRSS YDYDVLDYWG QGTTVTVSS    119

SEQ ID NO: 74            moltype = AA  length = 107
FEATURE                  Location/Qualifiers
REGION                   1..107
                         note = Synthetic
source                   1..107
                         mol_type = protein
                         organism = synthetic construct
SEQUENCE: 74
DIQMTQSPSS LSASVGDRVT ITCRASQDIS NFLNWYQQKP GQPVKLLIYY TSRLHSGVPS    60
RFSGSGSGTD FTLTISSLQP EDFATYFCQQ GHTLPYTFGQ GTKLEIK                 107

SEQ ID NO: 75            moltype = AA  length = 107
FEATURE                  Location/Qualifiers
REGION                   1..107
                         note = Synthetic
source                   1..107
                         mol_type = protein
                         organism = synthetic construct
SEQUENCE: 75
DIQMTQSPSS LSASVGDRVT ITCRASQDIS NFLNWYQQKP GQPVKLLIYY TSRLHSGVPS    60
RFSGSGSGTD FTLTISSLQP EDFATYYCQQ GHTLPYTFGQ GTKLEIK                 107

SEQ ID NO: 76            moltype = AA  length = 119
FEATURE                  Location/Qualifiers
REGION                   1..119
                         note = Synthetic
source                   1..119
                         mol_type = protein
                         organism = synthetic construct
SEQUENCE: 76
QVQLQESGPG LVKPSQTLSL TCTVTGYSIT SGYYWNWIRQ PPGKGLEWIG YITFDGANNY    60
NPSLKNRVSI SRDTSKNQFS LKLSSVTAED TATYYCTRSS YDYDVLDYWG QGTTVTVSS    119

SEQ ID NO: 77            moltype = AA  length = 120
FEATURE                  Location/Qualifiers
REGION                   1..120
                         note = Synthetic
source                   1..120
                         mol_type = protein
                         organism = synthetic construct
SEQUENCE: 77
QVQLVQSGAE VKKPGASVKV SCKASGYSFT DYYINWVRQA PGQGLEWMGW IYPGSGNTRY    60
SERFKGRVTI TRDTSASTAY MELSSLRSED TAVYYCARED YYPYHGMDYW GQGTLVTVSS   120

SEQ ID NO: 78            moltype = AA  length = 111
FEATURE                  Location/Qualifiers
REGION                   1..111
                         note = Synthetic
source                   1..111
                         mol_type = protein
                         organism = synthetic construct
SEQUENCE: 78
DIVLTQSPDS LAVSLGERAT INCRASESVD GYDNSFMHWY QQKPGQPPKL LIFRASNLES    60
GVPDRFSGSG SRTDFTLTIS SLQAEDVAVY YCQQSSEDPW TFGQGTKLEI K            111

SEQ ID NO: 79            moltype = AA  length = 120
FEATURE                  Location/Qualifiers
REGION                   1..120
                         note = Synthetic
source                   1..120
                         mol_type = protein
```

```
                              organism = synthetic construct
SEQUENCE: 79
QVQLVQSGAE VKKPGASVKV SCKASGYSFT DYDINWVRQA PGQGLEWMGW IYPGSGNTRY    60
SERFKGRVTI TRDTSASTAY MELSSLRSED TAVYYCARED YYPYHGMDYW GQGTLVTVSS   120

SEQ ID NO: 80              moltype = AA   length = 111
FEATURE                    Location/Qualifiers
REGION                     1..111
                           note = Synthetic
source                     1..111
                           mol_type = protein
                           organism = synthetic construct
SEQUENCE: 80
DIVMTQSPDS LAVSLGERAT INCRASESVD GYDNSFMHWY QQKPGQPPKL LIFRASNLES    60
GVPDRFSGSG SGTDFTLTIS SLQAEDVAVY YCQQSSEDPW TFGQGTKLEI K            111

SEQ ID NO: 81              moltype = AA   length = 330
FEATURE                    Location/Qualifiers
source                     1..330
                           mol_type = protein
                           organism = Homo sapiens
SEQUENCE: 81
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 82              moltype = AA   length = 330
FEATURE                    Location/Qualifiers
REGION                     1..330
                           note = Synthetic
source                     1..330
                           mol_type = protein
                           organism = synthetic construct
SEQUENCE: 82
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 83              moltype = AA   length = 107
FEATURE                    Location/Qualifiers
REGION                     1..107
                           note = Synthetic
source                     1..107
                           mol_type = protein
                           organism = synthetic construct
SEQUENCE: 83
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 84              moltype = AA   length = 447
FEATURE                    Location/Qualifiers
REGION                     1..447
                           note = Synthetic
source                     1..447
                           mol_type = protein
                           organism = synthetic construct
SEQUENCE: 84
EVQLVQSGSE LKKPGASVKV SCTASGFNIK DDYMYWVRQP PGKGLEWIGW IDPETGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 85              moltype = AA   length = 219
FEATURE                    Location/Qualifiers
REGION                     1..219
                           note = Synthetic
source                     1..219
                           mol_type = protein
                           organism = synthetic construct
```

```
SEQUENCE: 85
DIVMTQSPLS LPVTPGEPAS ISCRSSKSLL HSNGYTYLFW FQQRPGQSPR LLIYRMSNLA    60
SGVPDRFSGS GSGTDFTLKI SRVEAEDVGV YYCMQHLEYP FTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 86          moltype = AA  length = 447
FEATURE                Location/Qualifiers
REGION                 1..447
                       note = Synthetic
source                 1..447
                       mol_type = protein
                       organism = synthetic construct
SEQUENCE: 86
EVQLVQSGSE LKKPGASVKV SCTASGFNIK DDYMYWVRQP PGKGLEWIGW IDPESGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 87          moltype = AA  length = 447
FEATURE                Location/Qualifiers
REGION                 1..447
                       note = Synthetic
source                 1..447
                       mol_type = protein
                       organism = synthetic construct
SEQUENCE: 87
EVQLVQSGSE LKKPGASVKV SCTASGFNIK DDYMYWVRQP PGKGLEWIGW IDPENGDTEY    60
ASKFQDRVTV TADTSTNTAY MELSSLRSED TAVYYCTLWL RRGLDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 88          moltype = AA  length = 449
FEATURE                Location/Qualifiers
REGION                 1..449
                       note = Synthetic
source                 1..449
                       mol_type = protein
                       organism = synthetic construct
SEQUENCE: 88
QVQLQESGPG LVKPSQTLSL TCSVTGYSIT SGYYWNWIRQ PPGKGLEWMG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 89          moltype = AA  length = 214
FEATURE                Location/Qualifiers
REGION                 1..214
                       note = Synthetic
source                 1..214
                       mol_type = protein
                       organism = synthetic construct
SEQUENCE: 89
DIQMTQSPSS LSASVGDRVT ITCRASQDIS NFLNWYQQKP GQPVKLLIYY TSRLHSGVPS    60
RFSGSGSGTD FTLTISSLQP EDFATYFCQQ GHTLPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 90          moltype = AA  length = 214
FEATURE                Location/Qualifiers
REGION                 1..214
                       note = Synthetic
source                 1..214
                       mol_type = protein
                       organism = synthetic construct
SEQUENCE: 90
DIQMTQSPSS LSASVGDRVT ITCRASQDIS NFLNWYQQKP GQPVKLLIYY TSRLHSGVPS    60
```

```
RFSGSGSGTD FTLTISSLQP EDFATYYCQQ GHTLPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 91             moltype = AA   length = 449
FEATURE                   Location/Qualifiers
REGION                    1..449
                          note = Synthetic
source                    1..449
                          mol_type = protein
                          organism = synthetic construct
SEQUENCE: 91
QVQLQESGPG LVKPSQTLSL TCTVTGYSIT SGYYWNWIRQ PPGKGLEWIG YITFDGANNY     60
NPSLKNRVSI SRDTSKNQFS LKLSSVTAED TATYYCTRSS YDYDVLDYWG QGTTVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 92             moltype = AA   length = 450
FEATURE                   Location/Qualifiers
REGION                    1..450
                          note = Synthetic
source                    1..450
                          mol_type = protein
                          organism = synthetic construct
SEQUENCE: 92
QVQLVQSGAE VKKPGASVKV SCKASGYSFT DYYINWVRQA PGQGLEWMGW IYPGSGNTRY     60
SERFKGRVTI TRDTSASTAY MELSSLRSED TAVYYCARED YYPYHGMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 93             moltype = AA   length = 218
FEATURE                   Location/Qualifiers
REGION                    1..218
                          note = Synthetic
source                    1..218
                          mol_type = protein
                          organism = synthetic construct
SEQUENCE: 93
DIVLTQSPDS LAVSLGERAT INCRASESVD GYDNSFMHWY QQKPGQPPKL LIFRASNLES     60
GVPDRFSGSG SRTDFTLTIS SLQAEDVAVY YCQQSSEDPW TFGQGTKLEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 94             moltype = AA   length = 450
FEATURE                   Location/Qualifiers
REGION                    1..450
                          note = Synthetic
source                    1..450
                          mol_type = protein
                          organism = synthetic construct
SEQUENCE: 94
QVQLVQSGAE VKKPGASVKV SCKASGYSFT DYDINWVRQA PGQGLEWMGW IYPGSGNTRY     60
SERFKGRVTI TRDTSASTAY MELSSLRSED TAVYYCARED YYPYHGMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 95             moltype = AA   length = 218
FEATURE                   Location/Qualifiers
REGION                    1..218
                          note = Synthetic
source                    1..218
                          mol_type = protein
                          organism = synthetic construct
SEQUENCE: 95
DIVMTQSPDS LAVSLGERAT INCRASESVD GYDNSFMHWY QQKPGQPPKL LIFRASNLES     60
GVPDRFSGSG SGTDFTLTIS SLQAEDVAVY YCQQSSEDPW TFGQGTKLEI KRTVAAPSVF    120
IFPPSDEQLK SGTASVVCLL NNFYPREAKV QWKVDNALQS GNSQESVTEQ DSKDSTYSLS    180
```

```
STLTLSKADY EKHKVYACEV THQGLSSPVT KSFNRGEC                              218

SEQ ID NO: 96           moltype = AA  length = 108
FEATURE                 Location/Qualifiers
REGION                  1..108
                        note = Synthetic
source                  1..108
                        mol_type = protein
                        organism = synthetic construct
SEQUENCE: 96
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHT                  108

SEQ ID NO: 97           moltype = AA  length = 225
FEATURE                 Location/Qualifiers
REGION                  1..225
                        note = Synthetic
source                  1..225
                        mol_type = protein
                        organism = synthetic construct
SEQUENCE: 97
EVQLVQSGSE LKKPGASVKV SCTASGFNIK DDYMYWVRQP PGKGLEWIGW IDPETGDTEY     60
ASKFQDRVTV TADTSTNTAY MELSSLRSED TAVYYCTLWL RRGLDYWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKKVEPKSC DKTHT                     225

SEQ ID NO: 98           moltype = AA  length = 225
FEATURE                 Location/Qualifiers
REGION                  1..225
                        note = Synthetic
source                  1..225
                        mol_type = protein
                        organism = synthetic construct
SEQUENCE: 98
EVQLVQSGSE LKKPGASVKV SCTASGFNIK DDYMYWVRQP PGKGLEWIGW IDPESGDTEY     60
ASKFQDRVTV TADTSTNTAY MELSSLRSED TAVYYCTLWL RRGLDYWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKKVEPKSC DKTHT                     225

SEQ ID NO: 99           moltype = AA  length = 225
FEATURE                 Location/Qualifiers
REGION                  1..225
                        note = Synthetic
source                  1..225
                        mol_type = protein
                        organism = synthetic construct
SEQUENCE: 99
EVQLVQSGSE LKKPGASVKV SCTASGFNIK DDYMYWVRQP PGKGLEWIGW IDPENGDTEY     60
ASKFQDRVTV TADTSTNTAY MELSSLRSED TAVYYCTLWL RRGLDYWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKKVEPKSC DKTHT                     225

SEQ ID NO: 100          moltype = AA  length = 227
FEATURE                 Location/Qualifiers
REGION                  1..227
                        note = Synthetic
source                  1..227
                        mol_type = protein
                        organism = synthetic construct
SEQUENCE: 100
QVQLQESGPG LVKPSQTLSL TCSVTGYSIT SGYYWNWIRQ PPGKGLEWMG YITFDGANNY     60
NPSLKNRVSI SRDTSKNQFS LKLSSVTAED TATYYCTRSS YDYDVLDYWG QGTTVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHT                   227

SEQ ID NO: 101          moltype = AA  length = 227
FEATURE                 Location/Qualifiers
REGION                  1..227
                        note = Synthetic
source                  1..227
                        mol_type = protein
                        organism = synthetic construct
SEQUENCE: 101
QVQLQESGPG LVKPSQTLSL TCTVTGYSIT SGYYWNWIRQ PPGKGLEWIG YITFDGANNY     60
NPSLKNRVSI SRDTSKNQFS LKLSSVTAED TATYYCTRSS YDYDVLDYWG QGTTVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHT                   227

SEQ ID NO: 102          moltype = AA  length = 228
```

| FEATURE | Location/Qualifiers |
|---|---|
| REGION | 1..228 |
| | note = Synthetic |
| source | 1..228 |
| | mol_type = protein |
| | organism = synthetic construct |

SEQUENCE: 102

| | | | | | |
|---|---|---|---|---|---|
| QVQLVQSGAE | VKKPGASVKV | SCKASGYSFT | DYYINWVRQA | PGQGLEWMGW | IYPGSGNTRY | 60 |
| SERFKGRVTI | TRDTSASTAY | MELSSLRSED | TAVYYCARED | YYPYHGMDYW | GQGTLVTVSS | 120 |
| ASTKGPSVFP | LAPSSKSTSG | GTAALGCLVK | DYFPEPVTVS | WNSGALTSGV | HTFPAVLQSS | 180 |
| GLYSLSSVVT | VPSSSLGTQT | YICNVNHKPS | NTKVDKKVEP | KSCDKTHT | | 228 |

| SEQ ID NO: 103 | moltype = AA length = 228 |
|---|---|
| FEATURE | Location/Qualifiers |
| REGION | 1..228 |
| | note = Synthetic |
| source | 1..228 |
| | mol_type = protein |
| | organism = synthetic construct |

SEQUENCE: 103

| | | | | | |
|---|---|---|---|---|---|
| QVQLVQSGAE | VKKPGASVKV | SCKASGYSFT | DYDINWVRQA | PGQGLEWMGW | IYPGSGNTRY | 60 |
| SERFKGRVTI | TRDTSASTAY | MELSSLRSED | TAVYYCARED | YYPYHGMDYW | GQGTLVTVSS | 120 |
| ASTKGPSVFP | LAPSSKSTSG | GTAALGCLVK | DYFPEPVTVS | WNSGALTSGV | HTFPAVLQSS | 180 |
| GLYSLSSVVT | VPSSSLGTQT | YICNVNHKPS | NTKVDKKVEP | KSCDKTHT | | 228 |

| SEQ ID NO: 104 | moltype = AA length = 19 |
|---|---|
| FEATURE | Location/Qualifiers |
| REGION | 1..19 |
| | note = Synthetic |
| source | 1..19 |
| | mol_type = protein |
| | organism = synthetic construct |

SEQUENCE: 104

| | |
|---|---|
| MGWSCIILFL | VATATGVHS | 19 |

| SEQ ID NO: 105 | moltype = AA length = 760 |
|---|---|
| FEATURE | Location/Qualifiers |
| source | 1..760 |
| | mol_type = protein |
| | organism = Homo sapiens |

SEQUENCE: 105

| | | | | | |
|---|---|---|---|---|---|
| MMDQARSAFS | NLFGGEPLSY | TRFSLARQVD | GDNSHVEMKL | AVDEEENADN | NTKANVTKPK | 60 |
| RCSGSICYGT | IAVIVFFLIG | FMIGYLGYCK | GVEPKTECER | LAGTESPVRE | EPGEDFPAAR | 120 |
| RLYWDDLKRK | LSEKLDSTDF | TGTIKLLNEN | SYVPREAGSQ | KDENLALYVE | NQFREFKLSK | 180 |
| VWRDQHFVKI | QVKDSAQNSV | IIVDKNGRLV | YLVENPGGYV | AYSKAATVTG | KLVHANFGTK | 240 |
| KDFEDLYTPV | NGSIVIVRAG | KITFAEKVAN | AESLNAIGVL | IYMDQTKFPI | VNAELSFFGH | 300 |
| AHLGTGDPYT | PGFPSFNHTQ | FPPSRSSGLP | NIPVQTISRA | AAEKLFGNME | GDCPSDWKTD | 360 |
| STCRMVTSES | KNVKLTVSNV | LKEIKILNIF | GVIKGFVEPD | HYVVVGAQRD | AWGPGAAKSG | 420 |
| VGTALLLKLA | QMFSDMVLKD | GFQPSRSIIF | ASWSAGDFGS | VGATEWLEGY | LSSLHLKAFT | 480 |
| YINLDKAVLG | TSNFKVSASP | LLYTLIEKTM | QNVKHPVTGQ | FLYQDSNWAS | KVEKLTLDNA | 540 |
| APPFLAYSGI | PAVSFCFCED | TDYPYLGTTM | DTYKELIERI | PELNKVARAA | AEVAGQFVIK | 600 |
| LTHDVELNLD | YERYNSQLLS | FVRDLNQYRA | DIKEMGLSLQ | WLYSARGDFF | RATSRLTTDF | 660 |
| GNAEKTDRFV | MKKLNDRVMR | VEYHFLSPYV | SPKESPFRHV | FWGSGSHTLP | ALLENLKLRK | 720 |
| QNNGAFNETL | FRNQLALATW | TIQGAANALS | GDVWDIDNEF | | | 760 |

| SEQ ID NO: 106 | moltype = AA length = 760 |
|---|---|
| FEATURE | Location/Qualifiers |
| source | 1..760 |
| | mol_type = protein |
| | organism = Macaca mulatta |

SEQUENCE: 106

| | | | | | |
|---|---|---|---|---|---|
| MMDQARSAFS | NLFGGEPLSY | TRFSLARQVD | GDNSHVEMKL | GVDEEENTDN | NTKPNGTKPK | 60 |
| RCGGNICYGT | IAVIIFFLIG | FMIGYLGYCK | GVEPKTECER | LAGTESPARE | EPEEDFPAAP | 120 |
| RLYWDDLKRK | LSEKLDTTDF | TSTIKLLNEN | LYVPREAGSQ | KDENLALYIE | NQFREFKLSK | 180 |
| VWRDQHFVKI | QVKDSAQNSV | IIVDKNGGLV | YLVENPGGYV | AYSKAATVTG | KLVHANFGTK | 240 |
| KDFEDLDSPV | NGSIVIVRAG | KITFAEKVAN | AESLNAIGVL | IYMDQTKFPI | VKADLSFFGH | 300 |
| AHLGTGDPYT | PGFPSFNHTQ | FPPSQSSGLP | NIPVQTISRA | AAEKLFGNME | GDCPSDWKTD | 360 |
| STCKMVTSEN | KSVKLTVSNV | LKETKILNIF | GVIKGFVEPD | HYVVVGAQRD | AWGPGAAKSS | 420 |
| VGTALLLKLA | QMFSDMVLKD | GFQPSRSIIF | ASWSAGDFGS | VGATEWLEGY | LSSLHLKAFT | 480 |
| YINLDKAVLG | TSNFKVSASP | LLYTLIEKTM | QDVKHPVTGR | SLYQDSNWAS | KVEKLTLDNA | 540 |
| APPFLAYSGI | PAVSFCFCED | TDYPYLGTTM | DTYKELVERI | PELNKVARAA | AEVAGQFVIK | 600 |
| LTHDTELNLD | YERYNSQLLL | FLRDLNQYRA | DVKEMGLSLQ | WLYSARGDFF | RATSRLTTDF | 660 |
| RNAEKRDKFV | MKKLNDRVMR | VEYYFLSPYV | SPKESPFRHV | FWGSGSHTLS | ALLESLKLRR | 720 |
| QNNSAFNETL | FRNQLALATW | TIQGAANALS | GDVWDIDNEF | | | 760 |

| SEQ ID NO: 107 | moltype = AA length = 760 |
|---|---|
| FEATURE | Location/Qualifiers |
| source | 1..760 |
| | mol_type = protein |

```
                        organism = Macaca fascicularis
SEQUENCE: 107
MMDQARSAFS NLFGGEPLSY TRFSLARQVD GDNSHVEMKL GVDEEENTDN NTKANGTKPK    60
RCGGNICYGT IAVIIFFLIG FMIGYLGYCK GVEPKTECER LAGTESPARE EPEEDFPAAP   120
RLYWDDLKRK LSEKLDTTDF TSTIKLLNEN LYVPREAGSQ KDENLALYIE NQFREFKLSK   180
VWRDQHFVKI QVKDSAQNSV IIVDKNGGLV YLVENPGGYV AYSKAATVTG KLVHANFGTK   240
KDFEDLDSPV NGSIVIVRAG KITFAEKVAN AESLNAIGVL IYMDQTKFPI VKADLSFFGH   300
AHLGTGDPYT PGFPSFNHTQ FPPSQSSGLP NIPVQTISRA AAEKLFGNME GDCPSDWKTD   360
STCKMVTSEN KSVKLTVSNV LKETKILNIF GVIKGFVEPD HYVVVGAQRD AWGPGAAKSS   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QDVKHPVTGR SLYQDSNWAS KVEKLTLDNA   540
APPFLAYSGI PAVSFCFCED TDYPYLGTTM DTYKELVERI PELNKVARAA AEVAGQFVIK   600
LTHDTELNLD YERYNSQLLL FLRDLNQYRA DVKEMGLSLQ WLYSARGDFF RATSRLTTDF   660
RNAEKRDKFV MKKLNDRVMR VEYYFLSPYV SPKESPFRHV FWGSGSHTLS ALLESLKLRR   720
QNNSAFNETL FRNQLALATW TIQGAANALS GDVWDIDNEF                        760

SEQ ID NO: 108          moltype = AA   length = 763
FEATURE                 Location/Qualifiers
source                  1..763
                        mol_type = protein
                        organism = Mus musculus
SEQUENCE: 108
MMDQARSAFS NLFGGEPLSY TRFSLARQVD GDNSHVEMKL AADEEENADN NMKASVRKPK    60
RFNGRLCFAA IALVIFFLIG FMSGYLGYCK RVEQKEECVK LAETEETDKS ETMETEDVPT   120
SSRLYWADLK TLLSEKLNSI EFADTIKQLS QNTYTPREAG SQKDESLAYY IENQFHEFKF   180
SKVWRDEHYV KIQVKSSIGQ NMVTIVQSNG NLDPVESPEG YVAFSKPTEV SGKLVHANFG   240
TKKDFEELSY SVNGSLVIVR AGEITFAEKV ANAQSFNAIG VLIYMDKNKF PVVEADLALF   300
GHAHLGTGDP YTPGFPSFNH TQFPPSQSSG LPNIPVQTIS RAAAEKLFGK MEGSCPARWN   360
IDSSCKLELS QNQNVKLIVK NVLKERRILN IFGVIKGYEE PDRYVVVGAQ RDALGAGVAA   420
KSSVGTGLLL KLAQVFSDMI SKDGFRPSRS IIFASWTAGD FGAVGATEWL EGYLSSLHLK   480
AFTYINLDKV VLGTSNFKVS ASPLLYTLMG KIMQDVKHPV DGKSLYRDSN WISKVEKLSF   540
DNAAYPPLAY SGIPAVSFCF CEDADYPYLG TRLDTYEALT QKVPQLNQMV RTAAEVAGQL   600
IIKLTHDVEL NLDYEMYNSK LLSFMKDLNQ FKTDIRDMGL SLQWLYSARG DYFRATSRLT   660
TDFHNAEKTN RFVMREINDR IMKVEYHFLS PYVSPRESPF RHIFWGSGSH TLSALVENLK   720
LRQKNITAFN ETLFRNQLAL ATWTIQGVAN ALSGDIWNID NEF                    763

SEQ ID NO: 109          moltype = AA   length = 197
FEATURE                 Location/Qualifiers
REGION                  1..197
                        note = Synthetic
source                  1..197
                        mol_type = protein
                        organism = synthetic construct
SEQUENCE: 109
FVKIQVKDSA QNSVIIVDKN GRLVYLVENP GGYVAYSKAA TVTGKLVHAN FGTKKDFEDL    60
YTPVNGSIVI VRAGKITFAE KVANAESLNA IGVLIYMDQT KFPIVNAELS FFGHAHLGTG   120
DPYTPGFPSF NHTQFPPSRS SGLPNIPVQT ISRAAAEKLF GNMEGDCPSD WKTDSTCRMV   180
TSESKNVKLT VSNVLKE                                                 197

SEQ ID NO: 110          moltype = AA   length = 5
FEATURE                 Location/Qualifiers
REGION                  1..5
                        note = Synthetic
source                  1..5
                        mol_type = protein
                        organism = synthetic construct
SEQUENCE: 110
SYWMH                                                                5

SEQ ID NO: 111          moltype = AA   length = 17
FEATURE                 Location/Qualifiers
REGION                  1..17
                        note = Synthetic
source                  1..17
                        mol_type = protein
                        organism = synthetic construct
SEQUENCE: 111
EINPTNGRTN YIEKFKS                                                  17

SEQ ID NO: 112          moltype = AA   length = 7
FEATURE                 Location/Qualifiers
REGION                  1..7
                        note = Synthetic
source                  1..7
                        mol_type = protein
                        organism = synthetic construct
SEQUENCE: 112
GTRAYHY                                                              7
```

```
SEQ ID NO: 113           moltype = AA   length = 11
FEATURE                  Location/Qualifiers
REGION                   1..11
                         note = Synthetic
source                   1..11
                         mol_type = protein
                         organism = synthetic construct
SEQUENCE: 113
RASDNLYSNL A                                                                  11

SEQ ID NO: 114           moltype = AA   length = 7
FEATURE                  Location/Qualifiers
REGION                   1..7
                         note = Synthetic
source                   1..7
                         mol_type = protein
                         organism = synthetic construct
SEQUENCE: 114
DATNLAD                                                                       7

SEQ ID NO: 115           moltype = AA   length = 9
FEATURE                  Location/Qualifiers
REGION                   1..9
                         note = Synthetic
source                   1..9
                         mol_type = protein
                         organism = synthetic construct
SEQUENCE: 115
QHFWGTPLT                                                                     9

SEQ ID NO: 116           moltype = AA   length = 7
FEATURE                  Location/Qualifiers
REGION                   1..7
                         note = Synthetic
source                   1..7
                         mol_type = protein
                         organism = synthetic construct
SEQUENCE: 116
GYTFTSY                                                                       7

SEQ ID NO: 117           moltype = AA   length = 6
FEATURE                  Location/Qualifiers
REGION                   1..6
                         note = Synthetic
source                   1..6
                         mol_type = protein
                         organism = synthetic construct
SEQUENCE: 117
NPTNGR                                                                        6

SEQ ID NO: 118           moltype = AA   length = 6
FEATURE                  Location/Qualifiers
REGION                   1..6
                         note = Synthetic
source                   1..6
                         mol_type = protein
                         organism = synthetic construct
SEQUENCE: 118
TSYWMH                                                                        6

SEQ ID NO: 119           moltype = AA   length = 13
FEATURE                  Location/Qualifiers
REGION                   1..13
                         note = Synthetic
source                   1..13
                         mol_type = protein
                         organism = synthetic construct
SEQUENCE: 119
WIGEINPTNG RTN                                                                13

SEQ ID NO: 120           moltype = AA   length = 6
FEATURE                  Location/Qualifiers
REGION                   1..6
                         note = Synthetic
source                   1..6
                         mol_type = protein
                         organism = synthetic construct
SEQUENCE: 120
ARGTRA                                                                        6
```

```
SEQ ID NO: 121          moltype = AA   length = 7
FEATURE                 Location/Qualifiers
REGION                  1..7
                        note = Synthetic
source                  1..7
                        mol_type = protein
                        organism = synthetic construct
SEQUENCE: 121
YSNLAWY                                                                    7

SEQ ID NO: 122          moltype = AA   length = 10
FEATURE                 Location/Qualifiers
REGION                  1..10
                        note = Synthetic
source                  1..10
                        mol_type = protein
                        organism = synthetic construct
SEQUENCE: 122
LLVYDATNLA                                                                10

SEQ ID NO: 123          moltype = AA   length = 8
FEATURE                 Location/Qualifiers
REGION                  1..8
                        note = Synthetic
source                  1..8
                        mol_type = protein
                        organism = synthetic construct
SEQUENCE: 123
QHFWGTPL                                                                   8

SEQ ID NO: 124          moltype = AA   length = 116
FEATURE                 Location/Qualifiers
REGION                  1..116
                        note = Synthetic
source                  1..116
                        mol_type = protein
                        organism = synthetic construct
SEQUENCE: 124
QVQLQQPGAE LVKPGASVKL SCKASGYTFT SYWMHWVKQR PGQGLEWIGE INPTNGRTNY     60
IEKFKSKATL TVDKSSSTAY MQLSSLTSED SAVYYCARGT RAYHYWGQGT SVTVSS        116

SEQ ID NO: 125          moltype = AA   length = 107
FEATURE                 Location/Qualifiers
REGION                  1..107
                        note = Synthetic
source                  1..107
                        mol_type = protein
                        organism = synthetic construct
SEQUENCE: 125
DIQMTQSPAS LSVSVGETVT ITCRASDNLY SNLAWYQQKQ GKSPQLLVYD ATNLADGVPS     60
RFSGSGSGTQ YSLKINSLQS EDFGTYYCQH FWGTPLTFGA GTKLELK                  107

SEQ ID NO: 126          moltype = AA   length = 9
FEATURE                 Location/Qualifiers
REGION                  1..9
                        note = Synthetic
source                  1..9
                        mol_type = protein
                        organism = synthetic construct
SEQUENCE: 126
QHFAGTPLT                                                                  9

SEQ ID NO: 127          moltype = AA   length = 8
FEATURE                 Location/Qualifiers
REGION                  1..8
                        note = Synthetic
source                  1..8
                        mol_type = protein
                        organism = synthetic construct
SEQUENCE: 127
QHFAGTPL                                                                   8

SEQ ID NO: 128          moltype = AA   length = 116
FEATURE                 Location/Qualifiers
REGION                  1..116
                        note = Synthetic
source                  1..116
                        mol_type = protein
```

```
                          organism = synthetic construct
SEQUENCE: 128
EVQLVQSGAE VKKPGASVKV SCKASGYTFT SYWMHWVRQA PGQRLEWIGE INPTNGRTNY      60
IEKFKSRATL TVDKSASTAY MELSSLRSED TAVYYCARGT RAYHYWGQGT MVTVSS         116

SEQ ID NO: 129            moltype = AA   length = 107
FEATURE                   Location/Qualifiers
REGION                    1..107
                          note = Synthetic
source                    1..107
                          mol_type = protein
                          organism = synthetic construct
SEQUENCE: 129
DIQMTQSPSS LSASVGDRVT ITCRASDNLY SNLAWYQQKP GKSPKLLVYD ATNLADGVPS      60
RFSGSGSGTD YTLTISSLQP EDFATYYCQH FWGTPLTFGQ GTKVEIK                  107

SEQ ID NO: 130            moltype = AA   length = 330
FEATURE                   Location/Qualifiers
source                    1..330
                          mol_type = protein
                          organism = Homo sapiens
SEQUENCE: 130
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                     330

SEQ ID NO: 131            moltype = RNA   length = 25
FEATURE                   Location/Qualifiers
misc_feature              1..25
                          note = Synthetic
source                    1..25
                          mol_type = other RNA
                          organism = synthetic construct
SEQUENCE: 131
actgcgcgca ggtctagcca ggaag                                           25

SEQ ID NO: 132            moltype = AA   length = 446
FEATURE                   Location/Qualifiers
REGION                    1..446
                          note = Synthetic
source                    1..446
                          mol_type = protein
                          organism = synthetic construct
SEQUENCE: 132
QVQLQQPGAE LVKPGASVKL SCKASGYTFT SYWMHWVKQR PGQGLEWIGE INPTNGRTNY      60
IEKFKSKATL TVDKSSSTAY MQLSSLTSED SAVYYCARGT RAYHYWGQGT SVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCPPCPA PELLGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSRDELTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPGK                                         446

SEQ ID NO: 133            moltype = AA   length = 214
FEATURE                   Location/Qualifiers
REGION                    1..214
                          note = Synthetic
source                    1..214
                          mol_type = protein
                          organism = synthetic construct
SEQUENCE: 133
DIQMTQSPAS LSVSVGETVT ITCRASDNLY SNLAWYQQKQ GKSPQLLVYD ATNLADGVPS      60
RFSGSGSGTQ YSLKINSLQS EDFGTYYCQH FWGTPLTFGA GTKLELKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                214

SEQ ID NO: 134            moltype = AA   length = 446
FEATURE                   Location/Qualifiers
REGION                    1..446
                          note = Synthetic
source                    1..446
                          mol_type = protein
                          organism = synthetic construct
SEQUENCE: 134
EVQLVQSGAE VKKPGASVKV SCKASGYTFT SYWMHWVRQA PGQRLEWIGE INPTNGRTNY      60
IEKFKSRATL TVDKSASTAY MELSSLRSED TAVYYCARGT RAYHYWGQGT MVTVSSASTK     120
```

```
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSRDELTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 135          moltype = AA   length = 214
FEATURE                 Location/Qualifiers
REGION                  1..214
                        note = Synthetic
source                  1..214
                        mol_type = protein
                        organism = synthetic construct
SEQUENCE: 135
DIQMTQSPSS LSASVGDRVT ITCRASDNLY SNLAWYQQKP GKSPKLLVYD ATNLADGVPS     60
RFSGSGSGTD YTLTISSLQP EDFATYYCQH FWGTPLTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 136          moltype = AA   length = 226
FEATURE                 Location/Qualifiers
REGION                  1..226
                        note = Synthetic
source                  1..226
                        mol_type = protein
                        organism = synthetic construct
SEQUENCE: 136
QVQLQQPGAE LVKPGASVKL SCKASGYTFT SYWMHWVKQR PGQGLEWIGE INPTNGRTNY     60
IEKFKSKATL TVDKSSSTAY MQLSSLTSED SAVYYCARGT RAYHYWGQGT SVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCP                   226

SEQ ID NO: 137          moltype = AA   length = 226
FEATURE                 Location/Qualifiers
REGION                  1..226
                        note = Synthetic
source                  1..226
                        mol_type = protein
                        organism = synthetic construct
SEQUENCE: 137
EVQLVQSGAE VKKPGASVKV SCKASGYTFT SYWMHWVRQA PGQRLEWIGE INPTNGRTNY     60
IEKFKSRATL TVDKSASTAY MELSSLRSED TAVYYCARGT RAYHYWGQGT MVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCP                   226

SEQ ID NO: 138          moltype = AA   length = 7
FEATURE                 Location/Qualifiers
REGION                  1..7
                        note = Synthetic
source                  1..7
                        mol_type = protein
                        organism = synthetic construct
SEQUENCE: 138
ASSLNIA                                                                7

SEQ ID NO: 139          moltype = AA   length = 12
FEATURE                 Location/Qualifiers
REGION                  1..12
                        note = Synthetic
source                  1..12
                        mol_type = protein
                        organism = synthetic construct
SEQUENCE: 139
SKTFNTHPQS TP                                                         12

SEQ ID NO: 140          moltype = AA   length = 12
FEATURE                 Location/Qualifiers
REGION                  1..12
                        note = Synthetic
source                  1..12
                        mol_type = protein
                        organism = synthetic construct
SEQUENCE: 140
TARGEHKEEE LI                                                         12

SEQ ID NO: 141          moltype = AA   length = 9
FEATURE                 Location/Qualifiers
REGION                  1..9
```

```
                       note = Synthetic
source                 1..9
                       mol_type = protein
                       organism = synthetic construct
SEQUENCE: 141
CQAQGQLVC                                                                      9

SEQ ID NO: 142         moltype = AA   length = 9
FEATURE                Location/Qualifiers
REGION                 1..9
                       note = Synthetic
source                 1..9
                       mol_type = protein
                       organism = synthetic construct
SEQUENCE: 142
CSERSMNFC                                                                      9

SEQ ID NO: 143         moltype = AA   length = 9
FEATURE                Location/Qualifiers
REGION                 1..9
                       note = Synthetic
source                 1..9
                       mol_type = protein
                       organism = synthetic construct
SEQUENCE: 143
CPKTRRVPC                                                                      9

SEQ ID NO: 144         moltype = AA   length = 20
FEATURE                Location/Qualifiers
REGION                 1..20
                       note = Synthetic
source                 1..20
                       mol_type = protein
                       organism = synthetic construct
SEQUENCE: 144
WLSEAGPVVT VRALRGTGSW                                                         20

SEQ ID NO: 145         moltype = AA   length = 9
FEATURE                Location/Qualifiers
REGION                 1..9
                       note = Synthetic
source                 1..9
                       mol_type = protein
                       organism = synthetic construct
SEQUENCE: 145
CMQHSMRVC                                                                      9

SEQ ID NO: 146         moltype = AA   length = 7
FEATURE                Location/Qualifiers
REGION                 1..7
                       note = Synthetic
source                 1..7
                       mol_type = protein
                       organism = synthetic construct
SEQUENCE: 146
DDTRHWG                                                                        7

SEQ ID NO: 147         moltype = DNA   length = 1275
FEATURE                Location/Qualifiers
source                 1..1275
                       mol_type = genomic DNA
                       organism = Homo sapiens
SEQUENCE: 147
atggccctcc cgacaccctc ggacagcacc ctccccgcgg aagcccgggg acgaggacgg            60
cgacggagac tcgtttggac cccgagccaa agcgaggccc tgcgagcctg ctttgagcgg           120
aacccgtacc cgggcatcgc caccagagaa cggctggccc aggccatcgg cattccggag           180
cccagggtcc agatttggtt tcagaatgag aggtcacgcc agctgaggca gcaccggcgg           240
gaatctcggc cctggcccgg gagacgcggc cgccagaaag gccgcgaaa gcggaccgcc            300
gtcaccggat cccagaccgc cctgctcctc cgagcctttg agaaggatcg ctttccaggc           360
atcgccgccc gggaggagct ggccagagag acgggcctcc cggagtccag gattcagatc           420
tggtttcaga atcgaaggcg caggcacccg ggacagggtg gcaggcgcc cgcgcaggca            480
ggcggcctgt gcagcgcggc cccggcgggg ggtcaccctg ctccctcgtg ggtcgccttc           540
gcccacaccg gcgcgtgggg aacgggcgct tcccgcaccc acgtgccctg cgcgcctggg           600
gctctcccac aggggggcttt cgtgagccag gcagcgaggg ccgccccgc gctgcagccc           660
agccaggccc gccggcaga ggggatctcc caacctgccc cggcgcgcgg ggatttcgcc            720
tacgccgccc cggctcctcc ggacggggcg ctctcccacc ctcaggctcc tcggtggcct           780
ccgcacccgg gcaaaagccg ggaggaccgg gaccgcagc gcgacggcct gccgggcccc            840
tgcgcggtgc cacagcctgg gccgctcaa gcggggcgcc agggccaagg ggtgcttgcg            900
ccacccacgt cccaggggag tccgtggtgg ggctggggcc ggggtcccca ggtcgccggg           960
```

-continued

```
gcggcgtggg aaccccaagc cggggcagct ccacctcccc agcccgcgcc cccggacgcc    1020
tccgcctccg cgcggcaggg gcagatgcaa ggcatcccgg cgccctccca ggcgctccag    1080
gagccggcgc cctggtctgc actcccctgc ggcctgctgc tggatgagct cctggcgagc    1140
ccggagtttg tgcagcaggc gcaacctctc ctagaaacgg aggccccggg ggagctggag    1200
gcctcggaag aggccgcctc gctggaagca cccctcagcg aggaagaata ccgggctctg    1260
ctggaggagc tttag                                                     1275

SEQ ID NO: 148           moltype = DNA  length = 2024
FEATURE                  Location/Qualifiers
source                   1..2024
                         mol_type = genomic DNA
                         organism = Mus musculus
SEQUENCE: 148
atggcagaag ctggcagccc tgttggtggc agtggtgtgg cacgggaatc ccggcggcgc    60
aggaagacgg tttggcaggc ctggcaagag caggccctgc tatcaacttt caagaagaag    120
agatacctga gcttcaagga gaggaaggag ctggccaagc gaatgggggt ctcagattgc    180
cgcatccgcg tgtggtttca gaaccgcagg aatcgcagtg gagaggaggg gcatgcctca    240
aagaggtcca tcagaggctc caggaggcta gcctcgccac agctccagga agagcttgga    300
tccaggccac agggtagagg catgcgctca tctggcagaa ggcctcgcac tcgactcacc    360
tcgctacagc tcaggatcct agggcaagca tttgagagga acccacgacc aggctttgct    420
accagggagg agctggcgcg tgacacaggg ttgcccgagg acacgatcca catatggttt    480
caaaaccgaa gagctcggcg gcgccacagg aggggcaggc ccacagctca agatcaagac    540
ttgctggcgt cacaagggtc ggatgggggcc cctgcaggtc cggaaggcag agagcgtgaa    600
ggtgcccagg agaacttgtt gccacaggaa gaagcaggaa gtacgggcat ggataccctcg    660
agccctagcg acttgccctc cttctgcgga gagtcccagc ctttccaagt ggcacagccc    720
cgtggagcag gccaacaaga ggcccccact cgagcaggca acgcaggctc tctgaaaccc    780
ctccttgatc agctgctgga tgaagtccaa gtagaagagc ctgctccagc ccctctgaat    840
ttggatggaa accctggtgg cagggtgcat gaaggttccc aggagagctt ttggccacag    900
gaagaagcag gaagtacagg catggatact tctagcccca gcgactcaaa ctccttctgc    960
agagagtccc agccttccca agtggcacag ccctgtggga cgggccaaga agatgcccgc    1020
actcaagcag acagcacagg ccctctggaa ctcctcctcc ttgatcaact gctggacgaa    1080
gtccaaaagg aagagcatgt gccagtccca ctggattggg gtagaaatcc tgcagcagg    1140
gagcatgaag gttcccagga cagcttactg ccctgagg aagcagtaaa ttcgggcatg    1200
gatacctcga tccctagcat ctggccaacc ttctgcagaa aatcccagcc tccccaagtg    1260
gcacagccct ctggaccagg ccaagcacag gcccccactc aaggtgggaa cacggaccccc    1320
ctggagctct cctctatca actgttggat gaagtccaag tagaagagca tgctccagcc    1380
cctctgaatt gggatgtaga tcctggtggc agggtgcatg aaggtcgtg ggagagcttt    1440
tggccacagg aagaagcagg aagtacaggc ctggatactt caagcccccag cgactcaaac    1500
tccttcttca gagagtccaa gccttcccaa gtggcacagc gccgtggagc gggccaagaa    1560
gatgcccgca ctcaagcaga cagcacaggc cctctggaac tcctcctctt tgatcaactg    1620
ctggacgaag tccaaaagga gagcatgtg ccagccccac tggattgggg tagaaatcct    1680
ggcagcatgg agcatgaagg ttcccaggac agcttactgc ccctgagga agcagcaaat    1740
tcgggcatg atacctcgat ccctagcatc tggccagcct tctgcagaaa atcccagcct    1800
ccccaagtgg cacagccctc tggaccagcc caagcacagg ccccccattca aggtgggaac    1860
acggaccccc tggagctctt ccttgatcaa ctgctgaccg aagtccaact tgaggagcag    1920
gggcctgccc ctgtgaatgt ggaggaaaca tgggagcaaa tggacacaac acctatctgc    1980
ctctcacttc agaagaatat cagactcttc tagatatgct ctga                     2024

SEQ ID NO: 149           moltype = DNA  length = 25
FEATURE                  Location/Qualifiers
misc_feature             1..25
                         note = Synthetic
source                   1..25
                         mol_type = other DNA
                         organism = synthetic construct
SEQUENCE: 149
cctcttacct cagttacaat ttata                                          25

SEQ ID NO: 150           moltype = DNA  length = 25
FEATURE                  Location/Qualifiers
misc_feature             1..25
                         note = Synthetic
source                   1..25
                         mol_type = other DNA
                         organism = synthetic construct
SEQUENCE: 150
agttcagaga tatattaaaa tgccc                                          25

SEQ ID NO: 151           moltype = DNA  length = 25
FEATURE                  Location/Qualifiers
misc_feature             1..25
                         note = Synthetic
source                   1..25
                         mol_type = other DNA
                         organism = synthetic construct
SEQUENCE: 151
gggcatttta atatatctct gaact                                          25

SEQ ID NO: 152           moltype = RNA  length = 21
```

```
FEATURE                 Location/Qualifiers
misc_feature            1..21
                        note = Synthetic
source                  1..21
                        mol_type = other RNA
                        organism = synthetic construct
SEQUENCE: 152
tcctatgact gtagatttta t                                              21

SEQ ID NO: 153          moltype = RNA   length = 23
FEATURE                 Location/Qualifiers
misc_feature            1..23
                        note = Synthetic
source                  1..23
                        mol_type = other RNA
                        organism = synthetic construct
SEQUENCE: 153
ataaaatcta cagtcatagg aat                                            23

SEQ ID NO: 154          moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 154
tgtaataacc atatctacct t                                              21

SEQ ID NO: 155          moltype = RNA   length = 23
FEATURE                 Location/Qualifiers
misc_feature            1..23
                        note = Synthetic
source                  1..23
                        mol_type = other RNA
                        organism = synthetic construct
SEQUENCE: 155
aaggtagata tggttattac aaa                                            23

SEQ ID NO: 156          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 156
tgcgcactgc gcgcaggtct agccaggaag                                     30

SEQ ID NO: 157          moltype = DNA   length = 1574
FEATURE                 Location/Qualifiers
source                  1..1574
                        mol_type = genomic DNA
                        organism = Homo sapiens
SEQUENCE: 157
atggccctcc cgacaccctc ggacagcacc ctccccgcgg aagcccgggg acgaggacgg    60
cgacggagac tcgtttggac cccgagccaa agcgaggccc tgcgagcctg ctttgagcgg   120
aacccgtacc cggcatcgc caccagagaa cggctggccc aggccatcgg cattccggag   180
cccagggtcc agatttggtt tcagaatgag aggtcacgcc agctgaggca gcaccggcgg   240
gaatctcggc cctggcccgg gagacgcggc ccgccagaag gccggcgaaa gcggaccgcc   300
gtcaccggat cccagaccgc cctgctcctc cgagcctttg agaaggatcg cttttccaggc   360
atcgccgccc gggaggagct ggccagagag acgggcctcc cggagtccag gattcagatc   420
tggtttcaga atcgaagggc caggcacccg ggacagggtg gcagggcgcc cgcgcaggca   480
ggcggcctgt gcagcgcgc cccggcgggg ggtcaccctg ctccctcgtg ggtcgccttc   540
gcccacaccg gcgcgtgggg aacgggcgtt cccgcacccc acgtgccctg cgcgcctggg   600
gctctcccac aggggggcttt cgtgagccag gcagcgaggg ccgcccccgc gctgcagccc   660
```

```
agccaggccg cgccggcaga ggggatctcc caacctgccc cggcgcgcgg ggatttcgcc    720
tacgccgccc cggctcctcc ggacggggcg ctctcccacc ctcaggctcc tcgctggcct    780
ccgcaccagg gcaaaagccg ggaggaccgg gacccgagc gcgacggcct gccgggcccc    840
tgcgcggtgg cacagcctgg gcccgctcaa gcggggccgc agggccaagg ggtgcttgcg    900
ccacccacgt cccaggggag tccgtggtgg ggctggggcc ggggtcccca ggtcgccggg    960
gcggcgtggg aacccaagc cggggcagct ccacctcccc agcccgcgcc cccggacgcc   1020
tccgcctccg cgcggcaggg gcagatgcaa ggcatcccgg cgccctccca ggcgctccag   1080
gagccggcgc cctggtctgc actcccctgc ggcctgctgc tggatgagct cctggcgagc   1140
ccggagtttc tgcagcaggc gcaacctctc ctagaaacgg aggccccggg ggagctggag   1200
gcctcggaag aggccgcctc gctggaagca cccctcagcg aggaagaata ccgggctctg   1260
ctggaggagc tttaggacgc ggggtctagg cccggtgaga gactccacac cgcggagaac   1320
tgccattctt tcctgggcat cccggggatc ccagagccgg cccaggtacc agcagacctg   1380
cgcgcagtgc gcaccccggc tgacgtgcaa gggagctcgc tggcctctct gtgcccttgt   1440
tcttccgtga aattctggct gaatgtctcc ccccaccttc cgacgctgtc taggcaaacc   1500
tggattagag ttacatctcc tggatgatta gttcagagat atattaaaat gcccctccc    1560
tgtggatcct atag                                                     1574

SEQ ID NO: 158          moltype = DNA  length = 1710
FEATURE                 Location/Qualifiers
source                  1..1710
                        mol_type = genomic DNA
                        organism = Homo sapiens
SEQUENCE: 158
atggccctcc cgacaccctc ggacagcacc ctccccgcgg aagcccgggg acgaggacgg    60
cgacggagac tcgtttggac cccgagccaa agcgaggccc tgcgagcctg ctttgagcgg   120
aaccgtacc cgggcatcgc caccagagaa cggctgagcc aggccatcgg cattccggag   180
cccagggtcc agatttggtt tcagaatgag aggtcacgcc agctgaggca gcaccggcgg   240
gaatctcggc cctggcccgg gagacgcggc ccgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc cggagtccag gattcagatc   420
tggtttcaga atcgaagggc caggcacccg ggacagggtg gcagggcgcc cgcgcaggca   480
ggcggcctgt gcagcgcggc ccccggcggg ggtcaccctg ctccctcgtg ggtcgccttc   540
gcccacaccg gcgcgtgggg aacggggctt cccgcacccc acgtgccctg cgcgcctggg   600
gctctcccac aggggggctt cgtgagccag gcagcgaggg ccgcccccgc gctgcagccc   660
agccaggccg cgccggcaga ggggatctcc caacctgccc cggcgcgcgg ggatttcgcc   720
tacgccgccc cggctcctcc ggacggggcg ctctcccacc ctcaggctcc tcggtggcct   780
ccgcaccagg gcaaaagccg ggaggaccgg gacccgagc gcgacggcct gccgggcccc    840
tgcgcggtgg cacagcctgg gcccgctcaa gcggggccgc agggccaagg ggtgcttgcg    900
ccacccacgt cccaggggag tccgtggtgg ggctggggcc ggggtcccca ggtcgccggg    960
gcggcgtggg aacccaagc cggggcagct ccacctcccc agcccgcgcc cccggacgcc   1020
tccgcctccg cgcggcaggg gcagatgcaa ggcatcccgg cgccctccca ggcgctccag   1080
gagccggcgc cctggtctgc actcccctgc ggcctgctgc tggatgagct cctggcgagc   1140
ccggagtttc tgcagcaggc gcaacctctc ctagaaacgg aggccccggg ggagctggag   1200
gcctcggaag aggccgcctc gctggaagca cccctcagcg aggaagaata ccgggctctg   1260
ctggaggagc tttaggacgc ggggttggga cggggtcggg tggttcgggg cagggcggtg   1320
gcctctcttt cgcggggaac acctggctgg ctacggaggg gcgtgtctcc gccccgcccc   1380
ctccaccggg ctgaccggcc tgggattcct gccttctagg tctaggcccg gtgagagact   1440
ccactccgcg gagaactgcc tttctttcct gggcatcccg gggatcccag agccggccca   1500
ggtaccagca gacctgcgcg cagtgcgcac cccggctgac gtgcaaggga gctcgctggc   1560
ctctctgtgc ccttgttctt ccgtgaaatt ctggctgaat gtctcccccc accttccgac   1620
gctgtctagg caaacctgga ttagagttac atctcctgga tgattagttc agagatatat   1680
taaaatgccc cctccctgtg gatcctatag                                   1710
```